(12) United States Patent
Siegel et al.

(10) Patent No.: US 8,273,752 B2
(45) Date of Patent: Sep. 25, 2012

(54) SUBSTITUTED IMIDAZOPYRIMIDINES AND TRIAZOLOPYRIMIDINES

(75) Inventors: Stephan Siegel, Berlin (DE); Andreas Wilmen, Köln (DE); Susanne Röhrig, Hilden (DE); Niels Svenstrup, Velbert (DE); Mark Jean Gnoth, Mettmann (DE); Stefan Heitmeier, Wülfrath (DE); Ulrich Rester, Wuppertal (DE); Dmitry Zubov, Remscheid (DE); Jochen Strayle, Wuppertal (DE); Michael Sperzel, Kierspe (DE)

(73) Assignee: Bayer Intellectual Property GmbH, Monheim (DE)

( * ) Notice: Subject to any disclaimer, the term of this patent is extended or adjusted under 35 U.S.C. 154(b) by 229 days.

(21) Appl. No.: 12/529,711

(22) PCT Filed: Mar. 4, 2008

(86) PCT No.: PCT/EP2008/001682
§ 371 (c)(1),
(2), (4) Date: Jan. 11, 2010

(87) PCT Pub. No.: WO2008/113469
PCT Pub. Date: Sep. 25, 2008

(65) Prior Publication Data
US 2010/0113441 A1    May 6, 2010

(30) Foreign Application Priority Data

Mar. 16, 2007    (DE) .......................... 10 2007 012 645

(51) Int. Cl.
*A01N 43/90*   (2006.01)
*A61K 31/519*  (2006.01)
*C07D 487/00*  (2006.01)

(52) U.S. Cl. ................... 514/259.1; 514/259.5; 544/281
(58) Field of Classification Search .................. None
See application file for complete search history.

(56) References Cited

FOREIGN PATENT DOCUMENTS

| EP | 0641564 A1 | 3/1995 |
| WO | WO-01/83485 A1 | 11/2001 |
| WO | WO 03/014137 A1 | 2/2003 |
| WO | WO-2006/044687 A2 | 4/2006 |

OTHER PUBLICATIONS

Vippagunta et. al. Advanced Drug Delivery Reviews 48 (2001) 3-26.*
J. R. Woodgett: "A Common Denominator Linking Glycogen Metabolism, Nuclear Oncogenes and Development," Trends in Biochemical Sciences, vol. 16, May 1991, pp. 177-181.
A. Wodarz et al.: "Mechanisms of WNT Signaling in Development," Annu. Rev. Cell Dev. Biol., vol. 14, 1998, pp. 59-88.
P. Kirstetter et al.: "Activation of the Canonical WNT Pathway Leads to Loss of Hematopoietic Stem Cell Repopulation and Multilineage Differentiation Block," Nature Immunology, vol. 7, No. 10, Oct. 2006, pp. 1048-1056.
M. O'Brien et al.: "Mortality within 30 Days of Chemotherapy: a Clinical Governance Benchmarking Issue for Oncology Patients," British Journal of Cancer, vol. 95, 2006, pp. 1632-1636.

\* cited by examiner

*Primary Examiner* — Jeffrey Murray
(74) *Attorney, Agent, or Firm* — Karen King

(57) ABSTRACT

The invention relates to substituted imidazo- and triazolopyrimidines and processes for their preparation, and their use for the manufacture of medicaments for the treatment and/or prophylaxis of diseases, in particular of haematological disorders, preferably of leucopenias and neutropenias.

5 Claims, No Drawings

SUBSTITUTED IMIDAZOPYRIMIDINES AND TRIAZOLOPYRIMIDINES

This application is a National Stage Application filed under 35 U.S.C. §371 based on International Application No. PCT/EP2008/001682, filed Mar. 4, 2008, which claims priority to German Patent Application Number 102007012645.1, filed Mar. 16, 2007, the entire contents each of which are incorporated herein by reference. The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The invention relates to substituted imidazo- and triazolopyrimidines and processes for their preparation, and their use for the manufacture of medicaments for the treatment and/or prophylaxis of diseases, in particular of haematological disorders, preferably of leukopenias and neutropenias.

Glycogen synthase kinase 3 (GSK3) belongs to the families of serine/threonin kinases. Specific substrates are inter alia cytoskeletal proteins and transcription factors. Two isoforms, GSK3α and GSK3β, have been identified to date (Woodgett J R., Trends Biochem. Sci. (1991), 16(5), 177-81). Both isoforms are constitutively active in chiefly resting, non-proliferating cells.

GSK3β is of central importance within the Wnt/Wingless signal transduction pathway. The latter is one of the most important, evolutionarily conserved signalling systems. Wnt signals control very early patterning processes during embryogenesis, they induce mesoderm formation and many organs, and they control the proliferation and differentiation of stem cells (Wodarz A., Nusse R., Annu. Rev. Cell Dev. Biol. (1998), 14, 59-88; Kirstetter et al., Nat. Immunol. (2006), 7(10), 1048-56). There is intracellular compartmentalization of the Wnt signalling pathway, thus making it possible to control a wide variety of processes. Within the Wnt cascade, glycogen synthase kinase 3 forms part of a multiprotein complex to which belong inter alia the structural molecules axin, the tumour suppressor protein APC and the transcription cofactor β-catenin. In this connection, β-catenin is the principal substrate of GSK3β. The consequence of this GSK3β-mediated phosphorylation is the proteasomal degradation of β-catenin Inhibition of GSK3-activity leads to an accumulation of β-catenin in the cell with subsequent translocation into the cell nucleus. There, β-catenin acts as a cofactor in transcription complexes and thus is partly responsible for the expression of defined target genes.

Radiotherapies or chemotherapies are among the standard approaches to controlling cancer. Both types of therapy are nonspecific in relation to their target cells, i.e. not only tumour cells but also untransformed, proliferating cells are affected. These untransformed, proliferating cells also include haematopoietic progenitor cells which develop inter alia into neutrophilic granulocytes. A significant reduction in the number of neutrophils is referred to as neutropenia. A neutropenia induced by chemotherapy or radiotherapy results clinically in an increased susceptibility to infection. If the neutropenia is substantial there is an increase in the morbidity and, in some circumstances, also the mortality of a therapy (O'Brien et al., British Journal of Cancer (2006), 95, 1632-1636).

Inhibition of GSK3 activity leads to an increased rate of proliferation and differentiation of haematopoietic stem cells and can accordingly be utilized for therapeutic intervention in relation to a therapy-induced neutropenia.

WO2006/044687 describes the use of imidazopyrimidinylamines as kinase inhibitors for the treatment of cancer and WO01/083485 discloses imidazo- and triazolopyrimidines inter alia for the treatment of asthma and cancer. WO2005/044793 discloses inter alia the use of imidazopyrimidinylamines as CRF (corticotropin releasing factor) receptor antagonists for the treatment of depressions.

One object of the present invention is therefore to provide novel compounds as GSK3β inhibitors for the treatment of haematological disorders, preferably of neutropenia in humans and animals.

The invention relates to compounds of the formula

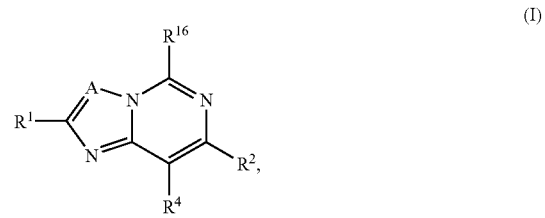

(I)

in which
A is N or $CR^{15}$,
where
$R^{15}$ is hydrogen, bromine or chlorine,
$R^1$ is hydrogen, hydroxy, amino, hydroxycarbonyl, aminocarbonyl, trifluoromethyl, trifluoromethoxy, cyano, $C_1$-$C_4$-alkoxy, $C_1$-$C_6$-alkylamino, alkylcarbonyl, $C_1$-$C_4$-alkoxycarbonyl, $C_1$-$C_6$-alkylaminocarbonyl, dihydroxypropylaminocarbonyl, dihydroxybutylaminocarbonyl, dihydroxypentylaminocarbonyl, $C_1$-$C_4$-alkylcarbonylamino, $C_1$-$C_4$-alkylsulphonylamino, 5- or 6-membered heterocyclylcarbonyl, —$CH_2R^{13}$ or —$CH_2CH_2R^{14}$,
where alkoxy, alkylamino, alkylcarbonyl, alkoxycarbonyl, alkylaminocarbonyl, alkylcarbonylamino and alkylsulphonylamino may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino and 5- or 6-membered heterocyclyl,
in which heterocyclyl may be substituted by 1 to 3 substituents, where the substituents are selected independently of one another from the group consisting of halogen, hydroxy, oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl,
and
where heterocyclylcarbonyl may be substituted by 1 to 3 substituents, where the substituents are selected independently of one another from the group consisting of halogen, hydroxy, oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl,
and
where
$R^{13}$ is hydroxy, amino, cyano, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino, 5- or 6-membered heterocyclyl or 5- or 6-membered heteroaryl,
in which alkoxy, alkylamino, alkoxycarbonyl, alkylaminocarbonyl and alkylcarbonylamino may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino, and in which heterocyclyl and heteroaryl may be substituted by 1 to 3 substituents, where the substituents are selected independently of one another from the group consisting of halogen, hydroxy, oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl, and where $R^{14}$ is hydroxy, amino, cyano, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino, 5- or 6-membered heterocyclyl or 5- or 6-membered heteroaryl, in which alkoxy, alkylamino, alkoxycarbonyl, alkylaminocarbonyl and alkylcarbonylamino may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino, and in which heterocyclyl and heteroaryl may be substituted by 1 to 3 substituents, where the substituents are selected independently of one another from the group consisting of halogen, hydroxy, oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl, $R^2$ is $C_6$-$C_{10}$-aryl or 5- to 10-membered heteroaryl, where aryl and heteroaryl may be substituted by 1 to 3 substituents, where the substituents are selected independently of one another from the group consisting of hydroxy, hydroxymethyl, amino, halogen, cyano, trifluoromethyl, trifluoromethoxy, aminocarbonyl, $C_1$-$C_4$-alkyl, $C_1$-$C_4$-alkoxy, $C_1$-$C_4$-alkoxymethyl, $C_1$-$C_4$-alkylamino, $C_1$-$C_4$-alkylaminomethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulphonyl, $C_1$-$C_4$-alkylsulphonylamino, $C_1$-$C_4$-alkylaminosulphonyl, phenyl, benzyloxy, 5- or 6-membered heterocyclyl, 5- or 6-membered heterocyclylcarbonyl, 5- or 6-membered heterocyclylmethyl and 5- or 6-membered heteroaryl, in which phenyl, benzyloxy, heterocyclyl, heterocyclylcarbonyl, heterocyclylmethyl and heteroaryl may be substituted by 1 to 3 substituents, where the substituents are selected independently of one another from the group consisting of halogen, cyano, trifluoromethyl, trifluoromethoxy, aminocarbonyl, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_1$-$C_4$-alkylcarbonylamino, or two of the substituents on the aryl form together with the carbon atoms to which they are bonded a 1,3-dioxolane or 1,4-dioxane, $R^4$ is hydrogen, halogen, cyano, trifluoromethyl, $C_1$-$C_3$-alkyl, methylthio or cyclopropyl, $R^{16}$ is a group of the formula

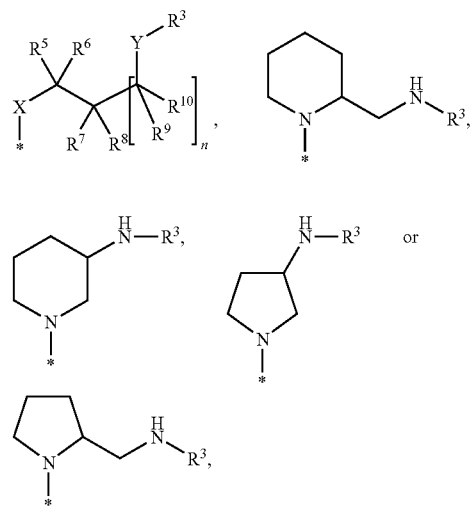

where

* is the point of attachment to the heterocycle, n is the number 0 or 1,

X is $NR^{11}$, S or O, where $R^{11}$ is hydrogen, $C_1$-$C_3$-alkyl or cyclopropyl, Y is $NR^{12}$, S or O, where $R^{12}$ is hydrogen, $C_1$-$C_3$-alkyl or cyclopropyl, $R^3$ is 2-pyridyl, pyrimid-2-yl, 2-aminopyrimid-4-yl, 2-cyclopropylaminopyrimid-4-yl, 2-methylaminopyrimid-4-yl, 2-ethylaminopyrimid-4-yl, 1,3-thiazol-2-yl, 1,3-thiazol-4-yl or 1,3-thiazol-5-yl, where 2-pyridyl, pyrimid-2-yl, 2-aminopyrimid-4-yl, 1,3-thiazol-2-yl, 1,3-thiazol-4-yl and 1,3-thiazol-5-yl are substituted by 1 to 3 substituents, where the substituents are selected independently of one another from the group consisting of halogen, cyano, nitro, amino, trifluoromethyl, trifluoromethoxy, aminocarbonyl, trifluoromethylcarbonyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_3$-$C_6$-cycloalkylcarbonyl, in which alkyl, alkoxy, alkylamino, alkylcarbonyl, alkoxycarbonyl, alkylaminocarbonyl and cycloalkylcarbonyl may be substituted by a substituent, where the substituent is selected from the group consisting of halogen, cyano, hydroxy, amino, trifluoromethyl and $C_3$-$C_6$-cycloalkyl, or $R^3$ is a group of the formula

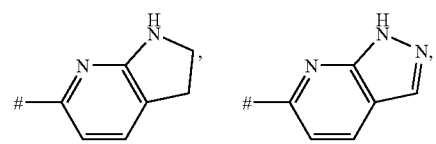

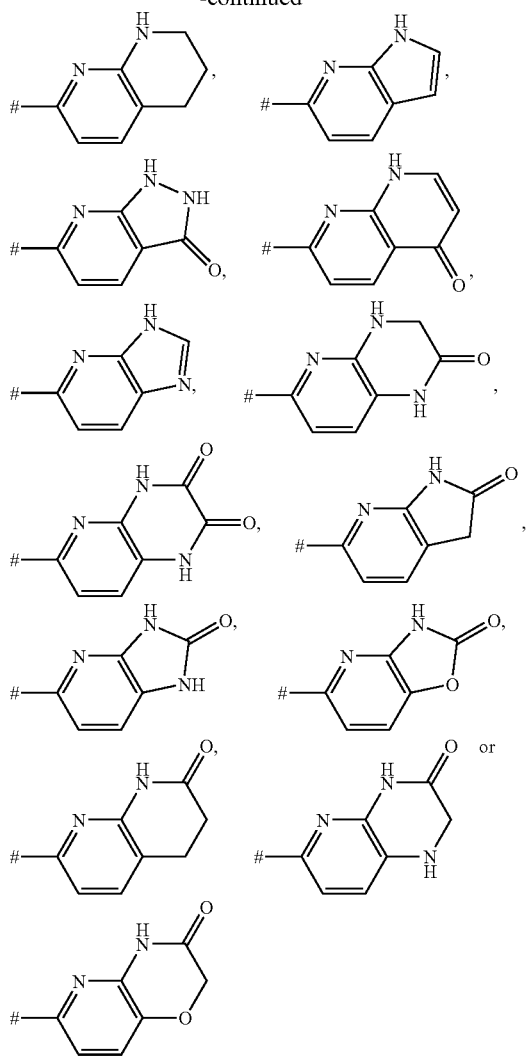

where # is the point of attachment to Y,
R[5] is hydrogen, $C_1$-$C_3$-alkyl or cyclopropyl,
R[6] is hydrogen or $C_1$-$C_3$-alkyl,
R[7] is hydrogen, $C_1$-$C_3$-alkyl or cyclopropyl,
R[8] is hydrogen or $C_1$-$C_3$-alkyl,
R[9] is hydrogen, $C_1$-$C_3$-alkyl or cyclopropyl,
R[10] is hydrogen or $C_1$-$C_3$-alkyl,
and the salts thereof, the solvates thereof and the solvates of the salts thereof.

Compounds according to the invention are the compounds of the formula (I) and the salts, solvates and solvates of the salts thereof, as well as the compounds encompassed by the formula (I) and mentioned below as exemplary embodiment, and the salts, solvates and solvates of the salts thereof, insofar as the compounds encompassed by formula (I) and mentioned below are not already salts, solvates and solvates of the salts.

The compounds of the invention may, depending on their structure, exist in stereoisomeric forms (enantiomers, diastereomers). The invention therefore encompasses the enantiomers or diastereomers and respective mixtures thereof. The stereoisomerically pure constituents can be isolated in a known manner from such mixtures of enantiomers and/or diastereomers.

Where the compounds of the invention can occur in tautomeric forms, the present invention encompasses all tautomeric forms.

Salts preferred for the purposes of the present invention are physiologically acceptable salts of the compounds of the invention. However, salts which are themselves unsuitable for pharmaceutical applications but can be used for example for isolating or purifying the compounds of the invention are also encompassed.

Physiologically acceptable salts of the compounds of the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases such as, for example and preferably, alkali metal salts (e.g. sodium and potassium salts), alkaline earth metal salts (e.g. calcium and magnesium salts) and ammonium salts derived from ammonia or organic amines having 1 to 16 C atoms, such as, for example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

Solvates refer for the purposes of the invention to those forms of the compounds of the invention which form a complex in the solid or liquid state through coordination with solvent molecules. Hydrates are a specific form of solvates in which the coordination takes place with water.

The present invention also encompasses prodrugs of the compounds according to the invention. The term "prodrugs" encompasses compounds which themselves may be biologically active or inactive but are converted during their residence time in the body into compounds according to the invention (for example by metabolism or hydrolysis).

For the purposes of the present invention, the substituents have, unless specified otherwise, the following meaning:

Alkyl per se and "alk" and "alkyl" in alkoxy, alkylamino, alkylcarbonyl, alkoxycarbonyl, alkylaminocarbonyl, alkylcarbonylamino, alkylsulphonyl, alkylsulphonylamino and alkylaminosulphonyl stand for a linear or branched alkyl radical having 1 to 6, preferably 1 to 4, carbon atoms, by way of example, and preferably for methyl, ethyl, n-propyl, isopropyl, n-butyl, tert-butyl, n-pentyl and n-hexyl.

Alkoxy stands by way of example and preferably for methoxy, ethoxy, n-propoxy, isopropoxy, n-butoxy and tert-butoxy.

Alkylamino stands for an alkylamino radical having one or two alkyl substituents (chosen independently of one another), by way of example and preferably for methylamino, ethylamino, n-propylamino, isopropylamino, tert-butylamino, N,N-dimethylamino, N,N-diethylamino, N-ethyl-N-methylamino, N-methyl-N-n-propylamino, N-isopropyl-N-n-propylamino and N-tert-butyl-N-methylamino. $C_1$-$C_4$-alkylamino stands for example for a monoalkylamino radical having 1 to 4 carbon atoms or for a dialkylamino radical having 1 to 4 carbon atoms in each alkyl substituent in each case.

Alkylcarbonyl stands by way of example and preferably for methylcarbonyl, ethylcarbonyl, n-propylcarbonyl, isopropylcarbonyl, n-butylcarbonyl and tert-butylcarbonyl.

Alkoxycarbonyl stands by way of example and preferably for methoxycarbonyl, ethoxycarbonyl, n-propoxycarbonyl, isopropoxycarbonyl, n-butoxycarbonyl and tert-butoxycarbonyl.

Alkylaminocarbonyl stands for an alkylaminocarbonyl radical having one or two alkyl substituents (chosen independently of one another), by way of example and preferably for methylaminocarbonyl, ethylaminocarbonyl, n-propylaminocarbonyl, isopropylaminocarbonyl, tert-butylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl and N-tert-butyl-N-methylaminocarbonyl. $C_1$-$C_4$-alkylaminocarbonyl stands for example for a monoalkylaminocarbonyl radical having 1 to 4 carbon atoms or for a dialkylaminocarbonyl radical having 1 to 4 carbon atoms in each alkyl substituent in each case.

Alkylcarbonylamino stands by way of example and preferably for methylcarbonylamino, ethylcarbonylamino, n-propylcarbonylamino, isopropylcarbonylamino, n-butylcarbonylamino and tert-butylcarbonylamino.

Alkylsulphonyl stands by way of example and preferably for methylsulphonyl, ethylsulphonyl, n-propylsulphonyl, isopropylsulphonyl, n-butylsulphonyl and tert-butylsulphonyl.

Alkylaminosulphonyl stands for an alkylaminosulphonyl radical having one or two alkyl substituents (chosen independently of one another), by way of example and preferably for methylaminosulphonyl, ethylaminosulphonyl, n-propylaminosulphonyl, isopropylaminosulphonyl, tert-butylaminosulphonyl, N,N-dimethylaminosulphonyl, N, N-diethylaminosulphonyl, N-ethyl-N-methylaminosulphonyl, N-methyl-N-n-propylaminosulphonyl, N-isopropyl-N-n-propylaminosulphonyl and N-tert-butyl-N-methylaminosulphonyl. $C_1$-$C_4$-alkylaminosulphonyl stands for example for a monoalkylaminosulphonyl radical having 1 to 4 carbon atoms or for a dialkylaminosulphonyl radical having 1 to 4 carbon atoms in each alkyl substituent in each case.

Alkylsulphonylamino stands by way of example and preferably for methylsulphonylamino, ethylsulphonylamino, n-propylsulphonylamino, isopropylsulphonylamino, n-butylsulphonylamino and tert-butylsulphonylamino.

Cycloalkyl stands for a monocyclic cycloalkyl group usually having 3 to 6 carbon atoms, and mention may be made by way of example and preferably of cyclopropyl, cyclobutyl, cyclopentyl and cyclohexyl for cycloalkyl.

Heterocyclyl stands for a monocyclic, heterocyclic radical having 5 or 6 ring atoms and up to 3, preferably up to 2 heteroatoms and/or heterogroups from the series N, O, S, SO, $SO_2$, where a nitrogen atom may also form an N-oxide. The heterocyclyl radicals may be saturated or partly unsaturated. 5- or 6-membered, monocyclic saturated heterocyclyl radicals having up to 2 heteroatoms from the series O, N and S are preferred, by way of example and preferably for pyrrolidin-2-yl, pyrrolidin-3-yl, pyrrolinyl, tetrahydrofuranyl, tetrahydrothienyl, pyranyl, piperidin-1-yl, piperidin-2-yl, piperidin-3-yl, piperidin-4-yl, thiopyranyl, morpholin-1-yl, morpholin-2-yl, morpholin-3-yl, piperazin-1-yl, piperazin-2-yl.

Heteroaryl stands for an aromatic, mono- or bicyclic radical usually having 5 to 10, preferably 5 or 6 ring atoms and up to 5, preferably up to 4 heteroatoms from the series S, O and N, where a nitrogen atom may also form an N-oxide, by way of example and preferably for thienyl, furyl, pyrrolyl, thiazolyl, oxazolyl, oxadiazolyl, pyrazolyl, imidazolyl, triazolyl, pyridyl, pyrimidyl, pyridazinyl, pyrazinyl, indolyl, indazolyl, benzofuranyl, benzothiophenyl, quinolinyl, isoquinolinyl, benzoxazolyl, benzimidazolyl.

Halogen stands for fluorine, chlorine, bromine and iodine, preferably for fluorine and chlorine.

In the formulae of the group which can stand for $R^3$, the end point of the line besides which a # stands in each case does not stand for a carbon atom or a $CH_2$ group but forms part of the bond to the atom to which $R^3$ is bonded.

In the formulae of the group which can stand for $R^{16}$, the end point of the line besides which a * stands in each case does not stand for a carbon atom or a $CH_2$ group but forms part of the bond to the atom to which $R^{16}$ is bonded.

Preference is given to compounds of the formula (I), in which

A is N or $CR^{15}$, where $R^{15}$ is hydrogen, bromine or chlorine, $R^1$ is hydrogen, hydroxy, amino, hydroxycarbonyl, aminocarbonyl, trifluoromethyl, trifluoromethoxy, cyano, $C_1$-$C_4$-alkoxy, $C_1$-$C_6$-alkylamino, $C_1$-$C_4$-alkylcarbonyl, $C_1$-$C_4$-alkoxycarbonyl, $C_1$-$C_6$-alkylaminocarbonyl, dihydroxypropylaminocarbonyl, dihydroxybutylaminocarbonyl, dihydroxypentylaminocarbonyl, $C_1$-$C_4$-alkylcarbonylamino, $C_1$-$C_4$-alkylsulphonylamino, 5- or 6-membered heterocyclylcarbonyl, —$CH_2R^{13}$ or —$CH_2CH_2R^{14}$, where alkoxy, alkylamino, alkylcarbonyl, alkoxycarbonyl, alkylaminocarbonyl, alkylcarbonylamino and alkylsulphonylamino may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino and 5- or 6-membered heterocyclyl, in which heterocyclyl may be substituted by 1 to 3 substituents, where the substituents are selected independently of one another from the group consisting of halogen, hydroxy, oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl, and where heterocyclylcarbonyl may be substituted by 1 to 3 substituents, where the substituents are selected independently of one another from the group consisting of halogen, hydroxy, oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl, and where $R^{13}$ is hydroxy, amino, cyano, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino, 5- or 6-membered heterocyclyl or 5- or 6-membered heteroaryl, in which alkoxy, alkylamino, alkoxycarbonyl, alkylaminocarbonyl and alkylcarbonylamino may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino, and in which heterocyclyl and heteroaryl may be substituted by 1 to 3 substituents, where the substituents are selected independently of one another from the group consisting of halogen, hydroxy, oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl, and where $R^{14}$ is hydroxy, amino, cyano, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino, 5- or 6-membered heterocyclyl or 5- or 6-membered heteroaryl, in which alkoxy, alkylamino, alkoxycarbonyl, alkylaminocarbonyl and alkylcarbonylamino may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino, and in which heterocyclyl and heteroaryl may be substituted by 1 to 3 substituents, where the substituents are selected independently of one another from the group consisting of halogen, hydroxy, oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl, $R^2$ is $C_6$-$C_{10}$-aryl or 5- to 10-membered heteroaryl, where aryl and heteroaryl may be substituted by 1 to 3 substituents, where the substituents are selected independently of one another from the group consisting of hydroxy, hydroxymethyl, amino, halogen, cyano, trifluoromethyl, trifluoromethoxy, aminocarbonyl, $C_1$-$C_4$-alkyl, $C_1$-$C_4$-alkoxy, $C_1$-$C_4$-alkoxymethyl, $C_1$-$C_4$-alkylamino, $C_1$-$C_4$-alkylaminomethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulphonyl, $C_1$-$C_4$-alkylsulphonylamino, $C_1$-$C_4$-alkylaminosulphonyl, phenyl, benzyloxy, 5- or 6-membered heterocyclyl, 5- or 6-membered heterocyclylcarbonyl, 5- or 6-membered heterocyclylmethyl and 5- or 6-membered heteroaryl, in which phenyl, benzyloxy, heterocyclyl, heterocyclylcarbonyl, heterocyclylmethyl and heteroaryl may be substituted by 1 to 3 substituents, where the substituents are selected independently of one another from the group consisting of halogen, cyano, trifluoromethyl, trifluoromethoxy, aminocarbonyl, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_1$-$C_4$-alkylcarbonylamino, or two of the substituents on the aryl form together with the carbon atoms to which they are bonded a 1,3-dioxolane or 1,4-dioxane, $R^4$ is hydrogen, halogen, cyano, trifluoromethyl, $C_1$-$C_3$-alkyl, methylthio or cyclopropyl, $R^{16}$ is a group of the formula

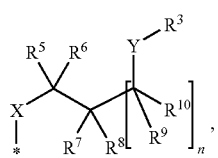 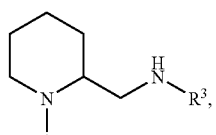

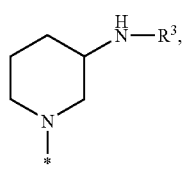 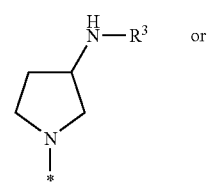 or

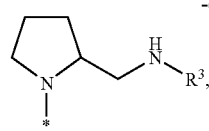

where

* is the point of attachment to the heterocycle, n is the number 0 or 1,

X is $NR^{11}$, S or O, where
$R^{11}$ is hydrogen, $C_1$-$C_3$-alkyl or cyclopropyl, Y is $NR^{12}$, S or O, where
$R^{12}$ is hydrogen, $C_1$-$C_3$-alkyl or cyclopropyl, $R^3$ is 2-pyridyl, pyrimid-2-yl, 2-aminopyrimid-4-yl, 2-cyclopropylaminopyrimid-4-yl, 2-methylaminopyrimid-4-yl, 2-ethylaminopyrimid-4-yl, 1,3-thiazol-2-yl, 1,3-thiazol-4-yl or 1,3-thiazol-5-yl, where 2-pyridyl, pyrimid-2-yl, 2-aminopyrimid-4-yl, 1,3-thiazol-2-yl, 1,3-thiazol-4-yl and 1,3-thiazol-5-yl are substituted by 1 to 3 substituents, where the substituents are selected independently of one another from the group consisting of halogen, cyano, nitro, amino, trifluoromethyl, trifluoromethoxy, aminocarbonyl, trifluoromethylcarbonyl, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_3$-$C_6$-cycloalkylcarbonyl, where alkyl, alkoxy, alkylamino, alkylcarbonyl, alkoxycarbonyl, alkylaminocarbonyl and cycloalkylcarbonyl may be substituted by a substituent, where the substituent is selected from the group consisting of halogen, cyano, hydroxy, amino, trifluoromethyl and $C_3$-$C_6$-cycloalkyl, $R^5$ is hydrogen, $C_1$-$C_3$-alkyl or cyclopropyl, $R^6$ is hydrogen or $C_1$-$C_3$-alkyl, $R^7$ is hydrogen, $C_1$-$C_3$-alkyl or cyclopropyl, $R^8$ is hydrogen or $C_1$-$C_3$-alkyl, $R^9$ is hydrogen, $C_1$-$C_3$-alkyl or cyclopropyl, $R^{10}$ is hydrogen or $C_1$-$C_3$-alkyl, and the salts thereof, the solvates thereof and the solvates of the salts thereof.

Preference is also given to compounds of the formula (I), in which

A is N or $CR^{15}$, where
$R^{15}$ is hydrogen or chlorine, $R^1$ is hydrogen, hydroxycarbonyl, aminocarbonyl, trifluoromethyl, cyano, $C_1$-$C_4$-alkyl, $C_1$-$C_4$-alkoxy, $C_1$-$C_6$-alkylamino, $C_1$-$C_4$-alkoxycarbonyl, $C_1$-$C_6$-alkylaminocarbonyl, dihydroxypropylaminocarbonyl, dihydroxybutylaminocarbonyl, dihydroxypentylaminocarbonyl, $C_1$-$C_4$-alkylcarbonylamino, $C_1$-$C_4$-alkylsulphonylamino, 5- or 6-membered heterocyclylcarbonyl, —$CH_2R^{13}$ or —$CH_2CH_2R^{14}$, where alkoxy, alkylamino, alkoxycarbonyl, alkylaminocarbonyl, alkylcarbonylamino and alkylsulphonylamino may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino and 5- or 6-membered heterocyclyl, in which heterocyclyl may be substituted by 1 to 3 substituents, where the substituents are selected independently of one another from the group consisting of halogen, hydroxy, oxo, $C_1$-$C_4$-alkyl, $C_1$-$C_4$-alkoxy and $C_1$-$C_4$-alkylamino, and where heterocyclylcarbonyl may be substituted by 1 to 3 substituents, where the substituents are selected independently of one another from the group consisting of halogen, hydroxy, oxo, $C_1$-$C_4$-alkyl, $C_1$-$C_4$-alkoxy and $C_1$-$C_4$-alkylamino, and where $R^{13}$ is hydroxy, amino, cyano, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino, 5- or 6-membered heterocyclyl or 5- or 6-membered heteroaryl, in which alkoxy, alkylamino, alkoxycarbonyl, alkylaminocarbonyl and alkylcarbonylamino may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino, and in which heterocyclyl and heteroaryl may be substituted by 1 to 3 substituents, where the substituents are selected independently of one another from the group consisting of halogen, hydroxy, oxo, $C_1$-$C_4$-alkyl, $C_1$-$C_4$-alkoxy and $C_1$-$C_4$-alkylamino, and where $R^{14}$ is hydroxy, amino, cyano, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino, 5- or 6-membered heterocyclyl or 5- or 6-membered heteroaryl, in which alkoxy, alkylamino, alkoxycarbonyl, alkylaminocarbonyl and alkylcarbonylamino may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino, and in which heterocyclyl and heteroaryl may be substituted by 1 to 3 substituents, where the substituents are selected independently of one another from the group consisting of halogen, hydroxy, oxo, $C_1$-$C_4$-alkyl, $C_1$-$C_4$-alkoxy and $C_1$-$C_4$-alkylamino, $R^2$ is $C_6$-$C_{10}$-aryl, thienyl, furyl, pyrrolyl, thiazolyl, oxazolyl, oxadiazolyl, pyrazolyl, imidazolyl, pyridyl, pyrimidyl, pyridazinyl, pyrazinyl, indolyl, indazolyl, quinolinyl, benzofuranyl or benzoxazolyl, where aryl, thienyl, furyl, pyrrolyl, thiazolyl, oxazolyl, oxadiazolyl, pyrazolyl, imidazolyl, pyridyl, pyrimidyl, pyridazinyl, pyrazinyl, indolyl, indazolyl, quinolinyl, benzofuranyl and benzoxazolyl may be substituted by 1 to 3 substituents, where the substituents are selected independently of one another from the group consisting of hydroxy, hydroxymethyl, amino, halogen, cyano, trifluoromethyl, trifluoromethoxy, aminocarbonyl, $C_1$-$C_4$-alkyl, $C_1$-$C_4$-alkoxy, $C_1$-$C_4$-alkoxymethyl, $C_1$-$C_4$ alkylamino, $C_1$-$C_4$-alkylaminomethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulphonyl, $C_1$-$C_4$-alkylsulphonylamino, $C_1$-$C_4$-alkylaminosulphonyl, phenyl, benzyloxy, 5- or 6-membered heterocyclyl, 5- or 6-membered heterocyclylcarbonyl, 5- or 6-membered heterocyclylmethyl and 5- or 6-membered heteroaryl, in which phenyl, benzyloxy, heterocyclyl, heterocyclylcarbonyl, heterocyclylmethyl and heteroaryl may be substituted by 1 to 3 substituents, where the substituents are selected independently of one another from the group consisting of halogen, cyano, trifluoromethyl, trifluoromethoxy, aminocarbonyl, $C_1$-$C_4$ alkyl, $C_1$-$C_4$-alkoxy, $C_1$-$C_4$ alkylamino, $C_1$-$C_4$-alkylcarbonyl, $C_1$-$C_4$-alkoxycarbonyl, $C_1$-$C_4$-alkylaminocarbonyl and $C_1$-$C_4$-alkylcarbonylamino, or two of the substituents on the aryl form together with the carbon atoms to which they are bonded a 1,3-dioxolane or 1,4-dioxane, $R^4$ is hydrogen, halogen, cyano, trifluoromethyl, $C_1$-$C_3$-alkyl or cyclopropyl, $R^{16}$ is a group of the formula

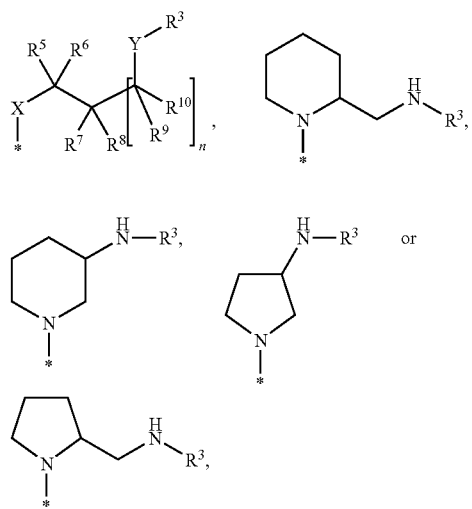

where

* is the point of attachment to the heterocycle, n is the number 0 or 1,

X is $NR^{11}$, S or O, where $R^{11}$ is hydrogen or methyl,

Y is $NR^{12}$, S or O, where $R^{12}$ is hydrogen or methyl, $R^3$ is 2-pyridyl, pyrimid-2-yl, 2-aminopyrimid-4-yl, 2-cyclopropylaminopyrimid-4-yl, 2-methylaminopyrimid-4-yl, 2-ethylaminopyrimid-4-yl, 1,3-thiazol-2-yl, 1,3-thiazol-4-yl or 1,3-thiazol-5-yl, where 2-pyridyl, pyrimid-2-yl, 2-aminopyrimid-4-yl, 1,3-thiazol-2-yl, 1,3-thiazol-4-yl and 1,3-thiazol-5-yl are substituted by 1 to 3 substituents, where the substituents are selected independently of one another from the group consisting of halogen, cyano, nitro, amino, trifluoromethyl, trifluoromethoxy, aminocarbonyl, trifluoromethylcarbonyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_3$-$C_6$-cycloalkylcarbonyl, in which alkyl, alkoxy, alkylamino, alkylcarbonyl, alkoxycarbonyl, alkylaminocarbonyl and cycloalkylcarbonyl may be substituted by a substituent, where the substituent is selected from the group consisting of halogen, cyano, hydroxy, amino, trifluoromethyl and $C_3$-$C_6$-cyclo alkyl, $R^5$ is hydrogen or methyl,
$R^6$ is hydrogen or methyl,
$R^7$ is hydrogen or methyl,
$R^8$ is hydrogen or methyl,
$R^9$ is hydrogen or methyl,
$R^{10}$ is hydrogen or methyl, and the salts thereof, the solvates thereof and the solvates of the salts thereof.

Preference is also given to compounds of the formula (I), in which

A is N or $R^{15}$,
where
$R^{15}$ is hydrogen, $R^1$ is hydrogen, trifluoromethyl, cyano, $C_1$-$C_4$-alkyl, $C_1$-$C_6$-alkylaminocarbonyl, dihydroxypropylaminocarbonyl, dihydroxybutylaminocarbonyl, dihydroxypentylaminocarbonyl, pyrrolidinylcarbonyl, piperidinylcarbonyl, morpholinylcarbonyl, piperazinylcarbonyl, —$CH_2R^{13}$ or —$CH_2CH_2R^{14}$, where alkylaminocarbonyl may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, pyrrolidinyl, piperidinyl, morpholinyl and piperazinyl, in which pyrrolidinyl, piperidinyl, morpholinyl and piperazinyl may be substituted by 1 to 3 substituents, where the substituents are selected independently of one another from the group consisting of halogen, hydroxy, oxo, $C_1$-$C_4$-alkyl, $C_1$-$C_4$-alkoxy and $C_1$-$C_4$-alkylamino, and where pyrrolidinylcarbonyl, piperidinylcarbonyl, morpholinylcarbonyl and piperazinylcarbonyl may be substituted by 1 to 3 substituents, where the substituents are selected independently of one another from the group consisting of halogen, hydroxy, oxo, $C_1$-$C_4$-alkyl, $C_1$-$C_4$-alkoxy and $C_1$-$C_4$-alkylamino, and where $R^{13}$ is hydroxycarbonyl, $C_1$-$C_4$-alkoxy, $C_1$-$C_4$-alkylamino, $C_1$-$C_4$-alkylaminocarbonyl, pyrrolidinyl, piperidinyl, morpholinyl, piperazinyl, pyrazolyl, imidazolyl, triazolyl or pyridyl, in which alkoxy, alkylamino and alkylaminocarbonyl may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino, and in which pyrrolidinyl, piperidinyl, morpholinyl, piperazinyl, pyrazolyl, imidazolyl, triazolyl and pyridyl may be substituted by 1 to 3 substituents, where the substituents are selected independently of one another from the group consisting of halogen, hydroxy, oxo, $C_1$-$C_4$-alkyl, $C_1$-$C_4$-alkoxy and $C_1$-$C_4$-alkylamino, $R^{14}$ is hydroxycarbonyl, $C_1$-$C_4$-alkoxy, $C_1$-$C_4$-alkylamino, $C_1$-$C_4$-alkylaminocarbonyl, pyrrolidinyl, piperidinyl, morpholinyl, piperazinyl, pyrazolyl, imidazolyl, triazolyl or pyridyl, in which alkoxy, alkylamino and alkylaminocarbonyl may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino, and in which pyrrolidinyl, piperidinyl, morpholinyl, piperazinyl, pyrazolyl, imidazolyl, triazolyl and pyridyl may be substituted by 1 to 3 substituents, where the substituents are selected independently of one another from the group consisting of halogen, hydroxy, oxo, $C_1$-$C_4$-alkyl, $C_1$-$C_4$-alkoxy and $C_1$-$C_4$-alkylamino, $R^2$ is phenyl, where phenyl may be substituted by 1 to 3 substituents, where the substituents are selected independently of one another from the group consisting of hydroxy, halogen, cyano, trifluoromethyl, trifluoromethoxy, aminocarbonyl, $C_1$-$C_4$-alkyl, $C_1$-$C_4$-alkoxy, $C_1$-$C_4$-alkoxymethyl, $C_1$-$C_4$-alkylaminomethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulphonyl, $C_1$-$C_4$-alkylsulphonylamino, $C_1$-$C_4$-alkylaminosulphonyl, phenyl, pyrrolidinyl, piperidinyl, morpholinyl, piperazinyl, pyrrolidinylmethyl, piperidinylmethyl, morpholinylmethyl and piperazinylmethyl, in which phenyl, pyrrolidinyl, piperidinyl, morpholinyl, piperazinyl, pyrrolidinylmethyl, piperidinylmethyl, morpholinylmethyl and piperazinylmethyl may be substituted by 1 to 3 substituents, where the substituents are selected independently of one another from the group consisting of halogen, cyano, trifluoromethyl, trifluoromethoxy and $C_1$-$C_4$-alkyl, $R^4$ is hydrogen or chlorine,
$R^{16}$ is a group of the formula

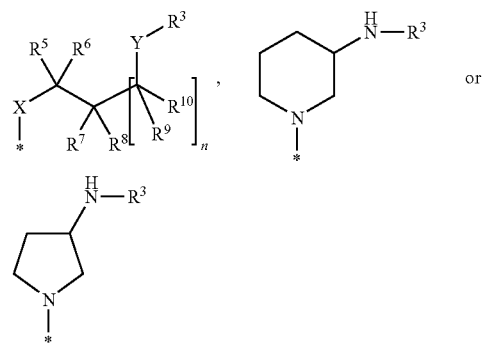

where
* is the point of attachment to the heterocycle,
n is the number 0,
X is $NR^{11}$, S or O,
where
$R^{11}$ is hydrogen or methyl,
Y is $NR^{12}$, S or O,
where
$R^{12}$ is hydrogen or methyl,
$R^3$ is 2-pyridyl, pyrimid-2-yl, 2-aminopyrimid-4-yl, 2-cyclopropylaminopyrimid-4-yl, 2-methylaminopyrimid-4-yl, 2-ethylaminopyrimid-4-yl, 1,3-thiazol-2-yl, 1,3-thiazol-4-yl or 1,3-thiazol-5-yl, where 2-pyridyl, pyrimid-2-yl, 2-aminopyrimid-4-yl, 1,3-thiazol-2-yl, 1,3-thiazol-4-yl and 1,3-thiazol-5-yl are substituted by 1 to 3 substituents, where the substituents are selected independently of one another from the group consisting of halogen, cyano, nitro, amino, trifluoromethyl, trifluoromethoxy, aminocarbonyl, trifluoromethylcarbonyl, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_3$-$C_6$-cycloalkylcarbonyl,
in which alkylamino, alkylcarbonyl, alkoxycarbonyl, alkylaminocarbonyl and cycloalkylcarbonyl may be substituted by a substituent, where the substituent is selected from the group consisting of halogen, cyano, hydroxy, amino, trifluoromethyl and $C_3$-$C_6$-cycloalkyl,
$R^5$ is hydrogen or methyl,
$R^6$ is hydrogen,
$R^7$ is hydrogen or methyl,
$R^8$ is hydrogen,
$R^9$ is hydrogen,
$R^{10}$ is hydrogen,
and the salts thereof, the solvates thereof and the solvates of the salts thereof.

Preference is also given to compounds of the formula (I) in which
A is N or $CR^{15}$,
where
$R^{15}$ is hydrogen,
$R^1$ is hydrogen, methyl or —$CH_2R^{13}$,
where
$R^{13}$ is morpholinyl,
$R^2$ is phenyl,
where phenyl may be substituted by 1 to 3 substituents, where the substituents are selected independently of one another from the group consisting of chlorine, fluorine trifluoromethyl, trifluoromethoxy and methyl,
$R^4$ is hydrogen,
$R^{16}$ is a group of the formula

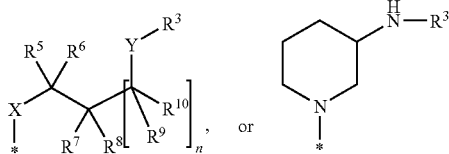

where
* is the point of attachment to the heterocycle,
n is the number 0,
X is $NR^{11}$ or O,
where
$R^{11}$ is hydrogen,
Y is $NR^{12}$ or O,
where
$R^{12}$ is hydrogen,
$R^3$ is 2-pyridyl or 1,3-thiazol-2-yl,
where 2-pyridyl and 1,3-thiazol-2-yl are substituted by 1 to 2 substituents, where the substituents are selected independently of one another from the group consisting of cyano, nitro, amino, trifluoromethylcarbonyl and methylcarbonyl,
$R^5$ is hydrogen or methyl,
$R^6$ is hydrogen,
$R^7$ is hydrogen or methyl,
$R^8$ is hydrogen,
$R^9$ is hydrogen,
$R^{10}$ is hydrogen,
and the salts thereof, the solvates thereof and the solvates of the salts thereof.

Preference is also given to compounds of the formula (I) in which
A is N or $CR^{15}$,
where
$R^{15}$ is hydrogen,
$R^1$ is hydrogen, methyl or —$CH_2R^{13}$,
where
$R^{13}$ is morpholinyl,
$R^2$ is phenyl,
where phenyl may be substituted by 1 to 3 substituents, where the substituents are selected independently of one another from the group consisting of chlorine, fluorine, trifluoromethyl, trifluoromethoxy and methyl,
$R^4$ is hydrogen,
$R^{16}$ is a group of the formula

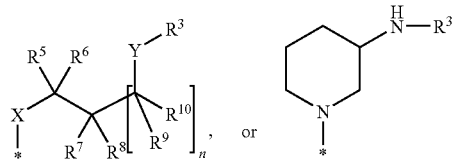

where
* is the point of attachment to the heterocycle,
n is the number 0,
X is $NR^{11}$,
where
$R^{11}$ is hydrogen,
Y is $NR^{12}$,
where
$R^{12}$ is hydrogen,
$R^3$ is 2-pyridyl or 1,3-thiazol-2-yl,
where 2-pyridyl and 1,3-thiazol-2-yl are substituted by 1 to 2 substituents, where the substituents are selected independently of one another from the group consisting of cyano, nitro, amino, trifluoromethylcarbonyl and methylcarbonyl,
$R^5$ is hydrogen or methyl,
$R^6$ is hydrogen,
$R^7$ is hydrogen or methyl,
$R^8$ is hydrogen,
$R^9$ is hydrogen,
$R^{10}$ is hydrogen,
and the salts thereof, the solvates thereof and the solvates of the salts thereof.

Preference is also given to compounds of the formula (I) in which
A is N or $CR^{15}$,
where
$R^{15}$ is hydrogen,
$R^1$ is hydrogen, methyl or —$CH_2R^{13}$,
where
$R^{13}$ is morpholinyl,
$R^2$ is phenyl,
where phenyl may be substituted by 1 to 3 substituents, where the substituents are selected independently of one another from the group consisting of chlorine, fluorine, trifluoromethyl, trifluoromethoxy and methyl,
$R^4$ is hydrogen, $R^{16}$ is a group of the formula

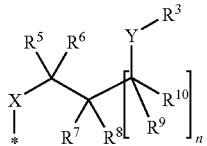

where
* is the point of attachment to the heterocycle,
n is the number 0,
X is $NR^{11}$,
  where
  $R^{11}$ is hydrogen,
Y is $NR^{12}$,
  where
  $R^{12}$ is hydrogen,
$R^3$ is 2-pyridyl or 1,3-thiazol-2-yl,
  where 2-pyridyl and 1,3-thiazol-2-yl are substituted by 1 to 2 substituents, where the substituents are selected independently of one another from the group consisting of cyano, nitro, amino, trifluoromethylcarbonyl and methylcarbonyl,
$R^5$ is hydrogen or methyl,
$R^6$ is hydrogen,
$R^7$ is hydrogen or methyl,
$R^8$ is hydrogen,
$R^9$ is hydrogen,
$R^{10}$ is hydrogen,
and the salts thereof, the solvates thereof and the solvates of the salts thereof.

Preference is also given to compounds of the formula (I) in which
A is N or $CR^{15}$,
  where
  $R^{15}$ is hydrogen,
$R^1$ is hydrogen, methyl or $—CH_2R^{13}$,
  where
  $R^{13}$ is morpholinyl,
$R^2$ is phenyl,
  where phenyl may be substituted by 1 to 3 substituents, where the substituents are selected independently of one another from the group consisting of chlorine, fluorine, trifluoromethyl, trifluoromethoxy and methyl,
$R^4$ is hydrogen,
$R^{16}$ is a group of the formula

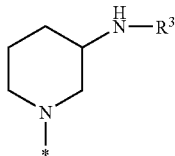

where
* is the point of attachment to the heterocycle,
$R^3$ is 2-pyridyl or 1,3-thiazol-2-yl,
  where 2-pyridyl and 1,3-thiazol-2-yl are substituted by 1 to 2 substituents, where the substituents are selected independently of one another from the group consisting of cyano, nitro, amino, trifluoromethylcarbonyl and methylcarbonyl,
and the salts thereof, solvates thereof and solvates of the salts thereof.

Preference is also given to compounds of the formula (I) in which
A is N or $CR^{15}$,
  where
  $R^{15}$ is hydrogen,
$R^1$ is $C_1$-$C_6$-alkylaminocarbonyl, 1,3-dihydroxyprop-2-ylaminocarbonyl, pyrrolidinylcarbonyl, piperidinylcarbonyl, morpholinylcarbonyl, piperazinylcarbonyl, $—CH_2R^{13}$ or $—CH_2CH_2R^{14}$,
  where alkylaminocarbonyl may be substituted by a substituent, where the substituent is selected from the group consisting of hydroxy, amino, aminocarbonyl, $C_1$-$C_4$-alkoxy, $C_1$-$C_4$ alkylamino, pyrrolidinyl, piperidinyl, morpholinyl and piperazinyl,
    in which pyrrolidinyl, piperidinyl, morpholinyl and piperazinyl may be substituted by 1 to 3 substituents, where the substituents are selected independently of one another from the group consisting of halogen, hydroxy, oxo, $C_1$-$C_4$-alkoxy and $C_1$-$C_4$-alkylamino,
  and
  where pyrrolidinylcarbonyl, piperidinylcarbonyl, morpholinylcarbonyl and piperazinylcarbonyl may be substituted by 1 to 3 substituents, where the substituents are selected independently of one another from the group consisting of halogen, hydroxy, oxo, alkyl, $C_1$-$C_4$-alkoxy and $C_1$-$C_4$-alkylamino,
  and
  where
  $R^{13}$ is $C_1$-$C_4$-alkoxy, $C_1$-$C_4$ alkylamino, $C_1$-$C_4$-alkylaminocarbonyl, pyrrolidinyl, piperidinyl, morpholinyl, piperazinyl, pyrazolyl, imidazolyl, triazolyl or pyridyl,
    in which alkoxy, alkylamino and alkylaminocarbonyl may be substituted by a substituent, where the substituent is selected from the group consisting of hydroxy, amino, aminocarbonyl, $C_1$-$C_4$-alkoxy, $C_1$-$C_4$ alkylamino, $C_1$-$C_4$-alkoxycarbonyl, $C_1$-$C_4$-alkylaminocarbonyl and $C_1$-$C_4$-alkylcarbonylamino,
    and
    in which pyrrolidinyl, piperidinyl, morpholinyl, piperazinyl, pyrazolyl, imidazolyl, triazolyl and pyridyl may be substituted by 1 to 3 substituents, where the substituents are selected independently of one another from the group consisting of halogen, hydroxy, oxo, $C_1$-$C_4$-alkyl, $C_1$-$C_4$-alkoxy and $C_1$-$C_4$-alkylamino,
  and
  where
  $R^{14}$ is $C_1$-$C_4$-alkoxy, $C_1$-$C_4$-alkylamino, $C_1$-$C_4$-alkylaminocarbonyl, pyrrolidinyl, piperidinyl, morpholinyl, piperazinyl, pyrazolyl, imidazolyl, triazolyl or pyridyl,
    in which alkoxy, alkylamino and alkylaminocarbonyl may be substituted by a substituent, where the substituent is selected from the group consisting of hydroxy, amino, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino,
    and
    in which pyrrolidinyl, piperidinyl, morpholinyl, piperazinyl, pyrazolyl, imidazolyl, triazolyl and pyridyl may be substituted by 1 to 3 substituents, where the substituents are selected independently of one another from the group consisting of halogen, hydroxy, oxo, $C_1$-$C_4$-alkyl, $C_1$-$C_4$-alkoxy and $C_1$-$C_4$-alkylamino,
$R^2$ is phenyl,
  where phenyl may be substituted by 1 to 3 substituents, where the substituents are selected independently of one another from the group consisting of chlorine, fluorine, trifluoromethyl, trifluoromethoxy and methyl,
$R^4$ is hydrogen, $R^{16}$ is a group of the formula

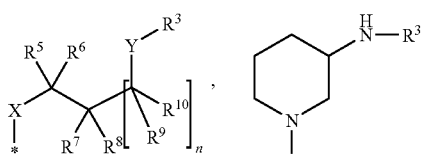,

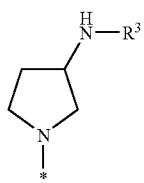

where
* is the point of attachment to the heterocycle,
n is the number 0,
X is $NR^{11}$, S or O,
  where
  $R^{11}$ is hydrogen or methyl,
Y is $NR^{12}$, S or O,
  where
  $R^{12}$ is hydrogen or methyl,
$R^3$ is 2-pyridyl or 1,3-thiazol-2-yl,
  where 2-pyridyl and 1,3-thiazol-2-yl are substituted by 1 to 2 substituents, where the substituents are selected independently of one another from the group consisting of cyano, nitro, amino, trifluoromethylcarbonyl and methylcarbonyl,
$R^5$ is hydrogen or methyl,
$R^6$ is hydrogen,
$R^7$ is hydrogen or methyl,
$R^8$ is hydrogen,
$R^9$ is hydrogen,
$R^{10}$ is hydrogen,
and the salts thereof, the solvates thereof and the solvates of the salts thereof.

Preference is also given to compounds of the formula (I), in which
A is N or $CR^{15}$,
  where
  $R^{15}$ is hydrogen,
$R^1$ is $C_1$-$C_4$-alkylaminocarbonyl, 1,3-dihydroxyprop-2-ylaminocarbonyl, piperazinylcarbonyl, —$CH_2R^{13}$ or —$CH_2CH_2R^{14}$,
  where alkylaminocarbonyl is substituted by a substituent, where the substituent is selected from the group consisting of hydroxy, amino, $C_1$-$C_4$-alkylamino, pyrrolidinyl, piperidinyl, morpholinyl and piperazinyl,
    in which pyrrolidinyl, piperidinyl, morpholinyl and piperazinyl may be substituted by 1 to 3 $C_1$-$C_4$-alkyl substituents,
  and
  where piperazinylcarbonyl may be substituted by 1 to 3 substituents, where the substituents are selected independently of one another from the group consisting of oxo, $C_1$-$C_4$-alkyl, $C_1$-$C_4$-alkoxy and $C_1$-$C_4$-alkylamino,
  and
  where
  $R^{13}$ is $C_1$-$C_4$-alkoxy, $C_1$-$C_4$-alkylamino, $C_1$-$C_4$-alkylaminocarbonyl, pyrrolidinyl, piperidinyl, morpholinyl or piperazinyl,
    in which alkoxy, alkylamino and alkylaminocarbonyl are substituted by a substituent, where the substituent is selected from the group consisting of hydroxy, amino, $C_1$-$C_4$-alkoxy and $C_1$-$C_4$-alkylamino,
    and
    in which pyrrolidinyl, piperidinyl, morpholinyl and piperazinyl may be substituted by 1 to 3 $C_1$-$C_4$-alkyl substituents,
  and
  where
  $R^{14}$ is $C_1$-$C_4$-alkoxy, $C_1$-$C_4$-alkylamino, $C_1$-$C_4$-alkylaminocarbonyl, pyrrolidinyl, piperidinyl, morpholinyl or piperazinyl,
    in which alkoxy, alkylamino and alkylaminocarbonyl are substituted by a substituent, where the substituent is selected from the group consisting of hydroxy, amino, $C_1$-$C_4$-alkoxy and $C_1$-$C_4$-alkylamino,
    and
    in which pyrrolidinyl, piperidinyl, morpholinyl and piperazinyl may be substituted by 1 to 3 $C_1$-$C_4$-alkyl substituents,
$R^2$ is phenyl,
  where phenyl may be substituted by 1 to 3 substituents, where the substituents are selected independently of one another from the group consisting of chlorine, fluorine, trifluoromethyl, trifluoromethoxy and methyl,
$R^4$ is hydrogen,
$R^{16}$ is a group of the formula

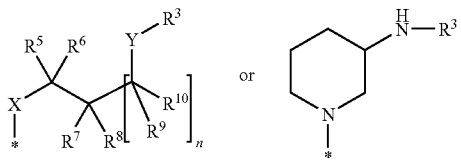

where
* is the point of attachment to the heterocycle,
n is the number 0,
X is $NR^{11}$ or O,
  where
  $R^{11}$ is hydrogen,
Y is $NR^{12}$ or O,
  where
  $R^{12}$ is hydrogen,
$R^3$ is 2-pyridyl or 1,3-thiazol-2-yl,
  where 2-pyridyl and 1,3-thiazol-2-yl are substituted by 1 to 2 substituents, where the substituents are selected independently of one another from the group consisting of cyano, nitro, amino, trifluoromethylcarbonyl and methylcarbonyl,
$R^5$ is hydrogen or methyl,
$R^6$ is hydrogen,
$R^7$ is hydrogen or methyl,
$R^8$ is hydrogen,
$R^9$ is hydrogen,
$R^{10}$ is hydrogen,
and the salts thereof, the solvates thereof and the solvates of the salts thereof.

Preference is also given to compounds of the formula (I) in which
A is N or $CR^{15}$,
  where
  $R^{15}$ is hydrogen,
$R^1$ is $C_1$-$C_4$-alkylaminocarbonyl, 1,3-dihydroxyprop-2-ylaminocarbonyl, piperazinylcarbonyl, —$CH_2R^{13}$ or —$CH_2CH_2R^{14}$, where alkylaminocarbonyl is substituted by a substituent, where the substituent is selected from the group consisting of hydroxy, amino, $C_1$-$C_4$-alkylamino, pyrrolidinyl, piperidinyl, morpholinyl and piperazinyl,
  in which pyrrolidinyl, piperidinyl, morpholinyl and piperazinyl may be substituted by 1 to 3 $C_1$-$C_4$-alkyl substituents,
and
where piperazinylcarbonyl may be substituted by 1 to 3 substituents, where the substituents are selected independently of one another from the group consisting of oxo, $C_1$-$C_4$-alkyl, $C_1$-$C_4$-alkoxy and $C_1$-$C_4$-alkylamino,
and
where
$R^{13}$ is $C_1$-$C_4$-alkoxy, $C_1$-$C_4$-alkylamino, $C_1$-$C_4$-alkylaminocarbonyl, pyrrolidinyl, piperidinyl, morpholinyl or piperazinyl,
  in which alkoxy, alkylamino and alkylaminocarbonyl are substituted by a substituent, where the substituent is selected from the group consisting of hydroxy, amino, $C_1$-$C_4$-alkoxy and $C_1$-$C_4$-alkylamino,
  and
  in which pyrrolidinyl, piperidinyl, morpholinyl and piperazinyl may be substituted by 1 to 3 $C_1$-$C_4$-alkyl substituents,
and
where
$R^{14}$ is $C_1$-$C_4$-alkoxy, $C_1$-$C_4$-alkylamino, $C_1$-$C_4$-alkylaminocarbonyl, pyrrolidinyl, piperidinyl, morpholinyl or piperazinyl,
  in which alkoxy, alkylamino and alkylaminocarbonyl are substituted by a substituent, where the substituent is selected from the group consisting of hydroxy, amino, $C_1$-$C_4$-alkoxy and $C_1$-$C_4$-alkylamino,
  and
  in which pyrrolidinyl, piperidinyl, morpholinyl and piperazinyl may be substituted by 1 to 3 $C_1$-$C_4$-alkyl substituents,
$R^2$ is phenyl,
  where phenyl may be substituted by 1 to 3 substituents, where the substituents are selected independently of one another from the group consisting of chlorine, fluorine, trifluoromethyl, trifluoromethoxy and methyl,
$R^4$ is hydrogen,
$R^{16}$ is a group of the formula

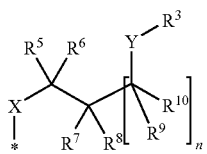

where
* is the point of attachment to the heterocycle,
n is the number 0,
X is $NR^{11}$,
  in which
  $R^{11}$ is hydrogen,
Y is $NR^{12}$,
  in which
  $R^{12}$ is hydrogen,
$R^3$ is 2-pyridyl or 1,3-thiazol-2-yl,
  where 2-pyridyl and 1,3-thiazol-2-yl are substituted by 1 to 2 substituents, where the substituents are selected independently of one another from the group consisting of cyano, nitro, amino, trifluoromethylcarbonyl and methylcarbonyl,
$R^5$ is hydrogen or methyl,
$R^6$ is hydrogen,
$R^7$ is hydrogen or methyl,
$R^8$ is hydrogen,
$R^9$ is hydrogen,
$R^{10}$ is hydrogen,
and the salts thereof, the solvates thereof and the solvates of the salts thereof.

Preference is also given to compounds of the formula (I) in which
A is N or $CR^{15}$,
  where
  $R^{15}$ is hydrogen,
$R^1$ is $C_1$-$C_4$-alkylaminocarbonyl, 1,3-dihydroxyprop-2-ylaminocarbonyl, piperazinylcarbonyl, —$CH_2R^{13}$ or —$CH_2CH_2R^{14}$,
  where alkylaminocarbonyl is substituted by a substituent, where the substituent is selected from the group consisting of hydroxy, amino, $C_1$-$C_4$-alkylamino, pyrrolidinyl, piperidinyl, morpholinyl and piperazinyl,
    in which pyrrolidinyl, piperidinyl, morpholinyl and piperazinyl may be substituted by 1 to 3 $C_1$-$C_4$-alkyl substituents,
  and
  where piperazinylcarbonyl may be substituted by 1 to 3 substituents, where the substituents are selected independently of one another from the group consisting of oxo, $C_1$-$C_4$ alkyl, $C_1$-$C_4$-alkoxy and $C_1$-$C_4$-alkylamino,
  and
  where
  $R^{13}$ is $C_1$-$C_4$-alkoxy, $C_1$-$C_4$ alkylamino, $C_1$-$C_4$-alkylaminocarbonyl, pyrrolidinyl, piperidinyl, morpholinyl or piperazinyl,
    in which alkoxy, alkylamino and alkylaminocarbonyl are substituted by a substituent, where the substituent is selected from the group consisting of hydroxy, amino, $C_1$-$C_4$-alkoxy and $C_1$-$C_4$-alkylamino,
    and
    in which pyrrolidinyl, piperidinyl, morpholinyl and piperazinyl may be substituted by 1 to 3 $C_1$-$C_4$-alkyl substituents,
  and
  where
  $R^{14}$ is $C_1$-$C_4$-alkoxy, $C_1$-$C_4$-alkylamino, $C_1$-$C_4$-alkylaminocarbonyl, pyrrolidinyl, piperidinyl, morpholinyl or piperazinyl,
    in which alkoxy, alkylamino and alkylaminocarbonyl are substituted by a substituent, where the substituent is selected from the group consisting of hydroxy, amino, $C_1$-$C_4$-alkoxy and $C_1$-$C_4$-alkylamino,
    and
    in which pyrrolidinyl, piperidinyl, morpholinyl and piperazinyl may be substituted by 1 to 3 $C_1$-$C_4$-alkyl substituents,
$R^2$ is phenyl,
  where phenyl may be substituted by 1 to 3 substituents, where the substituents are selected independently of one another from the group consisting of chlorine, fluorine, trifluoromethyl, trifluoromethoxy and methyl,
$R^4$ is hydrogen, $R^{16}$ is a group of the formula

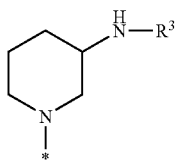

where
* is the point of attachment to the heterocycle,
$R^3$ is 2-pyridyl or 1,3-thiazol-2-yl,
  where 2-pyridyl and 1,3-thiazol-2-yl are substituted by 1 to 2 substituents, where the substituents are selected independently of one another from the group consisting of cyano, nitro, amino, trifluoromethylcarbonyl and methylcarbonyl,
and the salts thereof, the solvates thereof and the solvates of the salts thereof.

Preference is also given to compounds of the formula (I), which correspond to the formula

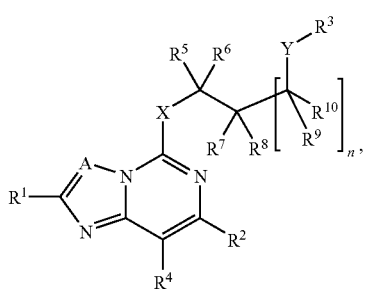

(Ia)

in which
A is N or CH,
n is the number 0 or 1,
X is $NR^{11}$, S or O,
  where
    $R^{11}$ is hydrogen, $C_1$-$C_3$-alkyl or cyclopropyl,
Y is $NR^{12}$, S or O,
  where
    $R^{12}$ is hydrogen, $C_1$-$C_3$-alkyl or cyclopropyl,
$R^1$ is hydrogen, hydroxy, amino, hydroxycarbonyl, aminocarbonyl, trifluoromethyl, trifluoromethoxy, cyano, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulphonylamino, —$CH_2R^{13}$ or —$CH_2CH_2R^{14}$,
  where alkoxy, alkylamino, alkylcarbonyl, alkoxycarbonyl, alkylaminocarbonyl, alkylcarbonylamino and alkylsulphonylamino may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino,
  and
  where
    $R^{13}$ is hydroxy, amino, cyano, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino or 5- or 6-membered heterocyclyl,
      in which alkoxy, alkylamino, alkoxycarbonyl, alkylaminocarbonyl and $C_1$-$C_4$-alkylcarbonylamino may be substituted by a substituent, where the substituent is selected from the group consisting of hydroxy, amino, hydroxycarbonyl, aminocarbonyl, $C_1$-$C_4$-alkoxy, $C_1$-$C_4$ alkylamino, $C_1$-$C_4$-alkoxycarbonyl, $C_1$-$C_4$-alkylaminocarbonyl and $C_1$-$C_4$-alkylcarbonylamino,
      and
      in which heterocyclyl may be substituted by 1 to 3 substituents, where the substituents are selected independently of one another from the group consisting of halogen, oxo, $C_1$-$C_4$-alkoxy, $C_1$-$C_4$ alkylamino, $C_1$-$C_4$ alkyl carbonyl, $C_1$-$C_4$-alkoxycarbonyl and $C_1$-$C_4$-alkylaminocarbonyl,
  and
  where
    $R^{14}$ is hydroxy, amino, cyano, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino or 5- or 6-membered heterocyclyl,
      in which alkoxy, alkylamino, alkoxycarbonyl, alkylaminocarbonyl and $C_1$-$C_4$-alkylcarbonylamino may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino,
      and
      in which heterocyclyl may be substituted by 1 to 3 substituents, where the substituents are selected independently of one another from the group consisting of halogen, oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl,
$R^2$ is $C_6$-$C_{10}$-aryl or 5- to 10-membered heteroaryl,
  where aryl and heteroaryl may be substituted by 1 to 3 substituents, where the substituents are selected independently of one another from the group consisting of hydroxy, hydroxymethyl, amino, halogen, cyano, trifluoromethyl, trifluoromethoxy, aminocarbonyl, $C_1$-$C_4$-alkyl, $C_1$-$C_4$-alkoxy, $C_1$-$C_4$-alkoxymethyl, $C_1$-$C_4$-alkylamino, $C_1$-$C_4$-alkylaminomethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulphonyl, $C_1$-$C_4$-alkylsulphonylamino, $C_1$-$C_4$-alkylaminosulphonyl, phenyl, benzyloxy, 5- or 6-membered heterocyclyl, 5- or 6-membered heterocyclylcarbonyl, 5- or 6-membered heterocyclylmethyl and 5- or 6-membered heteroaryl,
    in which phenyl, benzyloxy, heterocyclyl, heterocyclylcarbonyl, heterocyclylmethyl and heteroaryl may be substituted by 1 to 3 substituents, where the substituents are selected independently of one another from the group consisting of halogen, cyano, trifluoromethyl, trifluoromethoxy, aminocarbonyl, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_1$-$C_4$-alkylcarbonylamino,
  or
  two of the substituents on the aryl form together with the carbon atoms to which they are bonded a 1,3-dioxolane or 1,4-dioxane,
$R^3$ is 2-pyridyl, 2-aminopyrimid-4-yl, 1,3-thiazol-2-yl, 1,3-thiazol-4-yl or 1,3-thiazol-5-yl,
  where 2-pyridyl, 2-aminopyrimid-4-yl, 1,3-thiazol-2-yl, 1,3-thiazol-4-yl and 1,3-thiazol-5-yl are substituted by 1 to 3 substituents, where the substituents are selected independently of one another from the group consisting of halogen, cyano, nitro, amino, trifluoromethyl, trifluoromethoxy, aminocarbonyl, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_3$-$C_6$-cycloalkylcarbonyl, in which alkyl, alkoxy, alkylamino, alkylcarbonyl, alkoxycarbonyl, alkylaminocarbonyl and cycloalkylcarbonyl may be substituted by a substituent, where the substituent is selected from the group consisting of cyano, hydroxy, amino, trifluoromethyl and $C_3$-$C_6$-cycloalkyl, or $R^3$ is a group of the formula

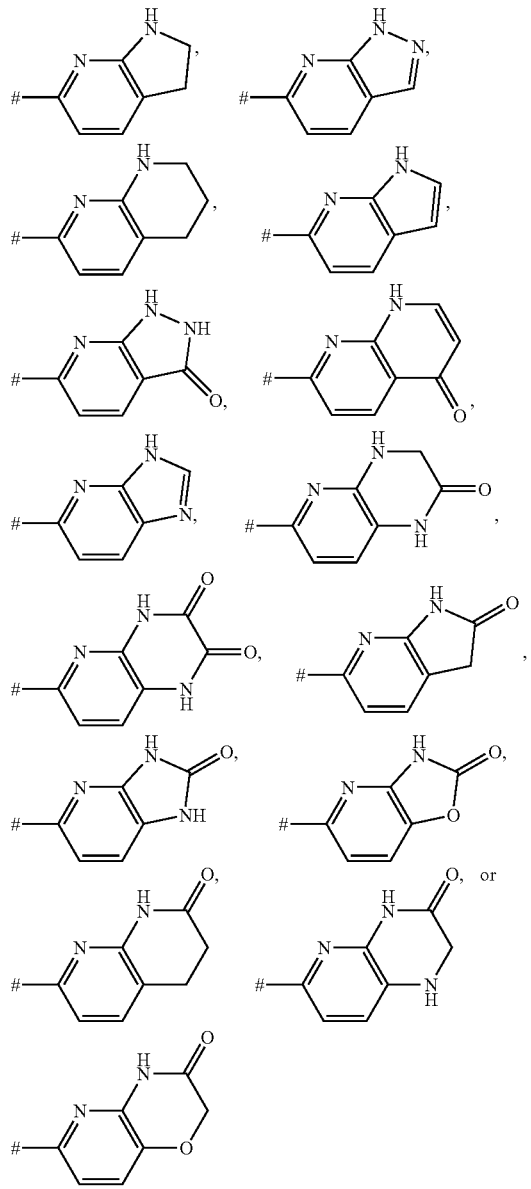

where # is the point of attachment to Y, $R^4$ is hydrogen, halogen, cyano, trifluoromethyl, $C_1$-$C_3$-alkyl, methylthio or cyclopropyl, $R^5$ is hydrogen, $C_1$-$C_3$-alkyl or cyclopropyl, $R^6$ is hydrogen or $C_1$-$C_3$-alkyl, $R^7$ is hydrogen, $C_1$-$C_3$-alkyl or cyclopropyl, $R^8$ is hydrogen or $C_1$-$C_3$-alkyl, $R^9$ is hydrogen, $C_1$-$C_3$-alkyl or cyclopropyl, $R^{10}$ is hydrogen or $C_1$-$C_3$-alkyl, and the salts thereof, the solvates thereof and the solvates of the salts thereof.

Preference is also given to compounds of the formula (Ia) in which

A is N or CH, n is the number 0 or 1,

X is $NR^{11}$, S or O, where $R^{11}$ is hydrogen or methyl,

Y is $NR^{12}$, S or O, where $R^{12}$ is hydrogen or methyl, $R^1$ is hydrogen, hydroxycarbonyl, aminocarbonyl, trifluoromethyl, cyano, $C_1$-$C_4$-alkyl, $C_1$-$C_4$-alkoxy, $C_1$-$C_4$-alkylamino, $C_1$-$C_4$-alkylaminocarbonyl, $C_1$-$C_4$-alkylcarbonylamino, $C_1$-$C_4$-alkylsulphonylamino or —$CH_2R^{13}$, where alkoxy, alkylamino, alkylaminocarbonyl, alkylcarbonylamino and alkylsulphonylamino may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino, and where $R^{13}$ is amino, cyano, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino or 5- or 6-membered heterocyclyl, in which alkoxy, alkylamino, alkoxycarbonyl, alkylaminocarbonyl and $C_1$-$C_4$-alkylcarbonylamino may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino, and in which heterocyclyl may be substituted by 1 to 3 substituents, where the substituents are selected independently of one another from the group consisting of halogen, oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl, $R^2$ is $C_6$-$C_{10}$-aryl, thienyl, furyl, pyrrolyl, thiazolyl, oxazolyl, oxadiazolyl, pyrazolyl, imidazolyl, pyridyl, pyrimidyl, pyridazinyl, pyrazinyl, indolyl, indazolyl, quinolinyl, benzofuranyl or benzoxazolyl, where aryl and thienyl, furyl, pyrrolyl, thiazolyl, oxazolyl, oxadiazolyl, pyrazolyl, imidazolyl, pyridyl, pyrimidyl, pyridazinyl, pyrazinyl, indolyl, indazolyl, benzofuranyl and benzoxazolyl may be substituted by 1 to 3 substituents, where the substituents are selected independently of one another from the group consisting of hydroxy, hydroxymethyl, amino, halogen, cyano, trifluoromethyl, trifluoromethoxy, aminocarbonyl, $C_1$-$C_4$-alkyl, $C_1$-$C_4$-alkoxy, $C_1$-$C_4$-alkoxymethyl, $C_1$-$C_4$-alkylamino, $C_1$-$C_4$-alkylaminomethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulphonyl, $C_1$-$C_4$-alkylsulphonylamino, $C_1$-$C_4$-alkylaminosulphonyl, phenyl, benzyloxy, 5- or 6-membered heterocyclyl, 5- or 6-membered heterocyclylcarbonyl, 5- or 6-membered heterocyclylmethyl and 5- or 6-membered heteroaryl, in which phenyl, benzyloxy, heterocyclyl, heterocyclyl-
carbonyl, heterocyclylmethyl and heteroaryl may be
substituted by 1 to 3 substituents, where the substitu-
ents are selected independently of one another from
the group consisting of halogen, cyano, trifluorom-
ethyl, trifluoromethoxy, aminocarbonyl, $C_1$-$C_4$-alkyl,
$C_1$-$C_4$-alkoxy, $C_1$-$C_4$-alkylamino, $C_1$-$C_4$-alkylcarbo-
nyl, $C_1$-$C_4$-alkoxycarbonyl, $C_1$-$C_4$-alkylaminocarbo-
nyl and $C_1$-$C_4$-alkylcarbonylamino, or two of the substituents on the aryl form together with the
carbon atoms to which they are bonded a 1,3-dioxolane
or 1,4-dioxane, $R^3$ is 2-pyridyl, 2-aminopyrimid-4-yl, 1,3-thiazol-2-yl, 1,3-
thiazol-4-yl or 1,3-thiazol-5-yl, where 2-pyridyl, 2-aminopyrimid-4-yl, 1,3-thiazol-2-yl,
1,3-thiazol-4-yl and 1,3-thiazol-5-yl are substituted by 1
to 3 substituents, where the substituents are selected
independently of one another from the group consisting
of halogen, cyano, nitro, amino, trifluoromethyl, trifluo-
romethoxy, aminocarbonyl, $C_1$-$C_4$-alkyl, $C_1$-$C_4$-alkoxy,
$C_1$-$C_4$-alkylamino, $C_1$-$C_4$-alkylcarbonyl, $C_1$-$C_4$-
alkoxycarbonyl, $C_1$-$C_4$-alkylaminocarbonyl and $C_3$-$C_6$-
cycloalkylcarbonyl, in which alkyl, alkoxy, alkylamino, alkylcarbonyl,
alkoxycarbonyl, alkylaminocarbonyl and cycloalkyl-
carbonyl may be substituted by a substituent, where
the substituent is selected from the group consisting
of cyano, hydroxy, amino, trifluoromethyl and $C_3$-$C_6$-
cycloalkyl, or $R^3$ is a group of the formula

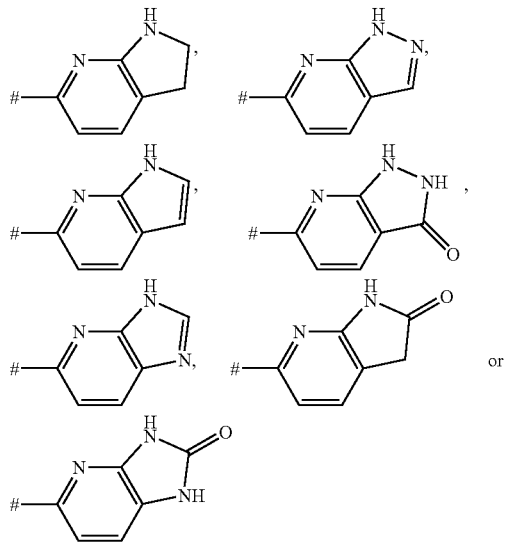

where # is the point of attachment to Y,
$R^4$ is hydrogen, halogen, cyano or trifluoromethyl,
$R^5$ is hydrogen or methyl,
$R^6$ is hydrogen or methyl,
$R^7$ is hydrogen or methyl,
$R^8$ is hydrogen or methyl,
$R^9$ is hydrogen or methyl,
$R^{10}$ is hydrogen or methyl,
and the salts thereof, the solvates thereof and the solvates of
the salts thereof.

Preference is also given to compounds of the formula (Ia)
in which
A is N or CH,
n is the number 0,
X is $NR^{11}$, S or O,
where
$R^{11}$ is hydrogen,
Y is $NR^{12}$, S or O,
where
$R^{12}$ is hydrogen or methyl,
$R^1$ is hydrogen, trifluoromethyl, methyl or —$CH_2R^{13}$,
where
$R^{13}$ is pyrrolidinyl, piperidinyl or morpholinyl,
$R^2$ is phenyl, naphthyl, thienyl, pyrazolyl, pyridyl, indolyl or
quinolinyl,
where phenyl, naphthyl, thienyl, pyrazolyl, pyridyl,
indolyl and quinolinyl may be substituted by 1 to 3
substituents, where the substituents are selected inde-
pendently of one another from the group consisting of
halogen, trifluoromethyl, trifluoromethoxy, aminocar-
bonyl, $C_1$-$C_4$-alkyl, $C_1$-$C_4$-alkoxy, $C_1$-$C_4$-alkoxycarbo-
nyl, $C_1$-$C_4$-alkylaminocarbonyl, $C_1$-$C_4$-alkylsulphonyl,
$C_1$-$C_4$-alkylsulphonylamino, benzyloxy, pyrrolidinyl,
piperidinyl, morpholinyl and morpholinylcarbonyl,
in which benzyloxy may be substituted by 1 to 3 sub-
stituents, where the substituents are selected indepen-
dently of one another from the group consisting of
halogen, or two of the substituents on the phenyl form together with the
carbon atoms to which they are bonded a 1,3-dioxolane
or 1,4-dioxane, $R^3$ is 2-pyridyl or 1,3-thiazol-2-yl, where 2-pyridyl and 1,3-thiazol-2-yl are substituted by 1 to
2 substituents, where the substituents are selected inde-
pendently of one another from the group consisting of
cyano, nitro, amino, trifluoromethyl and methylcarbo-
nyl, $R^4$ is hydrogen,
$R^5$ is hydrogen or methyl,
$R^6$ is hydrogen,
$R^7$ is hydrogen or methyl,
$R^8$ is hydrogen,
$R^9$ is hydrogen,
$R^{10}$ is hydrogen,
and the salts thereof, the solvates thereof and the solvates of
the salts thereof.

Preference is also given to compounds of the formula (I) or
(Ia), in which A is CH.

Preference is also given to compounds of the formula (I) or
(Ia), in which A is N.

Preference is also given to compounds of the formula (I) or
(Ia), in which n is the number 0.

Preference is also given to compounds of the formula (I) or
(Ia), in which X is $NR^{11}$, where $R^{11}$ is hydrogen.

Preference is also given to compounds of the formula (I) or
(Ia), in which Y is $NR^{12}$, where $R^{12}$ is hydrogen.

Preference is also given to compounds of the formula (I) or
(Ia) in which $R^1$ is hydrogen, trifluoromethyl or methyl.

Preference is also given to compounds of the formula (I) or
(Ia) in which $R^1$ is hydrogen or methyl.

Preference is also given to compounds of the formula (I) or
(Ia) in which $R^1$ is —$CH_2R^{13}$, where $R^{13}$ is morpholinyl.

Preference is also given to compounds of the formula (I) or
(Ia), in which
$R^3$ is 2-pyridyl or 1,3-thiazol-2-yl,
where 2-pyridyl and 1,3-thiazol-2-yl are substituted by 1 to
2 substituents, where the substituents are selected independently of one another from the group consisting of cyano, nitro, amino, trifluoromethyl and methylcarbonyl.

Preference is also given to compounds of the formula (I) or (Ia), in which

R³ is 2-pyridyl or 1,3-thiazol-2-yl, where 2-pyridyl and 1,3-thiazol-2-yl are substituted by 1 to 2 substituents, where the substituents are selected independently of one another from the group consisting of cyano, nitro, amino, trifluoromethylcarbonyl and methylcarbonyl.

Preference is also given to compounds of the formula (I) or (Ia) in which R⁴ is hydrogen.

Preference is also given to compounds of the formula (I) or (Ia) in which R⁵, R⁶, R⁸, R⁹ and R¹⁰ are hydrogen, and R⁷ is hydrogen or methyl.

Preference is also given to compounds of the formula (I) in which

R¹⁶ is a group of the formula

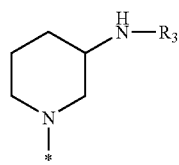

where

* is the point of attachment to the heterocycle,

R³ is 2-pyridyl or 1,3-thiazol-2-yl, where 2-pyridyl and 1,3-thiazol-2-yl are substituted by 1 to 2 substituents, where the substituents are selected independently of one another from the group consisting of cyano, nitro, amino, trifluoromethylcarbonyl and methylcarbonyl.

The invention further relates to a process for preparing compounds of the formula (I), or the salts thereof, solvates thereof or solvates of the salts thereof, where

[A] the compounds of the formula

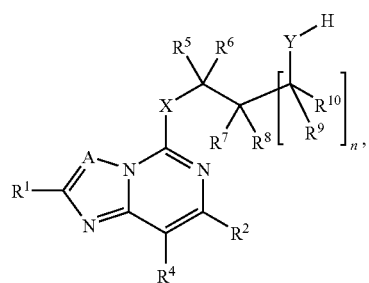

in which

A, n, X, Y, R¹, R², R⁴, R⁵, R⁶, R⁷, R⁸, R⁹ and R¹⁰ have the meaning indicated above, are reacted with compounds of the formula $$R^3-X^1 \qquad (III),$$

in which

R³ has the meaning indicated above, and

X¹ is halogen, preferably chlorine or fluorine, or

[B] the compounds of the formula

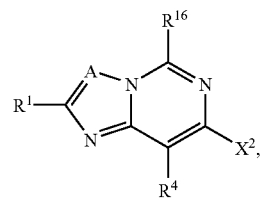

in which

A, R¹, R⁴ and R¹⁶ have the meaning indicated above, and

X² is iodine, bromine, chlorine or trifluoromethanesulphonyl, preferably iodine or bromine, are reacted with compounds of the formula $$Q-R^2 \qquad (V),$$

in which

R² has the meaning indicated above, and

Q is —B(OH)₂, a boronic acid ester, preferably boronic acid pinacol ester, —BF₃⁻K⁺, under Suzuki coupling conditions, or

[C] the compounds of the formula

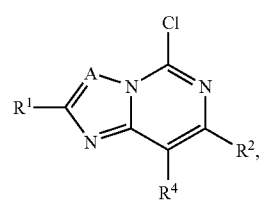

in which

A, R¹, R² and R⁴ have the meaning indicated above, are reacted with compounds of the formula $$H-R^{16} \qquad (IX),$$

in which

R¹⁶ has the meaning indicated above.

The reaction by process [A] generally takes place in inert solvents, where appropriate in the presence of a base, where appropriate in a microwave, preferably in a temperature range from 50° C. to 200° C. under atmospheric pressure up to 3 bar.

Examples of bases are alkali metal carbonates such as, for example, sodium, potassium or caesium carbonate, or organic bases such as trialkylamines, e.g. triethylamine, N-methylmorpholine, N-methylpiperidine, 4-dimethylaminopyridine or diisopropylethylamine, or other bases such as, for example, sodium hydride or potassium tert-butoxide, with preference for diisopropylethylamine or sodium hydride.

Examples of inert solvents are halo hydrocarbons such as methylene chloride or trichloromethane, alcohols such as methanol, ethanol, n-propanol or isopropanol, or ethers such as dioxane or tetrahydrofuran, or other solvents such as, for example, dimethyl sulphoxide, dimethylformamide or N-methylpyrrolidone, or mixtures of these solvents, with preference for isopropanol or dimethyl sulphoxide.

The reaction by process [B] generally takes place in inert solvents, in the presence of a catalyst, where appropriate in the presence of an additional reagent, where appropriate in a microwave, preferably in a temperature range from room temperature to 150° C. under atmospheric pressure up to 3 bar.

Examples of catalysts for Suzuki reaction conditions are usual palladium catalysts, with preference for catalysts such as, for example, dichlorobis(triphenylphosphine)palladium, tetrakistriphenylphosphinepalladium(0), palladium(II) acetate/tricyclohexylphosphine, bis(diphenylphosphaneferrocenyl)palladium(II) chloride, 1,3-bis(2,6-diisopropylphenyl)imidazol-2-ylidene(1,4-naphthoquinone)palladium dimer, allyl(chloro)(1,3-dimesityl-1,3-dihydro-2H-imidazol-2-ylidene)palladium or palladium(II) acetate/dicyclohexyl(2',4',6'-triisopropylbiphenyl-2-yl)phosphine. Tris(dibenzylideneacetone)dipalladium can also be employed as palladium source.

Examples of additional reagents are potassium acetate, caesium, potassium or sodium carbonate, potassium tert-butoxide, caesium fluoride or potassium phosphate, with preference for additional reagents such as, for example, potassium acetate and/or aqueous sodium carbonate solution.

Examples of inert solvents are ethers such as dioxane, tetrahydrofuran or 1,2-dimethoxyethane, hydrocarbons such as benzene, xylene or toluene, or carboxamides such as dimethylformamide or dimethylacetamide, alkyl sulphoxides such as dimethyl sulphoxide, or N-methylpyrrolidone or acetonitrile, or mixtures of the solvents with alcohols such as methanol or ethanol and/or water, with preference for dioxane or acetonitrile or a mixture of one of these solvents with water.

The reaction by process [C] takes place under the reaction conditions indicated for process [A].

The compounds of the formulae (III), (V) and (IX) are known or can be synthesized by known processes from the appropriate starting compounds.

The compounds of the formula (VI) are known, can be synthesized by known processes from the appropriate starting compounds, or can be prepared in analogy to the processes described in the example section (Example 1A to 6A).

The compounds of the formula (II) are known or can be prepared by reacting compounds of the formula

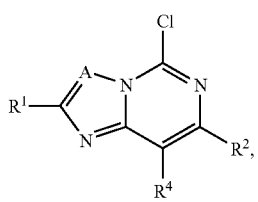
(VI)

in which
A, $R^1$, $R^2$ and $R^4$ have the meaning indicated above, with compounds of the formula

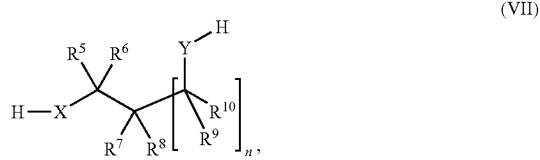
(VII)

in which
n, X, Y, $R^5$, $R^6$, $R^7$, $R^8$, $R^9$ and $R^{10}$ have the meaning indicated above.

The reaction takes place under the reaction conditions indicated for process [A].

The radical Y is protected during the reaction where appropriate with a protective group which is known to the skilled worker and which is eliminated after the reaction by standard processes.

The compounds of the formula (VII) are known or can be synthesized by known processes from the appropriate starting compounds.

The compounds of the formula (IV) are known or can be prepared by reacting compounds of the formula

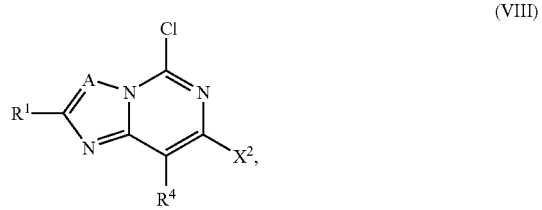
(VIII)

in which
A, $R^1$, $R^4$ and $X^2$ have the meaning indicated above, with compounds of the formula $$H-R^{16} \qquad (IX),$$

in which
$R^{16}$ has the meaning indicated above.

The reaction takes place under the reaction conditions indicated for process [A].

The compounds of the formula (VIII) are known, can be synthesized by known processes from the appropriate starting compounds, or can be prepared in analogy to the processes described in the example section (Example 9A to 11A and Example 50A to 53A).

The preparation of the starting compounds and the compounds of the formula (I) can be illustrated by the following synthesis schemes.

Scheme 1:

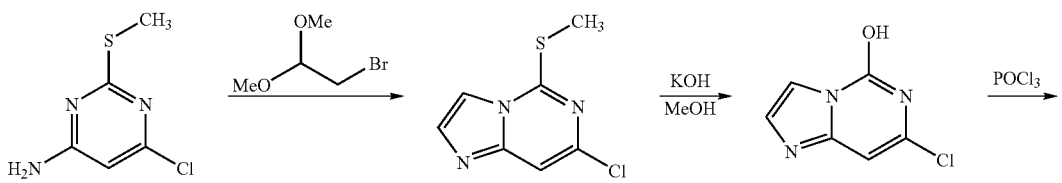

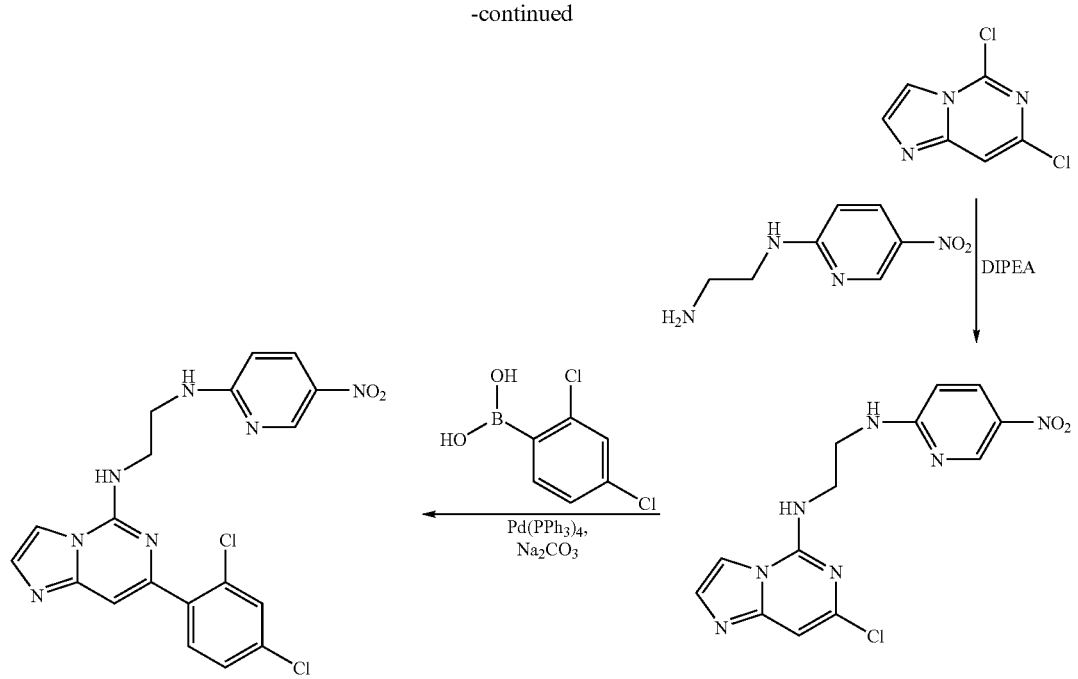
Scheme 2:
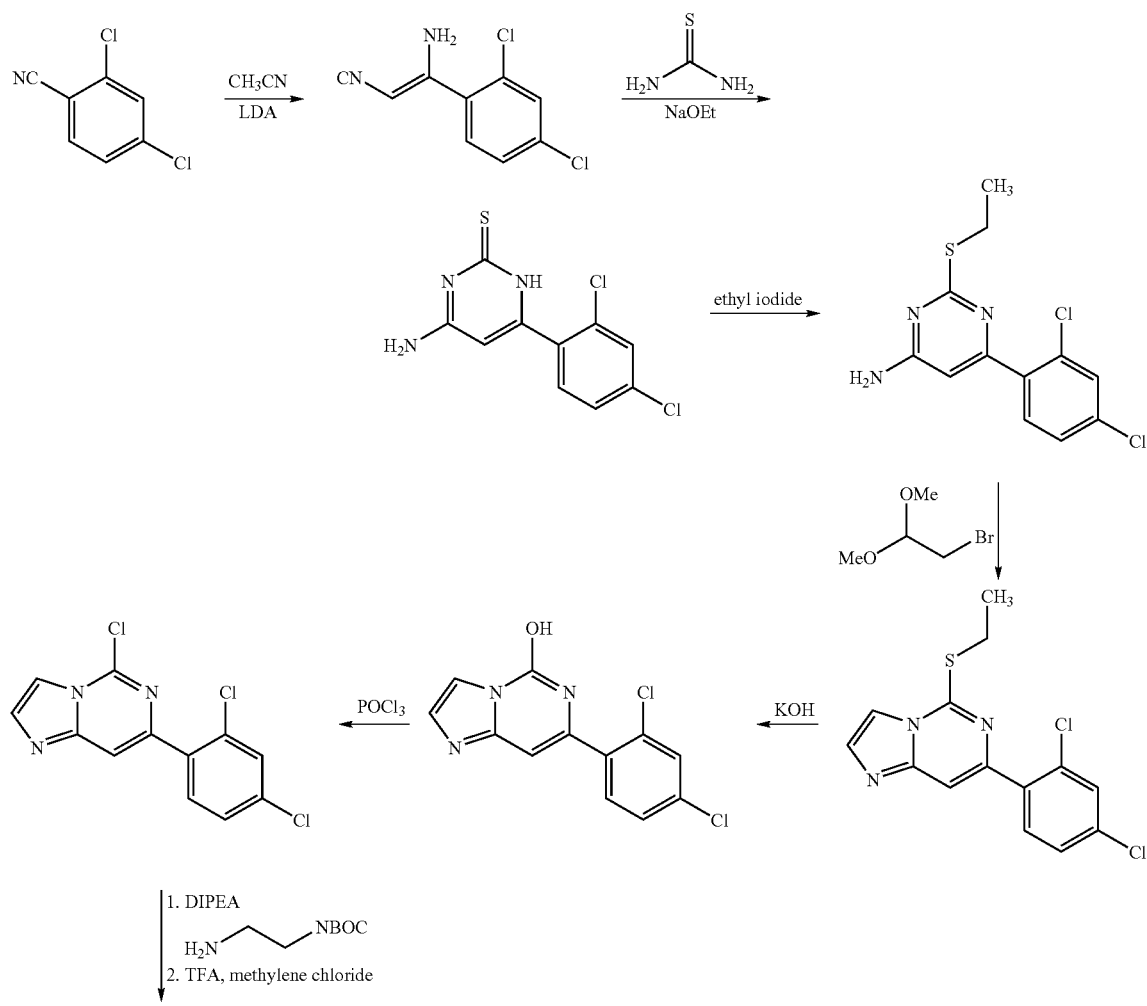

35
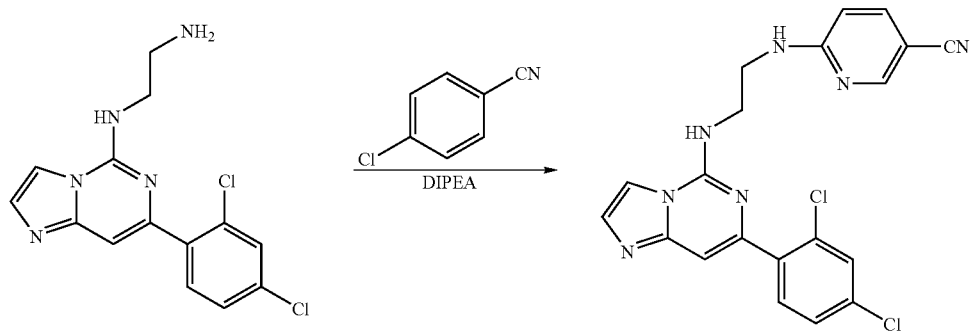
36
-continued
Scheme 3:
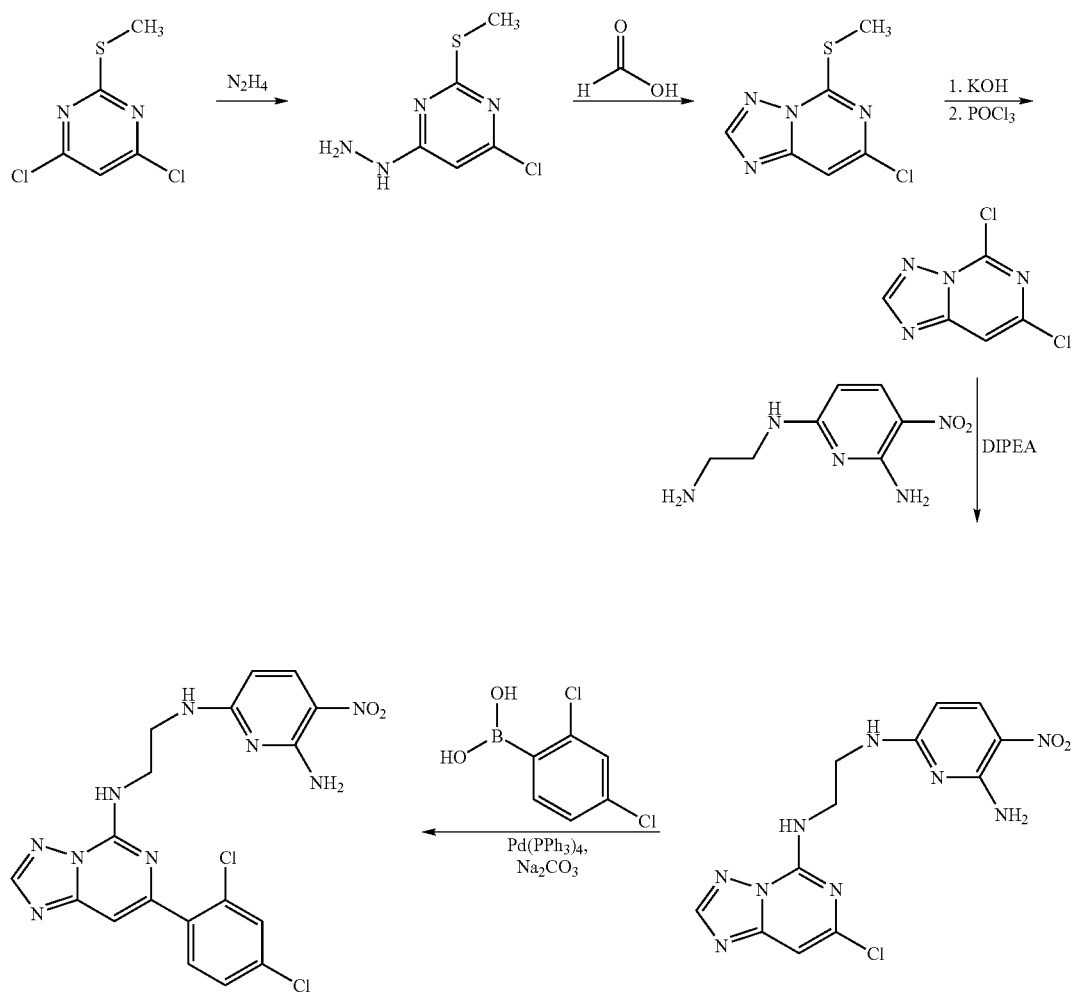

Scheme 4:
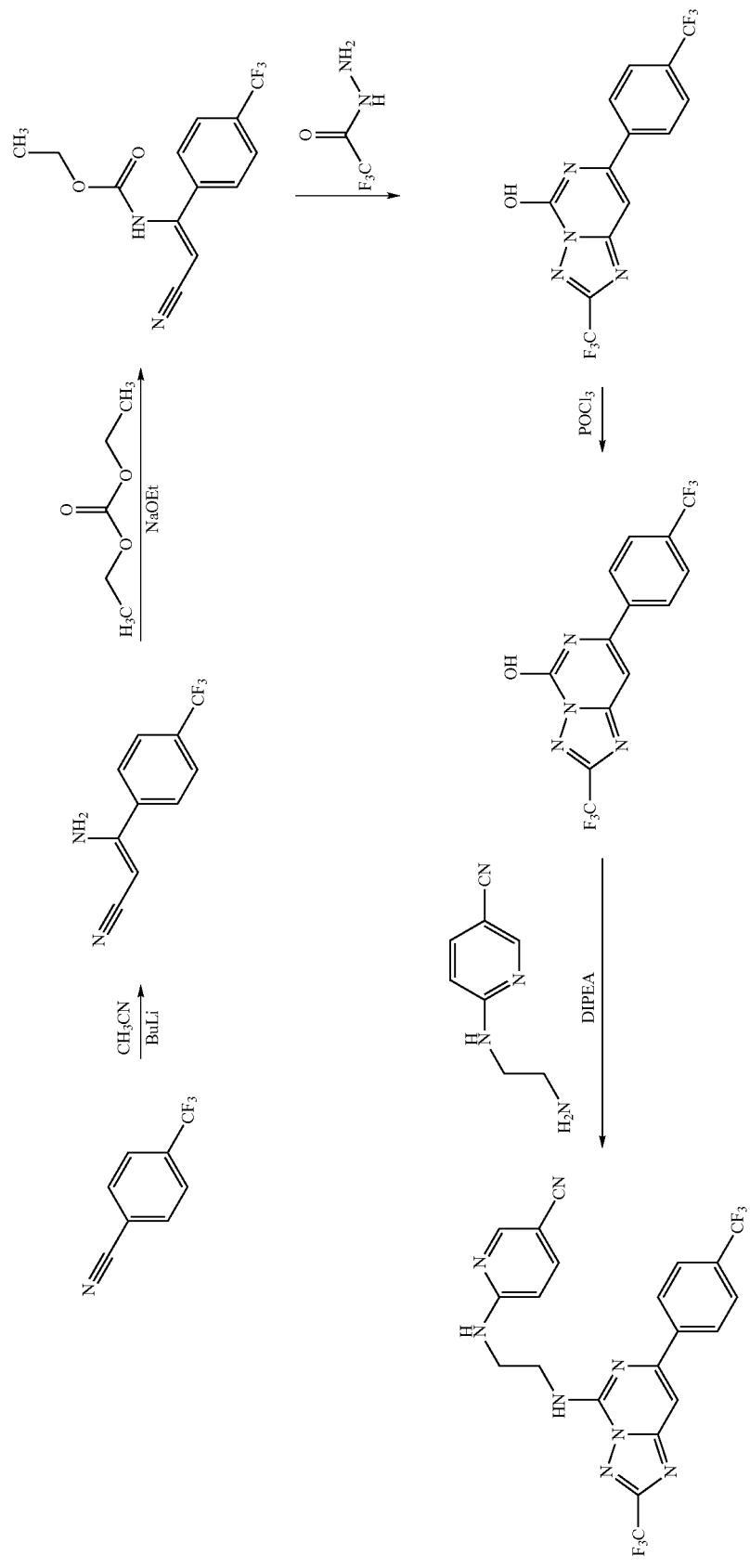

Scheme 5:

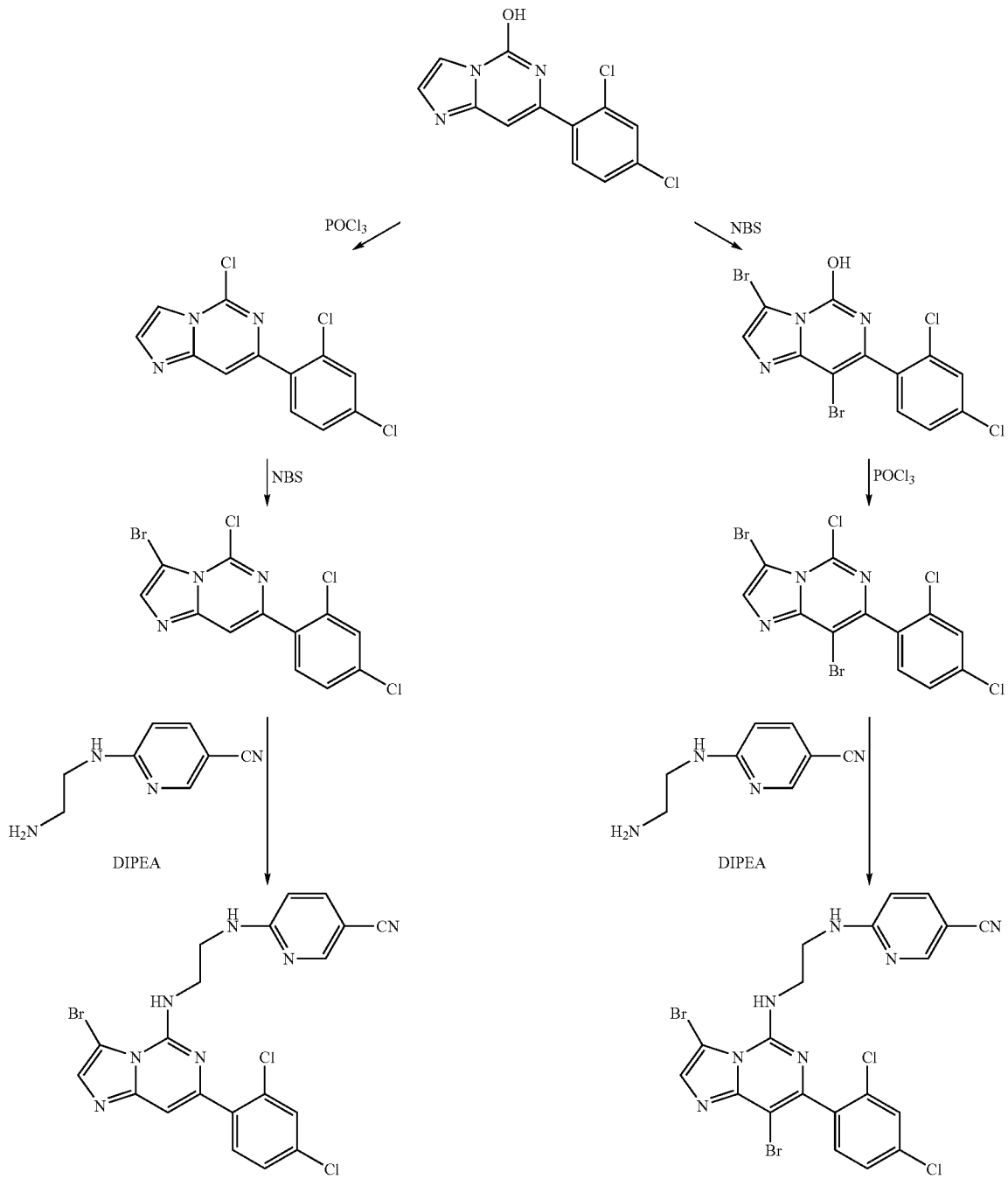

The compounds according to the invention show a valuable range of pharmacological and pharmacokinetic effects which could not have been predicted.

They are therefore suitable of use as medicaments for the treatment and/or prophylaxis of diseases in humans and animals.

The present invention further relates to the use of the compounds according to the invention for the treatment and/or prophylaxis of disorders, preferably haematological disorders, especially of leukopenias and neutropenia.

The compounds according to the invention are therefore suitable for the prophylaxis and/or treatment of neurodegenerative disorders such as, for example, Alzheimer's, Parkinson's, schizophrenia, degeneration, dementia, depression, aggression, cerebrovascular ischemia, sleep disorders, Huntington's chorea, neurotraumatic disorders such as, for example, stroke; type 2 diabetes mellitus and associated disorders such as, for example, the metabolic syndrome or obesity, type 1 diabetes mellitus, diabetic nephropathy, diabetic neuropathy, diabetic retinopathy, glomerulonephritis, hypercalcaemia, hyperglycaemia, hyperlipidaemia, glucose-galactose malabsorption, general endocrine dysfunctions such as, for example, pancreatitis; haematological disorders such as, for example, acquired and congenital neutropenia, granulocytopenia, acquired and congenital leucopenia, acquired and congenital anaemia, heamolytic anaemia, sickle cell anaemia, acquired and congenital thrombocytopenia, leukocyte dysfunctions, impairments of blood coagulation, ex vivo expansion of embryonic and adult stem cells, ex vivo differentiation of embryonic and adult stem cells, and of bone marrow, graft-versus-host reaction; cancer such as, for example, glaucoma, breast carcinoma, colon tumour, gastrointestinal tumours, Hodgkin's lymphoma, non-Hodgkin's lymphoma, Kaposi sarcoma, liver tumour, pancreatic tumour, skin tumour, bone marrow tumour, leukaemias such as, for example, acute lymphatic leukaemia, acute myeloid leukaemia, chronic myeloid leukaemia, chronic lymphatic leukaemia, prostate tumours, lung cancer, renal tumours; asthma, progressive, not completely reversible obstruction of the respiratory tract, pneumonia, pulmonary dysfunction; inflammatory disorders such as, for example, autoimmune diseases such as multiple sclerosis, rheumatoid arthritis, infections by gram-negative and gram-positive bacteria, viral infections, fungal infections such as, for example, by *Candida albicans*, HIV infections and HIV-associated infections, hepatitis of types A, B and C, parasitic infections; hair loss, reduced sperm motility, wound healing; osteoporosis, bone marrow disorders, bone and joint disorders; cardiovascular disorders such as, for example, cardiac defects, heart failure, cardiac fibrosis, cardiac arrhythmias, myocardial infarction, medicament- or substance-induced cardiotoxicity, atherosclerosis, high blood pressure.

The compounds according to the invention can additionally be employed also for efficient ex vivo expansion of adult haematopoietic stem cells from the bone marrow, from peripheral blood or umbilical cord blood.

These cells expanded in this way can then be used to curtail the cytopenias induced by myeloablative therapies or within the framework of therapeutic transplantation methods or for haematological systemic disorders such as, for example, leukaemias, or with cells which have been genetically manipulated after expansion for gene therapies.

The present invention further relates to the use of the compounds according to the invention for the treatment and/or prophylaxis of disorders, especially of the aforementioned disorders.

The present invention further relates to the use of the compounds according to the invention for the manufacture of a medicament for the treatment and/or prophylaxis of disorders, especially of the aforementioned disorders.

The present invention further relates to a method for the treatment and/or prophylaxis of disorders, in particular of the aforementioned disorders, by use of a therapeutically effective amount of a compound according to the invention.

The present invention further relates to medicaments comprising a compound according to the invention and one or more further active ingredients, in particular for the treatment and/or prophylaxis of the aforementioned disorders. Suitable active ingredients in the combination which may be mentioned by way of example and preferably are:

A combination of the compounds according to the invention with chemotherapeutic agents used clinically may lead to a significantly improved result of treatment for various neoplastic diseases. The chemotherapeutic agents are substances which either inhibit the rate of division of tumour cells and/or prevent neovascularization of solid tumours. These include substances inter alia from the group of taxanes such as, for example, paclitaxel, or docetaxel, substances which inhibit the mitosis of tumour cells, such as, for example, vinblastine, vincristine, vindesine or vinorelbine. Substances from the class of platinum derivatives such as, for example, cisplatin, carboplatin, oxaliplatin, nedaplatin or lobaplatin. The chemotherapeutic agents further include substances from the class of alkylating agents such as, for example, cyclophosphamide, ifosfamide, melphalan, chlorambucil, pipobroman, triethylene melamine, busulphan, carmustine, lomustine, streptozin, dacarbazine or temozolomide. The chemotherapeutic agents also include antimetabolites such as, for example, folic acid antagonists, pyrimidine analogues, purine analogues or adenosine deaminase inhibitors. This class of substances includes inter alia methotrexate, 5-fluorouracil, floxuridine, cytarabine, pentostatin and gemcitabine. Also employed as chemotherapeutic agents are natural products or derivatives thereof, which include inter alia enzymes, antitumour antibodies and lymphokines. These include for example bleomycin, dactinomycin, daunorubicin, doxorubicin, epirubicin, idarubicin, ara-V, paclitaxel, mithramycin, mitomycin-C, L-asparaginase, interferons (e.g. IFN-alpha) and etoposide. Other chemotherapeutic agents with antiproliferative and/or anti-angiogenic effect are sorafenib, sunitinib, bortezomib, DAST inhibitor (BAY 73-4506) inter alia.

The present invention further relates to a method for the ex vivo expansion of adult haematopoietic stem cells from bone marrow, from peripheral blood or umbilical cord blood, which is characterized in that an effective amount of the compound according to the invention is added.

The compounds of the invention can act systemically and/or locally. For this purpose, they can be administered in a suitable way such as, for example, by the oral, parenteral, pulmonary, nasal, sublingual, lingual, buccal, rectal, dermal, transdermal, conjunctival or otic route or as implant or stent.

The compounds of the invention can be administered in administration forms suitable for these administration routes.

Suitable for oral administration are administration forms which function according to the prior art and deliver the compounds of the invention rapidly and/or in modified fashion, and which contain the compounds of the invention in crystalline and/or amorphized and/or dissolved form, such as, for example, tablets (uncoated or coated tablets, for example having enteric coatings or coatings which are insoluble or dissolve with a delay and control the release of the compound of the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Oral administration is preferred.

Suitable for the other administration routes are, for example, pharmaceutical forms for inhalation (inter alia powder inhalers, nebulizers), nasal drops, solutions, sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (such as, for example, patches), milk, pastes, foams, dusting powders, implants or stents.

The compounds of the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as, for example, ascorbic acid), colours (e.g. inorganic pigments such as, for example, iron oxides) and masking flavours and/or odours.

The present invention further relates to medicaments which comprise at least one compound of the invention, preferably together with one or more inert, non-toxic, pharmaceutically suitable excipients, and to the use thereof for the aforementioned purposes.

It has generally proved advantageous on parenteral administration to administer amounts of about 5 to 500 mg every 24 hours to achieve effective results. The amount on oral administration is about 5 to 500 mg every 24 hours.

It may nevertheless be necessary where appropriate to deviate from the stated amounts, in particular as a function of the body weight, route of administration, individual response to the active ingredient, nature of the preparation and time or interval over which administration takes place.

The percentage data in the following tests and examples are, unless indicated otherwise, percentages by weight; parts are parts by weight. Solvent ratios, dilution ratios and concentration data of liquid/liquid solutions are in each case based on volume. The statement "w/v" means "weight/volume". Thus, for example, "10% w/v" means: 100 ml of solution or suspension comprise 10 g of substance.

A) EXAMPLES

Abbreviations

| | |
|---|---|
| abs. | absolute |
| Boc | tert-butoxycarbonyl |
| $CDCl_3$ | deuterochloroform |
| $CO_2$ | carbon dioxide |
| conc. | concentrated |
| d | day |
| DIEA | N,N-diisopropylethylamine |
| DMAP | 4-N,N-dimethylaminopyridine |
| DMF | dimethylformamide |
| DMSO | dimethyl sulphoxide |
| EDC | N'-(3-dimethylaminopropyl)-N-ethylcarbodiimide x HCl |
| eq. | equivalent |
| ESI | electrospray ionization (in MS) |
| h | hour |
| HOBt | 1-hydroxy-1H-benzotriazole x $H_2O$ |
| HPLC | high pressure, high performance liquid chromatography |
| LC-MS | coupled liquid chromatography-mass spectrometry |
| min | minutes |
| MS | mass spectrometry |
| MW | molecular weight [g/mol] |
| NMP | N-methylpyrrolidone |
| NMR | nuclear magnetic resonance spectroscopy |
| PyBOP | 1-benzotriazolyloxytripyrrolidinophosphonium hexafluorophosphate |
| $R_f$ | retention index (in TLC) |
| sat. | saturated |
| RP-HPLC | reverse phase HPLC |
| RT | room temperature |
| $R_t$ | retention time (in HPLC) |
| TBTU | (benzotriazol-1-yloxy)bisdimethylaminomethylium fluoroborate |
| TFA | trifluoroacetic acid |
| THF | tetrahydrofuran |

LC-MS Methods:

Method 1: Instrument: Micromass Quattro LCZ with HPLC Agilent series 1100; column: Phenomenex Synergi 2.5μ MAX-RR 100 A mercury 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 2: MS instrument type: Micromass ZQ; HPLC instrument type: Waters Alliance 2795; column: Merck Chromolith SpeedROD RP-18e 100 mm×4.6 mm; eluent A: water+500 μl of 50% formic acid/l; eluent B: acetonitrile+500 μl of 50% formic acid/l; gradient: 0.0 min 10% B→7.0 min 95% B→9.0 min 95% B; oven: 35° C.; flow rate: 0.0 min 1.0 ml/min→7.0 min 2.0 ml/min→9.0 min 2.0 ml/min; UV detection: 210 nm Method 3: MS instrument type: Micromass ZQ; HPLC instrument type: HP 1100 Series; UV DAD; column: Phenomenex Gemini 3μ 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 4: Instrument: Micromass Platform LCZ with HPLC Agilent series 1100; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 5: MS instrument type: Waters ZQ; HPLC instrument type: Waters Alliance 2795; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 210 nm.

Method 6: MS instrument type: Micromass ZQ; HPLC instrument type: Waters Alliance 2795; column: Phenomenex Synergi 2.5μ MAX-RP 100 A mercury 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 7: Instrument: Micromass Quattro LCZ with HPLC Agilent series 1100; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 208-400 nm.

Method 8: Instrument: Micromass QuattroPremier with Waters UPLC Acquity; column: Thermo Hypersil GOLD 1.9μ 50 mm×1 mm; eluent A: 1 l of water+0.5 ml of 50% formic acid, eluent B: 1 l of acetonitrile+0.5 ml of 50% formic acid; gradient: 0.0 min 90% A→0.1 min 90% A→1.5 min 10% A→2.2 min 10% A; oven: 50° C.; flow rate: 0.33 ml/min; UV detection: 210 nm.

Method 9: Instrument: Micromass Quattro Micro MS with HPLC Agilent series 1100; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→3.0 min 10% A→4.0 min 10%

A→4.01 min 100% A (flow rate: 2.5 ml/min)→5.00 min 100% A; oven: 50° C.; flow rate: 2 ml/min; UV detection: 210 nm.

Method 10: MS instrument type: Waters ZQ; HPLC instrument type: Agilent 1100 series; UV DAD; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→3.0 min 10% A→4.0 min 10% A→4.1 min 100% (flow rate: 2.5 ml/min); oven: 55° C.; flow rate: 2 ml/min; UV detection: 210 nm.
Starting Compounds Example 1A 3-Amino-3-(2,4-dichlorophenyl)acrylonitrile

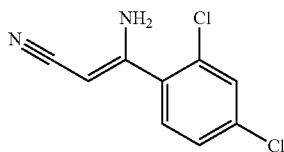

90 g (889.46 mmol) of diisopropylamine are introduced into 1660 ml of THF at −70° C. in a three-necked flask with mechanical stirrer under argon. 124.66 ml of N-butyllithium solution (2.5M in hexane, 758.66 mmol) are added dropwise at a rate such that the temperature does not rise above −60° C. The mixture is stirred for 10 min and then a solution of 32.22 g (784.82 mmol) of acetonitrile in 340 ml of THF is slowly added dropwise, and the suspension is stirred for 30 min. Then a solution of 90 g (523.21 mmol) of 2,4-dichlorobenzonitrile in 340 ml of THF is added dropwise, and the mixture is stirred at −70° C. for 20 min. It is allowed slowly to reach RT and is stirred at RT for a further 16 h. 600 ml of water are added, most of the THF is distilled off, and water and dichloromethane are added. The organic phase is washed with sat. aqueous sodium chloride solution. Removal of the solvent results in dark crystals which are purified by stirring with diethyl ether. 76.5 g (69% of theory) of the product are obtained as a solid.

LCMS (method 5): $R_t$=3.07 min. (m/z=213 (M+H)$^+$)
$^1$H-NMR (400 MHz, DMSO-d$_6$): δ=7.70 (d, 1H), 7.47 (dd, 1H), 7.40 (d, 1H), 7.02 (s, broad, 2H), 3.79 (s, 1H).

Example 2A

4-Amino-6-(2,4-dichlorophenyl)pyrimidine-2(1H)-thione

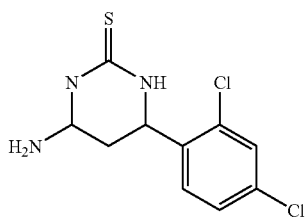

16.51 g (718.08 mmol) of sodium are dissolved in 353 ml of ethanol, and 40.996 g (538.56 mmol) of thiourea are added to the sodium ethanolate solution prepared in this way, followed by 76.5 g (359.04 mmol) of 3-amino-3-(2,4-dichlorophenyl)acrylonitrile. The mixture is heated under reflux for 18 h and, after cooling, 500 ml of water are added. The mixture is neutralized with 1M hydrochloric acid, and the precipitate which has separated out is filtered off with suction. The latter is washed with water, suspended in THF and again filtered off with suction. It is washed with 300 ml of petroleum ether and then dried under high vacuum. 67.5 g (55% of theory) of the product are obtained as a solid.

LCMS (method 3): $R_t$=1.54 min. (m/z=272 (M+H)$^+$)
$^1$H-NMR (400 MHz, DMSO-d$_6$): δ=12.30 (s, 1H), 7.78 (d, 1H), 7.75 (s, broad, 1H), 7.62 (s, broad, 1H), 7.53 (m, 2H), 5.89 (s, 1H).

Example 3A 6-(2,4-Dichlorophenyl)-2-(ethylthio)pyrimidine-4-amine

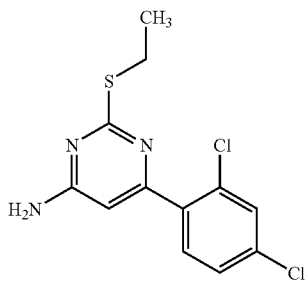

67.5 g (248 mmol) of 4-amino-6-(2,4-dichlorophenyl)pyrimidine-2(1H)-thione and 77.37 g (496.04 mmol) of iodoethane are dissolved in 560 ml of dry DMSO and, at RT, 270 ml of a saturated aqueous sodium bicarbonate solution are slowly added. The mixture is stirred at RT for 5 h and then 440 ml of water are added. The precipitate is filtered off with suction, washed with water and sucked dry. It is stirred twice with 100 ml of isopropanol each time and again filtered off with suction. It is washed once more with petroleum ether and the residue is dried under high vacuum. 50.0 g (67% of theory) of the product are obtained as a solid.

LCMS (method 5): $R_t$=3.49 min. (m/z=300 (M+H)$^+$)
$^1$H-NMR (400 MHz, DMSO-d$_6$): δ=7.73 (d, 1H), 7.60 (d, 1H), 7.53 (dd, 1H), 7.11 (s, 2H), 6.39 (s, 1H), 3.01 (q, 2H), 1.29 (t, 3H).

Example 4A 7-(2,4-Dichlorophenyl)-5-(ethylthio)imidazo[1,2-c]pyrimidine

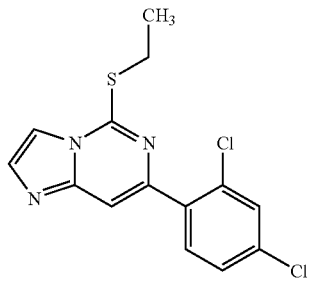

48.5 g (161.55 mmol) of 6-(2,4-dichlorophenyl)-2-(ethylthio)pyrimidine-4-amine (Example 3A) and 163.84 g (969.32 mmol) of bromoacetaldehyde dimethyl acetal are introduced into a mixture of 1164 ml of dioxane and 291 ml of water and heated under reflux for 16 h. The dioxane is substantially removed in vacuo, and 1000 ml of ethyl acetate and 1000 ml of saturated aqueous sodium bicarbonate solution are cautiously added. The phases are separated and a further extraction with ethyl acetate is carried out. The combined organic phases are washed with saturated aqueous sodium chloride solution, dried over sodium sulphate and then freed of solvent. The residue is purified by silica gel chromatography. 16.6 g (27% of theory) of the product are obtained and are reacted further in this form.

LCMS (method 5): $R_t$=3.84 min. (m/z=324 (M+H)$^+$)

$^1$H-NMR (400 MHz, DMSO-d$_6$): δ=7.92 (s, 1H), 7.79 (s, 2H), 7.78 (d, 1H), 7.71 (s, 1H), 7.59 (dd, 1H), 3.41 (q, 2H), 1.43 (t, 3H).

Example 5A 7-(2,4-Dichlorophenyl)imidazo[1,2-c]pyrimidin-5-ol

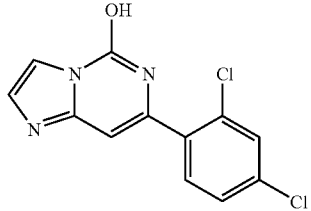

16.6 g (51.19 mmol) of 7-(2,4-dichlorophenyl)-5-(ethylthio)imidazo[1,2-c]pyrimidine are dissolved in 330 ml of methanol, and 77 ml of a 2 molar aqueous potassium hydroxide solution are added. The mixture is stirred at the reflux temperature for 2 h. After cooling, 300 ml of water are added and then, while cooling in ice, 140 ml of 0.1 molar hydrochloric acid. The mixture is then neutralized with saturated aqueous ammonium chloride solution and stirred for 10 min, and the solid is filtered off with suction. It is thoroughly washed with water and dried under high vacuum. 13.6 g (92% of theory) of the product are obtained as a solid.

MS (ES+): m/z=280 (M)$^+$.

$^1$H-NMR (400 MHz, DMSO-d$_6$): δ=11.90 (s, 1H), 7.83 (dd, 2H), 7.56-7.64 (m, 2H), 7.45 (d, 1H), 6.69 (s, 1H).

Example 6A

5-Chloro-7-(2,4-dichlorophenyl)imidazo[1,2-c]pyrimidine

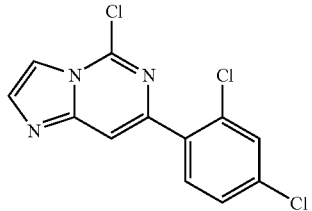

12.0 g (42.84 mmol) of 7-(2,4-dichlorophenyl)imidazo[1,2-c]pyrimidin-5-ol are introduced into 131.6 g (858.27 mmol) of phosphoryl chloride and heated at 120° C. for 5 h. A clear solution is produced after 10 min. The mixture is allowed to cool, and then 2000 ml of saturated aqueous sodium bicarbonate solution are cautiously added. Towards the end, about 100 g of solid sodium bicarbonate are also added, and the mixture is stirred at pH 7 for 10 min. The precipitate is filtered off with suction, thoroughly washed with water, suspended in a little isopropanol and sucked dry. It is then washed once more with petroleum ether and dried under high vacuum at 50° C. 11 g (81% of theory) of the product are obtained as a solid.

MS (CI+): m/z=298 (M)$^+$.

$^1$H-NMR (400 MHz, DMSO-d$_6$): δ=8.17 (s, 1H), 8.00 (s, 1H), 8.88 (d, 1H), 7.82 (d, 1H), 7.73 (d, 1H), 7.56 (dd, 1H).

Example 7A tert-Butyl (2-{[7-(2,4-dichlorophenyl)imidazo[1,2-c]pyrimidin-5-yl]amino}ethyl)carbamate

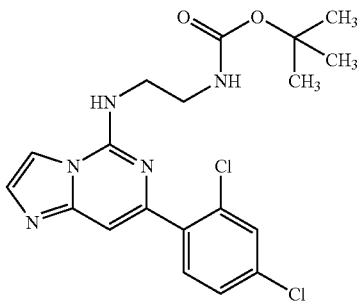

3.0 g (10.05 mmol) of 5-chloro-7-(2,4-dichlorophenyl)imidazo[1,2-c]pyrimidine, 2.41 g (15.07 mmol) of N-Boc-ethylenediamine and 3.89 g (30.15 mmol) of diisopropylethylamine are dissolved in 50 ml of DMSO and heated at 120° C. for 16 h. Ethyl acetate and water are added, and the removed organic phase is washed twice more with water. The organic phase is dried with magnesium sulphate. Removal of the solvent results in 4.49 g (99% of theory) of product.

LCMS (method 5): $R_t$=2.80 min. (m/z=422 (M+H)$^+$)

$^1$H-NMR (400 MHz, DMSO-d$_6$): δ=8.04 (s, 1H), 7.99 (t, 1H), 7.75 (d, 1H), 7.71 (d, 1H), 7.57 (d, 1H), 7.52 (dd, 1H), 7.11 (s, 1H), 6.95 (t, 1H), 3.53 (m, 2H), 3.2-3.32 (m, 2H), 1.33 (s, 9H).

Example 8A

N-[7-(2,4-Dichlorophenyl)imidazo[1,2-c]pyrimidin-5-yl]ethane-1,2-diamine trifluoroacetate

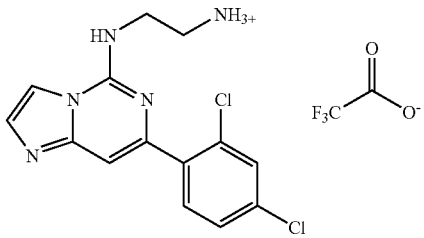

4.42 g (10.47 mmol) of tert-butyl (2-{[7-(2,4-dichlorophenyl)imidazo[1,2-c]pyrimidin-5-yl]amino}ethyl)carbamate are dissolved in 160 ml of dichloromethane, and 16 ml (209 mmol) of trifluoroacetic acid are added. The mixture is stirred at RT for 2 h and then removed from all volatile constituents in vacuo. 4.56 g (99% of theory) of product are obtained and are employed without further purification.

LCMS (method 4): $R_t$=2.23 min. (m/z=322 (M+H)$^+$)

$^1$H-NMR (400 MHz, DMSO-d$_6$): δ=8.90 (s, 1H), 8.20 (s, 1H), 8.04 (s, 1H), 7.90 (s, broad, 2H), 7.82 (d, 1H), 7.76 (d, 1H), 7.60 (dd, 1H), 7.42 (s, 1H), 3.80 (dd, 2H), 3.18 (dd, 2H).

Example 9A

7-Chloro-5-(methylthio)imidazo[1,2-c]pyrimidine

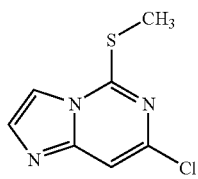

75 g (427 mmol) of 4-amino-6-chloro-2-(methylthio)pyrimidine are dissolved in 3000 ml of dioxane and 750 ml of water. 101.05 g (597.81 mmol) of bromoacetaldehyde dimethyl acetal are added, and the mixture is heated under reflux for 24 h. After the reaction is complete, the dioxane is removed in vacuo and the aqueous suspension is suspended in THF, filtered with suction and washed with some THF. Drying of the solid at 40° C. under high vacuum results in 56.5 g (66% of theory) of the product.

MS (ES+): m/z=200 (M+H)$^+$.

$^1$H-NMR (400 MHz, DMSO-d$_6$): δ=8.12 (s, 1H), 7.97 (s, 1H), 7.77 (s, 1H), 2.80 (s, 3H).

Example 10A

7-Chloroimidazo[1,2-c]pyrimidin-5-ol

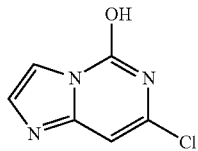

A solution of 73.25 g (366.87 mmol) of 7-chloro-5-(methylthio)imidazo[1,2-c]pyrimidine are dissolved in 732 ml of methanol, and 1275 ml of a 2 molar aqueous potassium hydroxide solution are added. The mixture is heated under reflux for 3 h. After the reaction is complete, the methanol is removed in vacuo, the mixture is neutralized with half-concentrated hydrochloric acid, and the crystals which have separated out are filtered off with suction. They are washed with methanol and water and then dried under high vacuum. 40.0 g (64% of theory) of the product are obtained.

LCMS (method 4): $R_t$=1.32 min. (m/z=170 (M+H)$^+$).

$^1$H-NMR (400 MHz, DMSO-d$_6$): δ=12.98 (s, 1H), 7.71 (s, 1H), 7.54 (s, 1H), 6.63 (s, 1H).

Example 11A 5,7-Dichloroimidazo[1,2-c]pyrimidine

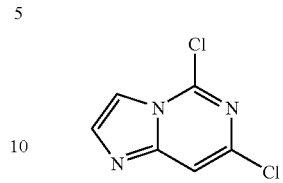

38.3 g (225.86 mmol) of 7-chloroimidazo[1,2-c]pyrimidin-5-ol are suspended in 450.2 g (2936 mmol) of phosphoryl chloride under argon and heated at 120° C. for 4 h. After this time, the excess phosphoryl chloride is removed in vacuo, and the residue is distilled together with toluene. The residue is suspended in water, the pH is brought to 7 with saturated aqueous sodium bicarbonate solution, and the precipitated solid is filtered off with suction. The latter is washed with water and dried over phosphorus pentoxide for 18 h. 33.5 g (67% of theory) of the product are obtained as a solid.

LCMS (method 6): $R_t$=1.01 min. (m/z=189 (M+H)$^+$).

$^1$H-NMR (400 MHz, DMSO-d$_6$): δ=8.11 (s, 1H), 7.94 (s, 1H), 7.81 (s, 1H).

Example 12A tert-Butyl {2-[(5-cyanopyridin-2-yl)amino]ethyl}carbamate

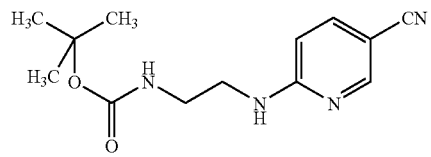

3.0 g (18.73 mmol) of N-Boc-ethylenediamine, 5.19 g (37.45 mmol) of 6-chloronicotinonitrile and 3.75 g (37.45 mmol) of potassium bicarbonate are suspended in 360 ml of DMF and heated at 90° C. for 16 h. Water is added to the mixture, which is then extracted three times with ethyl acetate. The combined organic phases are washed with saturated aqueous sodium chloride solution. After drying over magnesium sulphate, the solvent is removed. Drying under high vacuum results in 3.58 g (68% of theory) of the product.

LCMS (method 7): $R_t$=2.63 min. (m/z=263 (M+H)$^+$).

$^1$H-NMR (400 MHz, DMSO-d$_6$): δ=8.37 (d, 1H), 7.66 (d, 1H), 7.60 (s, br, 1H), 6.88 (t, 1H), 6.53 (d, 1H), 3.31 (dd, 2H), 3.08 (dd, 2H), 1.37 (s, 9H).

Example 13A

6-[(2-Aminoethyl)amino]nicotinonitrile trifluoroacetate

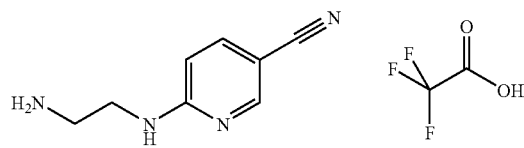

4.0 g (15.25 mmol) of tert-butyl {2-[(5-cyanopyridin-2-yl)amino]ethyl}carbamate (Example 12A) are dissolved in 150 ml of dichloromethane, and 17.39 g (152.5 mmol) of trifluoroacetic acid are slowly injected. The mixture is stirred at RT for 16 h and then all volatile constituents are removed in vacuo. 4.3 g (91% of theory) of the product are obtained as a resin.

LCMS (method 4): $R_t$=0.91 min. (m/z=161 (M−H)$^+$).

$^1$H-NMR (400 MHz, DMSO-d$_6$): δ=11.53 (s, br, 3H), 8.44 (d, 1H), 7.84 (s, br, 1H), 7.75 (dd, 1H), 6.61 (d, 1H), 3.55 (m, 2H), 3.0 (dd, 2H).

Example 14A tert-Butyl {2-[(6-amino-5-nitropyridin-2-yl)amino]ethyl}carbamate

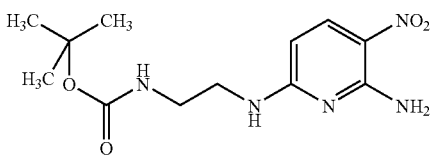

In analogy to the preparation of the cyanopyridine (Example 12A), 5.5 g (86% of theory) of the product are obtained from 3.0 g (18.73 mmol) of N-Boc-ethylenediamine and 6.5 g (37.4 mmol) of 6-chloro-3-nitropyridine-2-amine after purification by silica gel chromatography.

LCMS (method 4): $R_t$=3.05 min. (m/z=296 (M−H)$^+$).

$^1$H-NMR (400 MHz, DMSO-d$_6$): δ=8.13 (s, br, 1H), 7.94 (s, 1H), 7.92 (d, 1H), 7.71 (s, br, 1H), 6.87 (s, br, 1H), 5.94 (d, 1H), 3.37 (dd, 2H), 3.11 (dd, 2H), 1.37 (s, 9H).

Example 15A

N$^6$-(2-Aminoethyl)-3-nitropyridine-2,6-diamine trifluoroacetate

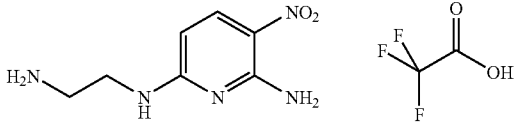

In analogy to the preparation of the cyanopyridine (Example 13A), 4.98 g (99% of theory) of the product are obtained from 5.5 g (16.1 mmol) of the aminopyridine (Example 14A) and 18.7 g (160.9 mmol) of trifluoroacetic acid after removal of all volatile constituents.

MS (CI): m/z=198 (M+H)$^+$.

$^1$H-NMR (400 MHz, DMSO-d$_6$): δ=8.15 (s, br, 2H), 8.03 (s, br, 1H), 8.00 (d, 1H), 7.79 (s, br, 2H), 5.97 (d, 1H), 3.51 (dd, 2H), 3.06 (dd, 2H).

Example 16A 6-({2-[(7-Chloroimidazo[1,2-c]pyrimidin-5-yl)amino]ethyl}amino)nicotinonitrile

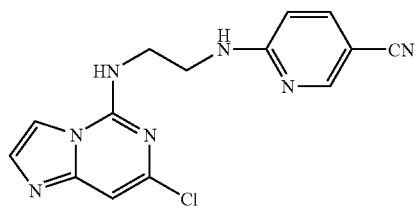

707 mg (3.20 mmol) of 5,7-dichloroimidazo[1,2-c]pyrimidine (Example 11A) are suspended in 25 ml of 2-propanol, and 1.35 g (3.52 mmol) of 6-[(2-aminoethyl)amino]nicotinonitrile trifluoroacetate (Example 13A) and 1.03 g (7.99 mmol) of DIPEA are added. The mixture is heated at 80° C. for 16 h. After this time, water is added and the precipitate which has separated out is filtered off with suction. It is washed with a little 2-propanol/water and the resulting solid is dried under high vacuum. 523 mg (50% of theory) of the product are obtained.

LCMS (method 3): $R_t$=1.31 min. (m/z=314 (M+H)$^+$)

$^1$H-NMR (400 MHz, DMSO-d$_6$): δ=8.37 (d, 1H), 8.33 (t, 1H), 7.93 (s, 1H), 7.80 (s, 1H), 7.68 (d, 1H), 7.50 (d, 1H), 6.90 (s, 1H), 6.56 (s, br, 1H), 3.62 (m, 2H), 3.31 (m, 2H).

Example 17A

N$^6$-{2-[7-Chloroimidazo[1,2-c]pyrimidin-5-yl)amino]ethyl}-3-nitropyridine-2,6-diamine

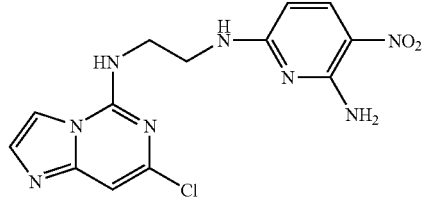

800 mg (4.13 mmol) of 5,7-dichloroimidazo[1,2-c]pyrimidine (Example 11A) are suspended in 20 ml of DMSO, and 1.62 g (4.54 mmol) of N$^6$-(2-aminoethyl)-3-nitropyridine-2,6-diamine trifluoroacetate (Example 15A) and 1.6 g (12.38 mmol) of DIPEA are added. The mixture is heated at 120° C. for 16 h. After this time, water is added, and the precipitate which has separated out is filtered off with suction. It is washed with a little 2-propanol/water and the resulting solid is dried under high vacuum. 1.34 g (92% of theory) of the product are obtained as a solid.

LCMS (method 7): $R_t$=1.44 min. (m/z=349 (M+H)$^+$)

$^1$H-NMR (400 MHz, DMSO-d$_6$): δ=8.29 (t, 1H), 8.15 (s, br, 1H), 8.09 (t, 1H), 7.95 (s, 1H), 7.93 (s, 1H), 7.69 (s, br, 1H), 7.50 (d, 1H), 6.92 (s, 1H), 5.92 (d, 1H), 3.67 (m, 4H).

Example 18A

4-Amino-2-(methylsulphonyl)-1,3-thiazole-5-carbonitrile

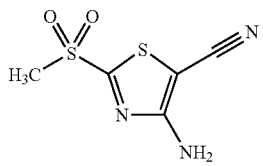

2.7 g (15.77 mmol) of 4-amino-2-(methylthio)-1,3-thiazole-5-carbonitrile are dissolved in 200 ml of dichloromethane, and 11.97 g (34.7 mmol) of 3-chloroperbenzoic acid are added. The mixture is stirred at RT for 30 min and then 6 ml of DMSO are added, and then saturated aqueous sodium bicarbonate solution, and the mixture is extracted three times with dichloromethane. Drying of the organic phase over magnesium sulphate and removal of the solvent result in 2.22 g (46% of theory) of the product as an oil, which is employed without further purification.

LCMS (method 3): $R_t$=1.19 min. (m/z=204 (M+H)$^+$).

Example 19A tert-Butyl {2-[(4-amino-5-cyano-1,3-thiazol-2-yl)amino]ethyl}carbamate

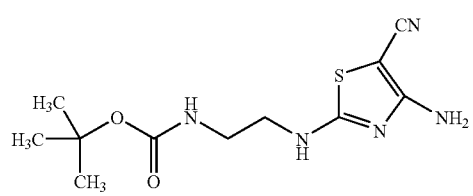

2.2 g (7.22 mmol) of 4-amino-2-(methylsulphonyl)-1,3-thiazole-5-carbonitrile (Example 18A) are dissolved in 24 ml of DMSO, and 1.74 g (10.84 mmol) of N-Boc-ethylenediamine and 933 mg (7.22 mmol) of DIPEA are added. The mixture is stirred at 120° C. for 16 h and, after the reaction is complete, water and ethyl acetate are added. The aqueous phase is extracted three times with ethyl acetate. The combined organic phases are dried over magnesium sulphate and purified by silica gel chromatography. 633 mg (31% of theory) of the product are obtained.

LCMS (method 6): $R_t$=1.45 min. (m/z=284 (M+H)$^+$)

$^1$H-NMR (400 MHz, DMSO-d$_6$): δ=8.35 (s, br, 1H), 6.90 (t, 1H), 6.68 (s, 2H), 3.22 (s, br, 2H), 3.07 (dd, 2H), 1.37 (s, 9H).

Example 20A

4-Amino-2-[(2-aminoethyl)amino]-1,3-thiazole-5-carbonitrile trifluoroacetate

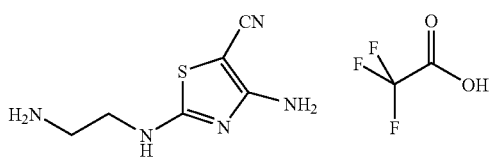

In analogy to the preparation of the cyanopyridine (Example 13A), 130 mg (96% of theory) of the product are obtained from 130 mg (0.46 mmol) of the Boc-protected amine (Example 19A) and 1.05 g (9.18 mmol) of trifluoroacetic acid after removal of all the volatile constituents.

LCMS (method 4): $R_t$=0.61 min. (m/z=184 (M+H)$^+$)

$^1$H-NMR (400 MHz, DMSO-d$_6$): δ=8.45 (t, 1H), 7.84 (s, br, 2H), 6.80 (s, br, 1H), 3.93 (s, 1H), 3.43 (dd, 2H), 3.01 (dd, 2H).

Example 21A

7-Chloro-5-(methylthio)-2-(trifluoromethyl)imidazo[1,2-c]pyrimidine

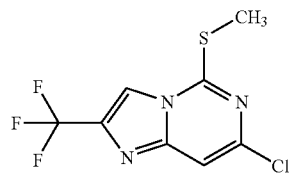

5 g (28.5 mmol) of 6-chloro-2-(methylthio)pyrimidine-4-amine and 6.26 g (42.7 mmol) of 3-chloro-1,1,1-trifluoropropanone are dissolved in 200 ml of DMF and heated at 120° C. for 16 h. After the reaction is complete, water is added and the mixture is extracted three times with ethyl acetate. The combined organic phases are dried over sodium sulphate and the product is purified by silica gel chromatography. Drying under high vacuum results in 3.5 g (45% of theory) of the product as a solid.

LCMS (method 5): $R_t$=3.40 min. (m/z=268 (M+H)$^+$)

$^1$H-NMR (400 MHz, DMSO-d$_6$): δ=8.65 (s, 1H), 7.75 (s, 1H), 2.78 (s, 3H).

Example 22A

7-Chloro-2-(trifluoromethyl)imidazo[1,2-c]pyrimidin-5-ol

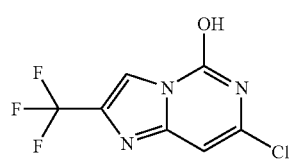

In analogy to the preparation of the hydroxypyrimidine (Example 10A), 2.27 g (67% of theory) of the product are obtained from 3.8 g (14.2 mmol) of the 7-chloro-5-(methylthio)-2-(trifluoromethyl)imidazo[1,2-c]pyrimidine (Example 21A) and 33 ml of 2 molar aqueous potassium hydroxide solution in 100 ml of methanol.

LCMS (method 3): $R_t$=1.73 min. (m/z=238 (M+H)$^+$)

$^1$H-NMR (400 MHz, DMSO-d$_6$): δ=8.40 (s, 1H), 6.94 (s, 1H).

Example 23A 5,7-Dichloro-2-(trifluoromethyl)imidazo[1,2-c]pyrimidine

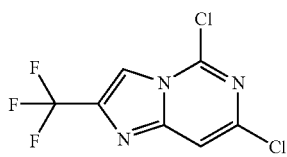

In analogy to the preparation of (Example 11A), 1.11 g (40% of theory) of the product are obtained from 2.76 g (8.95 mmol) of the 7-chloro-2-(trifluoromethyl)imidazo[1,2-c]pyrimidin-5-ol (Example 22A) and 38.7 g (252 mmol) of phosphoryl chloride.

LCMS (method 3): $R_t$=2.29 min. (m/z=256 (M+H)$^+$)

$^1$H-NMR (400 MHz, DMSO-$d_6$): δ=8.84 (s, 1H), 8.09 (s, 1H).

Example 24A

6-[(2-{[7-Chloro-2-(trifluoromethyl)imidazo[1,2-c]pyrimidin-5-yl]amino}ethyl)amino]-nicotinonitrile

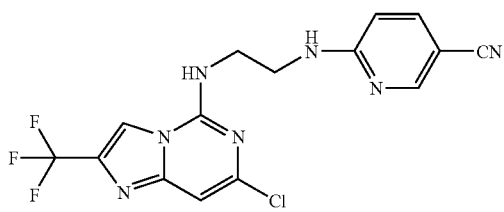

In analogy to the preparation of (Example 16A), 29 mg (19% of theory) of the product are obtained from 140 mg (0.41 mmol) of 5,7-dichloro-2-(trifluoromethyl)imidazo[1,2-c]pyrimidine (Example 23A) and 173.1 mg (0.45 mmol) of 6-[(2-aminoethyl)amino]nicotinonitrile trifluoroacetate (Example 13A).

LCMS (method 5): $R_t$=3.12 min. (m/z=382 (M+H)$^+$)

$^1$H-NMR (400 MHz, DMSO-$d_6$): δ=8.55 (t, 1H), 8.53 (s, 1H), 8.34 (d, 1H), 7.74 (s, 1H), 7.69 (d, 1H), 7.02 (s, 1H), 6.54 (s, 1H), 3.64 (m, 4H).

Example 25A $N^6$-(2-{[7-Chloro-2-(trifluoromethyl)imidazo[1,2-c]pyrimidin-5-yl]amino}ethyl)-3-nitropyridine-2,6-diamine

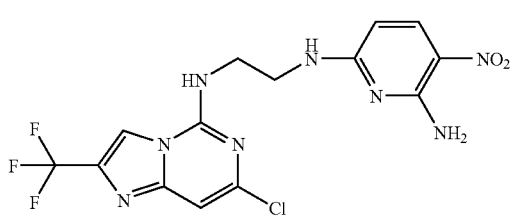

In analogy to the preparation of (Example 16A), 69 mg (38% of theory) of the product are obtained from 140 mg (0.41 mmol) of 5,7-dichloro-2-(trifluoromethyl)imidazo[1,2-c]pyrimidine (Example 23A) and 161 mg (0.45 mmol) of $N^6$-(2-aminoethyl)-3-nitropyridine-2,6-diamine trifluoroacetate (Example 15A).

LCMS (method 7): $R_t$=3.21 min. (m/z=417 (M+H)$^+$)

$^1$H-NMR (400 MHz, DMSO-$d_6$): δ=8.55 (s, 1H), 8.52 (t, 1H), 8.13 (s, br, 1H), 8.02 (t, 1H), 7.94 (d, 1H), 7.67 (s, br, 1H), 7.03 (s, 1H), 5.90 (d, 1H), 3.67 (m, 4H).

Example 26A

7-Chloro-2-(chloromethyl)-5-(methylthio)imidazo[1,2-c]pyrimidine

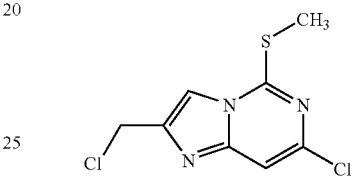

8 g (45.5 mmol) of 6-chloro-2-(methylthio)pyrimidine-4-amine and 5.78 g (45.55 mmol) of 1,3-dichloroacetone are dissolved in 53 ml of glacial acetic acid and heated at 105° C. for 16 h. After the reaction is complete, water is added and the precipitate is filtered off with suction. The crude product is further purified by silica gel chromatography. Drying under high vacuum results in 5.53 g (49% of theory) of product.

LCMS (method 4): $R_t$=3.33 min. (m/z=248 (M+H)$^+$)

$^1$H-NMR (400 MHz, DMSO-$d_6$): δ=7.99 (s, 1H), 7.58 (s, 1H), 4.85 (s, 2H), 2.76 (s, 3H).

Example 27A

7-Chloro-2-(chloromethyl)-5-(methylthio)imidazo[1,2-c]pyrimidine

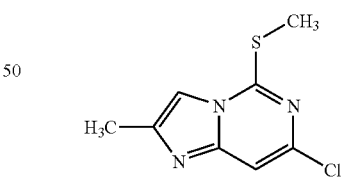

640 mg (2.58 mmol) of 7-chloro-2-(chloromethyl)-5-(methylthio)imidazo[1,2-c]pyrimidine (Example 26A) are dissolved in 32 ml of THF, and 6 g Raney nickel (suspension in water) are added and heated under reflux for 16 h. After the reaction is complete, the solvent is removed and the crude product is purified by silica gel chromatography. Drying under high vacuum results in 344.8 mg (63% of theory) of product.

LCMS (method 7): $R_t$=1.99 min. (m/z=214 (M+H)$^+$)

$^1$H-NMR (400 MHz, DMSO-$d_6$): δ=7.66 (s, 1H), 7.48 (s, 1H), 2.75 (s, 3H), 2.35 (s, 3H).

Example 28A

7-Chloro-2-methylimidazo[1,2-c]pyrimidin-5-ol

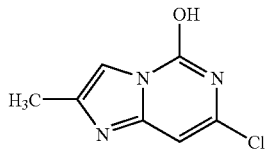

In analogy to the preparation of the hydroxypyrimidine (Example 10A), 652 mg (89% of theory) of the product are obtained from 850 mg (3.98 mmol) of the 7-chloro-2-(chloromethyl)-5-(methylthio)imidazo[1,2-c]pyrimidine (Example 27A) and 10 ml of 2 molar aqueous potassium hydroxide solution in 33 ml of methanol.

LCMS (method 4): $R_t$=1.89 min. (m/z=185 (M+H)$^+$)
$^1$H-NMR (400 MHz, DMSO-d$_6$): δ=13.07 (s, br, 1H), 7.43 (s, 1H), 6.52 (s, 1H), 2.27 (s, 3H).

Example 29A 5,7-Dichloro-2-methylimidazo[1,2-c]pyrimidine

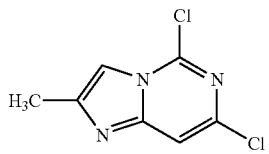

In analogy to the preparation of Example 11A, 501.6 mg (64% of theory) of the product are obtained from 716 mg (3.9 mmol) of the 7-chloro-2-methylimidazo[1,2-c]pyrimidin-5-ol (Example 28A) and 10.0 g (65.5 mmol) of phosphoryl chloride.

LCMS (method 6): $R_t$=1.22 min. (m/z=203 (M+H)$^+$)
$^1$H-NMR (400 MHz, DMSO-d$_6$): δ=7.87 (s, 1H), 7.80 (s, 1H), 2.38 (s, 3H).

Example 30A 6-({2-[(7-Chloro-2-methylimidazo[1,2-c]pyrimidin-5-yl)amino]ethyl}amino)nicotinonitrile

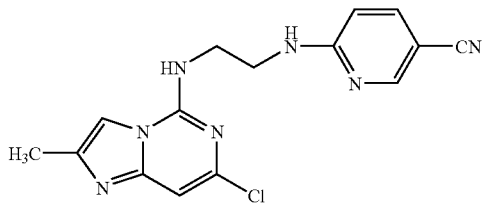

In analogy to the preparation of Example 17A, 129.9 mg (52% of theory) of the product are obtained from 150 mg (0.74 mmol) of 5,7-dichloro-2-methylimidazo[1,2-c]pyrimidine (Example 29A) and 313.3 mg (0.82 mmol) of 6-[(2-aminoethyl)amino]nicotinonitrile trifluoroacetate (Example 13A).

LCMS (method 6): $R_t$=1.01 min. (m/z=328 (M+H)$^+$)
$^1$H-NMR (400 MHz, DMSO-d$_6$): δ=8.36 (s, 1H), 8.15 (s, 1H), 7.78 (s, 1H), 7.68 (d, 1H), 7.63 (s, 1H), 6.78 (s, 1H), 6.56 (s, br, 1H), 3.60 (s, br, 4H), 2.27 (s, 3H).

Example 31A

N$^6$-{2-[(7-Chloro-2-methylimidazo[1,2-c]pyrimidin-5-yl)amino]ethyl}-3-nitropyridine-2,6-diamine

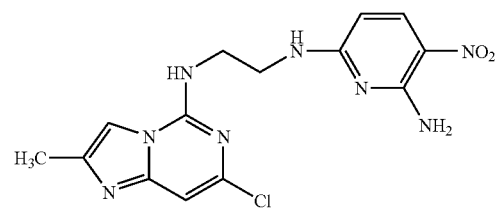

In analogy to the preparation of Example 16A, 320.9 mg (87% of theory) of the product are obtained from 200 mg (0.99 mmol) of 5,7-dichloro-2-methylimidazo[1,2-c]pyrimidine (Example 29A) and 389.5 mg (1.09 mmol) of N$^6$-(2-aminoethyl)-3-nitropyridine-2,6-diamine trifluoroacetate (Example 15A).

LCMS (method 6): $R_t$=0.96 min. (m/z=363 (M+H)$^+$)
$^1$H-NMR (400 MHz, DMSO-d$_6$): δ=8.16 (s, br, 1H), 8.10 (s, 1H), 8.07 (s, 1H), 7.93 (d, 1H), 7.68 (s, br, 1H), 7.65 (s, 1H), 6.79 (s, 1H), 5.92 (d, 1H), 3.65 (s, br, 4H), 2.27 (s, 3H).

Example 32A

7-Chloro-5-(methylthio)-2-(morpholin-4-ylmethyl)imidazo[1,2-c]pyrimidine

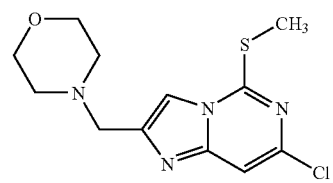

158 mg (1.81 mmol) of morpholine are introduced into 10 ml of DMF at 0° C., and 367 mg (3.63 mmol) of triethylamine and a catalytic amount of potassium iodide are added. A solution of 300 mg of 7-chloro-2-(chloromethyl)-5-(methylthio)imidazo[1,2-c]pyrimidine (Example 26A) in DMF is then slowly added dropwise. The mixture is allowed to reach RT and is stirred at this temperature for a further 16 h. Purification of the crude product by preparative HPLC and drying under high vacuum result in 221.8 mg (41% of theory) of product.

LCMS (method 6): $R_t$=0.52 min. (m/z=299 (M+H)$^+$)
$^1$H-NMR (400 MHz, DMSO-d$_6$): δ=7.73 (s, 1H), 7.53 (s, 1H), 3.61 (s, 2H), 3.57 (dd, 4H), 2.76 (s, 3H), 2.45 (dd, 4H).

Example 33A

7-Chloro-2-(morpholin-4-ylmethyl)imidazo[1,2-c]pyrimidin-5-ol hydrochloride

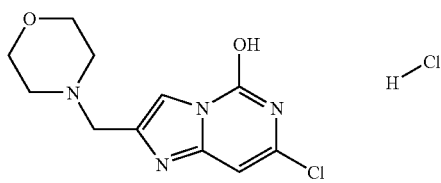

In analogy to the preparation of the hydroxypyrimidine of Example 10A, 194 mg (95% of theory) of the product are obtained from 200 mg (0.67 mmol) of the 7-chloro-5-(methylthio)-2-(morpholin-4-ylmethyl)imidazo[1,2-c]pyrimidine (Example 32A) and 1.7 ml of 2 molar aqueous potassium hydroxide solution in 3 ml of methanol and final acidification with hydrochloric acid.

LCMS (method 4): $R_t$=3.33 min. (m/z=248 (M+H)$^+$)
$^1$H-NMR (400 MHz, DMSO-d$_6$): δ=7.97 (s, 1H), 6.90 (s, 1H), 4.37 (s, 2H), 3.00-4.0 (m, 8H).

Example 34A 5,7-Dichloro-2-(morpholin-4-ylmethyl)imidazo[1,2-c]pyrimidine

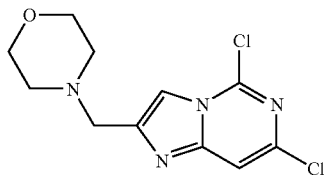

In analogy to the preparation of (Example 11A), 120.5 mg (71% of theory) of the product are obtained from 180 mg (3.9 mmol) of the 7-chloro-2-(morpholin-4-ylmethyl)imidazo-[1,2-c]pyrimidin-5-ol hydrochloride (Example 33A) and 1.06 g (6.9 mmol) of phosphoryl chloride.

LCMS (method 4): $R_t$=2.02 min. (m/z=287 (M+H)$^+$)
$^1$H-NMR (400 MHz, DMSO-d$_6$): δ=7.95 (s, 1H), 7.86 (s, 1H), 3.67 (s, 2H), 3.59 (dd, 4H), 3.32 (s, br, 4H).

Example 35A

N$^6$-(2-{[7-Chloro-2-(morpholin-4-ylmethyl)imidazo[1,2-c]pyrimidin-5-yl]amino}ethyl)-3-nitropyridine-2,6-diamine

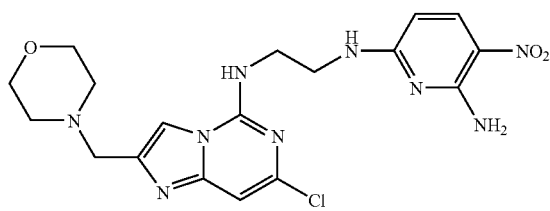

In analogy to the preparation of Example 17A, 74.6 mg (82% of theory) of the product are obtained from 60 mg (0.2 mmol) of 5,7-dichloro-2-(morpholin-4-ylmethyl)imidazo-[1,2-c]pyrimidine (Example 34A) and 79.8 mg (0.22 mmol) of N$^6$-(2-aminoethyl)-3-nitropyridine-2,6-diamine trifluoroacetate (Example 15A).

LCMS (method 6): $R_t$=0.86 min. (m/z=448 (M+H)$^+$)
$^1$H-NMR (400 MHz, DMSO-d$_6$): δ=8.18 (s, 1H), 8.08 (s, 1H), 7.93 (d, 1H), 7.82 (s, 1H), 7.64 (s, br, 1H), 6.83 (s, 1H), 5.92 (d, 1H), 3.65 (s, br, 4H), 3.58 (dd, 4H), 3.54 (s, 2H).

Example 36A tert-Butyl (2-{[7-(2,4-dichlorophenyl)imidazo[1,2-c]pyrimidin-5-yl]amino}propyl)carbamate

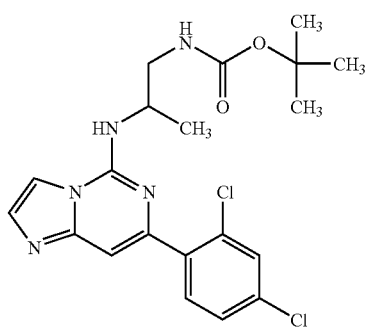

5-Chloro-7-(2,4-dichlorophenyl)imidazo[1,2-c]pyrimidine (Example 6A) (800 mg, 2.7 mmol), tert-butyl (2-aminopropyl)carbamate (700 mg, 4.0 mmol) and N,N-diisopropylethylamine (1.00 g, 8.0 mmol) are dissolved in DMSO (13 ml) and stirred at 120° C. under argon for 12 hours. The reaction mixture is diluted with water (100 ml) and extracted with ethyl acetate (3×75 ml). The combined organic phases are washed with saturated aqueous sodium chloride solution, dried over magnesium sulphate and concentrated. Removal of the solvent results in a foam which is taken up in diethyl ether. The product precipitates as solid from the diethyl ether solution and is filtered off with suction and dried. 800 mg (68% of theory) of the product are obtained as a solid.

LCMS (method 3): $R_t$=2.04 min. (m/z=437 (M+H)$^+$)
$^1$H-NMR (400 MHz, DMSO-d$_6$): δ=8.04 (s, 1H), 7.75 (dd, 1H), 7.70 (d, 1H), 7.56 (d, 1H), 7.51 (m, 2H), 7.10 (s, 1H), 6.96 (t, 1H), 4.34 (m, 1H), 3.21 (m, 2H), 1.32 (s, 9H), 1.23 (d, 3H).

Example 37A

N$^2$-[7-(2,4-Dichlorophenyl)imidazo[1,2-c]pyrimidin-5-yl]propane-1,2-diamine trifluoracetate

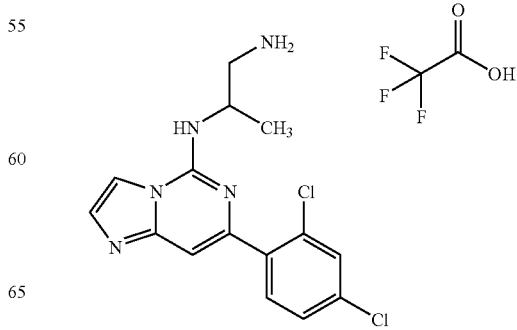

tert-Butyl (2-{[7-(2,4-dichlorophenyl)imidazo[1,2-c]pyrimidin-5-yl]amino}propyl)carbamate (Example 36A) (700 mg, 1.6 mmol) is dissolved in dichloromethane (20 ml), and trifluoroacetic acid (2.5 ml, 32 mmol) is added. The resulting solution is stirred at RT for 1 h, concentrated in a rotary evaporator and dried on the vacuum line. 1 g of the product is obtained.

LCMS (method 4): $R_t$=2.31 min. (m/z=337 (M+H)$^+$)

$^1$H-NMR (400 MHz, DMSO-d$_6$): δ=8.58 (br d, 1H), 8.28 (d, 1H), 8.06 (d, 1H), 7.94 (br s, 2H), 7.81 (d, 1H), 7.79 (d, 1H), 7.61 (dd, 1H), 7.44 (s, 1H), 4.58 (m, 1H), 3.14 (m, 2H), 1.35 (d, 3H).

Example 38A tert-Butyl {2-[(5-cyanopyridin-2-yl)amino]propyl}carbamate

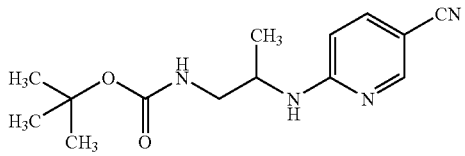

2-Chloro-5-cyanopyridine (477 mg, 3.4 mmol), tert-butyl (2-aminopropyl)carbamate (300 mg, 1.7 mmol) and potassium bicarbonate (345 mg, 3.4 mmol) are dissolved in DMF (10 ml) and stirred at 90° C. under argon for 12 h. The reaction mixture is diluted with water (100 ml) and extracted with ethyl acetate (3×75 ml). The combined organic phases are washed with saturated aqueous sodium chloride solution, dried over magnesium sulphate and concentrated. After removal of the solvent, the residue is purified by flash chromatography on silica gel (eluent: cyclohexane/ethyl acetate 10:1). 265 mg (55% of theory) of the product are obtained as a solid.

LCMS (method 4): $R_t$=3.21 min. (m/z=277 (M+H)$^+$)

$^1$H-NMR (400 MHz, DMSO-d$_6$): δ=8.37 (d, 1H), 7.66 (d, 1H), 7.37 (d, 1H), 6.87 (br t, 1H), 6.50 (d, 1H), 4.05 (m, 1H), 3.02 (m, 2H), 1.37 (s, 9H), 1.07 (d, 3H).

Example 39A tert-Butyl {2-[(6-amino-5-nitropyridin-2-yl)amino]propyl}carbamate

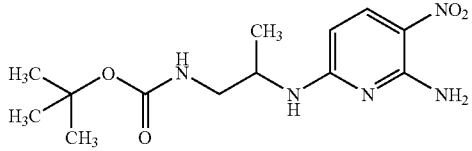

tert-Butyl {2-[(6-amino-5-nitropyridin-2-yl)amino]propyl}carbamate (Example 39A) is prepared in analogy to Example 38A from 2-amino-6-chloro-3-nitropyridine (637 mg, 3.7 mmol), tert-butyl (2-aminopropyl)carbamate (320 mg, 1.8 mmol) and potassium bicarbonate (368 mg, 3.7 mmol). 561 mg (98% of theory) of the product are obtained as a solid.

LCMS (method 3): $R_t$=2.10 min. (m/z=312 (M+H)$^+$)

$^1$H-NMR (400 MHz, DMSO-d$_6$): δ=8.13 (br m, 1H), 7.95 (d, 1H), 7.70 (br m 6.86 (br s, 1H), 5.92 (d, 1H), 4.19 (br m, 1H), 3.06 (br m, 2H), 1.34 (s, 9H), 1.09 (d, 3H).

Example 40A

6-[(2-Amino-1-methylethyl)amino]nicotinonitrile trifluoroacetate

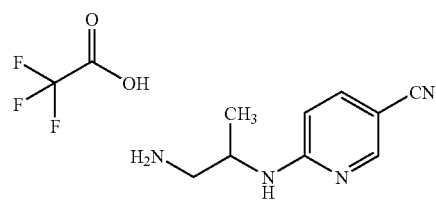

tert-Butyl {2-[(5-cyanopyridin-2-yl(amino]propyl}carbamate (Example 38A) (262 mg, 0.9 mmol) is introduced into dichloromethane (12 ml), trifluoroacetic acid (1.0 ml, 14 mmol) is added, and the reaction mixture is stirred at RT for 1 h. The solvent is evaporated and the product is dried on a vacuum line. The crude product isolated in this way still contains TFA, but can be reacted further in this form. 400 mg of the product are obtained.

LCMS (method 4): $R_t$=1.25 min. (m/z=177 (M+H)$^+$)

$^1$H-NMR (400 MHz, DMSO-d$_6$): δ=8.44 (d, 1H), 7.83 (br s, 3H), 7.74 (dd, 1H), 7.55 (d, 1H), 6.58 (d, 1H), 4.29 (br t, 1H), 3.45 (m, 1H), 2.94 (m, 2H), 1.19 (d, 3H).

Example 41A

N$^6$-(2-Amino-1-methylethyl)-3-nitropyridine-2,6-diamine trifluoroacetate

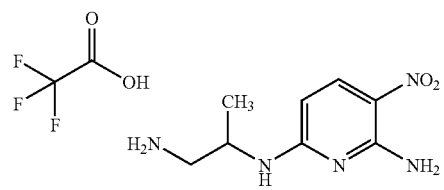

N$^6$-(2-Amino-1-methylethyl)-3-nitropyridine-2,6-diamine trifluoroacetate (Example 40A) is prepared in analogy to Example 40A from tert-butyl {2-[(6-amino-5-nitropyridin-2-yl)amino]propyl}carbamate (Example 39A) (560 mg, 1.8 mmol), trifluoroacetic acid (2.0 ml, 27 mmol) in dichloromethane (20 ml). 900 mg of the crude product are obtained thus as a solid.

LCMS (method 4): $R_t$=1.82 min. (m/z=212 (M+H)$^+$)

Example 42A tert-Butyl {2-[(5-cyanopyridin-2-yl)thio]ethyl}carbamate

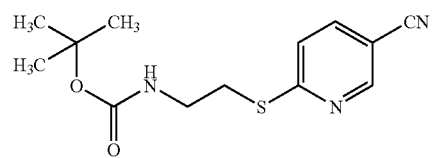

2-Chloro-5-cyanopyridine (500 mg, 3.6 mmol), tert-butyl (2-mercaptoethyl)carbamate (426 mg, 2.4 mmol) and 1,8-diazabicyclo(5.4.0)undec-7-ene (549 mg, 3.6 mmol) are dissolved in DMF (5 ml) and stirred at RT under argon for 12 h. The reaction mixture is diluted with water (100 ml) and extracted with ethyl acetate (3×75 ml). The combined organic phases are washed with saturated aqueous sodium chloride solution, dried over magnesium sulphate and concentrated. After removal of the solvent, the residue is purified by preparative RP-HPLC (gradient of eluent: water/acetonitrile 90:10 to 10:90). 612 mg (91% of theory) of the product are obtained as a solid.

LCMS (method 6): $R_t$=1.80 min. (m/z=280 (M+H)$^+$)

$^1$H-NMR (400 MHz, DMSO-d$_6$): δ=8.86 (d, 1H), 8.07 (dd, 1H), 7.54 (dd, 1H), 7.08 (br s, 1H), 3.24 (m, 4H), 1.36 (s, 9H).

Example 43A tert-Butyl {2-[(6-amino-5-nitropyridin-2-yl)thio]ethyl}carbamate

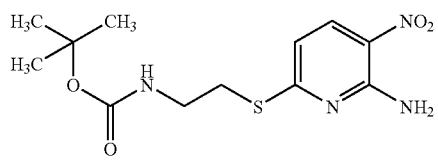

tert-Butyl {2-[(6-amino-5-nitropyridin-2-yl)thio]ethyl}carbamate (Example 43A) is prepared in analogy to Example 42A from 2-amino-6-chloro-3-nitropyridine (500 mg, 2.9 mmol), tert-butyl (2-mercaptoethyl)carbamate (255 mg, 1.4 mmol) and 1,8-diazabicyclo(5.4.0)undec-7-ene (439 mg, 2.9 mmol). 422 mg (93% of theory) of product are obtained.

LCMS (method 1): $R_t$=2.10 min. (m/z=315 (M+H)$^+$)

$^1$H-NMR (400 MHz, DMSO-d$_6$): δ=8.17 (d, 1H), 8.07 (br s, 1H), 7.03 (br t, 1H), 6.64 (d, 1H), 3.22 (m, 4H), 1.36 (s, 9H).

Example 44A tert-Butyl (2-{[7-(2,4-dichlorophenyl)imidazo[1,2-c]pyrimidin-5-yl]thio}ethyl)carbamate

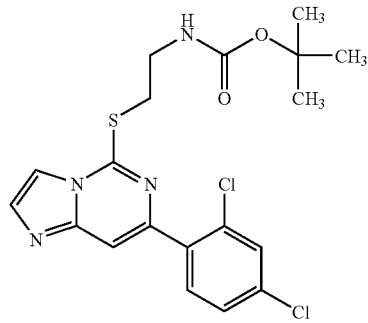

tert-Butyl (2-{[7-(2,4-dichlorophenyl)imidazo[1,2-c]pyrimidin-5-yl]thio}ethyl)carbamate (Example 44A) is synthesized in analogy to the preparation of Example 42A from 5-chloro-7-(2,4-dichlorophenyl)imidazo[1,2-c]pyrimidine (Example 6A) (500 mg, 17 mmol), tert-butyl (2-mercaptoethyl)carbamate (445 mg, 2.5 mmol) and 1,8-diazabicyclo(5.4.0)undec-7-ene (382 mg, 2.5 mmol). The crude product is purified by flash chromatography (eluent: cyclohexane/ethyl acetate), and 422 mg (93% of theory) of the product are obtained after evaporation of the solvent.

LCMS (method 1): $R_t$=2.40 min. (m/z=439 (M+H)$^+$)

Example 45A

6-[(2-Aminoethyl)thio]nicotinonitrile trifluoroacetate

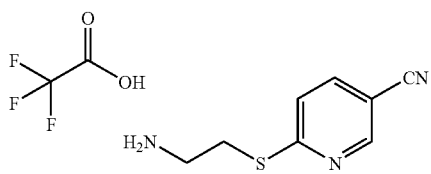

6-[(2-Aminoethyl)thio]nicotinonitrile trifluoroacetate (Example 45A) is prepared in analogy to Example 40A from tert-butyl {2-[(5-cyanopyridin-2-yl)thio]ethyl}carbamate (Example 42A) (580 mg, 2.1 mmol) and trifluoroacetic acid (3.2 ml, 42 mmol) in dichloromethane (20 ml). 500 mg of the product are obtained.

LCMS (method 4): $R_t$=1.01 min. (m/z=180 (M+H)$^+$)

$^1$H-NMR (400 MHz, DMSO-d$_6$): δ=8.89 (d, 1H), 8.13 (dd, 1H), 8.03 (br s, 3H), 7.62 (d, 1H), 3.43 (t, 2H), 3.14 (m, 2H).

Example 46A

6-[(2-Aminoethyl)thio]-3-nitropyridine-2-amine trifluoroacetate

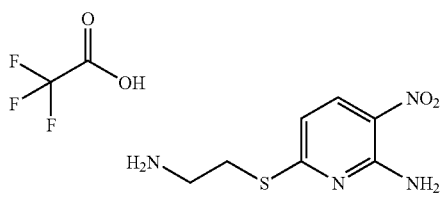

6-[(2-Aminoethyl)thio]-3-nitropyridine-2-amine trifluoroacetate (Example 46A) is prepared in analogy to Example 40A from tert-butyl {2-[(6-amino-5-nitropyridin-2-yl)thio]ethyl}carbamate (Example 43A) (380 mg, 1.2 mmol) and trifluoroacetic acid (1.9 ml, 24 mmol) in dichloromethane (20 ml). 400 mg of the product are obtained.

LCMS (method 4): $R_t$=2.03 min. (m/z=215 (M+H)$^+$)

$^1$H-NMR (400 MHz, DMSO-d$_6$): δ=8.20 (d, 1H), 8.12 (br s, 2H), 7.92 (br s, 3H), 6.69 (d, 1H), 3.35 (t, 2H), 3.16 (m, 2H).

Example 47A

2-{[7-(2,4-Dichlorophenyl)imidazo[1,2-c]pyrimidin-5-yl]thio}ethanamine trifluoroacetate

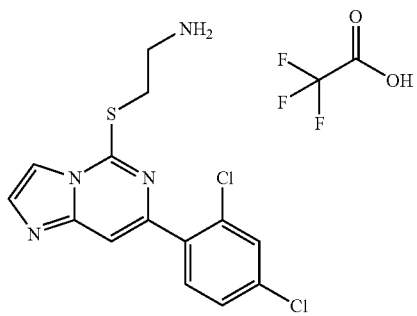

2-{[7-(2,4-Dichlorophenyl)imidazo[1,2-c]pyrimidin-5-yl]thio}ethanamine trifluoroacetate (Example 47A) is prepared in analogy to Example 40A from tert-butyl (2-{[7-(2,4-dichlorophenyl)imidazo[1,2-c]pyrimidin-5-yl]thio}ethyl) carbamate (Example 44A) (950 mg, 2.2 mmol) and trifluoroacetic acid (3.3 ml, 43 mmol) in dichloromethane (20 ml). The crude product consists of a 50:50 mixture of Example 47A and the regioisomeric product 2-{[7-(2,4-dichlorophenyl)imidazo[1,2-c]pyrimidin-5-yl]amino}ethanethiol. The mixture is processed further without purification.

Example 48A

2-[(6-Amino-5-nitropyridin-2-yl)amino]ethanol

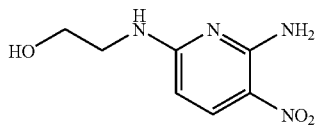

2-[(6-Amino-5-nitropyridin-2-yl)amino]ethanol (Example 48A) is prepared in analogy to Example 36A from 2-amino-6-chloro-3-nitropyridine (400 mg, 2.3 mmol) and 2-aminoethanol (282 mg, 4.6 mmol) in DMSO (110° C., 4 h). Removal of the solvent results in a crude product which is precipitated from dichloromethane. The product is filtered off with suction and dried. 283 mg (62% of theory) of the product are obtained.

LCMS (method 1): $R_f$=0.51 min. (m/z=199 (M+H)$^+$)
$^1$H-NMR (400 MHz, DMSO-d$_6$): δ=8.15 (br s, 1H), 8.02 (br t, 1H), 8.03 (d, 1H), 7.74 (br m, 1H), 6.00 (d, 1H), 4.79 (t, 1H), 3.54 (m, 2H), 3.43 (m, 2H).

Example 49A

2-{[7-(2,4-Dichlorophenyl)imidazo[1,2-c]pyrimidin-5-yl]amino}ethanol

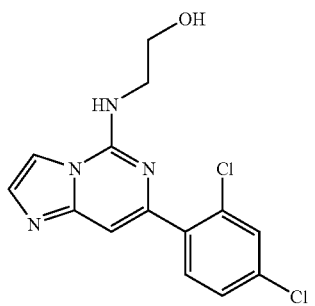

2-{[7-(2,4-Dichlorophenyl)imidazo[1,2-c]pyrimidin-5-yl]amino}ethanol (Example 49A) is prepared in analogy to Example 36A from 5-chloro-7-(2,4-dichlorophenyl)imidazo[1,2-c]-pyrimidine (Example 6A) (200 mg, 0.7 mmol) and 2-aminoethanol (82 mg, 1.3 mmol) in DMSO (80° C., 4 h). Removal of the solvent results in a crude product which is precipitated from dichloromethane. The product is filtered off with suction and dried. 216 mg (99% of theory) of product are obtained as a solid.

LCMS (method 3): $R_f$=1.44 min. (m/z=323 (M+H)$^+$)
$^1$H-NMR (400 MHz, DMSO-d$_6$): δ=8.15 (s, 1H), 8.12 (t, 1H), 7.74 (m, 2H), 7.58 (s, 1H), 7.54 (dd, 1H), 7.09 (s, 1H), 4.90 (br s, 1H), 3.67 (m, 2H), 2.85 (t, 2H).

Example 50A

4-Chloro-6-hydrazino-2-(methylthio)pyrimidine

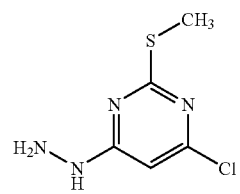

33 g (169.2 mmol) of 4,6-dichloro-2-(methylthio)pyrimidine are introduced into 300 ml of THF at −20° C., and 169 ml of a 1M solution of hydrazine in THF is added dropwise at a rate such that the temperature does not rise above −15° C. The mixture is stirred at 0° C. for a further 2 h. After the reaction is complete, the solvent is distilled off and the residue is stirred with diethyl ether. 18.4 g (57% of theory) of the product are obtained as a solid.

LCMS (method 4): $R_f$=2.43 min. (m/z=191 (M+H)$^+$)
$^1$H-NMR (400 MHz, DMSO-d$_6$): δ=7.26 (s, 1H), 6.48 (s, 1H), 6.39 (s, br, 1H), 3.82 (s, br, 2H), 2.51 (s, 3H).

Example 51A

7-Chloro-5-(methylthio)[1,2,4]triazolo[1,5-c]pyrimidine

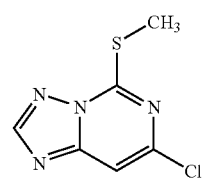

10 g (52.5 mmol) of 4-chloro-6-hydrazino-2-(methylthio)pyrimidine (Example 50A) are dissolved in 30 ml of formic acid and heated under reflux for 16 h. The crude mixture is removed from all volatile constituents in vacuo, and the residue is purified by chromatography on silica gel (dichloromethane/methanol 10+1). 2.58 g (24% of theory) of the product are obtained.

LCMS (method 6): $R_f$=0.97 min. (m/z=201 (M+H)$^+$)
$^1$H-NMR (400 MHz, DMSO-d$_6$): δ=8.78 (s, 1H), 7.45 (s, 1H), 2.84 (s, 3H).

Example 52A

7-Chloro[1,2,4]triazolo[1,5-c]pyrimidin-5-ol

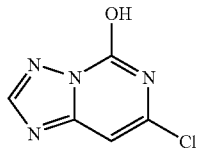

A solution of 2.58 g (12.9 mmol) of 7-chloro-5-(methylthio)[1,2,4]triazolo[1,5-c]pyrimidine (Example 51A) is dissolved in 300 ml of methanol, and 28 ml of a 2 molar aqueous potassium hydroxide solution are added. The mixture is heated under reflux for 3 h. After the reaction is complete, the methanol is removed in vacuo, the mixture is neutralized with half-concentrated hydrochloric acid, and the crystals which have separated out are filtered off with suction. They are washed with water and methanol and then dried under high vacuum. 1.82 g (83% of theory) of the product are obtained.

LCMS (method 4): $R_t$=1.72 min. (m/z=171 (M+H)$^+$).
$^1$H-NMR (400 MHz, DMSO-d$_6$): δ=8.40 (s, 1H), 7.06 (s, 1H).

Example 53A 5,7-Dichloro[1,2,4]triazolo[1,5-c]pyrimidine

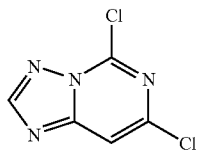

927 mg (4.19 mmol) of 7-chloro[1,2,4]triazolo[1,5-c]pyrimidin-5-ol (Example 52A) are suspended in 16.9 g (110.13 mmol) of phosphoryl chloride under argon and heated at 120° C. for 4 h. After this time, the excess phosphoryl chloride is removed in vacuo, and the residue is distilled together with toluene. The residue is suspended in water, the pH is brought to 7 with saturated aqueous sodium bicarbonate solution, and the precipitated solid is filtered off with suction. The latter is washed with water and dried over phosphorus pentoxide for 18 h. 389 mg (49% of theory) of the product are obtained.

LCMS (method 4): $R_t$=2.55 min. (m/z=189 (M+H)$^+$).
$^1$H-NMR (400 MHz, DMSO-d$_6$): δ=8.79 (s, 1H), 8.26 (s, 1H).

Example 54A 6-({2-[(7-Chloro[1,2,4]triazolo[1,5-c]pyrimidin-5-yl)amino]ethyl}amino)nicotinonitrile

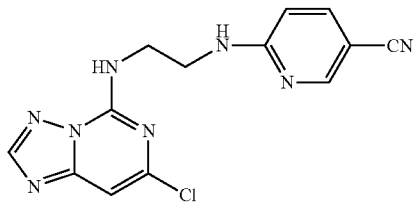

707 mg (3.20 mmol) of 5,7-dichloroimidazo[1,2-c]pyrimidine (Example 53A) are suspended in 25 ml of 2-propanol, and 1.35 g (3.52 mmol) of 6-[(2-aminoethyl)amino]nicotinonitrile trifluoroacetate (Example 13A) and 1.03 g (7.99 mmol) of DIPEA are added. The mixture is heated at 80° C. for 16 h. After this time, water is added and the precipitate which separates out is filtered off with suction. It is washed with a little 2-propanol/water, and the resulting solid is dried under high vacuum. 523 mg (50% of theory) of the product is obtained as a solid.

LCMS (method 3): $R_t$=1.31 min. (m/z=314 (M+H)$^+$)
$^1$H-NMR (400 MHz, DMSO-d$_6$): δ=8.37 (d, 1H), 8.33 (t, 1H), 7.93 (s, 1H), 7.80 (s, 1H), 7.68 (d, 1H), 7.50 (d, 1H), 6.90 (s, 1H), 6.56 (s, br, 1H), 3.62 (m, 2H), 3.31 (m, 2H).

Example 55A

N$^6$-{2-[(7-Chloro[1,2,4]triazolo[1,5-c]pyrimidin-5-yl)amino]ethyl}-3-nitropyridine-2,6-diamine

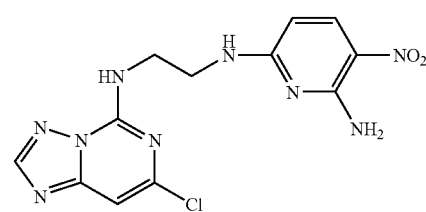

194 mg (3.20 mmol) of 5,7-dichloroimidazo[1,2-c]pyrimidine are suspended in 8 ml of 2-propanol, and 403.9 mg (1.13 mmol) of N$^6$-(2-aminoethyl)-3-nitropyridine-2,6-diamine trifluoroacetate and 331.7 mg (2.57 mmol) of DIPEA are added. The mixture is heated at 80° C. for 16 h. After this time, water is added, and the precipitate which separates out is filtered off with suction. It is washed with a little 2-propanol/water, and the resulting solid is dried under high vacuum. 265 mg (74% of theory) of the product are obtained as a solid.

LCMS (method 3): $R_t$=1.97 min. (m/z=350 (M+H)$^+$)
$^1$H-NMR (400 MHz, DMSO-d$_6$): δ=8.81 (t, 1H), 8.53 (s, 1H), 8.16 (s, br, 1H), 8.06 (t, 1H), 7.94 (d, 1H), 7.67 (s, br, 1H), 7.13 (s, 1H), 5.90 (d, 1H), 3.57-3.73 (m, 4H).

Example 56A tert-Butyl {3-[(6-amino-5-nitropyridin-2-yl)amino]propyl}carbamate

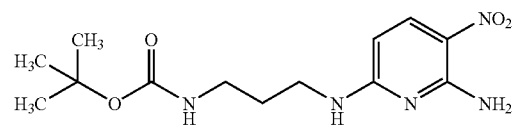

150.6 mg (0.864 mmol) of tert-butyl (3-aminopropyl)carbamate, 300 mg (1.73 mmol) of 6-chloro-3-nitropyridine-2-amine and 173 mg (1.73 mmol) of potassium bicarbonate are suspended in 10 ml of DMF and heated at 90° C. for 16 h. Water is added to the mixture, which is then extracted three times with ethyl acetate. Purification of the crude product by preparative HPLC and drying under high vacuum result in 195 mg (65% of theory) of product.

LCMS (method 7): $R_t$=2.85 min. (m/z=312 (M+H)$^+$)
$^1$H-NMR (400 MHz, DMSO-d$_6$): δ=8.12 (s, br, 1H), 7.91 (d, 1H), 7.73 (s, br, 1H), 6.84 (t, 1H), 5.93 (d, 1H), 4.09 (dd, 1H), 3.32 (m, 2H), 2.97 (q, 2H), 1.64 (m, 2H), 1.37 (s, 9H).

Example 57A

N⁶-(3-Aminopropyl)-3-nitropyridine-2,6-diamine trifluoroacetate

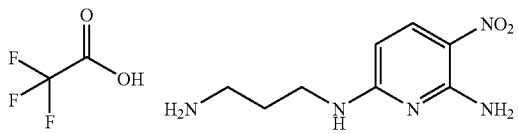

195 mg (0.56 mmol) of tert-butyl {3-[(6-amino-5-nitropyridin-2-yl)amino]propyl}carbamate (Example 56A) are dissolved in 6 ml of dichloromethane, and 656 mg (5.6 mmol) of trifluoroacetic acid are slowly injected. The mixture is stirred at RT for 16 h and then all the volatile constituents are removed in vacuo. 185 mg (96% of theory) of the product are obtained.

LCMS (method 4): $R_t$=1.41 min. (m/z=212 (M+H)⁺)
¹H-NMR (400 MHz, DMSO-$d_6$): δ=8.18 (s, br, 1H), 8.04 (t, 1H), 7.95 (d, 1H), 7.70 (s, br, 3H), 5.94 (d, 1H), 3.40 (dd, 2H), 2.82 (dd, 2H), 1.80 (pent, 2H).

Example 58A 6-({2-[(4-Amino-6-chloropyrimidin-2-yl)amino]ethyl}amino)pyridine-3-carbonitrile

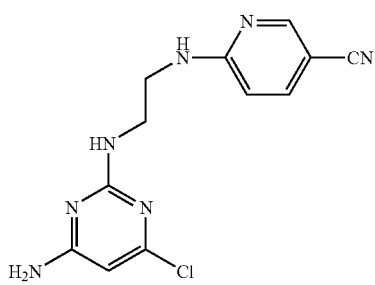

10.3 g (63 mmol) of 2,6-dichloropyrimidine-4-amine and 10.22 g (63 mmol) of 6-[(2-aminoethyl)amino]pyridine-3-carbonitrile are dissolved in 164 ml acetonitrile and heated under reflux conditions for 24 h. After cooling, the major amount of the precipitated product is filtered off with suction. 11.9 g (50% of theory) of the product are obtained as a solid.

LCMS (method 8): $R_t$=0.75 min. (m/z=290 (M+H)⁺)

Example 59A

Ethyl 7-chloro-5-({2-[(5-cyanopyridin-2-yl)amino]ethyl}amino)imidazo[1,2-c]pyrimidine-2-carboxylate

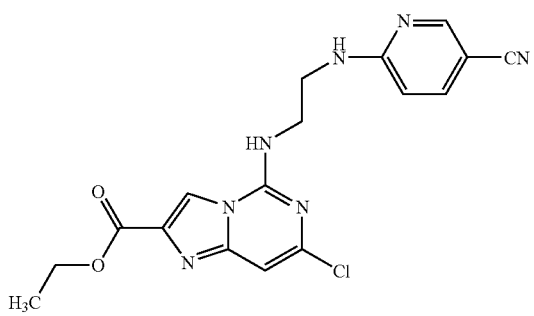

480 mg (1.66 mmol) of 6-({2-[(4-amino-6-chloropyrimidin-2-yl)amino]ethyl}amino)pyridine-3-carbonitrile and 538 mg (2.49 mmol) of ethyl bromopyruvate are dissolved in 8 ml of DMF and heated at 100° C. for 16 h. After the reaction is complete, the crude mixture is purified by preparative HPLC. 190 mg (27% of theory) of the product are obtained as a solid.

LCMS (method 1): $R_t$=1.69 min. (m/z=486 (M+H)⁺)
¹H-NMR (400 MHz, DMSO-$d_6$): δ=8.64 (s, 1H), 8.58 (t, 1H), 8.35 (d, 1H), 7.77 (m, 1H), 7.68 (d, 1H), 6.94 (s, 1H), 6.57 (d, 1H), 4.31 (q, 2H), 3.63 (m, 4H), 1.30 (t, 3H).

Example 60A tert-Butyl 3-[(5-cyanopyridin-2-yl)amino]piperidine-1-carboxylate

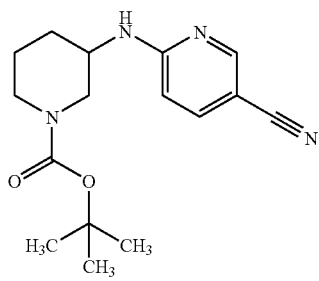

1.0 g (4.99 mmol) of tert-butyl 3-aminopiperidine-1-carboxylate and 1.383 g (9.99 mmol) of 6-chloropyridine-3-carbonitrile and 1.29 g (9.99 mmol) of diisopropylethylamine are suspended in 40 ml of DMSO and heated in a microwave at 140° C. for 45 min. The mixture is substantially freed of DMSO by kugelrohr distillation, water is added, and the precipitate which separates out is filtered off. Drying under high vacuum results in 2.24 g (46% of theory) of the product.

LCMS (method 3): $R_t$=2.23 min. (m/z=303 (M+H)⁺).

Example 61A 6-(Piperidin-3-ylamino)pyridine-3-carbonitrile hydrochloride

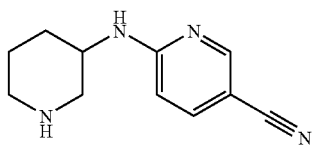

2.24 g (3.4 mmol) of tert-butyl 3-[(5-cyanopyridin-2-yl)amino]piperidine-1-carboxylate (Example 60A) are dissolved in 4.3 ml of a solution of hydrochloric acid in dioxane (4M) and stirred at RT for 3 h. After the reaction is complete, the solvent is completely removed. 1.74 g (90% of theory) of the product are obtained as a solid.

LCMS (method 8): $R_t$=0.27 min. (m/z=203 (M+H)⁺)
¹H-NMR (400 MHz, DMSO-$d_6$): δ=9.13 (m, 1H), 9.0 (m, 1H), 8.44 (d, 1H), 7.89 (m, 1H), 7.74 (dd, 1H), 6.63 (d, 1H), 5.58 (s, br), 4.19 (s, br, 1H), 3.57 (s, 1H), 3.34 (d, 1H), 3.14 (d, 1H), 2.88 (m, 1H), 2.7-2.81 (m, 1H), 1.82-2.0 (m, 2H), 1.63-1.79 (m, 1H), 1.48-1.59 (m, 1H).

Example 62A

2-Amino-6-[(2-{[7-chloro-2-(trifluoromethyl)imidazo[1,2-c]pyrimidin-5-yl]amino}ethyl)amino]-pyridine-3-carbonitrile

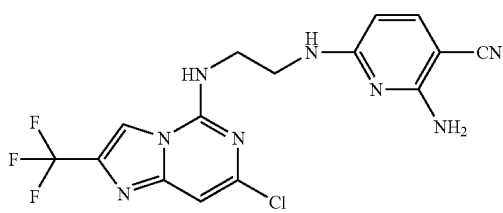

In analogy to the preparation of Example 16A, 433 mg (84% of theory) of the product are obtained as a solid from 338 mg (1.29 mmol) of 5,7-dichloro-2-(trifluoromethyl)imidazo[1,2-c]pyrimidine (Example 23A) and 338.4 mg (1.55 mmol) of 2-amino-6-[(2-aminoethyl)amino]pyridine-3-carbonitrile (Example 111A).

LCMS (method 3): $R_t$=2.12 min. (m/z=397 (M+H)$^+$)
$^1$H-NMR (400 MHz, DMSO-d$_6$): δ=8.56 (s, 1H), 8.49 (t, 1H), 7.32 (d, 1H), 7.23 (s, br, 1H), 7.01 (s, 1H), 6.27 (s, 2H), 5.79 (d, 1H), 3.59-3.67 (m, 2H), 3.50-3.58 (m, 2H).

Example 63A tert-Butyl 2-{[(5-cyanopyridin-2-yl)amino]methyl}pyrrolidine-1-carboxylate

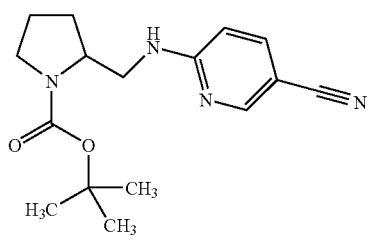

In analogy to the preparation of Example 60A, 214.5 mg (57% of theory) of the product are obtained as a solid from 250 mg (1.25 mmol) of tert-butyl 2-(aminomethyl)pyrrolidine-1-carboxylate and 345.9 mg (2.5 mmol) of 6-chloropyridine-3-carbonitrile.

LCMS (method 9): $R_t$=2.13 min. (m/z=303 (M+H)$^+$).
$^1$H-NMR (400 MHz, DMSO-d$_6$): δ=8.34 (s, 1H), 7.68 (s, br, 2H), 6.56 (d, 1H), 3.88 (s, 1H), 3.52 (s, br, 1H), 3.23 (m, 2H), 1.65-1.9 (m, 5H), 1.38 (s, 9H).

Example 64A

6-[(Pyrrolidin-2-ylmethyl)amino]pyridine-3-carbonitrile dihydrochloride

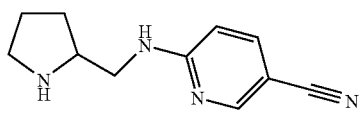

In analogy to the preparation of Example 61A, 117 mg (99% of theory) of the product are obtained as a solid from 190 mg (0.43 mmol) of tert-butyl 2-{[(5-cyanopyridin-2-yl)amino]methyl}pyrrolidine-1-carboxylate and 10 ml of hydrochloric acid in dioxane (4M).

LCMS (method 9): $R_t$=0.84 min. (m/z=203 (M+H)$^+$).
$^1$H-NMR (400 MHz, DMSO-d$_6$): δ=9.35 (s, br, 1H), 8.98 (s, br, 1H), 8.44 (s, 1H), 8.03 (s, 1H), 7.76 (dd, 1H), 6.67 (d, 1H), 5.10 (s, br), 3.71 (m, 1H), 3.62 (m, 2H), 3.67 (s, 1H), 3.08-3.25 (m, 2H), 1.98-2.09 (m, 1H), 1.80-1.98 (m, 2H), 1.59-1.70 (m, 1H).

Example 65A tert-Butyl 3-[(6-amino-5-nitropyridin-2-yl)amino]piperidine-1-carboxylate

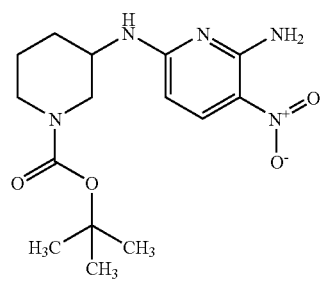

In analogy to the preparation of Example 60A, 615 mg (81% of theory) of the product are obtained as a solid from 500 mg (2.11 mmol) of tert-butyl 3-aminopiperidine-1-carboxylate hydrochloride and 771.7 mg (4.2 mmol) of 6-chloro-3-nitropyridine-2-amine.

LCMS (method 6): $R_t$=1.77 min. (m/z=338 (M+H)$^+$)
$^1$H-NMR (400 MHz, DMSO-d$_6$): δ=8.11 (s, br, 1H), 7.95 (d, 1H), 7.81 (d, 1H), 7.69 (s, br, 1H), 6.0 (d, 1H), 3.49 (s, br, 1H), 3.48 (s, 1H), 1.89 (m, 1H), 1.76 (m, 1H), 1.50 (m, 1H), 1.2-1.55 (s, 11H).

Example 66A

3-Nitro-N$^6$-piperidin-3-ylpyridine-2,6-diamine dihydrochloride

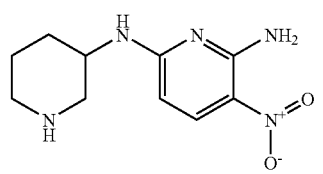

In analogy to the preparation of Example 61A, 500 mg (99% of theory) of the product are obtained as a solid from 610 mg (1.62 mmol) of tert-butyl 3-[(6-amino-5-nitropyridin-2-yl)amino]piperidine-1-carboxylate and 40 ml of hydrochloric acid in dioxane (4M).

LCMS (method 9): $R_t$=0.86 min. (m/z=238 (M+H)$^+$).
$^1$H-NMR (400 MHz, DMSO-d$_6$): δ=9.13 (s, br, 1H), 8.99 (s, br, 1H), 8.17 (s, 1H), 7.99 (d, 1H), 7.7 (s, br, 1H), 6.0 (d, 1H), 4.18 (s, br, 1H), 3.57 (s, 1H), 3.35 (d, 1H), 3.10 (m, 1H), 2.94 (m, 2H), 1.83-2.01 (m, 2H), 1.63-1.78 (m, 1H), 1.50-1.62 (m, 1H).

Example 67A tert-Butyl 3-[(5-cyanopyridin-2-yl)amino]piperidine-1-carboxylate

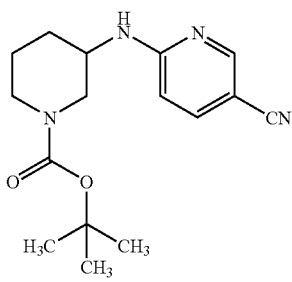

In analogy to the preparation of Example 60A, 85 mg (56% of theory) of the product are obtained as a solid from 100 mg (0.49 mmol) of tert-butyl 3-aminopiperidine-1-carboxylate hydrochloride and 138 mg (0.99 mmol) of 6-chloropyridine-3-carbonitrile.

LCMS (method 6): $R_t$=1.81 min. (m/z=303 (M+H)$^+$)
$^1$H-NMR (400 MHz, DMSO-d$_6$): δ=8.40 (d, 1H), 7.68 (d, 1H), 7.53 (d, 1H), 6.59 (d, 1H), 4.12 (s, br, 3H), 3.80 (s, br, 1H), 3.1-3.7 (m, 2H), 1.90 (m, 1H), 1.74 (m, 1H), 1.3-1.6 (m, 1H), 1.27 (s, 9H).

Example 68A 6-(Piperidin-3-ylamino)pyridine-3-carbonitrile dihydrochloride

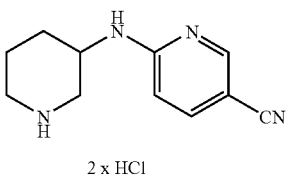

In analogy to the preparation of Example 61A, 1.74 g (90% of theory) of the product are obtained as a solid from 2.24 g (3.4 mmol) of tert-butyl 3-[(5-cyanopyridin-2-yl)amino]piperidine-1-carboxylate by reaction with hydrochloric acid in dioxane.

LCMS (method 8): $R_t$=0.27 min. (m/z=203 (M+H)$^+$)
$^1$H-NMR (400 MHz, DMSO-d$_6$): δ=9.13 (s, br, 1H), 8.99 (s, br, 1H), 8.44 (d, 1H), 7.89 (m, 1H), 7.74 (dd, 1H), 6.63 (d, 1H), 5.58 (s, br), 4.19 (m, 1H), 3.57 (s, 1H), 3.34 (d, 1H), 3.15 (d, 1H), 2.82-2.95 (m, 1H), 2.7-2.82 (m, 1H), 1.83-2.0 (m, 2H), 1.64-1.8 (m, 1H), 1.47-1.61 (m, 1H).

Example 69A

Methyl 4-amino-2-(methylsulphonyl)-1,3-thiazole-5-carboxylate

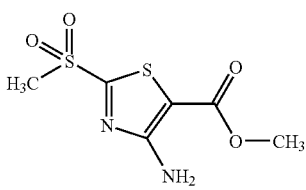

5.12 g (8.32 mmol) of Oxone® are dissolved in 170 ml of water and cooled to 5° C. A solution of 1 g (4.90 mmol) of methyl 4-amino-2-(methylsulphanyl)-1,3-thiazole-5-carboxylate in 18 ml of methanol is then added dropwise, and the solution is stirred at RT for 3 h. The major amount of methanol is removed and extracted three times with dichloromethane. The combined organic phases are dried with sodium sulphate. After removal of the solvent and drying of the residue under high vacuum, the resulting solid (824 mg (43% of theory)) is employed without further purification.

LCMS (method 3): $R_t$=1.52 min. (m/z=237 (M+H)$^+$)
$^1$H-NMR (400 MHz, DMSO-d$_6$): δ=7.36 (s, br, 2H), 3.79 (s, 3H), 3.45 (s, 3H).

Example 70A

1-[4-Amino-2-(methylsulphonyl)-1,3-thiazol-5-yl]ethanone

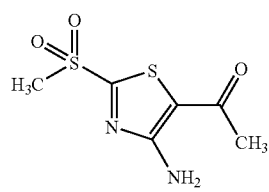

In analogy to the preparation of Example 69A, 395 mg (52% of theory) of the product are obtained as a solid from 500 mg (2.66 mmol) of 1-[4-amino-2-(methylsulphanyl)-1,3-thiazol-5-yl]ethanone by reaction with 2775 mg (4.52 mmol) of Oxone®. The reaction product still contains about 30% of the corresponding sulphoxide, which is not removed further.

LCMS (method 3): $R_t$=1.17 min. (m/z=221 (M+H)$^+$)
$^1$H-NMR (400 MHz, DMSO-d$_6$): δ=7.76 (s, br, 2H), 3.46 (s, 3H), 2.41 (s, 3H).

Example 71A 2-(Methylsulphonyl)-5-nitro-1,3-thiazole-4-amine

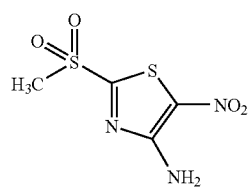

In analogy to the preparation of Example 18A, 116 mg (40% of theory) of the product are obtained from 250 mg (1.3 mmol) of 2-(methylsulphonyl)-5-nitro-1,3-thiazole-4-amine by reaction with 3-chloroperbenzoic acid.

LCMS (method 9): $R_t$=0.96 min. (m/z=224 (M+H)$^+$).

Example 72A tert-Butyl [2-({[(3,5-dimethyl-1H-pyrazol-1-yl)-(imino)methyl]carbamothioyl}-amino)ethyl]-carbamate

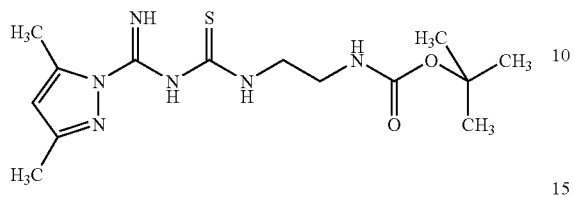

554.7 mg (4.94 mmol) of potassium tert-butoxide are dissolved in 12 ml of DMSO while cooling slightly in ice, and then 596.8 mg (2.96 mmol) of 3,5-dimethyl-1H-pyrazole-1-carboximidamide nitrate are added. A clear solution is produced after stirring for about 5 minutes. Then 500 mg (2.47 mmol) of tert-butyl (2-isothiocyanatoethyl)carbamate are added, and the icebath is removed. The mixture is heated at 60° C. for a further 3 h and the solution obtained in this way is employed for the further subsequent reactions.

Example 73A tert-Butyl (2-{[(2Z)-3-cyano-4-hydroxy-4-(trifluoromethyl)-1,3-thiazolidin-2-yliden]amino}ethyl)carbamate

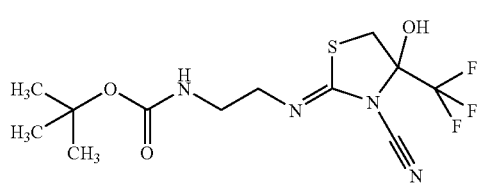

A solution of 484 mg (2.4 mmol) of 3-bromo-1,1,1-trifluoropropan-2-one in 12 ml of DMSO is added dropwise to the crude mixture from Example 72A while cooling in ice, and the mixture is then heated at 60° C. for 1 h. The crude mixture is poured into ice-water and extracted three times with ethyl acetate. After the combined organic phases have been dried, the solvent is completely removed and the residue is purified by subsequent purification by preparative HPLC. 640 mg (67% of theory) of the product are obtained as a solid.

LCMS (method 3): $R_t$=2.23 min. (m/z=355 (M+H)$^+$).
$^1$H-NMR (400 MHz, DMSO-d$_6$): δ=8.87 (s, 1H), 6.95 (t, 1H), 3.95 (d, 1H), 3.65 (d, 1H), 3.51-3.62 (m, 1H), 3.35 (m, 1H), 3.06-3.21 (m, 2H), 1.38 (s, 9H).

Example 74A (2Z)-2-[(2-Aminoethyl)imino]-4-hydroxy-4-(trifluoromethyl)-1,3-thiazolidine-3-carbonitrile hydrochloride

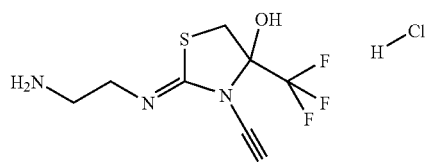

In analogy to the preparation of Example 61A, 400 mg (99% of theory) of the product are obtained as a solid from 436 mg (1.23 mmol) of tert-butyl (2-{[4-amino-5-(trifluoroacetyl)-1,3-thiazol-2-yl]amino}ethyl)carbamate and 20 ml of hydrochloric acid in dioxane (4M).

LCMS (method 8): $R_t$=0.26 min. (m/z=255 (M+H)$^+$).
$^1$H-NMR (400 MHz, DMSO-d$_6$): δ=9.31 (s, 3H), 7.94 (s, br, 2H), 3.92 (dd, 2H), 3.3-3.8 (m, 2H).

Example 75A tert-Butyl (2-{[4-amino-5-(cyclopropylcarbonyl)-1,3-thiazol-2-yl]amino}ethyl)carbamate

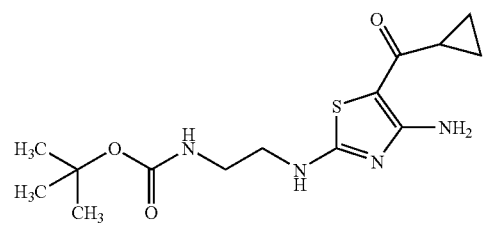

A solution of 404 mg (2.48 mmol) of 2-bromo-1-cyclopropylethanone in 15 ml of DMSO is added dropwise to 845 mg (2.48 mmol) of the crude mixture from Example 72A while cooling in ice, and the mixture is then heated at 100° C. for 1 h. The crude mixture is poured into ice-water and extracted three times with ethyl acetate. After the combined organic phases have been dried, the solvent is completely removed and the residue is purified by subsequent purification by preparative HPLC. 428 mg (48% of theory) of the product are obtained as a solid.

LCMS (method 9): $R_t$=1.73 min. (m/z=327 (M+H)$^+$)
$^1$H-NMR (400 MHz, CDCl$_3$): δ=5.58 (s, br, 2H), 6.35 (s, 1H), 4.91 (s, 1H), 3.3-3.5 (m, 4H), 1.65-1.74 (m, 1H), 1.45 (s, 9H), 1.06-1.12 (m, 2H), 0.78-0.88 (m, 2H).

Example 76A

{4-Amino-2-[(2-aminoethyl)amino]-1,3-thiazol-5-yl}(cyclopropyl)methanone dihydrochloride

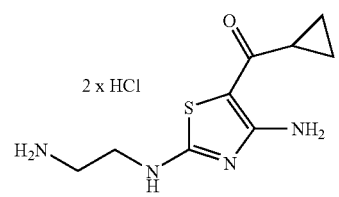

In analogy to the preparation of Example 61A, 400 mg (99% of theory) of the product are obtained as a solid from 420 mg (1.28 mmol) of tert-butyl (2-{[4-amino-5-(cyclopropylcarbonyl)-1,3-thiazol-2-yl]amino}ethyl)carbamate and 16 ml of hydrochloric acid in dioxane (4M).

LCMS (method 9): $R_t$=0.83 min. (m/z=227 (M+H)$^+$).
$^1$H-NMR (400 MHz, DMSO-d$_6$): δ=8.73 (s, 1H), 8.09 (s, br, 2H), 3.96 (s, br, 2H), 3.51 (dd, 2H), 3.02 (dd, 2H), 1.64 (m, 1H), 0.79-0.85 (m, 2H), 0.7-0.79 (m, 2H).

The following products and their precursors are obtained in analogy to the procedures described for Example 75A and Example 76A:

| Example | Structure | Characterization |
|---|---|---|
| 77A | 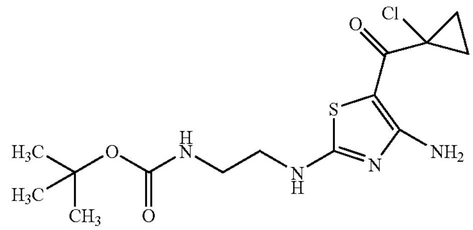 | LC/MS (method 8): $R_t$ = 1.03 min<br>MS (ESIpos): m/z = 361 (M + H)$^+$. |
| 78A | 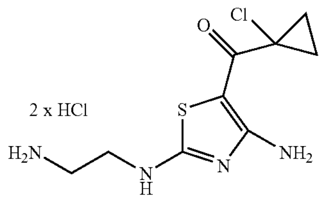 | LC/MS (method 8): $R_t$ = 0.35 min<br>MS (ESIpos): m/z = 261 (M + H)$^+$. |
| 79A | 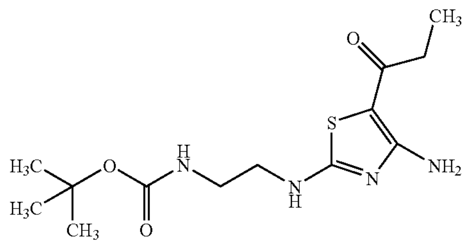 | LC/MS (method 6): $R_t$ = 1.36 min<br>MS (ESIpos): m/z = 315 (M + H)$^+$. |
| 80A | 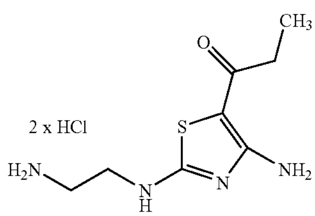 | LC/MS (method 9): $R_t$ = 0.77 min<br>MS (ESIpos): m/z = 215 (M + H)$^+$. |

Example 81A tert-Butyl 3-{[4-amino-5-(methoxycarbonyl)-1,3-thiazol-2-yl]amino}piperidine-1-carboxylate

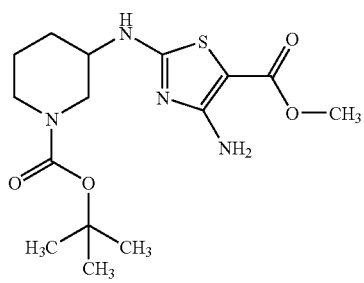

In analogy to the preparation of Example 60A, 158 mg (29% of theory) of the product are obtained as a solid from 335 mg (1.42 mmol) of tert-butyl 3-aminopiperidine-1-carboxylate hydrochloride and 3190 mg (2.84 mmol) of methyl 4-amino-2-(methylsulphonyl)-1,3-thiazole-5-carboxylate.

LCMS (method 8): $R_t$=1.06 min. (m/z=357 (M+H)$^+$)

$^1$H-NMR (400 MHz, DMSO-d$_6$): δ=8.32 (d, 1H), 6.79 (s, br, 2H), 3.60 (s, 3H), 3.55 (m, 2H), 1.89 (m, 1H), 1.71 (m, 1H), 1.5 (m, 1H), 1.35 (s, 11H).

Example 82A

Methyl 4-amino-2-(piperidin-3-ylamino)-1,3-thiazole-5-carboxylate dihydrochloride

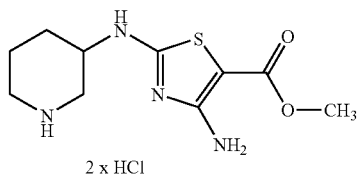

In analogy to the preparation of Example 61A, 130 mg (99% of theory) of the product are obtained as a solid from 150 mg (0.39 mmol) of tert-butyl 3-{[4-amino-5-(methoxycarbonyl)-1,3-thiazol-2-yl]amino}piperidine-1-carboxylate and 20 ml of hydrochloric acid in dioxane (4M).

LCMS (method 8): $R_t$=0.26 min. (m/z=257 (M+H)$^+$).

$^1$H-NMR (400 MHz, DMSO-d$_6$): δ=9.04 (s, br, 2H), 8.51 (d, 1H), 3.9 (m, 2H), 3.6 (s, 3H), 3.34 (d, 1H), 3.11 (d, 1H), 2.75-2.94 (m, 2H), 1.93-2.04 (m, 1H), 1.8-1.91 (m, 1H), 1.60-1.76 (m, 1H), 1.43-1.57 (m, 1H).

The following products and their precursors are obtained in analogy to the procedure described for Example 82A:

| Example | Structure | Characterization |
|---|---|---|
| 83A | 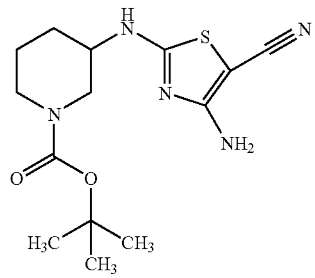 | LC/MS (method 7): $R_t$ = 2.25 min<br>MS (ESIpos): m/z = 390 (M + H)+. |
| 84A | 2 x HCl | LC/MS (method 1): $R_t$ = 1.58 min<br>MS (ESIpos): m/z = 458 (M + H)+. |
| 85A | 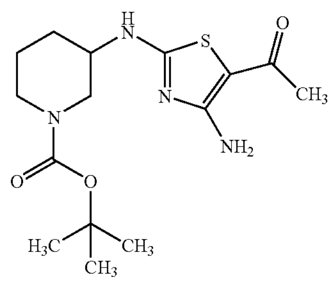 | LC/MS (method 4): $R_t$ = 4.54 min<br>MS (ESIpos): m/z = 455 (M + H)+. |
| 86A | 2 x HCl | LC/MS (method 4): $R_t$ = 4.54 min<br>MS (ESIpos): m/z = 455 (M + H)+. |
| 87A | 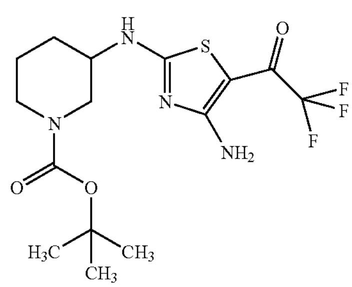 | LC/MS (method 4): $R_t$ = 4.54 min<br>MS (ESIpos): m/z = 455 (M + H)+. |
| 88A | 2 x HCl | LC/MS (method 4): $R_t$ = 4.54 min<br>MS (ESIpos): m/z = 455 (M + H)+. |

Example 89A

4-Amino-2-[(2-hydroxyethyl)amino]-1,3-thiazole-5-carbonitrile

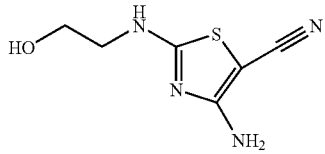

Example 89A is prepared in analogy to Example 48A from 4-amino-2-(methylsulphonyl)-1,3-thiazole-5-carbonitrile (Example 18A) (499 mg, 2.45 mmol) and 2-aminoethanol (300 mg, 4.91 mmol) in DMSO (80° C., 20 h). Removal of the solvent results in a crude product 527 mg (50% of theory) which is employed without further purification.

LCMS (method 8): $R_t$=0.26 min. (m/z=185 (M+H)$^+$)

Example 90A 2-(Chloromethyl)-7-(2,4-dichlorophenyl)-5-(ethylsulphanyl)imidazo[1,2-c]pyrimidine

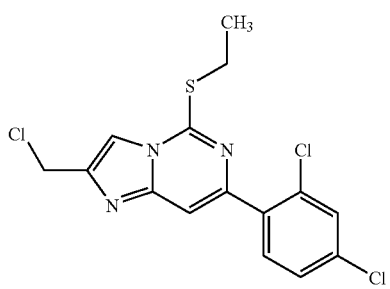

3 g (9.99 mmol) of 6-(2,4-dichlorophenyl)-2-(ethylsulphanyl)pyrimidine-4-amine (Example 3A) are added to a solution of 1.395 g (10.99 mmol) of 1,3-dichloropropan-2-one in 33 ml of dry ethanol, and the mixture is then heated under reflux conditions for 20 h. The solvent is substantially removed and the residue is purified by preparative HPLC. 1.5 g (37% of theory) of the product are obtained.

LCMS (method 3): $R_t$=3.04 min. (m/z=372 (M+H)$^+$)
$^1$H-NMR (400 MHz, DMSO-d$_6$): δ=8.0 (s, 1H), 7.79 (dd, 1H), 7.78 (s, 1H), 7.69 (s, 1H), 7.59 (dd, 1H), 4.9 (s, 2H), 3.4 (q, 2H), 1.45 (t, 3H).

Example 91A 7-(2,4-Dichlorophenyl)-5-(ethylsulphanyl)-2-(morpholin-4-ylmethyl)imidazo[1,2-c]pyrimidine

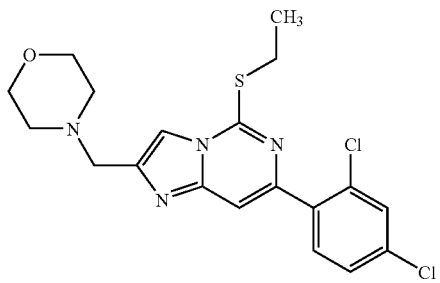

102 mg (1.17 mmol) of morpholine are introduced into 7 ml of DMF at 0° C., and 236 mg (0.78 mmol) of triethylamine and a catalytic amount of potassium iodide are added. A solution of 290 mg of 2-(chloromethyl)-7-(2,4-dichlorophenyl)-5-(ethylsulphanyl)imidazo[1,2-c]pyrimidine (Example 91A) in DMF is then slowly added dropwise. The mixture is allowed to reach RT and is stirred at this temperature for a further 16 h. Purification of the crude product by preparative HPLC and drying under high vacuum result in 214 mg (43% of theory) of product.

LCMS (method 3): $R_t$=1.95 min. (m/z=423 (M+H)$^+$)
$^1$H-NMR (400 MHz, DMSO-d$_6$): δ=7.78 (m, 1H), 7.74 (d, 1H), 7.63 (s, 1H), 7.58 (dd, 1H), 3.65 (s, 2H), 3.58 (dd, 4H), 3.40 (q, 2H), 2.47 (m, 4H), 1.42 (t, 3H).

Example 92A 7-(2,4-Dichlorophenyl)-5-(ethylsulphanyl)-2-[(4-methylpiperazin-1-yl)methyl]imidazo[1,2-c]-pyrimidine

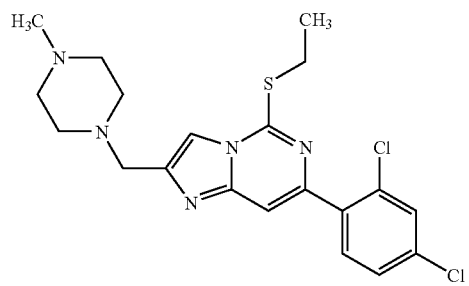

In analogy to Example 91A, 465 mg (99% of theory) of the product are obtained from 400 mg (0.44 mmol) of 2-(chloromethyl)-7-(2,4-dichlorophenyl)-5-(ethylsulphanyl)imidazo[1,2-c]-pyrimidine (Example 91A) and 161 mg (0.179 mmol) of methylpiperazine.

LCMS (method 6): $R_t$=1.33 min. (m/z=436 (M+H)$^+$)

Example 93A 7-(2,4-Dichlorophenyl)-2-(morpholin-4-ylmethyl)imidazo[1,2-c]pyrimidin-5-ol

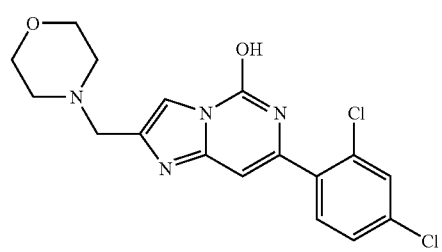

In analogy to the preparation of the hydroxypyrimidine of Example 10A, 104 mg (99% of theory) of the product are obtained from 114 mg (0.27 mmol) of 7-(2,4-dichlorophenyl)-5-(ethylsulphanyl)-2-(morpholin-4-ylmethyl)imidazo[1,2-c]pyrimidine (Example 92A) and 1.7 ml of 2 molar aqueous potassium hydroxide solution in 3 ml of methanol and final acidification with hydrochloric acid.

LCMS (method 10): $R_t$=1.31 min. (m/z=379 (M+H)$^+$)
$^1$H-NMR (400 MHz, DMSO-d$_6$): δ=11.85 (s, br, 1H), 7.81 (d, 1H), 7.65 (s, 1H), 7.61 (d, 1H), 7.57 (dd, 1H), 6.62 (s, 1H), 3.57 (dd, 4H), 3.52 (s, 2H), 2.45 (m, 4H).

Example 94A 7-(2,4-Dichlorophenyl)-2-[(4-methylpiperazin-1-yl)methyl]imidazo[1,2-c]pyrimidin-5-ol

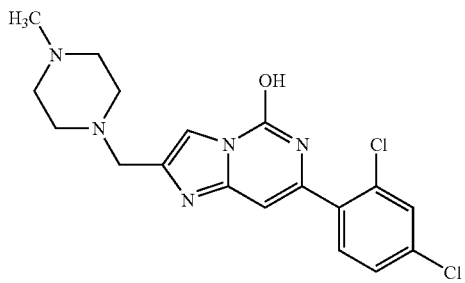

In analogy to Example 10A, 500 mg (97% of theory) of the product are obtained from 675 mg (1.31 mmol) of 7-(2,4-dichlorophenyl)-5-(ethylsulphanyl)-2-[(4-methylpiperazin-1-yl)methyl]-imidazo[1,2-c]pyrimidine (Example 93A) by heating in methanolic potassium hydroxide solution.
LCMS (method 6): $R_t$=0.71 min. (m/z=392 (M+H)$^+$)

Example 95A

5-Chloro-7-(2,4-dichlorophenyl)-2-(morpholin-4-ylmethyl)imidazo[1,2-c]pyrimidine

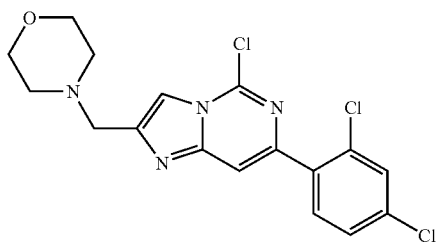

103 mg (0.267 mmol) of 7-(2,4-dichlorophenyl)-2-(morpholin-4-ylmethyl)imidazo[1,2-c]-pyrimidin-5-ol (Example 93A) are introduced in 5 ml (53.64 mmol) of phosphoryl chloride and heated at the reflux temperature for 3 h. The mixture is allowed to cool and is added cautiously to an ice/water mixture. The precipitate which separates out is filtered off. Drying under high vacuum results in 105 mg (99% of theory) of the product.
LCMS (method 8): $R_t$=0.93 min. (m/z=397 (M+H)$^+$)
$^1$H-NMR (400 MHz, DMSO-$d_6$): δ=8.01 (s, br, 1H), 7.93 (s, 1H), 7.80 (d, 1H), 7.72 (d, 1H), 7.59 (dd, 1H), 3.73 (s, br, 2H), 3.61 (m, 4H), 3.32 (m, 4H).

Example 96A

5-Chloro-7-(2,4-dichlorophenyl)-2-[(4-methylpiperazin-1-yl)methyl]imidazo[1,2-c]pyrimidine

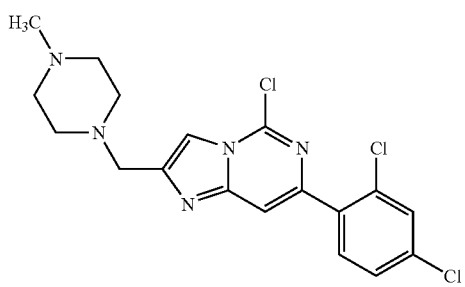

In analogy to Example 95A, 42 mg (17% of theory) of the product are obtained from 225 mg (0.49 mmol) of 7-(2,4-dichlorophenyl)-2-[(4-methylpiperazin-1-yl)methyl]imidazo[1,2-c]-pyrimidin-5-ol (Example 94A) by reaction with phosphoryl chloride.
LCMS (method 3): $R_t$=1.71 min. (m/z=410 (M+H)$^+$)

Example 97

1-[7-Chloro-5-(methylsulphanyl)imidazo[1,2-c]pyrimidin-2-yl]-N,N-dimethylmethanamine

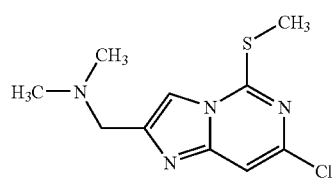

In analogy to Example 32A, 154 mg (31% of theory) of the product are obtained from 300 mg (1.21 mmol) of 7-chloro-2-(chloromethyl)-5-(methylsulphanyl)imidazo[1,2-c]pyrimidine (Example 26A) and 81.8 mg (1.81 mmol) of dimethylamine.
LCMS (method 7): $R_t$=0.89 min. (m/z=257 (M+H)$^+$)

Example 98A

7-Chloro-2-[(dimethylamino)methyl]imidazo[1,2-c]pyrimidin-5-ol

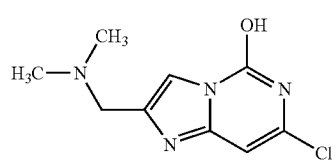

In analogy to Example 33A, 150 mg (98% of theory) of the product are obtained from 150 mg (0.58 mmol) of 1-[7-chloro-5-(methylsulphanyl)imidazo[1,2-c]pyrimidin-2-yl]-N,N-dimethylmethanamine (Example 97A) by heating in methanolic potassium hydroxide solution.
LCMS (method 4): $R_t$=0.97 min. (m/z=227 (M+H)$^+$)

Example 99A 1-(5,7-Dichloroimidazo[1,2-c]pyrimidin-2-yl)-N,N-dimethylmethanamine

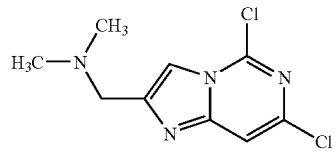

In analogy to Example 11A, 30 mg (18% of theory) of the product are obtained from 131 mg (0.58 mmol) of 7-chloro-2-[(dimethylamino)methyl]imidazo[1,2-c]pyrimidin-5-ol (Example 98A) by reaction with phosphoryl chloride.
LCMS (method 4): $R_t$=1.95 min. (m/z=245 (M+H)$^+$)

Example 100A

N[6]-[2-({7-Chloro-2-[(dimethylamino)methyl]imidazo[1,2-c]pyrimidin-5-yl}amino)ethyl]-3-nitropyridine-2,6-diamine

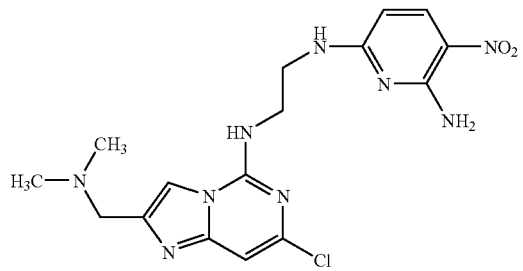

In analogy to the preparation of Example 17A, 11 mg (5% of theory) of the product are obtained from 147 mg (0.58 mmol) of 1-(5,7-dichloroimidazo[1,2-c]pyrimidin-2-yl)-N,N-dimethylmethanamine (Example 99A) and 228 mg (0.638 mmol) of N[6]-(2-aminoethyl)-3-nitropyridine-2,6-diamine trifluoroacetate (Example 15A).

LCMS (method 1): $R_t$=1.00 min. (m/z=406 (M+H)$^+$)

Example 101A

7-Chloro-2-ethyl-5-(methylsulphanyl)[1,2,4]triazolo[1,5-c]pyrimidine

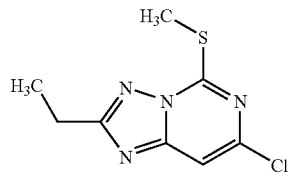

3 g (13.2 mmol) of 4-chloro-6-hydrazino-2-(methylthio)pyrimidine (Example 50A) are dissolved in 15 ml of triethyl orthopropionate and 10 ml of propionic acid and heated under reflux for 1 h. The mixture is added to water, adjusted to pH=7 with sodium hydroxide solution and extracted three times with dichloromethane. The collected organic phases are dried with magnesium sulphate and the solvent is completely removed. 2.3 g (54% of theory) of the product are obtained as a solid which is employed without further purification.

LCMS (method 9): $R_t$=1.64 min. (m/z=229 (M+H)$^+$).
$^1$H-NMR (400 MHz, DMSO-d$_6$): δ=7.64 (s, 1H), 3.38 (q, 2H), 2.70 (s, 3H), 1.41 (t, 3H).

Example 102A

7-Chloro-2-ethyl[1,2,4]-triazolo[1,5-c]pyrimidin-5-ol

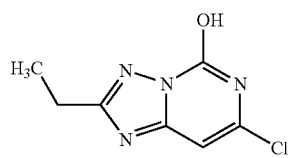

In analogy to Example 33A, 242 mg (99% of theory) of the product are obtained from 280 mg (1.22 mmol) of 7-chloro-2-ethyl-5-(methylsulphanyl)[1,2,4]triazolo[1,5-c]pyrimidine (Example 101A) by heating in methanolic potassium hydroxide solution.

LCMS (method 3): $R_t$=0.86 min. (m/z=199 (M+H)$^+$)

Example 103A 5,7-Dichloro-2-ethyl[1,2,4]triazolo[1,5-c]pyrimidine

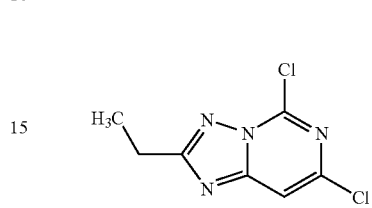

In analogy to Example 11A, 285 mg (80% of theory) of the product are obtained from 312 mg (1.57 mmol) of 7-chloro-2-ethyl[1,2,4]triazolo[1,5-c]pyrimidin-5-ol (Example 102A) by reaction with phosphoryl chloride.

LCMS (method 9): $R_t$=1.61 min. (m/z=217 (M+H)$^+$)
$^1$H-NMR (400 MHz, DMSO-d$_6$): δ=8.11 (s, 1H), 2.90 (q, 2H), 1.33 (t, 3H).

Example 104A 6-({2-[(7-Chloro-2-ethyl[1,2,4]triazolo[1,5-c]pyrimidin-5-yl)amino]ethyl}amino)pyridine-3-carbonitrile trifluoroacetate

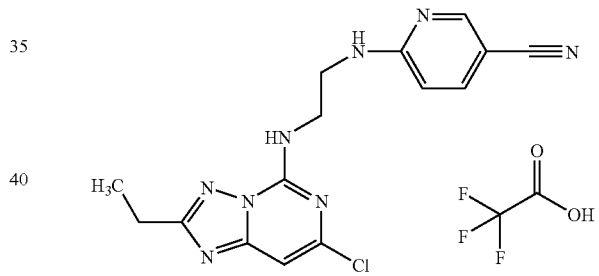

In analogy to Example 54A, 64 mg (23% of theory) of the product are obtained from 150 mg (0.62 mmol) of 5,7-dichloro-2-ethyl[1,2,4]triazolo[1,5-c]pyrimidine (Example 103A) by reaction with 297 mg (1.07 mmol) of 6-[(2-aminoethyl)amino]pyridine-3-carbonitrile.

LCMS (method 3): $R_t$=2.17 min. (m/z=343 (M+H)$^+$).
$^1$H-NMR (400 MHz, DMSO-d$_6$): δ=8.64 (t, 1H), 8.35 (d, 1H), 7.75 (m, 1H), 7.68 (m, 1H), 6.99 (s, 1H), 6.55 (s, br, 1H), 3.55-3.68 (m, 4H), 2.81 (q, 2H), 1.31 (t, 3H).

Example 105A tert-Butyl (6-chloropyridin-2-yl)carbamate

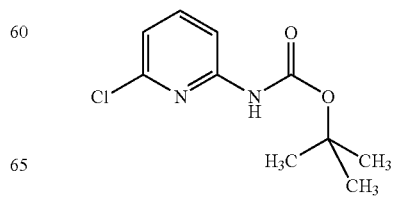

23.4 g (181.8 mmol) of 2-chloro-5-aminopyridine are mixed with 150 ml of THF under argon and cooled to 0° C. 73.3 g (400 mmol) of bis(trimethylsilyl)sodium amide and 43.65 g (200 mmol) of di-tert-butyl dicarbonate, dissolved in 150 ml of THF, are added dropwise. After 15 min, the cooling bath is removed and stirring is continued at RT for 15 min. The THF is removed in a rotary evaporator, and the residue is mixed and extracted with ethyl acetate and 0.5 N hydrochloric acid. The organic phase is separated off, dried over magnesium sulphate and concentrated in a rotary evaporator. The reaction mixture is chromatographed on silica gel (mobile phase dichloromethane/methanol 100%→100:3). 36.54 g (88% of theory) of the product are obtained as a solid.

LCMS (method 3): $R_t$=2.41 min. (m/z=175 (M+H)$^+$).
$^1$H-NMR (400 MHz, DMSO-d$_6$): d=10.11 (s, 1H), 7.78 (d, 2H), 7.1 (t, 1H), 1.47 (s, 9H).

Example 106A tert-Butyl (6-chloro-3-formylpyridin-2-yl)carbamate

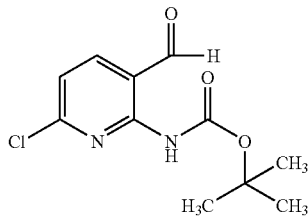

The reaction takes place under argon, the apparatus is heat-dried and operated with a KPG stirrer. 15 g (65.6 mmol) of tert-butyl (6-chloropyridin-2-yl)carbamate (Example 25A) and 19 g (164 mmol) of 1,2-bis(dimethylamino)ethane are introduced into 270 ml of THF and cooled to −78° C. 102.5 ml (164 mmol) of butyllithium (1.6N) are added dropwise. After the dropwise addition is complete, the reaction is slowly warmed to −10° C. and kept at −10° C. for 2 h and then cooled again to −78° C., and 10 ml (131 mmol) of DMF are added. The reaction is slowly warmed to RT, and the reaction mixture is added to 1 l of ethyl acetate and 350 ml of 1N hydrochloric acid and stirred for 15 min, and the organic phase is separated off. It is washed with water and saturated sodium bicarbonate solution, dried over magnesium sulphate and concentrated in a rotary evaporator. The residue is mixed with diethyl ether and the solid is filtered off with suction and dried. 12.3 g (73% of theory) of the product are obtained as a solid.

LCMS (method 3): $R_t$=2.19 min. (m/z=255 (M+H)$^-$).
$^1$H-NMR (400 MHz, DMSO-d$_6$): δ=10.37 (s, 1H), 9.83 (s, 1H), 8.2 (d, 1H), 7.42 (d, 1H), 1.46 (s, 9H).

Example 107A tert-Butyl {6-chloro-3-[(hydroxyimino)methyl]pyridin-2-yl}carbamate

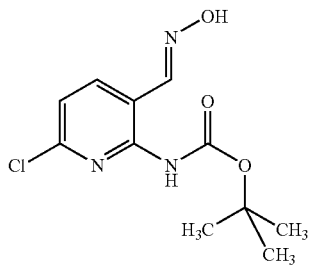

15.45 g (60.2 mmol) of tert-butyl (6-chloro-3-formylpyridin-2-yl)carbamate (Example 106A) are introduced into 750 ml of ethanol, and a solution of 225 ml of water and 9.38 g (120.4 mmol) of sodium acetate is added and stirred for 5 min. A solution of 225 ml of water and 8.36 g (114.4 mmol) of hydroxylamine hydrochloride is added, and the mixture is stirred at RT for 4 h. The reaction mixture is concentrated in a rotary evaporator at 20° C. The residue is taken up in ethyl acetate and washed twice with saturated sodium hydroxide carbonate solution and once with saturated sodium chloride solution. The organic phase is separated off, dried over magnesium sulphate and concentrated in a rotary evaporator at 20° C. 15.5 g (80% of theory) of the product are obtained as a solid.

LCMS (method 3): $R_t$=2.08 min. (m/z=270 (M+H)$^-$).
$^1$H-NMR (400 MHz, DMSO-d$_6$): δ=11.71 (s, 1H), 9.91 (s, 1H), 8.14 (s, 1H), 8.02 (d, 1H), 7.3 (d, 1H), 1.49 (s, 9H).

Example 108A

2-Amino-6-chloropyridine-3-carbaldehyde oxime hydrochloride

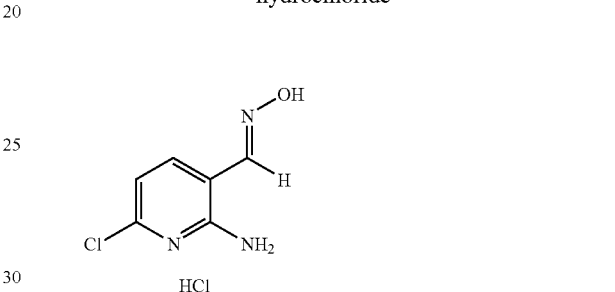

15.5 g (57 mmol) of tert-butyl {6-chloro-3-[(hydroxyimino)methyl]pyridin-2-yl}carbamate (Example 107A) are dissolved in 285 ml of 4N hydrogen chloride in dioxane and stirred for 30 min. The reaction mixture is concentrated to one half, and an equal portion of diethyl ether is added. The reaction mixture is stirred for 20 min and the product is filtered off and washed with diethyl ether. 11 g (94% of theory) of the product are obtained as a solid.

LCMS (method 6): $R_t$=1.09 min. (m/z=172 (M+H)$^+$)
$^1$H-NMR (400 MHz, DMSO-d$_6$): δ=8.27 (s, 1H), 7.61 (d, 1H), 6.65 (d, 1H).

Example 109A

2-Amino-6-chloropyridine-3-carbonitrile

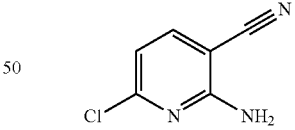

11.15 g (53.6 mmol) of 2-amino-6-chloropyridine-3-carbaldehyde oxime hydrochloride (Example 108A) are introduced into dioxane, 13 ml (161 mmol) of pyridine are added, and the mixture is cooled to 0° C. 8.3 ml (58.95 mmol) of trifluoroacetic anhydride are added, and the reaction is allowed to warm to RT and then stirred at 60° C. for 2 h. The reaction mixture is taken up in a mixture of ethyl acetate and sodium bicarbonate solution. The organic phase is washed with saturated aqueous sodium chloride solution, dried over magnesium sulphate and concentrated in a rotary evaporator. The residue is suspended in 3:1 dichloromethane:diethyl ether, and the solid is filtered off with suction and dried. 5.56 g (66% of theory) of the product are obtained as a solid.

LCMS (method 6): $R_t$=1.0 min. (m/z=154 (M+H)$^+$).
$^1$H-NMR (400 MHz, DMSO-d$_6$): δ=7.91 (d, 1H), 7.38 (s, 2H), 6.69 (d, 1H).

Example 110A tert-Butyl {2-[(6-amino-5-cyanopyridin-2-yl)amino]ethyl}carbamate

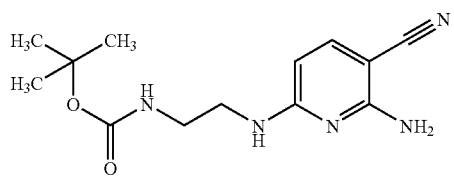

2 g (13 mmol) of 2-amino-6-chloropyridine-3-carbonitrile (Example 109A) are introduced into 15 ml of DMSO, and 2.71 g (16.93 mmol) of N-Boc-ethyleneamine and 3.4 ml (19.54 mmol) of N,N-diisopropylethylamine are added. The reaction mixture is irradiated in a microwave reactor at 115° C. for 1.5 h. The reaction mixture is taken up in a mixture of ethyl acetate and water. The organic phase is washed with saturated aqueous sodium chloride solution, dried over magnesium sulphate and concentrated in a rotary evaporator. 23.38 g (88% of theory) of the product are obtained as a solid.

LCMS (method 3): $R_t$=1.7 min. (m/z=278 (M+H)$^+$)
$^1$H-NMR (400 MHz, DMSO-d$_6$): δ=7.3 (s, 1H), 7.0 (br, s, 1H), 6.83 (s, 1H), 6.25 (s, 2H), 5.78 (d, 1H), 3.25 (q, 2H), 3.06 (q, 2H), 1.36 (s, 9H).

Example 111A

2-Amino-6-[(2-aminoethyl)amino]pyridine-3-carbonitrile dihydrochloride

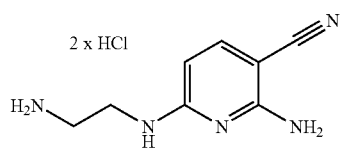

6.76 g (24.38 mmol) of tert-butyl {2-[(6-amino-5-cyanopyridin-2-yl)amino]ethyl}carbamate (Example 110A) are dissolved in 122 ml of 4N hydrogen chloride in dioxane and stirred for 30 min. The reaction mixture is concentrated to one half, and an equal portion of diethyl ether is added. The reaction mixture is stirred for 20 min, and the product is filtered off and washed with diethyl ether. 5.43 g (89% of theory) of the product are obtained as a solid.

LCMS (method 6): $R_t$=0.92 min. (m/z=177 (M+H)$^+$)
$^1$H-NMR (400 MHz, DMSO-d$_6$): δ=8.1 (s, 2H), 7.5 (d, 1H), 5.96 (d, 1H), 3.53 (q, 2H), 3.0 (q, 2H).

Example 112A 4-(Trifluoroacetyl)morpholine

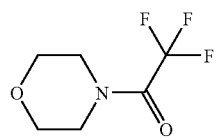

15 g (172 mmol) of morpholine are introduced into 750 ml of dichloromethane and, at 0° C., 29 ml (206 mmol) of trifluoroacetic anhydride and 119 ml (688 mmol) of N,N-diisopropylethylamine are added. The reaction mixture is warmed to RT and stirred at RT for 3 h. The reaction mixture is concentrated and the residue is taken up in ethyl acetate and washed successively with aqueous sodium bicarbonate solution, 1N hydrochloric acid and again with aqueous sodium bicarbonate solution. The organic phase is dried over magnesium sulphate and concentrated in a rotary evaporator. 28 g (88% of theory) of the product are obtained as an oil.

LCMS (method 9): $R_t$=1.22 min. (m/z=184 (M+H)$^+$)
$^1$H-NMR (400 MHz, DMSO-d$_6$): δ=3.65 (m, 2H), 3.56 (m, 2H).

Example 113A tert-Butyl [6-chloro-3-(trifluoroacetyl)pyridin-2-yl]carbamate

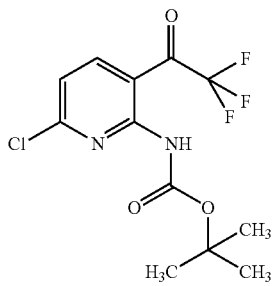

8 g (35 mmol) of tert-butyl (6-chloropyridin-2-yl)carbamate (Example 105A) are introduced into 100 ml of THF and cooled to −50° C. 55 ml (87 mmol) of butyllithium (1.6N) are added dropwise. After the dropwise addition is complete, the reaction is slowly warmed to −10° C. and kept at 0° C. for 2 h. It is then cooled again to −40° C., and 12.8 g (70 mmol) of 4-(trifluoroacetyl)morpholine (Example 35A), dissolved in 4 ml of THF, are added. The reaction solution is stirred at −40° C. for 1 h and then, at −40° C., poured into 1 l of ethyl acetate and 350 ml of ammonium chloride solution and extracted. The organic phase is separated off, dried over magnesium sulphate and concentrated in a rotary evaporator. The reaction mixture is chromatographed on silica gel (mobile phase cyclohexane/ethyl acetate 10:1). 9 g (79% of theory) of the product are obtained as an oil.

$^1$H-NMR (400 MHz, DMSO-d$_6$): δ=10.957 (s, 1H), 7.99 (d, 1H), 7.4 (d, 1H), 1.43 (s, 9H).

Example 114A tert-Butyl [6-({2-[(tert-butoxycarbonyl)amino]ethyl}amino)-3-(trifluoroacetyl)pyridin-2-yl]-carbamate

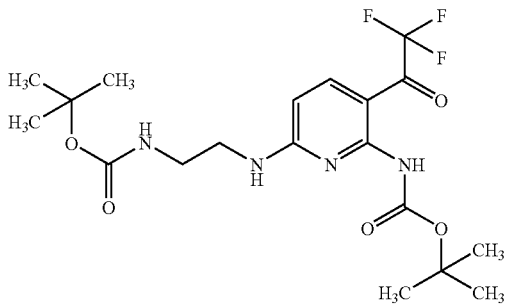

5 g (15.4 mmol) of tert-butyl [6-chloro-3-(trifluoroacetyl)pyridin-2-yl]carbamate (Example 113A) are introduced into 37.5 ml of DMSO, and 3.2 g (20 mmol) of N-Boc-ethylenediamine and 4 ml (23 mmol) of N,N-diisopropylethylamine are added. The reaction mixture is irradiated in a microwave reactor at 90° C. for 0.5 h. The reaction mixture is taken up in a mixture of ethyl acetate and water. The organic phase is washed with saturated aqueous sodium chloride solution, dried over magnesium sulphate and concentrated in a rotary evaporator. The reaction mixture is chromatographed on silica gel (mobile phase cyclohexane/ethyl acetate 5:1→1:1). 2.5 g (34% of theory) of the product are obtained as a solid.

LCMS (method 6): $R_t$=2.44 min. (m/z=449 (M+H)$^+$).

$^1$H-NMR (400 MHz, DMSO-d$_6$): δ=10.75 (s, 1H), 8.44 (s, 1H), 7.70 (d, 1H), 6.77 (s, 1H), 6.28 (d, 1H), 3.48 (br, s, 2H), 3.17 (br, s, 2H), 1.46 (s, 9H), 1.30 (s, 9H).

Example 115A

1-{2-Amino-6-[(2-aminoethyl)amino]pyridin-3-yl}-2,2,2-trifluoroethanone hydrochloride

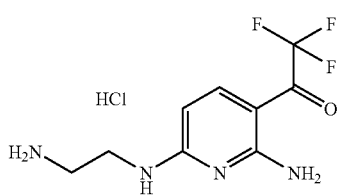

2.5 g (5.57 mmol) of tert-butyl [6-({2-[(tert-butoxycarbonyl)amino]ethyl}amino)-3-(trifluoroacetyl)pyridin-2-yl]carbamate (Example 114A) dissolved in 15 ml of 4N hydrogen chloride in dioxane and stirred for 20 h. The reaction mixture is concentrated to one half, and an equal portion of diethyl ether is added. The reaction mixture is stirred for 20 min, and the product is filtered off and washed with diethyl ether. 1.4 g (89% of theory) of the product are obtained as a solid.

LCMS (method 6): $R_t$=0.73 min. (m/z=249 (M+H)$^+$).

Example 116A tert-Butyl [6-chloro-3-acetylpyridin-2-yl]carbamate

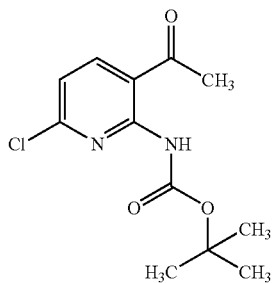

0.65 g (2.9 mmol) of tert-butyl (6-chloropyridin-2-yl)carbamate (Example 105A) is introduced into 10 ml of THF and cooled to −50° C. 4.5 ml (7.2 mmol) of butyllithium (1.6 M) are added dropwise. After the dropwise addition is complete, the reaction is slowly warmed to −10° C. and kept at 0° C. for 2 h. It is then cooled to −40° C. again, and 740 mg (5.7 mmol) of N-acetylmorpholine dissolved in 4 ml of THF are added. The reaction solution is stirred at −40° C. for 1 h and then, at −40° C., poured into 1 l of ethyl acetate and 350 ml of ammonium chloride solution and extracted. The organic phase is separated off, dried over magnesium sulphate and concentrated in a rotary evaporator. The reaction mixture is chromatographed on silica gel (mobile phase cyclohexane/ethyl acetate 2:1). 218 mg (28% of theory) of the product are obtained as an oil.

LCMS (method 8): $R_t$=1.16 min. (m/z=269 (M−H)$^-$)

Example 117A tert-Butyl {3-acetyl-6-[(2-{[7-(2,4-dichlorophenyl)imidazo[1,2-c]pyrimidin-5-yl]amino}ethyl)-amino]pyridin-2-yl}carbamate

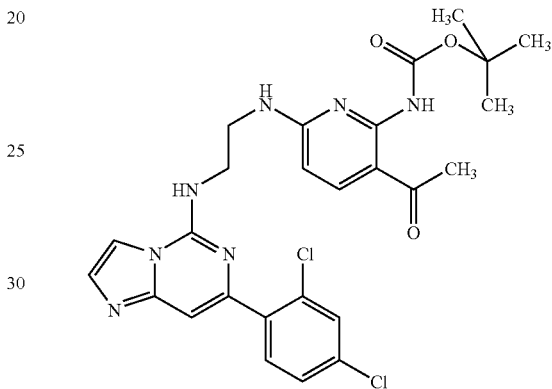

The compound is prepared as described in Example 1 from N-[7-(2,4-dichlorophenyl)imidazo-[1,2-c]pyrimidin-5-yl]ethane-1,2-diamine trifluoroacetate (Example 8A) and tert-butyl [6-chloro-3-acetylpyridin-2-yl]carbamate (Example 116A).

LCMS (method 6): $R_t$=1.61 min. (m/z=556 (M+H−Boc)$^+$)

Example 118A

Methyl 2-[(tert-butoxycarbonyl)amino]-6-chloropyridine-3-carboxylate

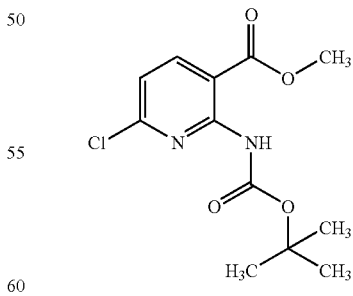

2.0 g (8.7 mmol) of tert-butyl (6-chloropyridin-2-yl)carbamate (Example 105A) are introduced into 50 ml of THF and cooled to −78° C. 13.7 ml (22 mmol) of butyllithium (1.6 M) are added dropwise. After the dropwise addition is complete, the reaction is slowly warmed to −10° C. and kept at −10° C. for 2 h. It is then cooled to −78° C. again, and 870 mg (9.2 mmol) of methyl chloroformate are added. The reaction solution is warmed to RT over 12 h and then the reaction mixture is poured into 150 ml of ethyl acetate and 80 ml of hydrochloric acid solution (1N) and stirred for 15 min. The organic phase is separated off, washed with water and saturated sodium bicarbonate solution, dried over magnesium sulphate and concentrated in a rotary evaporator. The reaction mixture is chromatographed on silica gel (mobile phase cyclohexane/ethyl acetate 10:1). 1018 mg (33% of theory) of the product are obtained as an oil.

LCMS (method 8): $R_t$=1.25 min. (m/z=187 (M+H-Boc)$^+$)

Example 119A

Methyl 2-[(tert-butoxycarbonyl)amino]-6-({2-[(tert-butoxycarbonyl)amino]ethyl}amino)pyridine-3-carboxylate

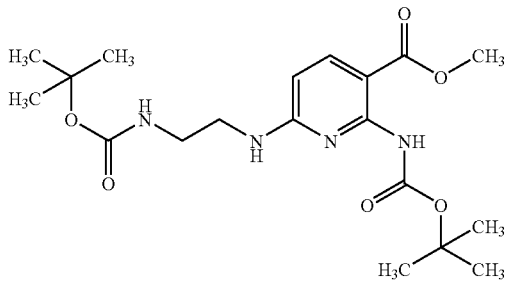

The compound is prepared from 650 mg (2.3 mmol) of methyl 2-[(tert-butoxycarbonyl)amino]-6-chloropyridine-3-carboxylate (Example 118A) and 363 mg (2.3 mmol) of N-Boc-ethylenediamine as described in Example 114A. 500 mg (50% of theory) of the product are obtained as a solid.

LCMS (method 8): $R_t$=1.32 min. (m/z=411 (M+H)$^+$).

Example 120A

Methyl 2-amino-6-[(2-aminoethyl)amino]pyridine-3-carboxylate dihydrochloride

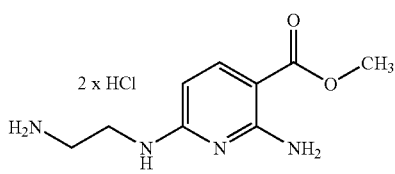

The compound is prepared from 496 mg (1.2 mmol) of methyl 2-[(tert-butoxycarbonyl)amino]-6-({2-[(tert-butoxycarbonyl)amino]ethyl}amino)pyridine-3-carboxylate as described in Example 115A. 363 mg (82% of theory) of the product are obtained as a solid.

LCMS (method 9): $R_t$=0.75 min. (m/z=212 (M+H-2HCl)$^+$).

Example 121A

3-Bromo-5-chloro-7-(2,4-dichlorophenyl)imidazo[1,2-c]pyrimidine

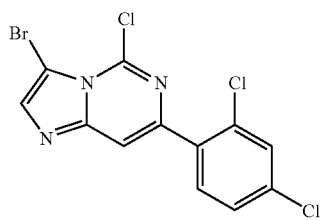

200 mg (0.67 mmol) of 5-chloro-7-(2,4-dichlorophenyl)imidazo[1,2-c]pyrimidine (Example 6A) are suspended in chloroform (30 ml), 238 mg (1.34 mmol) of N-bromosuccinimide are added, and the reaction mixture is stirred at RT for 12 h. The reaction mixture is diluted with ethyl acetate (100 ml) and water (75 ml), and the organic phase is separated off, dried over magnesium sulphate and concentrated in a rotary evaporator. The residue is stirred with acetonitrile (20 ml) and then diethyl ether (20 ml), and the solid is filtered off with suction and dried. 103 mg (41% of theory) of the product are isolated.

LCMS (method 3): $R_t$=2.78 min. (m/z=378 (M+H)$^+$)

Example 122A 3,5-Dichloro-7-(2,4-dichlorophenyl)imidazo[1,2-c]pyrimidine

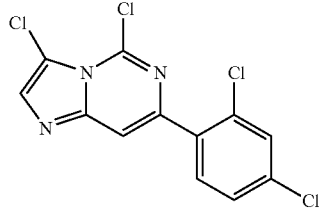

300 mg (1.0 mmol) of 5-chloro-7-(2,4-dichlorophenyl)imidazo[1,2-c]pyrimidine (Example 6A) are suspended in chloroform (15 ml), 240 mg (1.8 mmol) of N-chlorosuccinimide are added, and the reaction mixture is stirred at RT for 12 h. The reaction mixture is diluted with ethyl acetate (100 ml) and water (75 ml), and the organic phase is separated off, dried over magnesium sulphate and concentrated in a rotary evaporator. The residue is stirred with diethyl ether (20 ml), and the solid is filtered off with suction and dried. 63 mg (18% of theory) of the product are isolated.

LCMS (method 8): $R_t$=1.42 min. (m/z=334 (M+H)$^+$)

Example 123A 3,8-Dibromo-7-(2,4-dichlorophenyl)imidazo[1,2-c]pyrimidin-5-ol

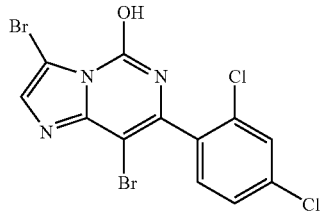

500 mg (1.8 mmol) of 7-(2,4-dichlorophenyl)imidazo[1,2-c]pyrimidin-5-ol (Example 5A) are suspended in chloroform (25 ml), 314 mg (1.8 mmol) of N-bromosuccinimide are added, and the reaction mixture is stirred at RT for 12 h. The solid is filtered off, the filtrate is diluted with ethyl acetate (100 ml) and water (75 ml), and the organic phase is separated off, dried over magnesium sulphate and concentrated in a rotary evaporator. The residue is purified by preparative HPLC. 101 mg (12% of theory) of the product are obtained.

LCMS (method 8): $R_t$=1.12 min. (m/z=438 (M+H)$^+$)

Example 124A 3,8-Dichloro-7-(2,4-dichlorophenyl)imidazo[1,2-c]pyrimidin-5-ol

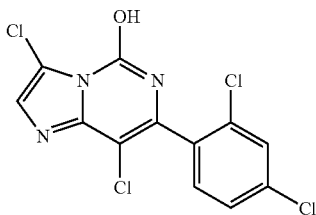

500 mg (1.8 mmol) of 7-(2,4-dichlorophenyl)imidazo[1,2-c]pyrimidin-5-ol (Example 5A) are suspended in chloroform (15 ml), 477 mg (3.6 mmol) of N-chlorosuccinimide are added, and the reaction mixture is stirred at 50° C. for 12 h. The reaction mixture is added at RT to ethyl acetate (100 ml) and diluted with water (75 ml), and the organic phase is separated off, dried over magnesium sulphate and concentrated in a rotary evaporator. The residue is stirred in acetonitrile and filtered, and the filtrate is purified by preparative HPLC. 214 mg (26% of theory) of the crude product are obtained and are reacted further without further purification.

LCMS (method 8): $R_t$=1.11 min. (m/z=350 (M+H)$^+$)

Example 125A 3,8-Dibromo-5-chloro-7-(2,4-dichlorophenyl)imidazo[1,2-c]pyrimidine

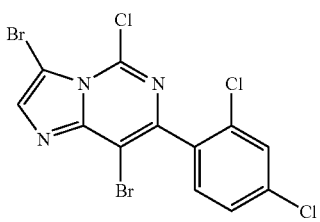

575 mg (1.3 mmol) of 3,8-dibromo-7-(2,4-dichlorophenyl)imidazo[1,2-c]pyrimidin-5-ol (Example 123A) are introduced into phosphoryl chloride (5 ml), 900 mg (4 mmol) of benzyltriethylammonium chloride are added, and the reaction mixture is stirred at 120° C. for 12 h. The reaction mixture is slowly poured, while stirring vigorously, into saturated sodium bicarbonate solution, and solid sodium bicarbonate (approx. 3 g) is added until a pH of 10 is reached. The mixture is stirred for 10 min, ethyl acetate (100 ml) is added and shaken, and the organic phase is separated off, washed with water and dried over magnesium sulphate and concentrated in a rotary evaporator. The residue is purified by silica gel chromatography (cyclohexane/ethyl acetate 10:1). 480 mg (80% of theory) of the product are obtained.

LCMS (method 3): $R_t$=2.91 min. (m/z=454 (M+H)$^+$)

Example 126A 3,5,8-Trichloro-7-(2,4-dichlorophenyl)imidazo[1,2-c]pyrimidine

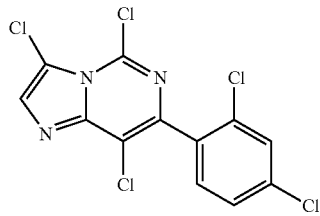

200 mg (0.4 mmol) of 3,8-dichloro-7-(2,4-dichlorophenyl)imidazo[1,2-c]pyrimidin-5-ol (Example 124A) are introduced into phosphoryl chloride (2 ml), 300 mg (1.3 mmol) of benzyltriethylammonium chloride are added, and the reaction mixture is stirred at 120° C. for 12 h. The reaction mixture is slowly added, with vigorous stirring, to saturated sodium bicarbonate solution, and solid sodium bicarbonate (approx. 1.5 g) is added until a pH of 10 is reached. The mixture is stirred for 10 min, ethyl acetate (100 ml) is added and shaken, and the organic phase is separated off, washed with water and dried over magnesium sulphate and concentrated in a rotary evaporator. The residue is purified by silica gel chromatography (cyclohexane/ethyl acetate 10:1). 150 mg (94% of theory) of the product are obtained.

LCMS (method 8): $R_t$=1.45 min. (m/z=366 (M+H)$^+$)

Example 127A (2Z)-3-Amino-3-[4-(trifluoromethyl)phenyl]prop-2-enonitrile

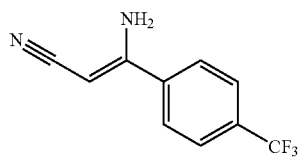

28.1 g (278 mmol) of diisopropylamine are introduced into 450 ml of THF at −70° C. in a three-neck flask with mechanical stirrer under argon. 148 ml of N-butyllithium solution (1.6 M in hexane, 237 mmol) are added dropwise at such a rate that the temperature does not rise above −60° C. The mixture is stirred for 10 min and then a solution of 12.9 ml (245 mmol) of acetonitrile in 100 ml of THF is slowly added dropwise, and the suspension is stirred for 30 min. Then a solution of 28 g (164 mmol) of 4-(trifluoromethyl)benzonitrile in 100 ml of THF is added dropwise, and the mixture is stirred at −70° C. for 20 min. It is allowed to reach RT slowly and is stirred at RT for a further 16 h. 150 ml of water are added, most of the THF is distilled off, and water and dichloromethane are added. The organic phase is washed with saturated aqueous sodium chloride solution. Removal of the solvent results in dark crystals which are purified by stirring with diisopropyl ether (40 ml once, 20 ml twice). The crystals are filtered off, washed with petroleum ether and dried. 27 g (78% of theory) of the product are obtained as a solid.

LCMS (method 9): $R_t$=2.05 min. (m/z=213 (M+H)$^+$)

$^1$H-NMR (400 MHz, DMSO-d$_6$): d=7.79 (s, 4H), 7.98 (br s, 1H), 4.30 (s, 1H).

Example 128A

Ethyl [2-cyano-1-(2,4-dichlorophenyl)ethenyl]carbamate

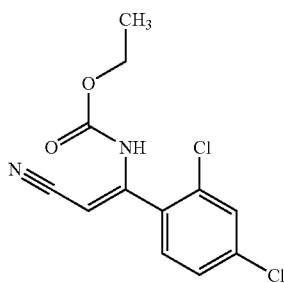

4.85 g (211 mmol) of sodium are dissolved in ethanol (260 ml), 30.0 g (141 mmol) of 3-amino-3-(2,4-dichlorophenyl)acrylonitrile and 36.59 g (310 mmol) of diethyl carbonate are added, and the reaction solution is stirred under reflux for 4 h. Ethyl acetate and water are added to the reaction mixture, and the pH is adjusted to pH=5 with concentrated hydrochloric acid. The organic phase is separated off, dried over magnesium sulphate and concentrated in a rotary evaporator. The residue is chromatographed on silica gel (mobile phase cyclohexane/ethyl acetate 7:1 to 1:1); the product has $R_f$=0.5 in cyclohexane/ethyl acetate 1:1. 17.1 g (43% of theory) of the product are obtained.

LCMS (method 6): $R_t$=1.87 min. (m/z=285 (M+H)$^+$)

$^1$H-NMR (400 MHz, DMSO-d$_6$): d=10.35 (s, 1H), 7.79 (d, 1H), 7.54 (m, 2H), 6.16 (s, 1H), 4.13 (q, 2H), 1.22 (t, 3H).

Example 129A

Ethyl {2-cyano-1-[4-(trifluoromethyl)phenyl]ethenyl}carbamate

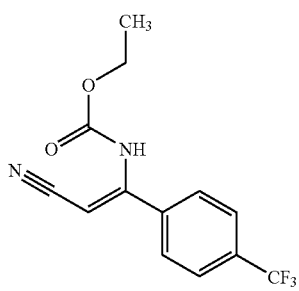

4.88 g (212 mmol) of sodium are dissolved in ethanol (260 ml), 30.0 g (141 mmol) of 3-amino-3-(2,4-dichlorophenyl)acrylonitrile and 36.75 g (311 mmol) of diethyl carbonate are added, and the reaction solution is stirred under reflux for 5 h. Ethyl acetate and water are added to the reaction mixture, and the pH is adjusted to pH=5 with 2M hydrochloric acid. The organic phase is separated off, dried over magnesium sulphate and concentrated in a rotary evaporator. The residue is chromatographed on silica gel (mobile phase cyclohexane/ethyl acetate 9:1 to 2:1). 13.3 g (33% of theory) of the product are obtained as a mixture of E and Z isomers.

LCMS (method 6): $R_t$=1.92 min. (m/z=285 (M+H)$^+$)

Example 130A 7-(2,4-Dichlorophenyl)-2-(trifluoromethyl)[1,2,4]triazolo[1,5-c]pyrimidin-5-ol

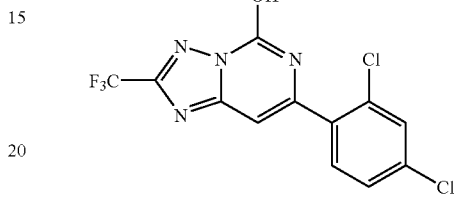

2.10 g (7.4 mmol) of ethyl [2-cyano-1-(2,4-dichlorophenyl)ethenyl]carbamate (Example 128A) and 0.95 g (7.4 mmol) of 2,2,2-trifluoroacetohydrazide are dissolved in NMP (10 ml) under argon and stirred in a flask with a calcium chloride drying tube at an oil-bath temperature of 160° C. for 4 h. The reaction mixture is cooled to RT, and water (20 ml) is added. Ethyl acetate (150 ml) and water (100 ml) are added, and the organic phase is separated off, dried with magnesium sulphate and concentrated. The residue is chromatographed on silica gel (mobile phase cyclohexane/ethyl acetate 4:1 to 1:1). 0.97 g (38% of theory) of the product is obtained.

LCMS (method 8): $R_t$=1.17 min. (m/z=349 (M+H)$^+$)

$^1$H-NMR (400 MHz, DMSO-d$_6$): d=12.82 (br s, 1H), 7.88 (d, 1H), 7.65 (m, 2H), 7.07 (s, 1H).

Example 131A 2-(Trifluoromethyl)-7-[4-(trifluoromethyl)phenyl][1,2,4]triazolo[1,5-c]pyrimidin-5-ol

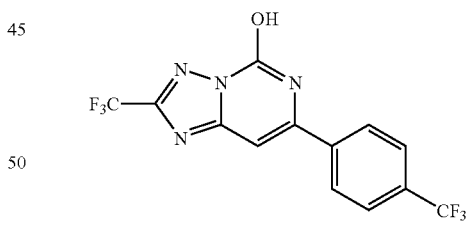

2.42 g (8.5 mmol) of ethyl {2-cyano-1-[4-(trifluoromethyl)phenyl]ethenyl}carbamate (Example 129A) and 1.09 g (8.5 mmol) of 2,2,2-trifluoroacetohydrazide are dissolved in NMP (10 ml) and stirred in a flask with a calcium chloride drying tube at an oil-bath temperature of 160° C. for 4 h. The reaction mixture is cooled to RT and ethyl acetate (150 ml) and water (100 ml) are added. The organic phase is separated off, dried with magnesium sulphate and concentrated. The residue is stirred with diethyl ether (25 ml), and the solid is filtered off and dried. 0.67 g (23% of theory) of the product is obtained.

LCMS (method 3): $R_t$=2.29 min. (m/z=349 (M+H)$^+$)

$^1$H-NMR (400 MHz, DMSO-d$_6$): d=12.81 (br s, 1H), 8.05 (d, 2H), 7.95 (d, 2H), 7.37 (s, 1H).

Example 132A

Ethyl 7-(2,4-dichlorophenyl)-5-hydroxy-[1,2,4]-triazolo[1,5-c]pyrimidine-2-carboxylate

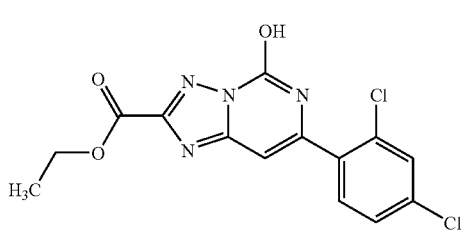

3.0 g (10.5 mmol) of ethyl [2-cyano-1-(2,4-dichlorophenyl)ethenyl]carbamate (Example 128A) and 1.39 g (10.5 mmol) of ethyl hydrazino(oxo)acetate are dissolved in NMP (16 ml) and stirred in a flask with a calcium chloride drying tube at an oil-bath temperature of 160° C. for 4 h. The reaction mixture is cooled to RT and ethyl acetate (150 ml) and water (100 ml) are added. The organic phase is separated off, dried with magnesium sulphate and concentrated. The residue is chromatographed on silica gel (mobile phase cyclohexane/ethyl acetate 10:1 to 1:1, then with dichloromethane/methanol 100:1). The crude product is concentrated, mixed with water and stirred for 1 h. The solid is filtered off with suction and dried; 1.31 g (35% of theory) of the product are obtained.

LCMS (method 8): $R_t$=1.00 min. (m/z=353 (M+H)$^+$)

$^1$H-NMR (400 MHz, DMSO-$d_6$): d=12.63 (br s, 1H), 7.88 (d, 1H), 7.63 (d, 2H), 6.99 (s, 1H), 4.42 (q, 2H), 1.46 (t, 3H).

Example 133A

Ethyl 5-hydroxy-7-[4-(trifluoromethyl)phenyl][1,2,4]triazolo[1,5-c]pyrimidine-2-carboxylate

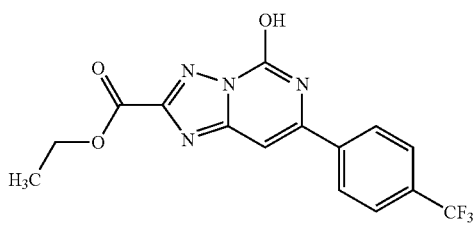

2.4 g (8.4 mmol) of ethyl {2-cyano-1-[4-(trifluoromethyl)phenyl]ethenyl}carbamate (Example 129A) and 1.24 g (8.4 mmol) of ethyl hydrazino(oxo)acetate are dissolved in NMP (16 ml) and stirred in a flask with a calcium chloride drying tube at an oil-bath temperature of 160° C. for 4 h. The reaction mixture is cooled to RT and poured into water (100 ml), and the precipitate is filtered off, washed with water and diethyl ether and dried. 1.90 g (64% of theory) of the crude product are obtained.

LCMS (method 8): $R_t$=1.01 min. (m/z=353 (M+H)$^+$)

Example 134A 7-(2,4-Dichlorophenyl)-2-(morpholin-4-ylmethyl)[1,2,4]triazolo[1,5-c]pyrimidin-5-ol

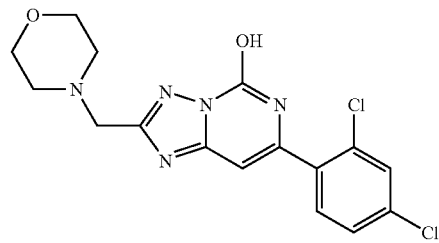

1.33 g (4.7 mmol) of ethyl [2-cyano-1-(2,4-dichlorophenyl)ethenyl]carbamate (Example 128A) and 740 mg (4.7 mmol) of 2-morpholin-4-ylacetohydrazide are dissolved in NMP (6 ml) and stirred in a flask with a calcium chloride drying tube at an oil-bath temperature of 160° C. for 3 h. The reaction mixture is cooled to RT and ethyl acetate (100 ml) and water (50 ml) are added. The organic phase is separated off, dried with magnesium sulphate and concentrated. The residue is chromatographed on silica gel (mobile phase dichloromethane/methanol 100:1 to 50:1). 1.25 g (70% of theory) of the product are obtained.

LCMS (method 8): $R_t$=0.68 min. (m/z=380 (M+H)$^+$)

$^1$H-NMR (400 MHz, DMSO-$d_6$): d=12.37 (br s, 1H), 7.85 (d, 1H), 7.64 (m, 2H), 6.85 (s, 1H), 4.44 (br s, 2H), 3.71 (s, 2H), 3.59 (m, 4H), 3.40 (s, 2H).

Example 135A 2-(Morpholin-4-ylmethyl)-7-[4-(trifluoromethyl)phenyl][1,2,4]-triazolo[1,5-c]pyrimidin-5-ol

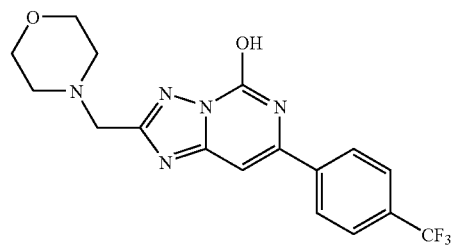

2.4 g (8.4 mmol) of ethyl {2-cyano-1-[4-(trifluoromethyl)phenyl]ethenyl}carbamate (Example 129A) and 1.34 g (8.4 mmol) of 2-morpholin-4-ylacetohydrazide are dissolved in NMP (12 ml) and stirred in a flask with a calcium chloride drying tube at an oil-bath temperature of 190° C. for 4 h. The reaction mixture is cooled to RT and ethyl acetate (150 ml) and water (100 ml) are added. The organic phase is washed with saturated sodium bicarbonate solution, separated off, dried with magnesium sulphate and concentrated. The residue is chromatographed on silica gel (mobile phase cyclohexane/ethyl acetate 10:1 to 1:1, then with dichloromethane/methanol 100:1). 850 mg (26% of theory) of the product are obtained.

LCMS (method 8): $R_t$=0.74 min. (m/z=380 (M+H)$^+$)

$^1$H-NMR (400 MHz, DMSO-$d_6$): d=12.36 (br s, 1H), 8.05 (d, 2H), 7.92 (d, 2H), 7.18 (s, 1H), 4.45 (m, 2H), 3.70 (s, 2H), 3.60 (m, 4H), 3.29 (s, 2H).

Example 136A 7-(2,4-Dichlorophenyl)-2-methyl[1,2,4]triazolo[1,5-c]pyrimidin-5-ol

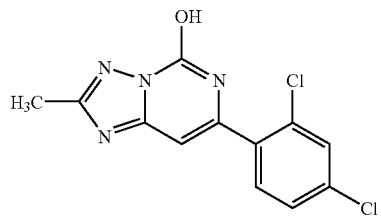

In analogy to Example 11A, 686 mg (60% of theory) of the product are obtained from 1000 mg (3.5 mmol) of ethyl [(Z)-2-cyano-1-(2,4-dichlorophenyl)ethenyl]carbamate (Example 129A) by reaction with 289 mg (3.5 mmol) of acetohydrazide.

LCMS (method 3): $R_t$=1.75 min. (m/z=295 (M+H)$^+$)
$^1$H-NMR (400 MHz, DMSO-d$_6$): d=12.35 (s, 1H), 7.84 (d, 1H), 5.57-7.66 (m, 2H), 6.79 (s, 1H), 2.43 (s, 3H).

Example 137A 7-(2,4-Dichlorophenyl)[1,2,4]triazolo[1,5-c]pyrimidin-5-ol

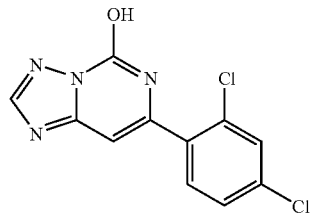

500 mg (1.75 mmol) of ethyl [2-cyano-1-(2,4-dichlorophenyl)ethenyl]carbamate (Example 128A) and 182 mg (1.75 mmol) of hydrazino(oxo)acetic acid are dissolved in NMP (2 ml) under argon and stirred in a flask with a calcium chloride drying tube at an oil-bath temperature of 160° C. for 4 h. The reaction mixture is cooled to RT, mixed with water (20 ml) and stirred for 20 min. Ethyl acetate (150 ml) and water (100 ml) are added and the organic phase is separated off, dried with magnesium sulphate and concentrated. The residue is stirred with diethyl ether/dichloromethane, and the solid is filtered off and dried. 150 mg (31% of theory) of the product are obtained.

LCMS (method 8): $R_t$=0.85 min. (m/z=281 (M+H)$^+$)
$^1$H-NMR (400 MHz, DMSO-d$_6$): d=12.45 (br s, 1H), 8.49 (s, 1H), 7.86 (d, 1H), 7.63 (m, 2H), 6.92 (s, 1H).

Example 138A 7-(4-Trifluoromethylphenyl)[1,2,4]-triazolo[1,5-c]pyrimidin-5-ol

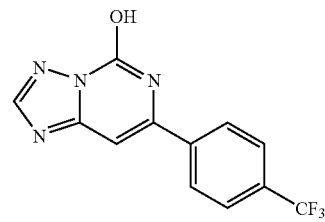

2.00 g (7.0 mmol) of ethyl [2-cyano-1-(4-trifluoromethylphenyl)ethenyl]carbamate (Example 129A) and 0.73 g (7.0 mmol) of hydrazino(oxo)acetic acid are dissolved in NMP (7 ml) under argon and stirred in a flask with a calcium chloride drying tube at an oil-bath temperature of 160° C. for 4 h. The reaction mixture is cooled to RT, mixed with water (20 ml) and stirred for 20 min. Ethyl acetate (150 ml) and water (100 ml) are added, and the organic phase is separated off, dried with magnesium sulphate and concentrated. The residue is suspended in water in an ultrasonic bath for 10 min. and then stirred for 30 min. The solid is filtered off and dried. 0.97 g (38% of theory) of the product are obtained.

LCMS (method 3): $R_t$=1.73 min. (m/z=281 (M+H)$^+$)
$^1$H-NMR (400 MHz, DMSO-d$_6$): d=12.44 (br s, 1H), 8.47 (s, 1H), 8.05 (d, 2H), 7.92 (d, 2H), 7.26 (s, 1H).

The following products are obtained in analogy to the procedures described for the preceding examples:

| Ex. | Structure | LC/MS: retention time [min] (method) | Characterization | Yield [of theory] |
|---|---|---|---|---|
| 139A | (structure shown) | 0.90 (method 8) | $^1$H-NMR (400 MHz, DMSO-d$_6$): d = 12.31 (s, 1H), 8.04 (d, 2H), 7.90 (d, 2H), 7.13 (s, 1H), 2.45 (s, 3H). | 18% |

| Ex. | Structure | LC/MS: retention time [min] (method) | Characterization | Yield [of theory] |
|---|---|---|---|---|
| 140A | 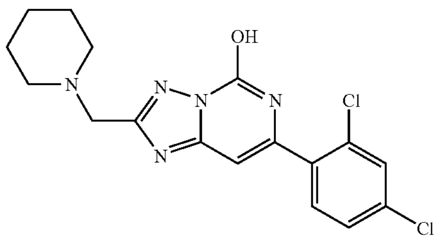 | 0.91 (method 6) | ¹H-NMR (400 MHz, DMSO-d$_6$): d = 12.28 (br s, 1H), 7.83 (d, 1H), 7.63 (m, 2H), 6.78 (s, 1H, 3.65 (s, 2H), 2.48 (m, 4H), 1.50 (m, 4H), 1.37 (m, 2H). | 96% |
| 141A | 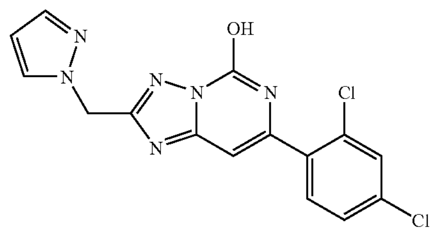 | 0.93 (method 8) | ¹H-NMR (400 MHz, DMSO-d$_6$): d = 12.44 (s, 1H), 7.87 (d, 1H), 7.85 (s, 1H), 7.62 (d, 2H), 7.46 (d, 1H), 6.85 (s, 1H), 6.30 (d, 1H), 5.57 (s, 2H). | 84% |
| 142A | 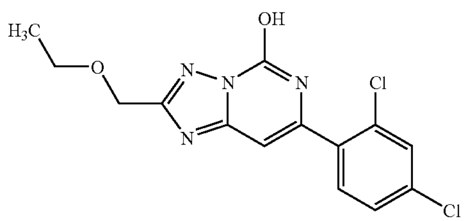 | 2.58 (method 3) | ¹H-NMR (400 MHz, DMSO-d$_6$): d = 12.40 (s, 1H), 7.85 (d, 1H), 7.60-7.66 (m, 2H), 6.86 (s, 1H), 4.60 (s, 2H), 3.57 (q, 2H), 1.15 (s, 3H). | — |
| 143A | 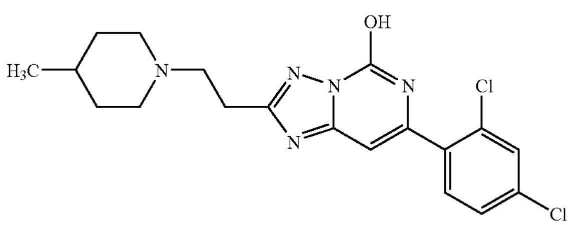 | 0.81 (method 8) | m/z = 406 (M + H)⁺ | 31% |
| 144A | 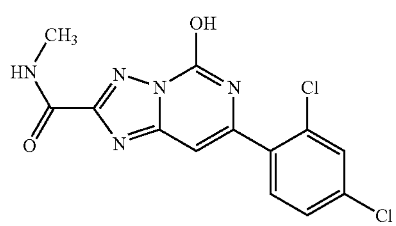 | 0.84 (method 8) | m/z = 338 (M + H)⁺ | 39% |
| 145A | 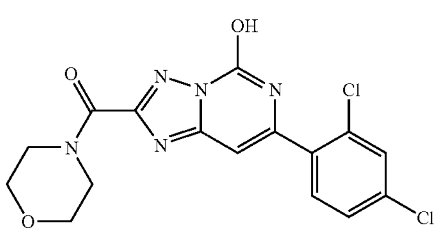 | 0.88 (method 8) | m/z = 394 (M + H)⁺ | 62% |

Example 146A

5-Chloro-7-(2,4-dichlorophenyl)-2-(trifluoromethyl)[1,2,4]triazolo[1,5-c]pyrimidine

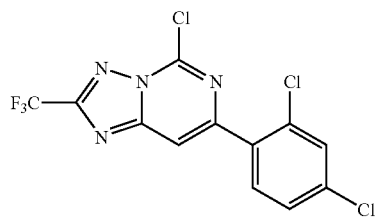

950 mg (2.7 mmol) of 7-(2,4-dichlorophenyl)-2-(trifluoromethyl)[1,2,4]triazolo[1,5-c]pyrimidin-5-ol (Example 130A) are introduced into phosphoryl chloride (10 ml), 1.86 g (8.2 mmol) of benzyltriethylammonium chloride are added, and the reaction mixture is stirred at 120° C. for 12 h. The reaction mixture is slowly poured, with vigorous stirring, into saturated sodium bicarbonate solution and ice, and solid sodium bicarbonate (approx. 5 g) is added until a pH of 8 is reached. The solid is filtered off with suction. The reaction vessel is washed out with dichloromethane, and the organic phase is dried over magnesium sulphate, concentrated and combined with the filtered solid. The crude product is purified by silica gel chromatography (cyclohexane/ethyl acetate 10:1). 784 mg (78% of theory) of the product are obtained.

LCMS (method 8): $R_t$=1.50 min. (m/z=367 (M+H)$^+$)

Example 147A

5-Chloro-2-(trifluoromethyl)-7-[4-(trifluoromethyl)phenyl][1,2,4]triazolo[1,5-c]pyrimidine

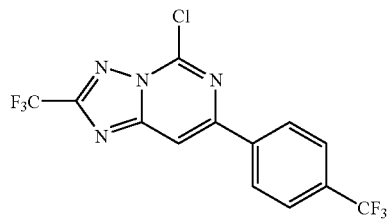

650 mg (1.9 mmol) of 2-(trifluoromethyl)-7-[4-(trifluoromethyl)phenyl][1,2,4]triazolo[1,5-c]-pyrimidin-5-ol (Example 131A) are introduced into phosphoryl chloride (10 ml), 1.28 g (5.6 mmol) of benzyltriethylammonium chloride are added, and the reaction mixture is stirred at 120° C. for 12 h. The reaction mixture is slowly poured, with vigorous stirring, into saturated sodium bicarbonate solution (50 ml) and ice, and solid sodium bicarbonate (approx. 1 g) is added until a pH of 8 is reached. The solid is filtered off with suction. 635 mg (93% of theory) of the crude product are obtained.

LCMS (method 8): $R_t$=1.48 min. (m/z=367 (M+H)$^+$)

$^1$H-NMR (400 MHz, DMSO-d$_6$): d=8.90 (s, 18.46 (d, 2H), 7.97 (d, 2H).

Example 148A

Ethyl-5-chloro-7-(2,4-dichlorophenyl)[1,2,4]triazolo[1,5-c]pyrimidine-2-carboxylate

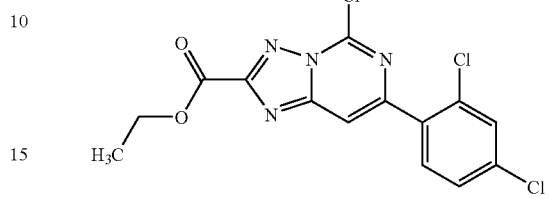

1311 mg (3.7 mmol) of ethyl 7-(2,4-dichlorophenyl)-5-hydroxy[1,2,4]triazolo[1,5-c]pyrimidine-2-carboxylate (Example 132A) are introduced into phosphoryl chloride (15 ml), 2.54 g (11.1 mmol) of benzyltriethylammonium chloride are added, and the reaction mixture is stirred at 120° C. for 12 h. The reaction mixture is slowly poured, while stirring vigorously, into saturated sodium bicarbonate solution (150 ml) and ice, and solid sodium bicarbonate (approx. 10 g) is added until a pH of 8 is reached. The solid is filtered off with suction. 635 mg (93% of theory) of the product are obtained.

LCMS (method 3): $R_t$=2.60 min. (m/z=371 (M+H)$^+$)

$^1$H-NMR (400 MHz, DMSO-d$_6$): d=8.40 (s, 1H), 7.88 (d, 1H), 7.75 (d, 1H), 7.65 (dd, 1H), 4.47 (q, 2H), 1.40 (t, 3H).

Example 149A

Ethyl 5-chloro-7-[4-(trifluoromethyl)phenyl][1,2,4]triazolo[1,5-c]pyrimidine-2-carboxylate

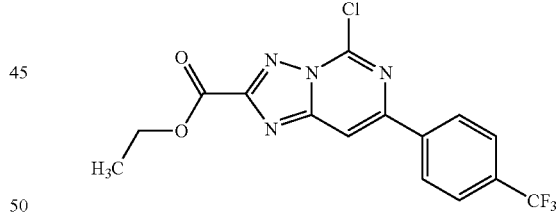

2300 mg (6.5 mmol) of ethyl 5-hydroxy-7-[4-(trifluoromethyl)phenyl][1,2,4]triazolo-[1,5-c]pyrimidine-2-carboxylate (Example 133A) are introduced into phosphoryl chloride (30 ml), 5.95 g (26.1 mmol) of benzyltriethylammonium chloride are added, and the reaction mixture is stirred at 120° C. for 20 h. The reaction mixture is slowly poured, while stirring vigorously, into saturated sodium bicarbonate solution (200 ml) and ice, and solid sodium bicarbonate (approx. 20 g) is added until a pH of 8 is reached. The solid is filtered off with suction and washed with water and diethyl ether and dried. 2300 mg (92% of theory) of the product are obtained.

LCMS (method 3): $R_t$=1.34 min. (m/z=371 (M+H)$^+$)

$^1$H-NMR (400 MHz, DMSO-d$_6$): d=8.80 (s, 1H), 8.45 (d, 2H), 7.95 (d, 2H), 4.47 (q, 2H), 1.39 (t, 3H).

Example 150A

5-Chloro-7-(2,4-dichlorophenyl)-2-(morpholin-4-ylmethyl)[1,2,4]triazolo[1,5-c]pyrimidine

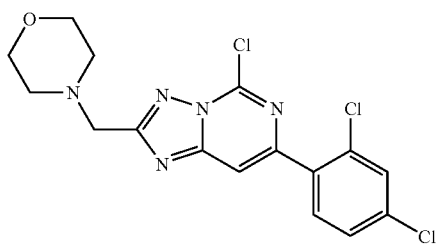

1250 mg (3.3 mmol) of 7-(2,4-dichlorophenyl)-2-(morpholin-4-ylmethyl)[1,2,4]triazolo-[1,5-c]pyrimidin-5-ol (Example 134A) are introduced into phosphoryl chloride (20 ml), 2.25 g (9.9 mmol) of benzyltriethylammonium chloride are added, and the reaction mixture is stirred at 120° C. for 12 h. The reaction mixture is slowly poured, while stirring vigorously, into saturated sodium bicarbonate solution (150 ml) and ice, and solid sodium bicarbonate (approx. 10 g) is added until a pH of 8 is reached. The solid is filtered off with suction and dried. 508 mg (39% of theory) of the product are obtained.

LCMS (method 8): $R_t$=1.01 min. (m/z=398 (M+H)$^+$)

Example 151A

5-Chloro-2-(morpholin-4-ylmethyl)-7-[4-(trifluoromethyl)phenyl][1,2,4]triazolo[1,5-c]pyrimidine

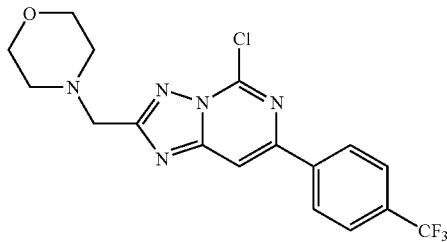

850 mg (2.2 mmol) of 2-(morpholin-4-ylmethyl)-7-[4-(trifluoromethyl)phenyl][1,2,4]triazolo-[1,5-c]pyrimidin-5-ol (Example 135A) are introduced into phosphoryl chloride (20 ml), 1.98 g (8.7 mmol) of benzyltriethylammonium chloride are added, and the reaction mixture is stirred at 120° C. for 2 h. The reaction mixture is slowly poured, while stirring vigorously, into ice-water, and solid sodium bicarbonate is added until a pH of 8 is reached. The reaction mixture is extracted with ethyl acetate (150 ml), and the organic phase is separated off, dried (magnesium sulphate) and concentrated. The residue is chromatographed on silica gel (mobile phase dichloromethane/ethanol 100:1 to 20:1). 650 mg (75% of theory) of the product are obtained as a solid.

LCMS (method 8): $R_t$=1.04 min. (m/z=398 (M+H)$^+$)

Example 152A

5-Chloro-7-(2,4-dichlorophenyl)-2-methyl[1,2,4]triazolo[1,5-c]pyrimidine

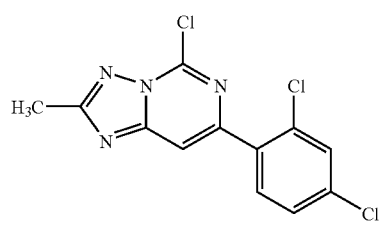

In analogy to Example 53A, 676 mg (49% of theory) of the product are obtained from 685 mg (2.31 mmol) of 7-(2,4-dichlorophenyl)-2-methyl[1,2,4]triazolo[1,5-c]pyrimidin-5-ol (Example 136A) by reaction in 6 ml of phosphoryl chloride and 1.59 g (6.96 mmol) of benzyltriethylammonium chloride.

LCMS (method 3): $R_t$=2.44 min. (m/z=313 (M+H)$^+$)

$^1$H-NMR (400 MHz, DMSO-d$_6$): d=8.14 (s, 1H), 7.84 (d, 1H), 7.73 (d, 1H), 7.62 (dd, 1H), 2.58 (s, 3H).

Example 153A

5-Chloro-7-[4-(trifluoromethyl)phenyl][1,2,4]triazolo[1,5-c]pyrimidine

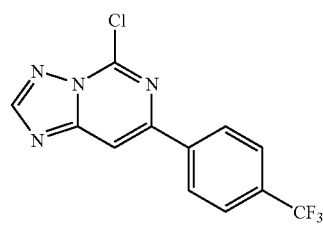

1320 mg (4.7 mmol) of 7-[4-(trifluoromethyl)phenyl][1,2,4]triazolo[1,5-c]pyrimidin-5-ol (Example 138A) are introduced into phosphoryl chloride (20 ml), 3.20 g (14 mmol) of benzyltriethylammonium chloride are added, and the reaction mixture is stirred at 120° C. for 4 h. The reaction mixture is slowly poured, while stirring vigorously, into saturated sodium bicarbonate solution (150 ml) and ice, and solid sodium bicarbonate (approx. 10 g) is added until a pH of 8 is reached. The solid is filtered off with suction. 1300 mg (92% of theory) of the crude product are obtained.

LCMS (method 6): $R_t$=2.00 min. (m/z=299 (M+H)$^+$)

$^1$H-NMR (400 MHz, DMSO-d$_6$): d=8.81 (s, 1H), 8.74 (s, 1H), 8.45 (d, 2H), 7.94 (d, 2H).

Example 154A

5-Chloro-7-[2,4-dichlorophenyl][1,2,4]triazolo[1,5-c]pyrimidine

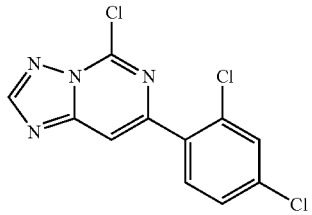

2.07 g (7.4 mmol) of 7-[2,4-dichlorophenyl][1,2,4]triazolo[1,5-c]pyrimidin-5-ol (Example 137A) are introduced into phosphoryl chloride (20 ml), 5.0 g (22 mmol) of benzyltriethylammonium chloride are added, and the reaction mixture is stirred at 120° C. for 16 h. The reaction mixture is concentrated and cautiously poured onto ice, while stirring vigorously, and the mixture is stirred for 10 min. The solid is filtered off with suction. 1100 mg (50% of theory) of the product are obtained.

LCMS (method 3): $R_t$=2.39 min. (m/z=299 (M+H)$^+$)

$^1$H-NMR (400 MHz, DMSO-d$_6$): d=8.84 (s, 1H), 8.29 (s, 1H), 7.85 (d, 1H), 7.75 (d, 1H), 7.64 (dd, 1H).

The following products are obtained in analogy to the procedures described for the preceding examples:

| Ex. | Structure | LC/MS: retention time [min] (method) | Characterization | Yield [of theory] |
|---|---|---|---|---|
| 155A | 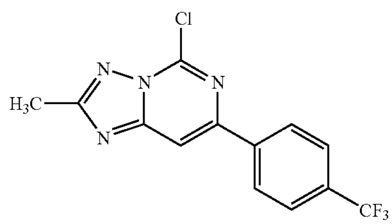 | 1.28 (method 8) | $^1$H-NMR (400 MHz, DMSO-d$_6$): d = 8.59 (s, 1H), 8.43 (d, 2H), 7.93 (d, 2H), 2.59 (s, 3H). | 82% |
| 156A | 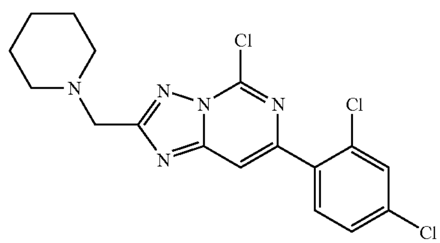 | 1.51 (method 3) | $^1$H-NMR (400 MHz, DMSO-d$_6$): d = 10.54 (br s, 1H), 8.35 (s, 1H), 7.89 (d, 1H), 7.74 (d, 1H), 7.66 (dd, 1H), 4.74 (br s, 2H), 3.04 (br m, 2H), 3.07 (br m, 2H), 1.78 (br m, 6H). | 6% |
| 157A | 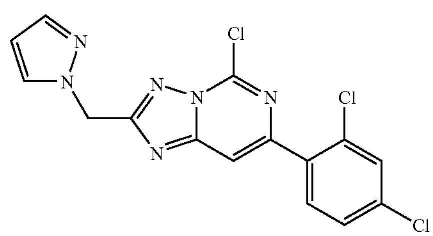 | 2.45 (method 3) | $^1$H-NMR (400 MHz, DMSO-d$_6$): d = 8.22 (s, 1H), 7.93 (d, 1H), 7.84 (d, 1H), 7.73 (d, 1H), 7.63 (dd, 1H), 7.47 (d, 1H), 6.32 (t, 1H), 5.73 (s, 2H). | 73% |
| 158A | 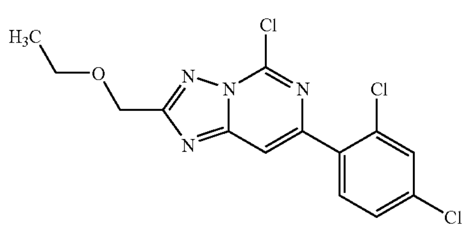 | 2.58 (method 3) | $^1$H-NMR (400 MHz, DMSO-d$_6$): d = 8.22 (s, 1H), 7.85 (d, 1H), 7.72 (d, 1H), 7.63 (dd, 1H), 4.75 (s, 2H), 3.62 (q, 2H), 1.17 (s, 3H). | — |
| 159A | 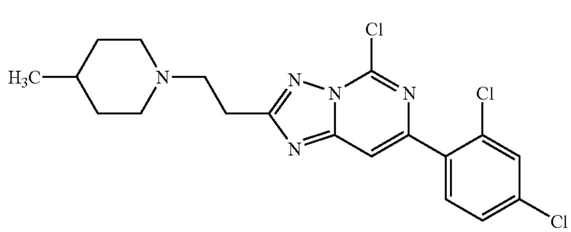 | 1.04 (method 8) | m/z = 424 (M + H)$^+$ | 58% |

| Ex. | Structure | LC/MS: retention time [min] (method) | Characterization | Yield [of theory] |
|---|---|---|---|---|
| 160A | 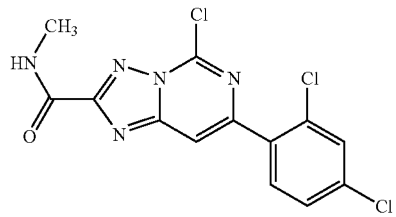 | 2.09 (method 9) | m/z = 356 (M + H)⁺ | 95% |
| 161A | 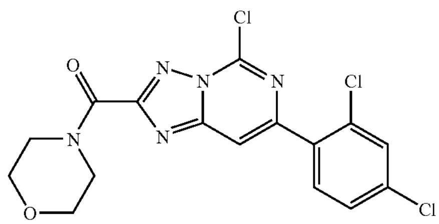 | 2.19 (method 9) | m/z = 412 (M + H)⁺ | 94% |

Exemplary Embodiments

Example 1

6-[(2-{[7-(2,4-Dichlorophenyl)imidazo[1,2-c]pyrimidin-5-yl]amino}ethyl)amino]nicotinonitrile

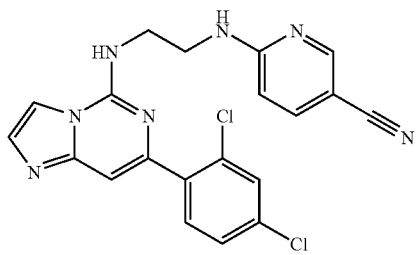

50 mg (0.155 mmol) of the amine (Example 8A) are introduced into 2 ml of isopropanol, 32.3 mg (0.233 mmol) of 6-chloronicotinonitrile and 30.09 mg (0.233 mmol) of DIPEA are added, and the mixture is heated in a microwave at 150° C. for 1 h. Purification by preparative HPLC results in 47 mg (71% of theory) of the product.

LCMS (method 5): $R_t$=2.34 min. (m/z=424 (M+H)⁺)

¹H-NMR (400 MHz, DMSO-d₆): d=8.36 (t, 1H), 8.05 (t, 1H), 7.98 (s, 1H), 7.76 (s, br, 1H), 7.71 (d, 1H), 7.65 (d, 1H), 7.60 (m, 1H), 7.58 (s, 1H), 7.50 (dd, 1H), 7.10 (s, 1H), 6.51 (d, 1H), 3.69 (t, 2H), 3.66 (t, br, 2H).

Example 2

N-[7-(2,4-Dichlorophenyl)imidazo[1,2-c]pyrimidin-5-yl]-N'-[5-(trifluoromethyl)pyridin-2-yl]ethane-1,2-diamine

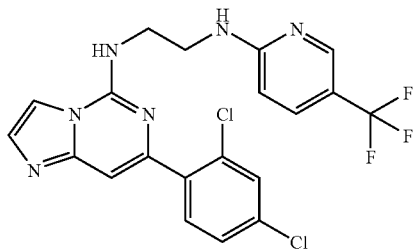

50 mg (0.155 mmol) of the amine (Example 8A) are introduced into 3 ml of dry DMSO, 51.2 mg (0.31 mmol) of 2-fluoro-5-(trifluoromethyl)pyridine and 31.1 mg (0.31 mmol) of potassium bicarbonate are added, and the mixture is heated at 130° C. under argon for 16 h. Purification by preparative HPLC results in 22 mg (30% of theory) of the product as a solid.

LCMS (method 3): $R_t$=2.06 min. (m/z=468 (M+H)⁺)

¹H-NMR (400 MHz, DMSO-d₆): d=8.27 (s, 1H), 8.07 (t, 1H), 8.00 (s, 1H), 7.71 (d, 1H), 7.66 (d, 1H), 7.58 (d, 1H), 7.54 (m, broad, 2H), 7.49 (dd, 1H), 7.10 (s, 1H), 6.57 (d, 1H), 3.68 (t, 2H), 3.64 (t, 2H).

Example 3

1-{6-[(2-{[7-(2,4-Dichlorophenyl)imidazo[1,2-c]pyrimidin-5-yl]amino}ethyl)amino]pyridin-3-yl}ethanone

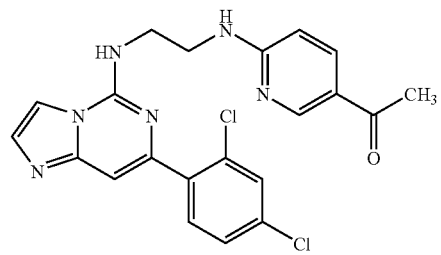

50 mg (0.155 mmol) of the amine (Example 8A) are introduced into 3 ml of dry N-methylpyrrolidine, 48.3 mg (0.31 mmol) of 1-(6-chloropyridin-3-yl)ethanone and 40.1 mg (0.31 mmol) of DIPEA are added, and the mixture is heated in a microwave at 130° C. for 1.5 h. Purification by preparative HPLC results in 11 mg (15% of theory) of the product as a solid.

LCMS (method 5): $R_t$=1.82 min. (m/z=439 (M−H)⁺)

¹H-NMR (400 MHz, DMSO-d₆): d=8.76 (s, br, 1H), 8.53 (d, 1H), 8.19 (s, 1H), 8.00 (s, 1H), 7.76 (d, 2H), 7.75 (dd, 1H), 7.66 (d, 1H), 7.53 (dd, 1H), 7.33 (s, 1H), 6.45 (d, 1H), 3.78 (dt, 2H), 3.69 (dt, 2H), 2.40 (s, 3H).

Example 4

N⁶-(2-{[7-(2,4-Dichlorophenyl)imidazo[1,2-c]pyrimidin-5-yl]amino}ethyl)-3-nitropyridine-2,6-diamine

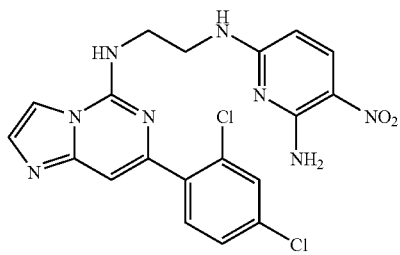

In analogy to the procedure for preparing Example 3, 30.1 mg (53% of theory) of the product are obtained as a solid from 40 mg (0.124 mmol) of the amine (Example 8A) and 43.1 mg (0.25 mmol) of 2-amino-6-chloro-3-nitropyridine after purification by preparative HPLC.

LCMS (method 3): $R_t$=1.68 min. (m/z=459 (M+H)⁺)

¹H-NMR (400 MHz, DMSO-d₆): d=8.10 (t, 1H), 8.04 (t, 1H), 8.00 (s, 1H), 7.88 (d, 1H), 7.70 (d, 1H), 7.65 (d, 1H), 7.58 (d, 1H), 7.46 (d, 1H), 7.11 (s, 1H), 5.88 (d, 1H), 3.73 (dt, 2H), 3.69 (dt, 2H).

Example 5

4-Amino-2-[(2-{[7-(2,4-dichlorophenyl)imidazo[1,2-c]pyrimidin-5-yl]amino}ethyl)amino]-1,3-thiazole-5-carbonitrile

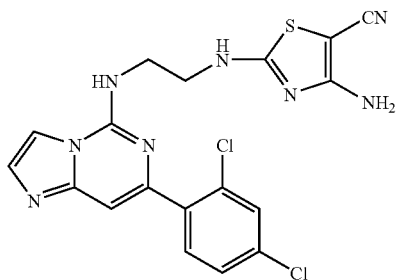

214.27 mg (0.72 mmol) of chloropyrimidine (Example 6A) are introduced into 28 ml of dry DMSO, 320 mg (1.08 mmol) of 4-amino-2-[(2-aminoethyl)amino]-1,3-thiazole-5-carbonitrile trifluoroacetate (Example 20A) and 742 mg (5.74 mmol) of DIPEA are added, and the mixture is heated at 120° C. under argon for 16 h. Water is added, and the mixture is neutralized with 1N hydrochloric acid and extracted three times with ethyl acetate. The combined organic phases are freed of solvent, and the residue is purified by preparative HPLC. 48.4 mg (14% of theory) of the product are obtained as a solid.

LCMS (method 6): $R_t$=1.18 min. (m/z=445 (M+H)⁺)

¹H-NMR (400 MHz, DMSO-d₆): d=8.53 (t, 1H), 8.08 (t, 1H), 8.00 (s, 1H), 7.99 (s, 1H), 7.71 (d, 1H), 7.66 (d, 1H), 7.59 (s, 1H), 7.51 (dd, 1H), 7.13 (s, 1H), 6.70 (s, 1H), 3.70 (dt, 2H), 3.56 (dt, 2H).

Example 6

N-[7-(2,4-Dichlorophenyl)imidazo[1,2-c]pyrimidin-5-yl]-N'-(5-nitropyridin-2-yl)ethane-1,2-diamine

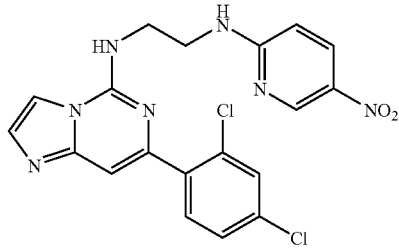

In analogy to the procedure for preparing Example 7A, the product is obtained as a solid by reacting 5-chloro-7-(2,4-dichlorophenyl)imidazo[1,2-c]pyrimidine (Example 6A) with N-(5-nitropyridin-2-yl)ethane-1,2-diamine.

LCMS (method 5): $R_t$=2.48 min. (m/z=444 (M+H)⁺)

¹H-NMR (400 MHz, DMSO-d₆): d=8.85 (s, 1H), 8.30 (s, 1H), 8.10 (s, 1H), 8.05 (s, 1H), 7.98 (s, 1H), 7.68 (s, 1H), 7.64 (d, 1H), 7.57 (d, 1H), 7.46 (dd, 1H), 7.10 (s, 1H), 6.48 (d, 1H), 3.73 (m, 4H).

Example 7

6-{[2-({7-[4-(Trifluoromethyl)phenyl]imidazo[1,2-c]pyrimidin-5-yl}amino)ethyl]amino}-nicotinonitrile

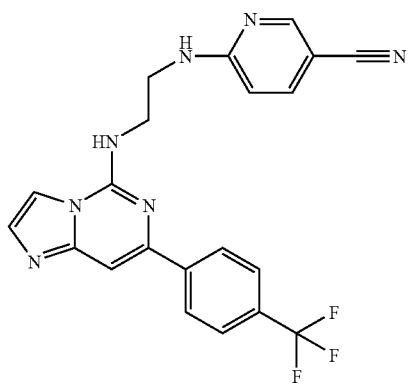

50 mg (0.123 mmol) of 6-({2-[(7-chloroimidazo[1,2-c]pyrimidin-5-yl)amino]ethyl}amino)-nicotinonitrile (Example 16A), 23.3 mg (0.123 mmol) of [4-(trifluoromethyl)phenyl]boronic acid and 14.18 mg (0.012 mmol) of tetrakis(triphenylphosphine)palladium(0) are introduced into a mixture of 2.5 ml of dioxane and 0.83 ml of saturated aqueous sodium carbonate solution under argon. The mixture is degassed with argon and then heated in a microwave at 150° C. for 30 min. Cooling is followed by filtration through an Extrelut® cartridge. Purification by preparative HPLC results in 43 mg (83% of theory) of the product as a solid.

LCMS (method 3): $R_t$=1.79 min. (m/z=424 (M+H)⁺)

¹H-NMR (400 MHz, DMSO-d₆): d=8.85 (t, 1H), 8.40 (s, 1H), 8.28 (d, 2H), 8.21 (d, 1H), 8.06 (d, 1H), 7.85 (d, 2H), 7.80 (t, 1H), 7.71 (s, 1H), 7.58 (d, 1H), 6.46 (d, 1H), 3.89 (dd, 2H), 3.71 (dd, 2H).

The following products are obtained by palladium-catalysed coupling with the appropriate boronic acids in analogy to the procedure described for Example 7:

| Example | Structure | Characterization |
|---|---|---|
| 8 | 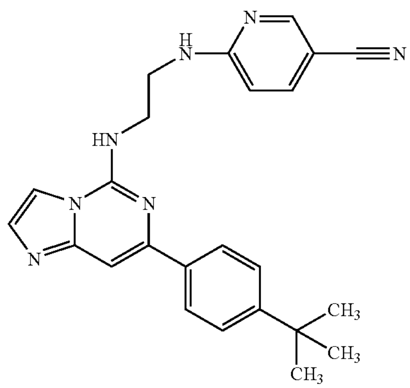 | LC/MS (method): R$_t$ = 2.89 min<br>MS (ESIpos): m/z = 412 (M + H)$^+$. |
| 9 | 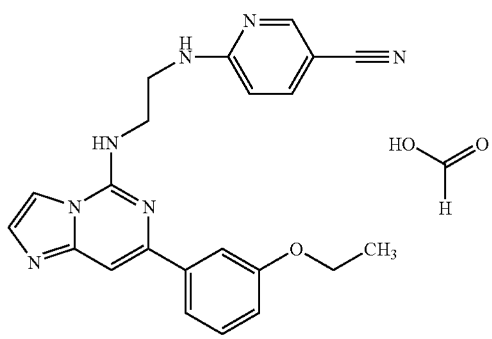 | LC/MS (method 3): R$_t$ = 1.60 min<br>MS (ESIpos): m/z = 400 (M + H)$^+$. |
| 10 | 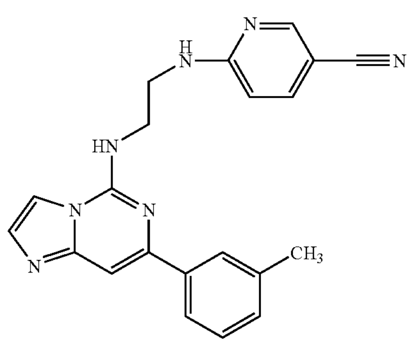 | LC/MS (method 3): R$_t$ = 1.59 min<br>MS (ESIpos): m/z = 370 (M + H)+. |
| 11 | 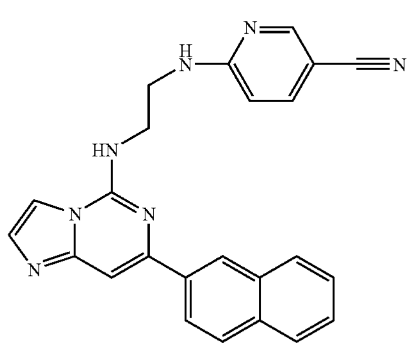 | LC/MS (method 5): R$_t$ = 2.28 min<br>MS (ESIpos): m/z = 406 (M + H)+. |

-continued
| Example | Structure | Characterization |
|---|---|---|
| 12 | 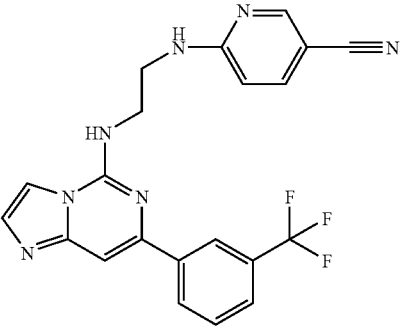 | LC/MS (method 3): $R_t$ = 1.74 min<br>MS (ESIpos): m/z = 424 (M + H)+. |
| 13 | 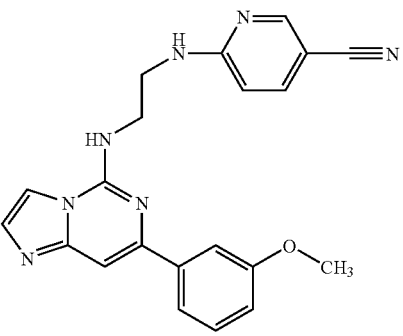 | LC/MS (method 3): $R_t$ = 1.51 min<br>MS (ESIpos): m/z = 386 (M + H)+. |
| 14 | 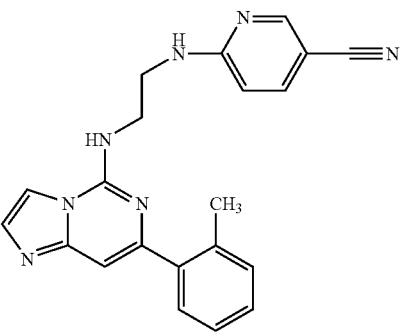 | LC/MS (method 3): $R_t$ = 1.53 min<br>MS (ESIpos): m/z = 370 (M + H)+. |
| 15 | 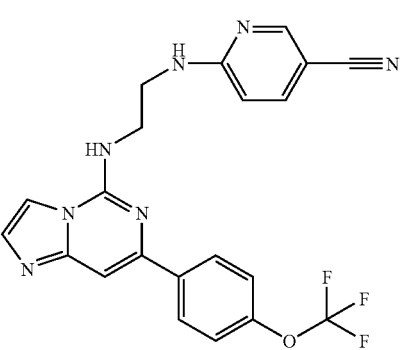 | LC/MS (method 3): $R_t$ = 1.80 min<br>MS (ESIpos): m/z = 440 (M + H)+. |

-continued
| Example | Structure | Characterization |
|---|---|---|
| 16 | 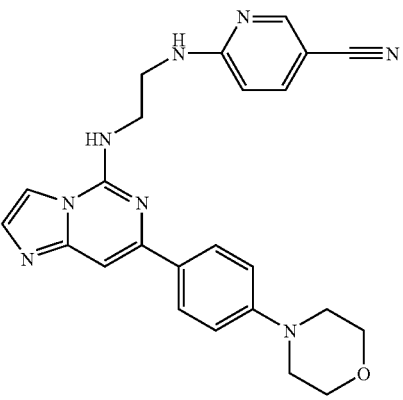 | LC/MS (method 2): R$_t$ = 2.64 min<br>MS (ESIpos): m/z = 441 (M + H)+. |
| 17 | 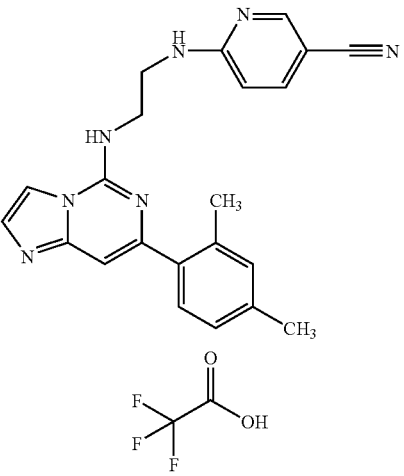 | LC/MS (method 3): R$_t$ = 1.61 min<br>MS (ESIpos): m/z = 384 (M + H)+. |
| 18 | 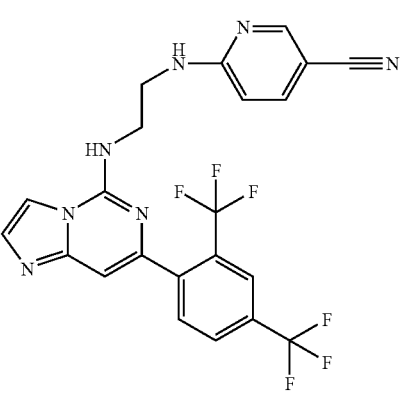 | LC/MS (method 7): R$_t$ = 2.90 min<br>MS (ESIpos): m/z = 492 (M + H)+. |
| 19 | 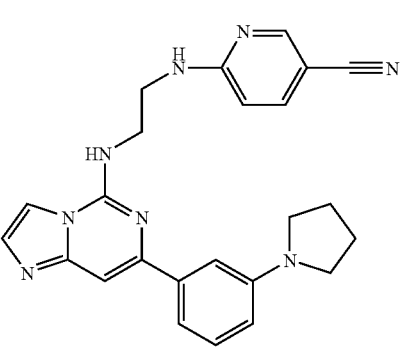 | LC/MS (method 3): R$_t$ = 1.74 min<br>MS (ESIpos): m/z = 425 (M + H)+. |

-continued

| Example | Structure | Characterization |
|---|---|---|
| 20 | 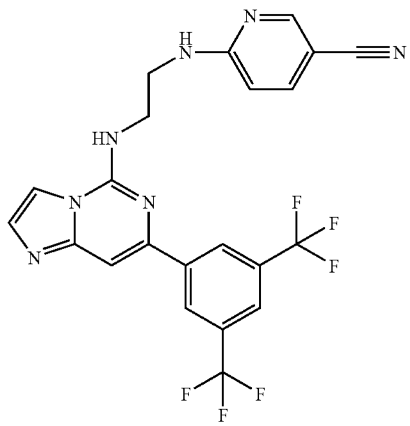 | LC/MS (method 3): R$_t$ = 2.07 min<br>MS (ESIpos): m/z = 492 (M + H)+. |
| 21 | 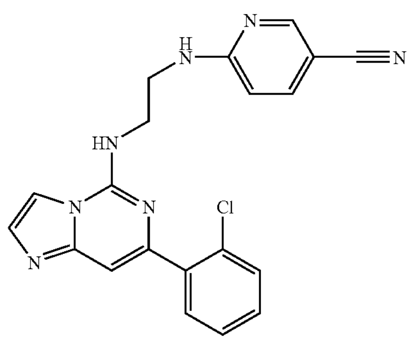 | LC/MS (method 5): R$_t$ = 1.94 min<br>MS (ESIpos): m/z = 390 (M + H)+. |
| 22 | 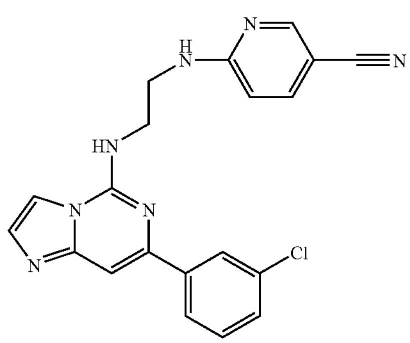 | LC/MS (method 5): R$_t$ = 2.13 min<br>MS (ESIpos): m/z = 390 (M + H)+. |
| 23 | 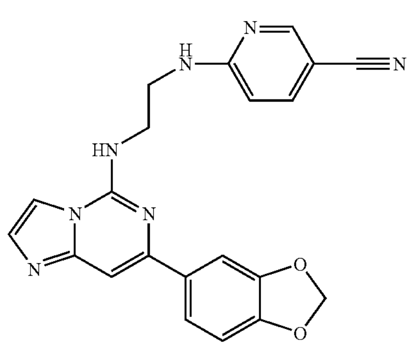 | LC/MS (method 7): R$_t$ = 2.09 min<br>MS (ESIpos): m/z = 400 (M + H)+. |

-continued
| Example | Structure | Characterization |
|---|---|---|
| 24 | 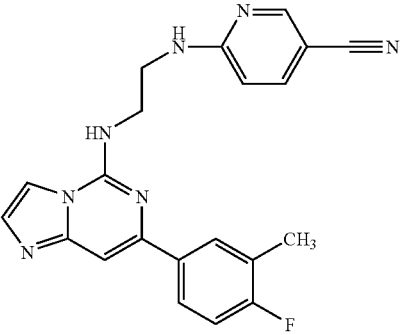 | LC/MS (method 5): R$_t$ = 2.16 min<br>MS (ESIpos): m/z = 388 (M + H)+. |
| 25 | 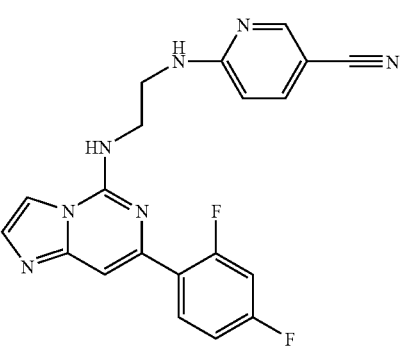 | LC/MS (method 6): R$_t$ = 1.1 min<br>MS (ESIpos): m/z = 392 (M + H)+. |
| 26 | 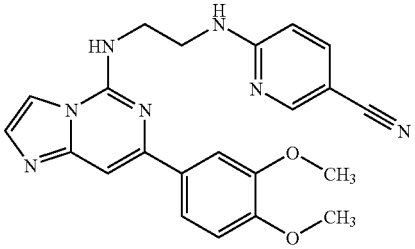 | LC/MS (method 7): R$_t$ = 1.94 min<br>MS (ESIpos): m/z = 416 (M + H)+. |
| 27 | 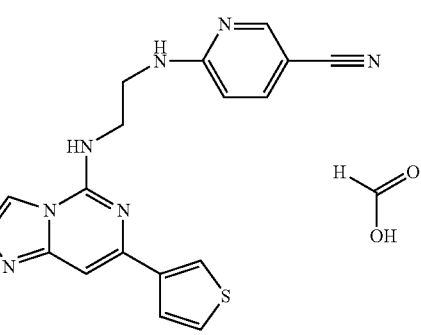 | LC/MS (method 5): R$_t$ = 1.83 min<br>MS (ESIpos): m/z = 362 (M + H)+. |
| 28 | 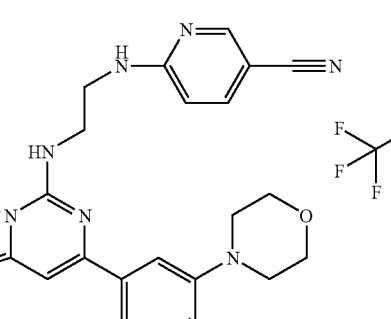 | LC/MS (method 6): R$_t$ = 1.01 min<br>MS (ESIpos): m/z = 441 (M + H)+. |

| Example | Structure | Characterization |
|---|---|---|
| 29 | 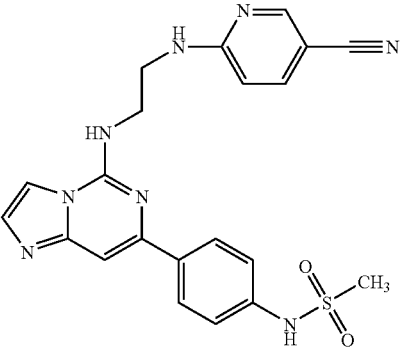 | LC/MS (method 6): $R_t$ = 0.87 min<br>MS (ESIpos): m/z = 449 (M + H)+. |
| 30 | 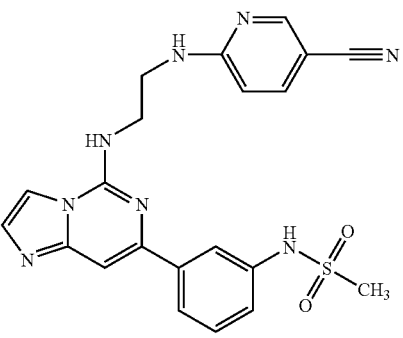 | LC/MS (method 6): $R_t$ = 1.09 min<br>MS (ESIpos): m/z = 449 (M + H)+. |

The following products are obtained by palladium-catalysed coupling with the appropriate boronic acids in analogy to the procedure described for Example 7 starting from $N^6$-{2-[(7-chloroimidazo[1,2-c]pyrimidin-5-yl)amino]ethyl}-3-nitropyridine-2,6-diamine (Example 17A):

| Example | Structure | Characterization |
|---|---|---|
| 31 | 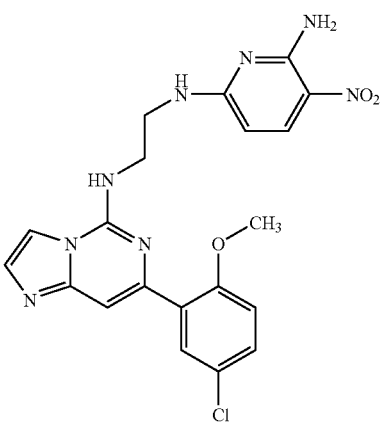 | LC/MS (method 6): $R_t$ = 1.30 min<br>MS (ESIpos): m/z = 455 (M + H)$^+$. |

| Example | Structure | Characterization |
|---|---|---|
| 32 | 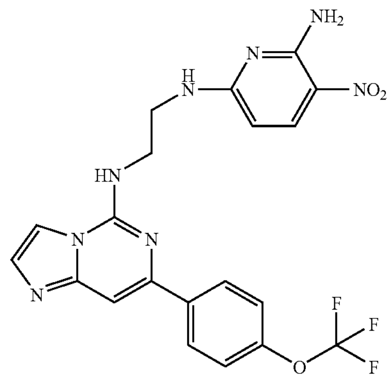 | LC/MS (method 4): $R_t$ = 3.07 min<br>MS (ESIpos): m/z = 475 (M + H)$^+$. |
| 33 | 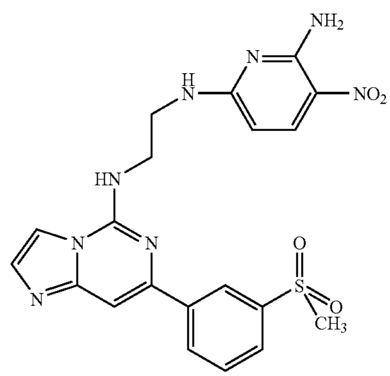 | LC/MS (method 7): $R_t$ = 1.65 min<br>MS (ESIpos): m/z = 469 (M + H)+. |
| 34 | 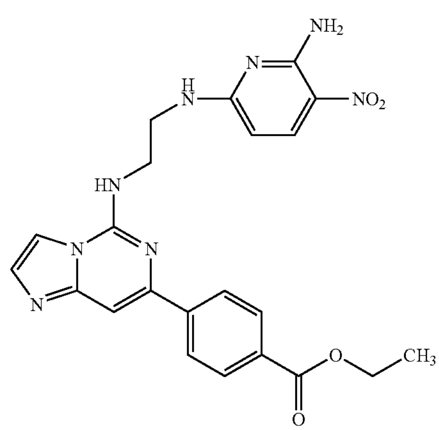 | LC/MS (method 7): $R_t$ = 2.34 min<br>MS (ESIpos): m/z = 463 (M + H)+. |

-continued
| Example | Structure | Characterization |
|---|---|---|
| 35 | 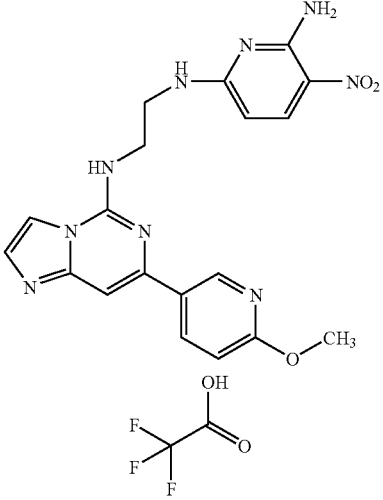 | LC/MS (method 6): $R_t$ = 0.91 min<br>MS (ESIpos): m/z = 422 (M + H)+. |
| 36 | 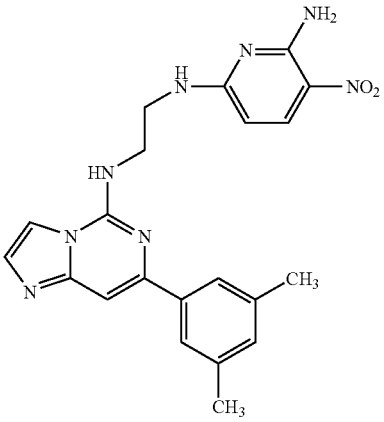 | LC/MS (method 7): $R_t$ = 2.49 min<br>MS (ESIpos): m/z = 419 (M + H)+. |
| 37 | 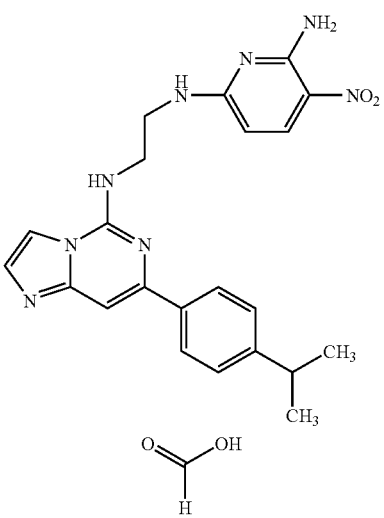 | LC/MS (method 3): $R_t$ = 1.74 min<br>MS (ESIpos): m/z = 433 (M + H)+. |

-continued
| Example | Structure | Characterization |
|---------|-----------|------------------|
| 38 | 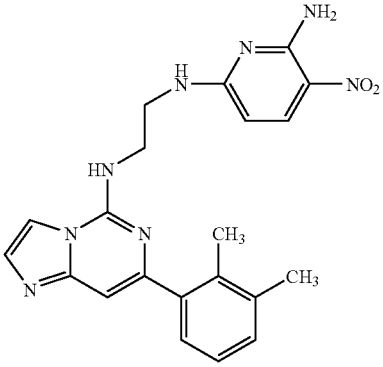 | LC/MS (method 6): R$_t$ = 1.29 min<br>MS (ESIpos): m/z = 419 (M + H)+. |
| 39 | 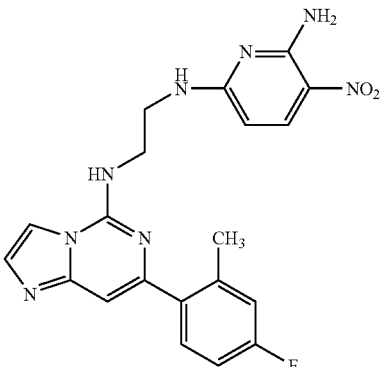 | LC/MS (method 3): R$_t$ = 1.54 min<br>MS (ESIpos): m/z = 423 (M + H)+. |
| 40 | 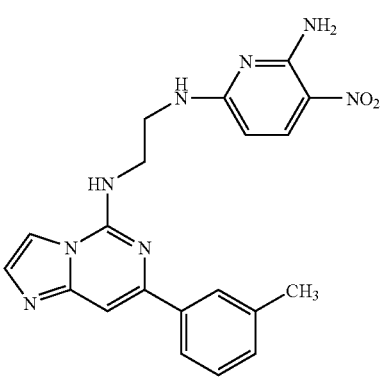 | LC/MS (method 3): R$_t$ = 1.55 min<br>MS (ESIpos): m/z = 405 (M + H)+. |

| Example | Structure | Characterization |
|---------|-----------|------------------|
| 41 | 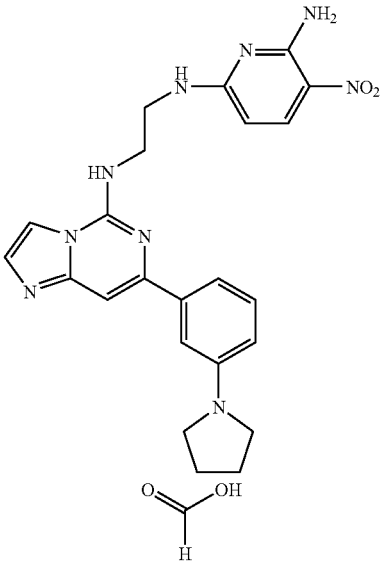 | LC/MS (method 5): R$_t$ = 2.31 min<br>MS (ESIpos): m/z = 460 (M + H)+. |
| 42 | 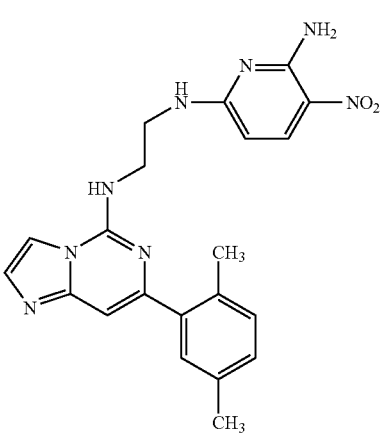 | LC/MS (method 3): R$_t$ = 1.58 min<br>MS (ESIpos): m/z = 419 (M + H)+. |
| 43 | 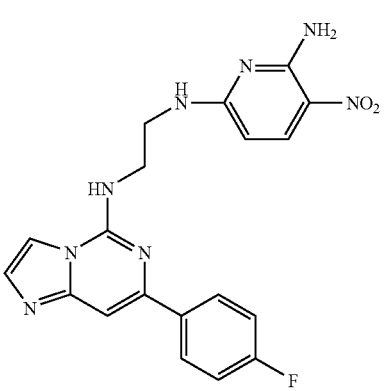 | LC/MS (method 3): R$_t$ = 1.50 min<br>MS (ESIpos): m/z = 409 (M + H)+. |

-continued
| Example | Structure | Characterization |
|---|---|---|
| 44 | 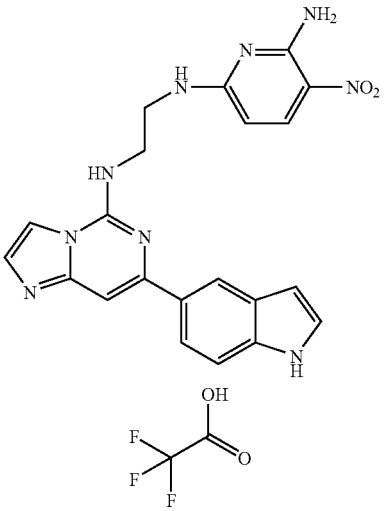 | LC/MS (method 6): $R_t$ = 1.70 min<br>MS (ESIpos): m/z = 530 (M + H)+. |
| 45 | 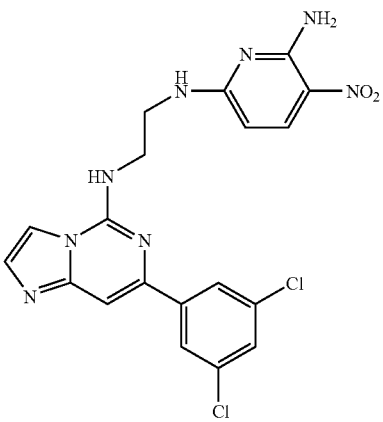 | LC/MS (method 7): $R_t$ = 2.68 min<br>MS (ESIpos): m/z = 459 (M + H)+. |
| 46 | 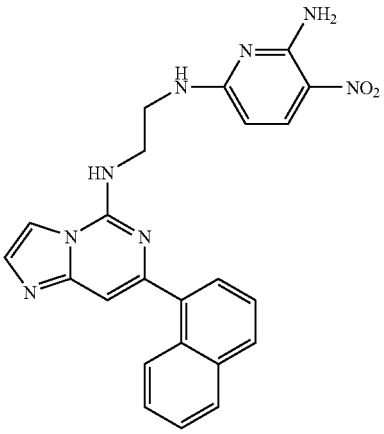 | LC/MS (method 3): $R_t$ = 1.60 min<br>MS (ESIpos): m/z = 441 (M + H)+. |

| Example | Structure | Characterization |
|---|---|---|
| 47 | 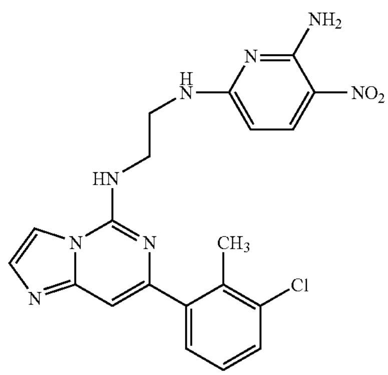 | LC/MS (method 7): R$_t$ = 3.08 min<br>MS (ESIpos): m/z = 439 (M + H)+. |
| 48 | 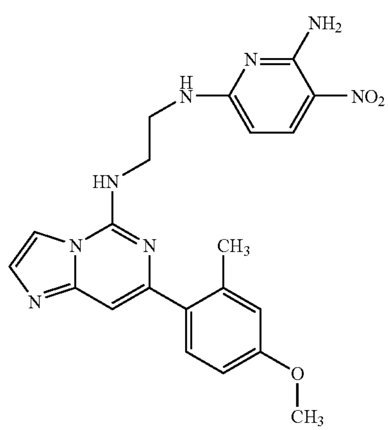 | LC/MS (method 3): R$_t$ = 1.45 min<br>MS (ESIpos): m/z = 435 (M + H)+. |
| 49 | 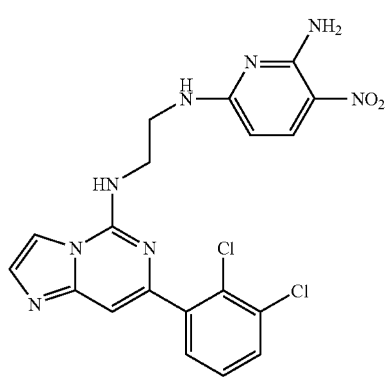 | LC/MS (method 3): R$_t$ = 1.66 min<br>MS (ESIpos): m/z = 459 (M + H)+. |
| 50 | 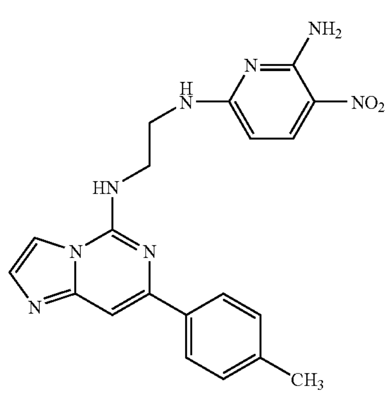 | LC/MS (method 3): R$_t$ = 1.59 min<br>MS (ESIpos): m/z = 405 (M + H)+. |

-continued
| Example | Structure | Characterization |
|---------|-----------|------------------|
| 51 | 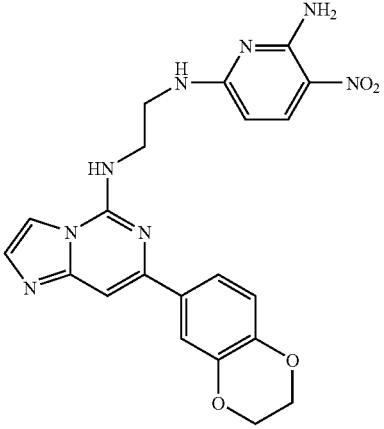 | LC/MS (method 7): $R_t$ = 2.01 min<br>MS (ESIpos): m/z = 449 (M + H)+. |
| 52 | 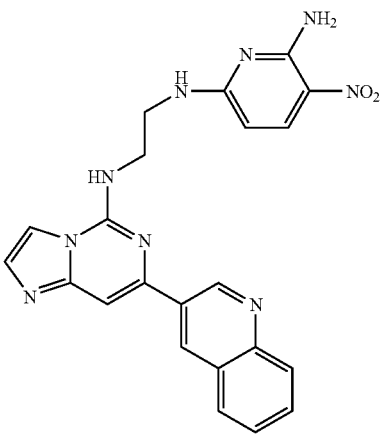 | LC/MS (method 5): $R_t$ = 2.90 min<br>MS (ESIpos): m/z = 441 (M + H)+. |
| 53 | 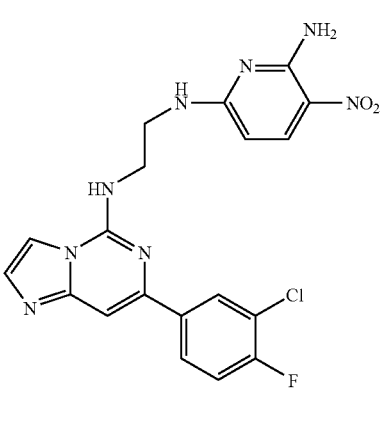 | LC/MS (method 3): $R_t$ = 1.65 min<br>MS (ESIpos): m/z = 443 (M + H)+. |

-continued
| Example | Structure | Characterization |
|---|---|---|
| 54 | 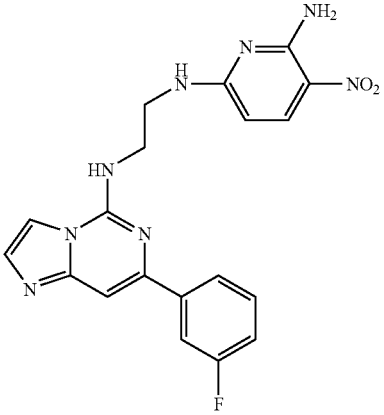 | LC/MS (method 3): $R_t$ = 1.51 min<br>MS (ESIpos): m/z = 409 (M + H)+. |
| 55 | 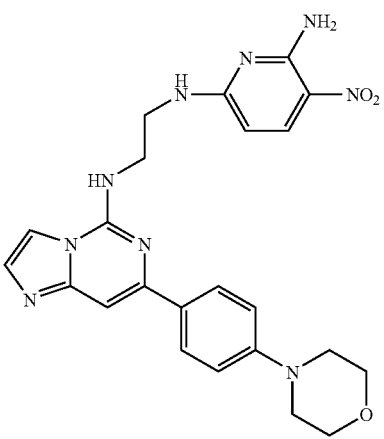 | LC/MS (method 6): $R_t$ = 1.01 min<br>MS (ESIpos): m/z = 476 (M + H)+. |
| 56 | 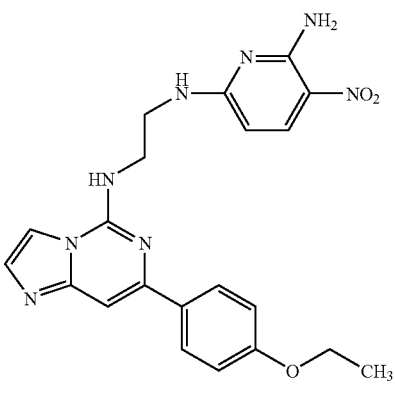 | LC/MS (method 6): $R_t$ = 1.12 min<br>MS (ESIpos): m/z = 435 (M + H)+. |

-continued
| Example | Structure | Characterization |
|---|---|---|
| 57 | 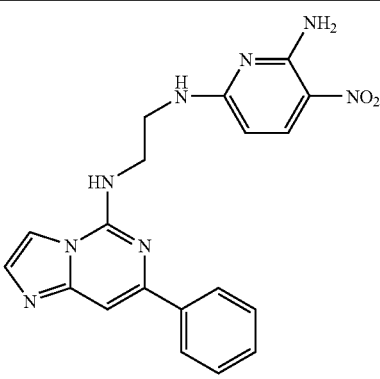 | LC/MS (method 3): $R_t$ = 1.45 min<br>MS (ESIpos): m/z = 391 (M + H)+. |
| 58 | 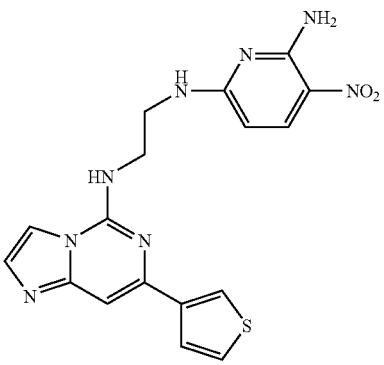 | LC/MS (method 5): $R_t$ = 2.94 min<br>MS (ESIpos): m/z = 397 (M + H)+. |
| 59 | 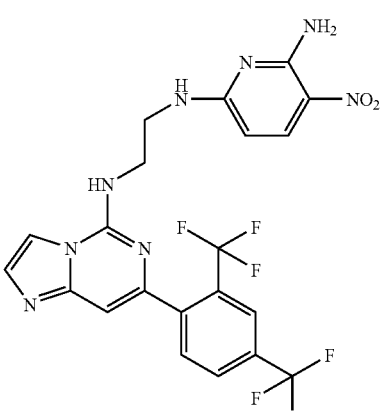 | LC/MS (method 5): $R_t$ = 2.71 min<br>MS (ESIpos): m/z = 527 (M + H)+. |
| 60 | 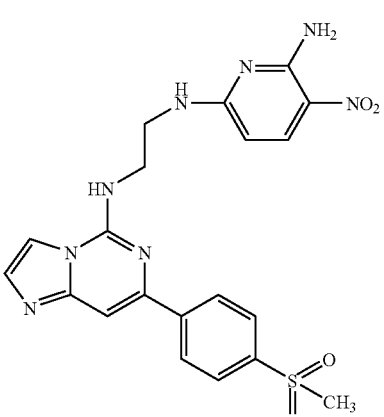 | LC/MS (method 5): $R_t$ = 1.42 min<br>MS (ESIpos): m/z = 469 (M + H)+. |

-continued

| Example | Structure | Characterization |
|---|---|---|
| 61 | 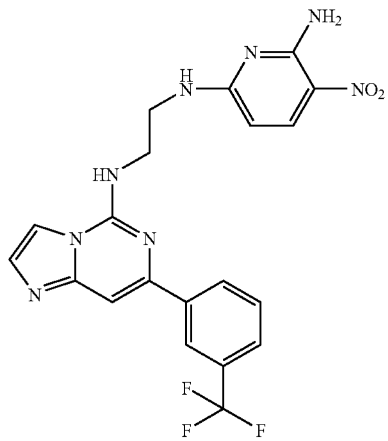 | LC/MS (method 3): R$_t$ = 1.70 min<br>MS (ESIpos): m/z = 459 (M + H)+. |
| 62 | 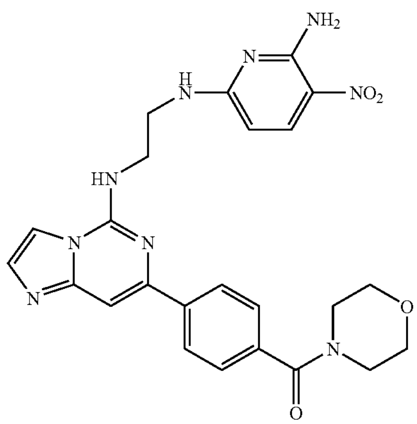 | LC/MS (method 6): R$_t$ = 1.02 min<br>MS (ESIpos): m/z = 504 (M + H)+. |
| 63 | 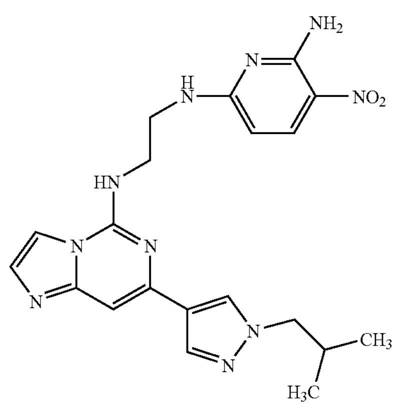 | LC/MS (method 3): R$_t$ = 1.45 min<br>MS (ESIpos): m/z = 437 (M + H)+. |
| 64 | 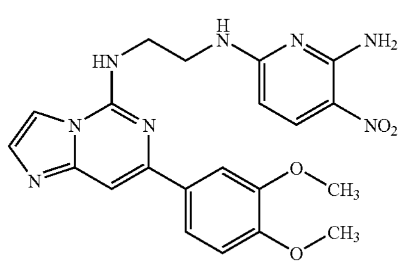 | LC/MS (method 3): R$_t$ = 1.37 min<br>MS (ESIpos): m/z = 451 (M + H)+. |

-continued

| Example | Structure | Characterization |
|---|---|---|
| 65 | 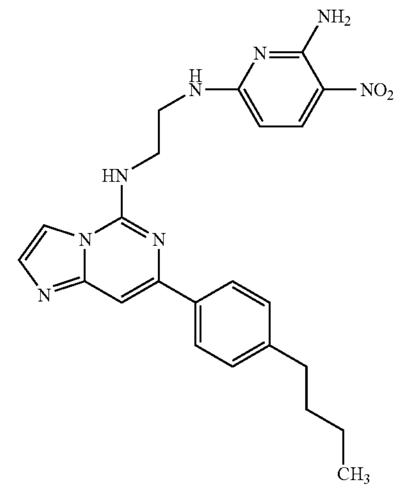 | LC/MS (method 6): R$_t$ = 1.43 min<br>MS (ESIpos): m/z = 447 (M + H)+. |
| 66 | 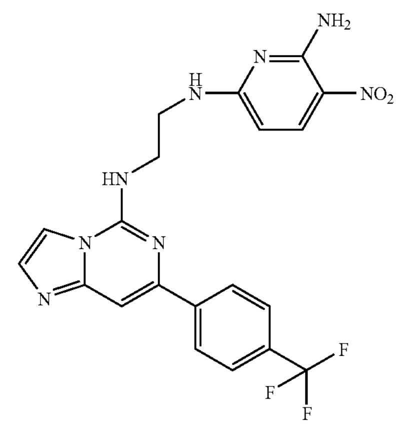 | LC/MS (method 5): R$_t$ = 2.35 min<br>MS (ESIpos): m/z = 459 (M + H)+. |
| 67 | 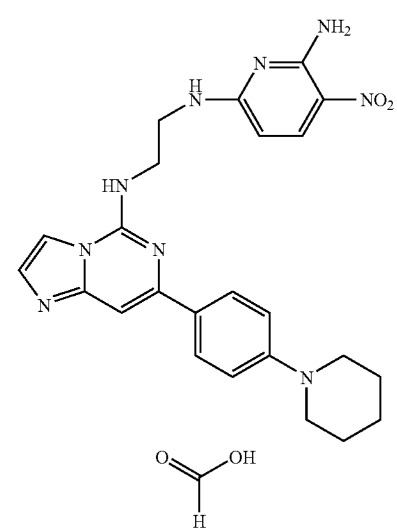 | LC/MS (method): R$_t$ = 2.08 min<br>MS (ESIpos): m/z = 474 (M + H)+. |

-continued
| Example | Structure | Characterization |
|---|---|---|
| 68 | 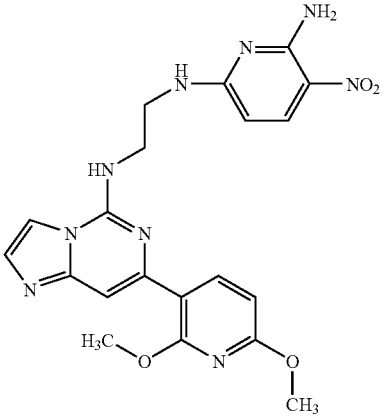 | LC/MS (method 6): $R_t$ = 1.31 min<br>MS (ESIpos): m/z = 452 (M + H)+. |
| 69 | 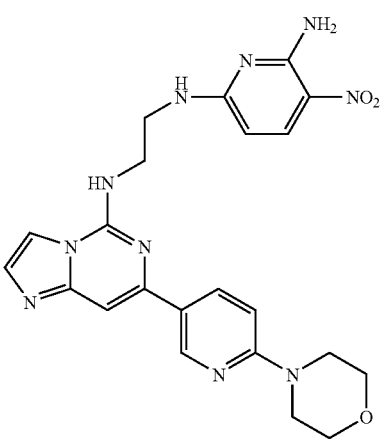 | LC/MS (method 6): $R_t$ = 0.79 min<br>MS (ESIpos): m/z = 477 (M + H)+. |
| 70 | 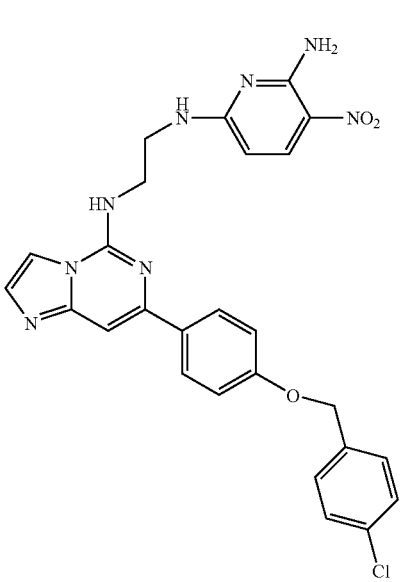 | LC/MS (method 5): $R_t$ = 2.91 min<br>MS (ESIpos): m/z = 531 (M + H)+. |

-continued

| Example | Structure | Characterization |
|---------|-----------|------------------|
| 71 | 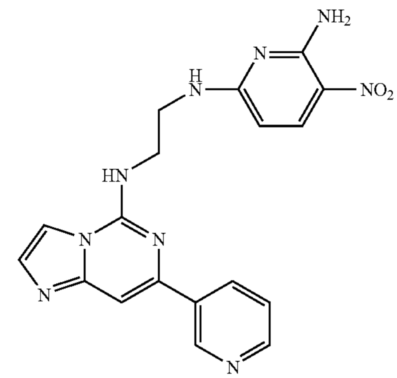 | LC/MS (method 6): R$_t$ = 0.63 min<br>MS (ESIpos): m/z = 392 (M + H)+. |
| 72 | 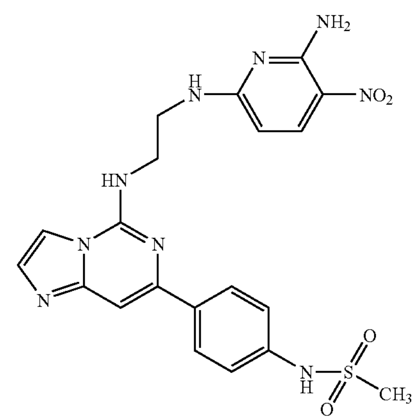 | LC/MS (method 6): R$_t$ = 0.84 min<br>MS (ESIpos): m/z = 484 (M + H)+. |
| 73 | 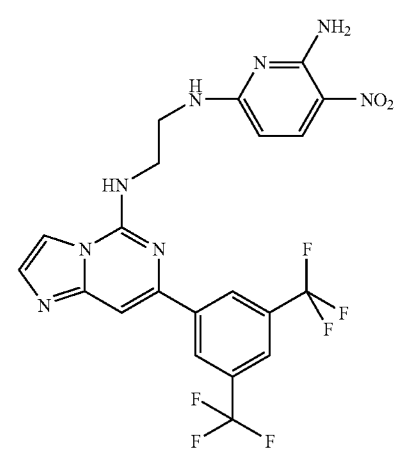 | LC/MS (method 3): R$_t$ = 2.03 min<br>MS (ESIpos): m/z = 527 (M + H)+. |

| Example | Structure | Characterization |
|---|---|---|
| 74 | 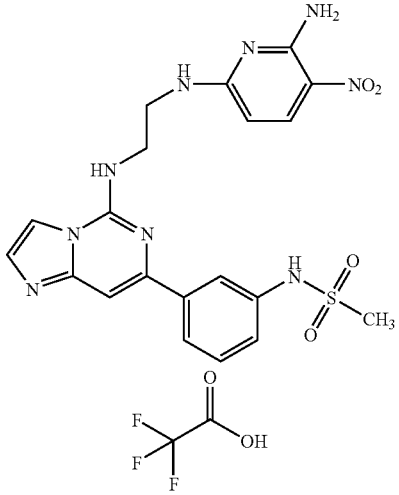 | LC/MS (method 6): $R_t$ = 0.86 min<br>MS (ESIpos): m/z = 484 (M + H)+. |
| 75 | 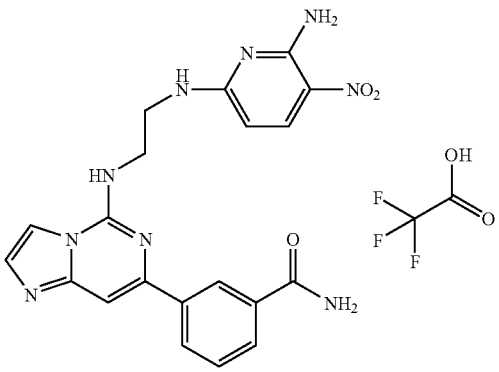 | LC/MS (method 6): $R_t$ = 0.71 min<br>MS (ESIpos): m/z = 434 (M + H)+. |

Example 76

$N^6$-(2-{[7-(2,4-Dichlorophenyl)imidazo[1,2-c]pyrimidin-5-yl]amino}ethyl)-$N^6$-methyl-3-nitropyridine-2,6-diamine formate

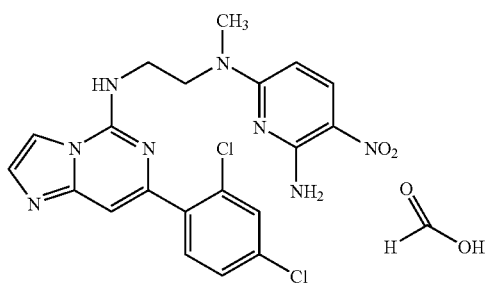

In analogy to the procedure for preparing Example 5, the product is obtained by reacting 5-chloro-7-(2,4-dichlorophenyl)imidazo[1,2-c]pyrimidine (Example 6A) with $N^6$-(2-aminoethyl)-$N^6$-methyl-3-nitropyridine-2,6-diamine formate (preparation analogous to Example 14A).

LCMS (method 7): $R_t$=2.67 min. (m/z=473 (M+H)$^+$)

$^1$H-NMR (400 MHz, DMSO-$d_6$): d=12.74 (s, 1H), 8.20 (s, 1H), 8.13 (s, 1H), 7.97 (s, 1H), 7.93 (s, 1H), 7.73 (s, 1H), 7.67 (d, 1H), 7.58 (s, 1H), 7.49 (d, 1H), 7.10 (s, 1H), 6.37 (s, br, 1H), 6.10 (s, br, 1H), 3.73 (s, br, 2H), 3.14 (s, br, 2H), 2.54 (s, 3H).

Example 77

$N^6$-(2-{[7-(2,4-Dichlorophenyl)-2-methylimidazo[1,2-c]pyrimidin-5-yl]amino}ethyl)-3-nitropyridine-2,6-diamine

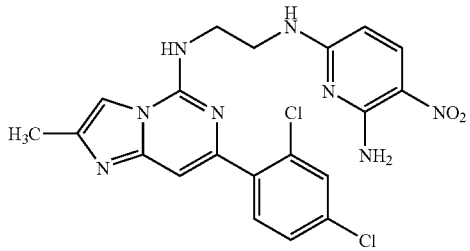

In analogy to the procedure described for Example 7, 9.3 mg (13% of theory) of the product are obtained starting from 60 mg (0.15 mmol) of $N^6$-{2-[(7-chloro-2-methylimidazo[1,2-c]pyrimidin-5-yl)amino]ethyl}-3-nitropyridine-2,6-diamine (Example 23A) by coupling with 29.3 mg (0.15 mmol) of (2,4-dichlorophenyl)boronic acid and subsequent purification by preparative HPLC.

LCMS (method 7): $R_t$=2.67 min. (m/z=473 (M+H)$^+$)

$^1$H-NMR (400 MHz, DMSO-$d_6$): d=8.05 (s, br, 1H), 7.88 (d, 1H), 7.83 (s, 1H), 7.68 (d, 1H), 7.65 (d, 1H), 7.45 (d, 1H), 7.00 (s, 1H), 5.90 (d, 1H), 3.71 (s, br, 4H), 3.67 (s, br, 4H), 2.32 (s, 3H).

Example 78

6-[(2-{[7-(2,4-Dichlorophenyl)-2-methylimidazo[1,2-c]pyrimidin-5-yl]amino}ethyl)amino]-nicotinonitrile

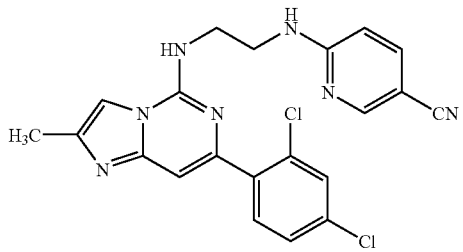

In analogy to the procedure described for Example 7, 11.9 mg (7% of theory) of the product are obtained starting from 120 mg (0.36 mmol) of 6-({2-[(7-chloro-2-methylimidazo[1,2-c]pyrimidin-5-yl)amino]ethyl}amino)nicotinonitrile (Example 30A) by coupling with 68.4 mg (0.36 mmol) of (2,4-dichlorophenyl)boronic acid and subsequent purification by preparative HPLC.

LCMS (method 3): $R_t$=1.76 min. (m/z=438 (M+H)$^+$)

$^1$H-NMR (400 MHz, DMSO-$d_6$): d=8.67 (s, br, 1H), 8.32 (s, 1H), 7.93 (s, 1H), 7.77 (d, 1H), 7.70 (s, br, 2H), 7.65 (d, 1H), 7.57 (dt, 1H), 7.29 (s, 1H), 6.48 (d, 1H), 3.74 (dd, 2H), 3.65 (dd, 2H), 2.45 (s, 3H).

Example 79

N$^6$-(2-{[7-(2,4-Dichlorophenyl)-2-(trifluoromethyl)imidazo[1,2-c]pyrimidin-5-1]amino}ethyl)-3-nitropyridine-2,6-diamine

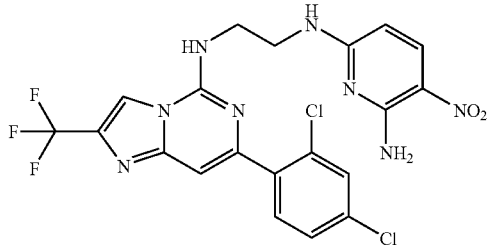

In analogy to the procedure described for Example 7, 23.5 mg (30% of theory) of the product are obtained as a solid starting from 68 mg (0.15 mmol) of N$^6$-{2-[(7-chloro-2-methylimidazo[1,2-c]pyrimidin-5-yl)amino]ethyl}-3-nitropyridine-2,6-diamine (Example 25A) by coupling with 28 mg (0.15 mmol) of (2,4-dichlorophenyl)boronic acid and subsequent purification by preparative HPLC.

LCMS (method 3): $R_t$=2.84 min. (m/z=527 (M+H)$^+$)

$^1$H-NMR (400 MHz, DMSO-$d_6$): d=8.61 (s, 1H), 8.23 (t, 1H), 8.12 (s, br, 1H), 8.04 (t, 1H), 7.87 (d, 1H), 7.72 (s, 1H), 7.63 (d, 2H), 7.47 (d, 1H), 7.19 (s, 1H), 5.86 (d, 1H), 3.75 (dd, 2H), 3.68 (dd, 2H).

Example 80

6-[(2-{[7-(2,4-Dichlorophenyl)-2-(trifluoromethyl)imidazo[1,2-c]pyrimidin-5-yl]amino}ethyl)-amino]nicotinonitrile

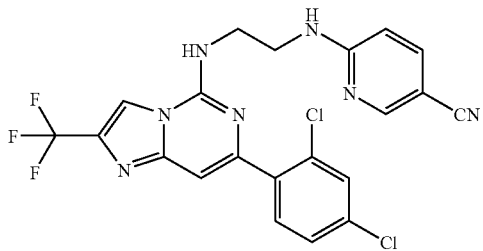

In analogy to the procedure described for Example 7, 11.4 mg (33% of theory) of the product are obtained as a solid starting from 29 mg (0.07 mmol) of 6-[(2-{[7-chloro-2-(trifluoromethyl)imidazo[1,2-c]pyrimidin-5-yl]amino}ethyl)amino]nicotinonitrile (Example 24A) by coupling with 13 mg (0.07 mmol) of (2,4-dichlorophenyl)boronic acid and subsequent purification by preparative HPLC.

LCMS (method 5): $R_t$=3.89 min. (m/z=492 (M+H)$^+$)

$^1$H-NMR (400 MHz, DMSO-$d_6$): d=8.59 (s, 1H), 8.32 (d, 2H), 7.74 (s, br, 2H), 7.62 (d, 1H), 7.58 (d, 1H), 7.52 (d, 1H), 7.18 (s, 1H), 6.48 (d, 1H), 3.70 (dd, 2H), 3.65 (dd, 2H).

Example 81

N$^6$-(2-{[7-(2,4-Dichlorophenyl)-2-(morpholin-4-ylmethyl)imidazo[1,2-c]pyrimidin-5-yl]amino}ethyl)-3-nitropyridine-2,6-diamine trifluoroacetate

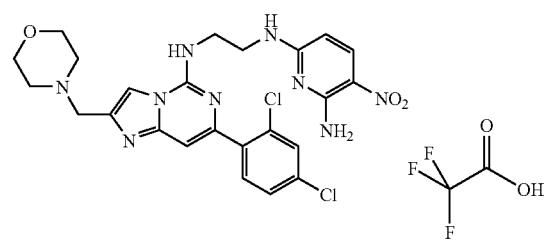

In analogy to the procedure described for Example 7, 7.9 mg (8% of theory) of the product are obtained starting from 60 mg (0.13 mmol) of N$^6$-(2-{[7-chloro-2-(morpholin-4-ylmethyl)imidazo[1,2-c]pyrimidin-5-yl]amino}ethyl)-3-nitropyridine-2,6-diamine (Example 35A) by coupling with 25.6 mg (0.07 mmol) of (2,4-dichlorophenyl)boronic acid and subsequent purification by preparative HPLC.

LCMS (method 6): $R_t$=1.28 min. (m/z=558 (M+H)$^+$)

$^1$H-NMR (400 MHz, DMSO-$d_6$): d=8.21 (s, br, 1H), 8.10 (s, 1H), 8.03 (s, br, 1H), 7.89 (d, 1H), 7.72 (s, 1H), 7.66 (d, 1H), 7.49 (d, 1H), 7.13 (s, 1H), 5.89 (d, 1H), 5.74 (s, 1H), 4.47 (s, br, 2H), 3.82 (m, br, 8H), 3.74 (s, br, 2H), 3.69 (s, br, 2H).

Example 82

6-[(2-{[7-(2,4-Dichlorophenyl)imidazo[1,2-c]pyrimidin-5-yl]amino}propyl)amino]-nicotinonitrile

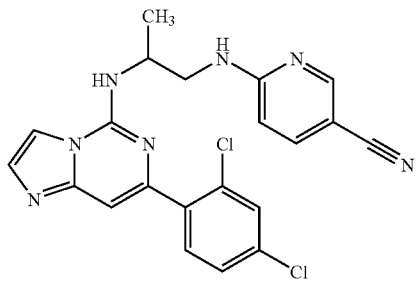

The amine (Example 37A) (300 mg, 0.46 mmol), 2-chloro-5-cyanopyridine (129 mg, 0.93 mmol) and N,N-diisopropylethylamine (600 mg, 4.6 mmol) are introduced into DMSO (6 ml), and heated at 150° C. in a microwave oven for 30 min. The reaction mixture is poured into water and extracted with ethyl acetate (3×25 ml). The combined organic phases are washed with saturated aqueous sodium chloride solution, dried over magnesium sulphate and concentrated. The residue is taken up in acetonitrile, and the product precipitates and is washed with acetonitrile and dried. 87 mg (41% of theory) of the product are obtained as a solid.

LCMS (method 3): $R_t$=1.86 min. (m/z=439 (M+H)$^+$)
$^1$H-NMR (400 MHz, DMSO-d$_6$): d=8.31 (d, 1H), 8.07 (s, 1H), 7.76 (t, 1H), 7.70 (d, 1H), 7.65 (d, 1H), 7.59 (d, 1H), 7.52 (m, 3H), 7.10 (s, 1H), 6.50 (br s, 1H), 4.56 (br m, 1H), 3.45 (m, 2H), 1.31 (d, 3H).

Enantiomer separation of 6-[(2-{[7-(2,4-dichlorophenyl)imidazo[1,2-c]pyrimidin-5-yl]amino}propyl)amino]nicotinonitrile (Example 82) is carried out under the following conditions:

A sample of Example 82 (87 mg) is taken up in ethanol:acetonitrile (4:1, 100 ml) and chromatographed on a Daicel Chiralpak AD-H 250 mm×20 mm column (flow rate: 15 ml/min; detection at 230 nm; volume injected: 500 µl; eluent iso-hexane:ethanol:N,N-diisopropylethylamine (350:150:1), temperature: 40° C.). Two fractions are isolated:
Example Ent-A-82: 27 mg of product are isolated in >99% ee.
Retention time 4.38 min
Example Ent-B-82: 24 mg of product are isolated in >99% ee.
Retention time 5.85 min

Example 83

N$^6$-(2-{[7-(2,4-Dichlorophenyl)imidazo[1,2-c]pyrimidin-5-yl]amino}propyl)-3-nitropyridine-2,6-diamine

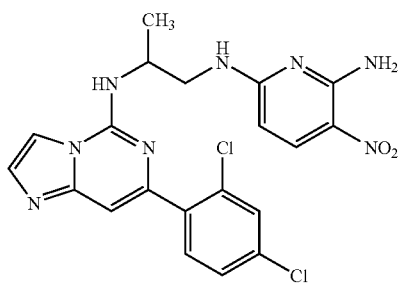

N$^6$-(2-{[7-(2,4-Dichlorophenyl)imidazo[1,2-c]pyrimidin-5-yl]amino}propyl)-3-nitropyridine-2,6-diamine (Example 83) is prepared in analogy to Example 82 from Example 37A (300 mg, 0.47 mmol), 2-amino-6-chloro-3-nitropyridine (161 mg, 0.93 mmol) and N,N-diisopropylethylamine (600 mg, 4.6 mmol). The crude product is reprecipitated from N,N-dimethylformamide and acetonitrile. The product is filtered off and washed with acetonitrile and dried. 99 mg (45% of theory) of the product are obtained as a solid.

LCMS (method 3): $R_t$=1.78 min. (m/z=473 (M+H)$^+$)
$^1$H-NMR (400 MHz, DMSO-d$_6$): d=8.07 (br m, 3H), 7.85 (d, 1H), 7.64 (m, 3H), 7.58 (m, 2H), 7.38 (dd, 1H), 7.12 (s, 1H), 5.38 (d, 1H), 4.60 (br m, 1H), 3.75 (m, 1H), 3.47 (s, 1H), 1.33 (d, 3H).

Enantiomer separation of N$^6$-(2-{[7-(2,4-dichlorophenyl)imidazo[1,2-c]pyrimidin-5-yl]-amino}propyl)-3-nitropyridine-2,6-diamine (Example 83) is carried out under the following conditions:

A sample of 99 mg of Example 83 is taken up in hot ethanol:acetonitrile (4:1, 80 ml) and chromatographed on a Daicel Chiralpak AD-H 5 µM 250 mm×20 mm column (flow rate: 15 ml/min; detection at 220 nm; volume injected 700 µl; eluent isohexane:ethanol:N,N-diisopropylethylamine (350:150:1), temperature: 40° C.). Two fractions are isolated:
Example Ent-A-83: 23 mg of product are isolated in >99.5% ee.
Retention time 4.88 min
Example Ent-B-83: 28 mg of product are isolated in >98% ee.
Retention time 5.93 min

Example 84

6-[(2-{[7-(2,4-Dichlorophenyl)imidazo[1,2-c]pyrimidin-5-yl]amino}-1-methylethyl)amino]-nicotinonitrile

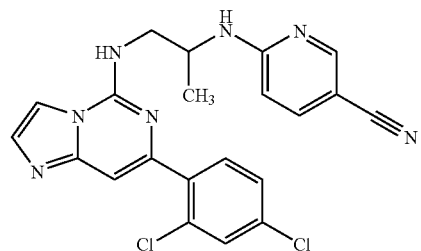

6-[(2-{[7-(2,4-Dichlorophenyl)imidazo[1,2-c]pyrimidin-5-yl]amino}-1-methylethyl)amino]-nicotinonitrile (Example 84) is prepared in analogy to Example 82 from Example 40A (187 mg, 0.63 mmol), 5-chloro-7-(2,4-dichlorophenyl)imidazo[1,2-c]pyrimidine (Example 6A) (273 mg, 0.94 mmol) and N,N-diisopropylethylamine (810 mg, 6.3 mmol). The crude product is precipitated from acetonitrile, and the product is filtered off and washed with acetonitrile and diethyl ether and dried. 220 mg (75% of theory) of the product are obtained as a solid.

LCMS (method 3): $R_t$=1.85 min. (m/z=438 (M+H)$^+$)
$^1$H-NMR (400 MHz, DMSO-d$_6$): d=8.29 (d, 1H), 8.08 (s, 2H), 7.72 (s, 1H), 7.65 (d, 1H), 7.58 (d, 2H), 7.50 (d, 2H), 7.11 (s, 1H), 6.49 (br s, 1H), 4.43 (br m, 1H), 3.80 (br m, 1H), 3.55 (br m, 1H), 1.22 (d, 3H).

Enantiomer separation of 6-[(2-{[7-(2,4-dichlorophenyl)imidazo[1,2-c]pyrimidin-5-yl]amino}-1-methylethyl)amino]nicotinonitrile (Example 84) is carried out under the following conditions:

A sample of 220 mg of Example 84 is taken up in hot 2-propanol:acetonitrile (4:1, 160 ml) and chromatographed on a Daicel Chiralpak AD-H 5 μm 250 mm×20 mm column (flow rate: 15 ml/min; detection at 220 nm; volume injected: 500 μl; eluent isohexane:2-propanol:N,N-diisopropylethylamine (400:100:1), temperature: 40° C.). Two fractions are isolated:

Example Ent-A-84: 63 mg of product are isolated in >99% ee.

Retention time 5.22 min

Example Ent-B-84: 59 mg of product can be isolated in >97% ee.

Retention time 5.98 min

Example 85

$N^6$-(2-{[7-(2,4-Dichlorophenyl)imidazo[1,2-c]pyrimidin-5-yl]amino}-1-methylethyl)-3-nitropyridine-2,6-diamine

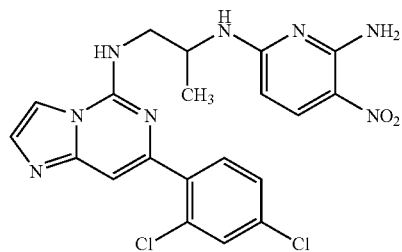

$N^6$-(2-{[7-(2,4-Dichlorophenyl)imidazo[1,2-c]pyrimidin-5-yl]amino}-1-methylethyl)-3-nitropyridine-2,6-diamine (Example 85) is prepared in analogy to Example 82 from Example 41A (467 mg, 1.0 mmol), 5-chloro-7-(2,4-dichlorophenyl)imidazo[1,2-c]pyrimidine (Example 6A) (200 mg, 0.67 mmol) and N,N-diisopropylethylamine (866 mg, 6.7 mmol). The crude product is precipitated from acetonitrile, and the product is filtered off and washed with acetonitrile and diethyl ether and dried. 234 mg (72% of theory) of product are obtained as a solid.

LCMS (method 3): $R_t$=1.80 min. (m/z=473 (M+H)$^+$)

$^1$H-NMR (400 MHz, DMSO-d$_6$): d=8.04 (br s, 2H), 7.94 (br t, 1H), 7.87 (d, 1H), 7.83 (d, 1H), 7.69 (s, 1H), 7.64 (d, 1H), 7.57 (s, 1H), 7.41 (br m, 2H), 7.12 (s, 1H), 5.83 (d, 1H), 4.48 (br t, 1H), 3.43 (m, 1H), 3.54 (m, 1H), 1.25 (d, 3H).

Enantiomer separation of $N^6$-(2-{[7-(2,4-dichlorophenyl)imidazo[1,2-c]pyrimidin-5-yl]amino}-1-methylethyl)-3-nitropyridine-2,6-diamine (Example 85) is carried out under the following conditions:

A sample of 234 mg of Example 85 is taken up in hot methanol:dichloromethane:tert-butyl methyl ether (15:15:35, 65 ml) and chromatographed on a Daicel Chiralpak IA 5 μm 250 mm×20 mm column (flow rate: 15 ml/min; detection at 230 nm; volume injected: 700 μl; eluent tert-butyl methyl ether:methanol:N,N-diisopropylethylamine (225:25:1), temperature: 40° C.) Two fractions are isolated:

Example Ent-A-85: 27 mg of product are isolated in >98.5% ee.

Retention time 6.10 min

Example Ent-B-85: 55 mg of product are isolated in >96% ee.

Retention time 7.49 min

Example 86

6-[(2-{[7-(2,4-Dichlorophenyl)imidazo[1,2-c]pyrimidin-5-yl]amino}ethyl)thio]nicotinonitrile

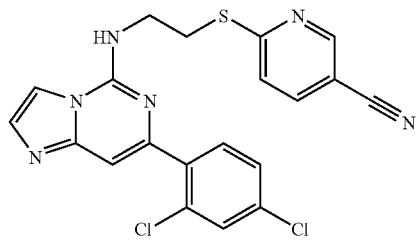

6-[(2-{[7-(2,4-Dichlorophenyl)imidazo[1,2-c]pyrimidin-5-yl]amino}ethyl)thio]nicotinonitrile (Example 86) is prepared in analogy to Example 82 from Example 45A (179 mg, 1.0 mmol), 5-chloro-7-(2,4-dichlorophenyl)imidazo[1,2-c]pyrimidine (Example 6A) (358 mg, 12 mmol) and N,N-diisopropylethylamine (1.7 ml, 10 mmol). 169 mg (38% of theory) of product are obtained as a solid after purification by preparative RP-HPLC (gradient of eluent: water:acetonitrile 90:10 to 10:90)

LCMS (method 3): $R_t$=2.06 min. (m/z=441 (M+H)$^+$)

$^1$H-NMR (400 MHz, DMSO-d$_6$): d=9.71 (t, 1H), 8.73 (d, 1H), 8.64 (m, 1H), 8.16 (d, 1H), 7.93 (dd, 1H), 7.81 (d, 1H), 7.68 (d, 1H), 7.58 (dd, 1H), 7.53 (d, 1H), 7.42 (s, 1H), 3.94 (m, 2H), 3.57 (t, 2H).

Example 87

N-{2-[(6-Amino-5-nitropyridin-2-yl)thio]ethyl}-7-(2,4-dichlorophenyl)imidazo[1,2-c]pyrimidine-5-amine

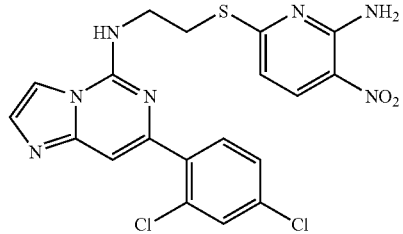

N-{2-[(6-Amino-5-nitropyridin-2-yl)thio]ethyl}-7-(2,4-dichlorophenyl)imidazo[1,2-c]pyrimidine-5-amine (Example 87) is prepared in analogy to Example 82 from Example 46A (129 mg, 0.6 mmol), 5-chloro-7-(2,4-dichlorophenyl)imidazo[1,2-c]pyrimidine (Example 6A) (197 mg, 0.7 mmol) and N,N-diisopropylethylamine (1.0 ml, 6 mmol). 83 mg (29% of theory) of product are obtained as a solid after purification by preparative RP-HPLC (gradient of eluent: water:acetonitrile 90:10 to 10:90). Example 89 is isolated as subsidiary component.

LCMS (method 1): $R_t$=1.70 min. (m/z=476 (M+H)$^+$)

$^1$H-NMR (400 MHz, DMSO-d$_6$): d=9.28 (br m, 1H), 8.42 (br m, 1H), 8.14 (br s, 2H), 7.98 (d, 1H), 7.77 (d, 1H), 7.71 (d, 1H), 7.56 (dd, 1H), 7.37 (s, 1H), 6.66 (d, 1H), 3.94 (m, 2H), 3.50 (m, 2H).

Example 88

6-[(2-{[7-(2,4-Dichlorophenyl)imidazo[1,2-c]pyrimidin-5-yl]thio}ethyl)amino]nicotinonitrile

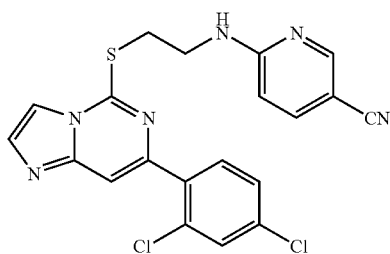

6-[(2-{[7-(2,4-Dichlorophenyl)imidazo[1,2-c]pyrimidin-5-yl]thio}ethyl)amino]nicotinonitrile (Example 88) is prepared in analogy to Example 82 from Example 47A (200 mg, 0.4 mmol), 2-chloro-5-cyanopyridine (75 mg, 0.5 mmol) and N,N-diisopropylethylamine (0.8 ml, 4 mmol). 92 mg (47% of theory) of product are obtained as solid after purification by preparative RP-HPLC (gradient of eluent: water:acetonitrile 90:10 to 10:90).

LCMS (method 1): $R_t$=1.66 min. (m/z=441 (M+H)$^+$)

$^1$H-NMR (400 MHz, DMSO-d$_6$): d=9.53 (br t, 1H), 8.71 (d, 1H), 8.52 (m, 1H), 8.13 (d, 1H), 7.94 (dd, 1H), 7.81 (d, 1H), 7.69 (d, 1H), 7.59 (dd, 1H), 7.53 (dd, 1H), 7.42 (s, 1H), 3.93 (m, 2H), 3.58 (t, 2H).

Example 89

$N^6$-(2-{[7-(2,4-Dichlorophenyl)imidazo[1,2-c]pyrimidin-5-yl]thio}ethyl)-3-nitropyridine-2,6-diamine

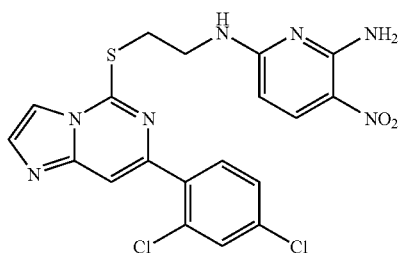

$N^6$-(2-{[7-(2,4-Dichlorophenyl)imidazo[1,2-c]pyrimidin-5-yl]thio}ethyl)-3-nitropyridine-2,6-diamine (Example 89) is prepared in analogy to Example 82 from Example 46A (129 mg, 0.6 mmol), 5-chloro-7-(2,4-dichlorophenyl)imidazo[1,2-c]pyrimidine (Example 6A) (197 mg, 0.7 mmol) and N,N-diisopropylethylamine (1.0 ml, 6 mmol). 949 mg (32% of theory) of product are obtained as solid after purification by preparative RP-HPLC (gradient of eluent: water:acetonitril 90:10 to 10:90). Example 87 is isolated as subsidiary component.

LCMS (method 1): $R_t$=2.00 min. (m/z=476 (M+H)$^+$)

$^1$H-NMR (400 MHz, DMSO-d$_6$): d=8.38 (br s, 1H), 8.26 (d, 1H), 8.17 (d, 1H), 7.96 (s, 1H), 7.86 (d, 1H), 7.77 (m, 2H), 7.55 (dd, 1H), 6.20 (br, 2H), 5.85 (d, 1H), 3.80 (m, 4H).

Example 90

$N^6$-(2-{[7-(2,4-Dichlorophenyl)imidazo[1,2-c]pyrimidin-5-yl]oxy}ethyl)-3-nitropyridine-2,6-diamine

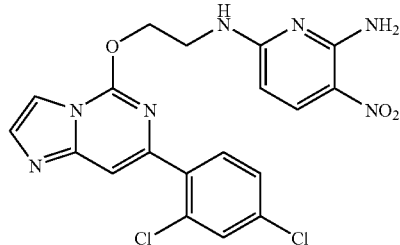

2-[(6-Amino-5-nitropyridin-2-yl)amino]ethanol (Example 48A) is introduced into DMF (3 ml) at 0° C., and sodium hydride (60% oil dispersion, 15 mg, 0.4 mmol) is added. The mixture is stirred at 0° C. for 10 min. 5-Chloro-7-(2,4-dichlorophenyl)imidazo[1,2-c]pyrimidine (Example 6A) (125 mg, 0.4 mmol) in DMF (1 ml) is added dropwise, and the reaction mixture is stirred at RT for 12 h. Glacial acetic acid (200 μl) is added, and the reaction mixture is poured into water and extracted with ethyl acetate (3×50 ml). The combined organic phases are washed with saturated aqueous sodium chloride solution, dried over magnesium sulphate and concentrated. The residue is precipitated from acetonitrile, filtered off, washed with acetonitrile and dried. 36 mg (18% of theory) of product are obtained as a solid.

LCMS (method 3): $R_t$=2.24 min. (m/z=460 (M+H)$^+$)

$^1$H-NMR (400 MHz, DMSO-d$_6$): d=8.17 (br t, 1H), 8.13 (br s, 2H), 7.93 (d, 1H), 7.88 (s, 1H), 7.75 (d, 1H), 7.71 (d, 1H), 7.68 (d, 1H), 7.55 (s, 1H), 7.51 (dd, 1H), 5.93 (d, 1H), 4.81 (m, 2H), 3.88 (m, 2H).

Example 91

N-{2-[(6-Amino-5-nitropyridin-2-yl)oxy]ethyl}-7-(2,4-dichlorophenyl)imidazo[1,2-c]-pyrimidine-5-amine

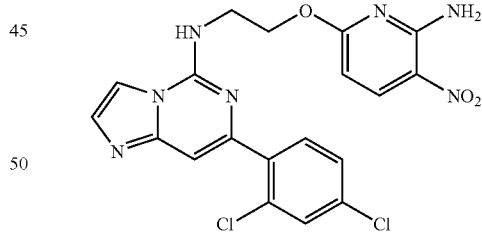

N-{2-[(6-Amino-5-nitropyridin-2-yl)oxy]ethyl}-7-(2,4-dichlorophenyl)imidazo[1,2-c]-pyrimidine-5-amine (Example 91) is prepared in analogy to Example 90 from Example 49A (156 mg, 0.5 mmol), 2-amino-6-chloro-3-nitropyridine (70 mg, 0.4 mmol) and sodium hydride (60% oil dispersion, 15 mg, 0.4 mmol). 70 mg (38% of theory) of the product are obtained as a solid after purification of the crude product by preparative RP-HPLC (gradient of eluent: water:acetonitrile 90:10 to 10:90).

LCMS (method 1): $R_t$=1.54 min. (m/z=460 (M+H)$^+$)

$^1$H-NMR (400 MHz, DMSO-d$_6$): d=9.32 (br m, 1H), 8.50 (br s, 1H), 8.15 (d, 1H), 8.09 (m, 3H), 7.77 (d, 1H), 7.70 (d, 1H), 7.55 (dd, 1H), 7.40 (s, 1H), 6.04 (d, 1H), 4.59 (m, 2H), 4.03 (m, 2H).

Example 92

6-[(2-{[7-(2,4-Dichlorophenyl)[1,2,4]triazolo[1,5-c]pyrimidin-5-yl]amino}ethyl)amino]-nicotinonitrile

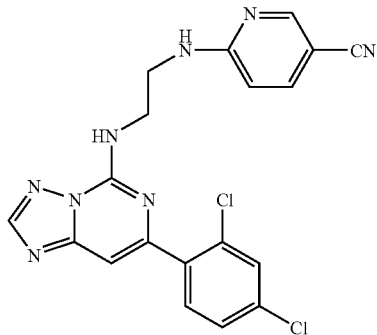

60 mg (0.19 mmol) of 6-({2-[(7-chloro[1,2,4]triazolo[1,5-c]pyrimidin-5-yl)amino]ethyl}amino)nicotinonitrile (Example 54A), 35.6 mg (0.19 mmol) of (2,4-dichlorophenyl)boronic acid and 21.6 mg (0.019 mmol) of tetrakis(triphenylphosphine)palladium(0) are introduced into a mixture of 4 ml of dioxane and 1.3 ml of saturated aqueous sodium carbonate solution under argon. The mixture is degassed with argon and then heated in a microwave at 150° C. for 30 min. Cooling is followed by filtration through an Extrelut® cartridge. Purification by preparative HPLC results in 15.3 mg (19% of theory) of the product as a solid.

LCMS (method 5): $R_t$=3.41 min. (m/z=425 (M+H)$^+$)

$^1$H-NMR (400 MHz, DMSO-d$_6$): d=8.55 (s, 1H), 8.48 (t, 1H), 8.32 (d, 1H), 7.73 (s, 1H), 7.71 (t, 1H), 7.59 (d, 1H), 7.55 (dd, 1H), 7.51 (d, 1H), 7.24 (s, 1H), 6.48 (s, br, 1H), 3.72 (dd, 2H), 3.63 (s, br, 2H).

Example 93

6-{[2-({7-[4-(Trifluoromethyl)phenyl][1,2,4]triazolo[1,5-c]pyrimidin-5-yl}amino)ethyl]amino}-nicotinonitrile

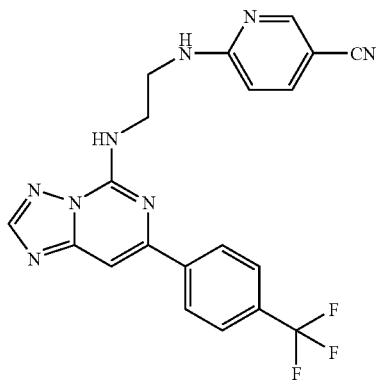

50 mg (0.16 mmol) of 6-({2-[(7-chloro[1,2,4]triazolo[1,5-c]pyrimidin-5-yl)amino]ethyl}amino)-nicotinonitrile (Example 54A), 29.5 mg (0.16 mmol) of [4-(trifluoromethyl)phenyl]boronic acid and 18 mg (0.016 mmol) of tetrakis(triphenylphosphine)palladium(0) are introduced into a mixture of 3.3 ml of dioxane and 1.1 ml of saturated aqueous sodium carbonate solution under argon. The mixture is degassed with argon and then heated in a microwave at 150° C. for 30 min Cooling is followed by filtration through an Extrelut® cartridge. Purification by preparative HPLC results in 6.5 mg (10% of theory) of the product as a solid.

LCMS (method 5): $R_t$=3.42 min. (m/z=425 (M+H)$^+$)

$^1$H-NMR (400 MHz, DMSO-d$_6$): d=8.54 (s, 1H), 8.45 (t, 1H), 8.42 (s, br, 1H), 8.22 (d, 2H), 7.78 (d, 2H), 7.76 (t, 1H), 7.72 (s, 1H), 7.54 (s, br, 1H), 6.44 (s, br, 1H), 3.85 (dd, 2H), 3.68 (m, 2H).

Example 94

N$^6$-(2-{[7-(2,4-Dichlorophenyl)[1,2,4]triazolo[1,5-c]pyrimidin-5-yl]amino}ethyl)-3-nitropyridine-2,6-diamine

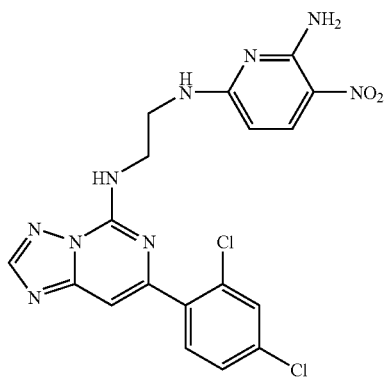

60 mg (0.16 mmol) of N$^6$-{2-[(7-chloro[1,2,4]triazolo[1,5-c]pyrimidin-5-yl)amino]ethyl}-3-nitropyridine-2,6-diamine (Example 6A), 30.3 mg (0.16 mmol) of (2,4-dichlorophenyl)boronic acid and 18.4 mg (0.016 mmol) of tetrakis(triphenylphosphine)palladium(0) are introduced into a mixture of 3.4 ml of dioxane and 1.1 ml of saturated aqueous sodium carbonate solution under argon. The mixture is degassed with argon and then heated in a microwave at 150° C. for 30 min Cooling is followed by filtration through an Extrelut® cartridge. Purification by preparative HPLC results in 10.9 mg (13% of theory) of the product as a solid.

LCMS (method 5): $R_t$=3.40 min. (m/z=460 (M+H)$^+$)

$^1$H-NMR (400 MHz, DMSO-d$_6$): δ=8.58 (s, 1H), 8.53 (t, 1H), 8.14 (s, br, 1H), 8.07 (t, 1H), 7.85 (d, 1H), 7.72 (s, 1H), 7.63 (s, br, 1H), 7.60 (d, 1H), 7.43 (d, 1H), 7.26 (s, 1H), 5.84 (d, 1H), 3.76 (m, 2H), 3.65 (m, 2H).

Example 95

N$^6$-(2-{[7-(3,5-Dimethylphenyl)[1,2,4]triazolo[1,5-c]pyrimidin-5-yl]amino}ethyl)-3-nitropyridine-2,6-diamine

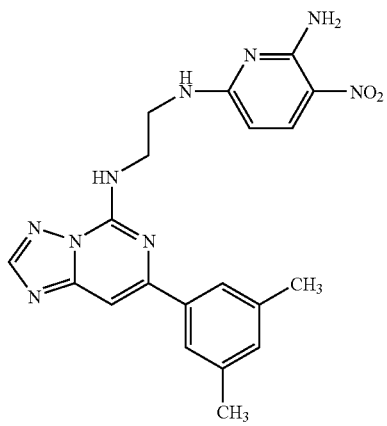

In analogy to the procedure described for Example 94, 39.9 mg (72% of theory) of the product are obtained as a solid starting from 50 mg (0.133 mmol) of N⁶-{2-[(7-chloro[1,2,4]triazolo-[1,5-c]pyrimidin-5-yl)amino]ethyl}-3-nitropyridine-2,6-diamine (Example 55A) by coupling with 19.9 mg (0.13 mmol) of (3,5-dimethylphenyl)boronic acid and subsequent purification by preparative HPLC.

LCMS (method 5): $R_t$=3.42 min. (m/z=420 (M+H)⁺)

¹H-NMR (400 MHz, DMSO-$d_6$): d=8.50 (s, 1H), 8.37 (t, 1H), 8.18 (s, br, 1H), 8.12 (t, 1H), 7.83 (d, 1H), 7.74 (s, br, 1H), 7.67 (s, 2H), 7.53 (s, 1H), 7.04 (s, 1H), 5.83 (d, 1H), 3.86 (m, 2H), 3.71 (dd, 2H), 2.28 (s, 6H).

Example 96

3-Nitro-N⁶-[2-({7-[4-(trifluoromethyl)phenyl][1,2,4]triazolo[1,5-c]pyrimidin-5-yl}amino)ethyl]-pyridine-2,6-diamine

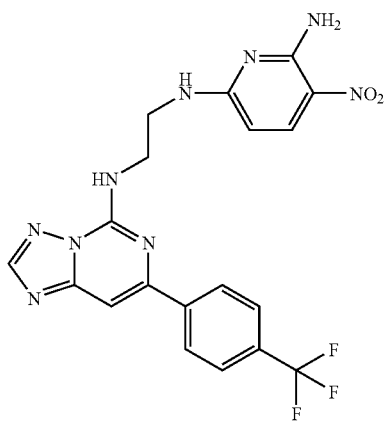

In analogy to the procedure described for Example 94, 2.3 mg (4% of theory) of the product are obtained as solid starting from 50 mg (0.133 mmol) of N⁶-{2-[(7-chloro[1,2,4]triazolo-[1,5-c]pyrimidin-5-yl)amino]ethyl}-3-nitropyridine-2,6-diamine (Example 55A) by coupling with 25.2 mg (0.13 mmol) of [4-(trifluoromethyl)phenyl]boronic acid and subsequent purification by preparative HPLC.

LCMS (method 5): $R_t$=3.41 min. (m/z=460 (M+H)⁺)

¹H-NMR (400 MHz, DMSO-$d_6$): d=8.55 (s, 1H), 8.47 (t, 1H), 8.24 (d, 3H), 8.08 (t, 1H), 7.77 (d, 1H), 7.73 (s, 1H), 7.70 (d, 3H), 5.79 (d, 1H), 3.92 (dd, 2H), 3.69 (dd, 2H).

Example 97

3-Nitro-N⁶-(2-{[7-(3-pyrrolidin-1-ylphenyl)[1,2,4]triazolo[1,5-c]pyrimidin-5-yl]amino}-ethyl)pyridine-2,6-diamine

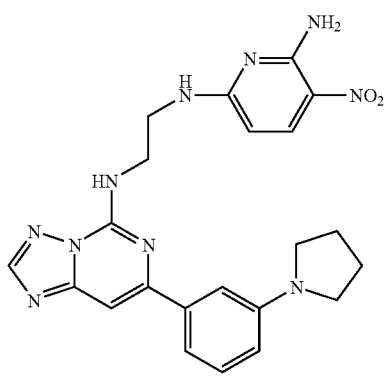

In analogy to the procedure described for Example 94, 17.5 mg (28% of theory) of the product are obtained as a solid starting from 50 mg (0.133 mmol) of N⁶-{2-[(7-chloro[1,2,4]triazolo-[1,5-c]pyrimidin-5-yl)amino]ethyl}-3-nitropyridine-2,6-diamine (Example 55A) by coupling with 25.3 mg (0.13 mmol) of (3-pyrrolidin-1-ylphenyl)boronic acid and subsequent purification by preparative HPLC.

LCMS (method 5): $R_t$=3.46 min. (m/z=461 (M+H)⁺)

¹H-NMR (400 MHz, DMSO-$d_6$): d=8.48 (s, 1H), 8.34 (t, 1H), 8.18 (s, br, 1H), 8.08 (t, 1H), 7.84 (d, 1H), 7.67 (s, br, 1H), 7.53 (s, 1H), 7.28 (d, 1H), 7.25 (s, 1H), 7.13 (t, 1H), 6.60 (d, 1H), 5.85 (d, 1H), 3.85 (dd, 2H), 3.74 (dd, 2H), 3.25 (m, 4H), 1.91-1.96 (m, 4H).

Example 98

N⁶-(3-{[7-(2,4-Dichlorophenyl)imidazo[1,2-c]pyrimidin-5-yl]amino}propyl)-3-nitropyridine-2,6-diamine

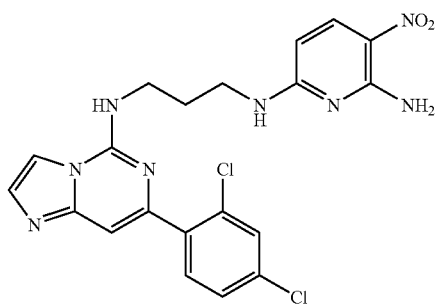

104 mg (0.32 mmol) of the amine (Example 57A) are introduced into 3 ml of isopropanol, 73.6 mg (0.25 mmol) of 5-chloro-7-(2,4-dichlorophenyl)imidazo[1,2-c]pyrimidine and 95.6 mg (0.74 mmol) of DIPEA are added, and the mixture is heated in a microwave at 150° C. for 2 h. Purification by preparative HPLC results in 96 mg (82% of theory) of the product.

LCMS (method 7): $R_t$=2.53 min. (m/z=475 (M+H)⁺)

¹H-NMR (400 MHz, DMSO-$d_6$): d=8.10 (s, br, 1H), 8.01 (s, 1H), 7.97 (t, 1H), 7.90 (m, 2H), 7.70 (s, 1H), 7.69 (d, 1H), 7.58 (d, 1H), 7.49 (dd, 1H), 7.10 (s, 1H), 5.89 (d, 1H), 3.59 (dd, 2H), 3.45 (dd, 2H), 3.16 (d, 1H), 1.97 (pent, 2H).

The following products are obtained in analogy to the procedure described for Example 7 by palladium-catalysed coupling with the appropriate boronic acids.

| Example | Structure | Characterization |
|---|---|---|
| 99 | 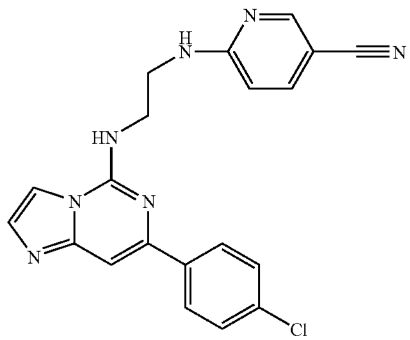 | LC/MS (method 7): R$_t$ = 2.25 min<br>MS (ESIpos): m/z = 390 (M + H)$^+$. |
| 100 | 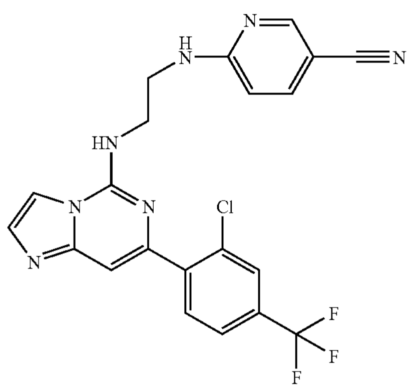 | LC/MS (method 1): R$_t$ = 1.58 min<br>MS (ESIpos): m/z = 458 (M + H)$^+$. |
| 101 | 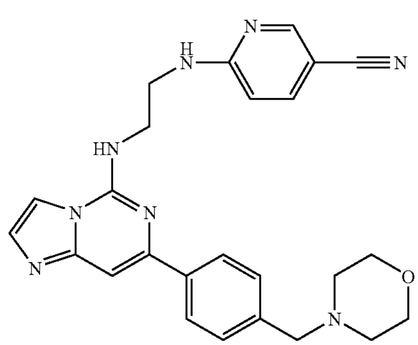 | LC/MS (method 4): R$_t$ = 4.54 min<br>MS (ESIpos): m/z = 455 (M + H)$^+$. |

Example 102

N[6]-[2-({2-Methyl-7-[4-(trifluoromethyl)phenyl]imidazo[1,2-c]pyrimidin-5-yl}amino)ethyl]-3-nitropyridine-2,6-diamine

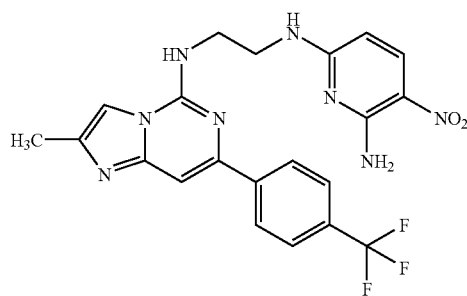

In analogy to the procedure described for Example 7, 30.2 mg (48% of theory) of the product are obtained starting from 50 mg (0.13 mmol) of N[6]-{2-[(7-chloro-2-methylimidazo[1,2-c]pyrimidin-5-yl)amino]ethyl}-3-nitropyridine-2,6-diamine (Example 31A) by coupling with 30.2 mg (0.15 mmol) of [4-(trifluoromethyl)phenyl]boronic acid and subsequent purification by preparative HPLC.

LCMS (method 1): $R_t$=1.46 min. (m/z=473 (M+H)$^+$)

$^1$H-NMR (400 MHz, DMSO-d$_6$): d=8.69 (s, br, 1H), 8.30 (d, 2H), 8.03 (t, 1H), 7.95 (s, 1H), 7.75-7.8 (m, 3H), 7.67 (s, 1H), 5.76 (d, 1H), 3.93 (s, br, 2H), 3.7 (s, br, 2H), 2.45 (s, 3H).

Example 103

N[6]-(2-{[7-(3,4-Dimethoxyphenyl)-2-methylimidazo[1,2-c]pyrimidin-5-yl]amino}ethyl)-3-nitropyridine-2,6-diamine

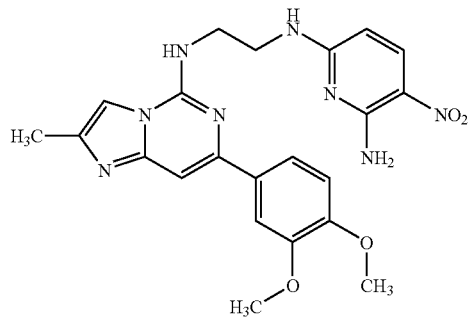

In analogy to the procedure described for Example 7, 57 mg (39% of theory) of the product are obtained starting from 120 mg (0.32 mmol) of N[6]-{2-[(7-chloro-2-methylimidazo[1,2-c]pyrimidin-5-yl)amino]ethyl}-3-nitropyridine-2,6-diamine (Example 31A) by coupling with 69 mg (0.38 mmol) of (3,4-dimethoxyphenyl)boronic acid and subsequent purification by preparative HPLC.

LCMS (method 1): $R_t$=1.17 min. (m/z=465 (M+H)$^+$)

$^1$H-NMR (400 MHz, DMSO-d$_6$): d=8.61 (s, br, 1H), 8.03 (t, br, 1H), 7.89 (s, 1H), 7.81 (d, 1H), 7.70 (d, 1H), 7.68 (s, 1H), 7.50 (s, 1H), 6.97 (d, 1H), 5.79 (d, 1H), 3.90 (s, br, 2H), 3.85 (s, 3H), 3.82 (s, 3H), 3.72 (s, br, 2H), 2.44 (s, 3H).

Example 104

N[6]-(2-{[7-(4-tert-Butylphenyl)-2-methylimidazo[1,2-c]pyrimidin-5-yl]amino}ethyl)-3-nitropyridine-2,6-diamine

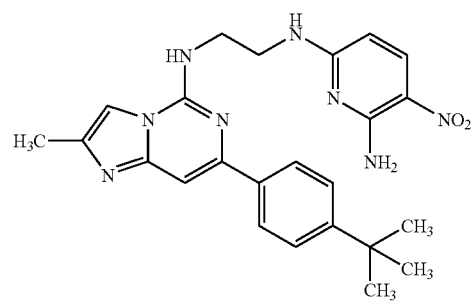

In analogy to the procedure described for Example 7, 34 mg (23% of theory) of the product are obtained starting from 120 mg (0.32 mmol) of N[6]-{2-[(7-chloro-2-methylimidazo[1,2-c]pyrimidin-5-yl)amino]ethyl}-3-nitropyridine-2,6-diamine (Example 31A) by coupling with 68 mg (0.38 mmol) of (4-tert-butylphenyl)boronic acid and subsequent purification by preparative HPLC.

LCMS (method 1): $R_t$=1.57 min. (m/z=461 (M+H)$^+$)

$^1$H-NMR (400 MHz, DMSO-d$_6$): d=8.59 (s, br, 1H), 8.19 (s, br, 1H), 8.04 (t, 1H), 7.95 (d, 2H), 7.90 (s, 1H), 7.77 (d, 1H), 7.7 (s, br, 1H), 7.45 (s, 1H), 7.41 (d, 2H), 5.75 (d, 1H), 3.93 (m, 2H), 3.68 (m, 2H), 2.44 (s, 3H), 1.30 (s, 9H).

Example 105

N[6]-(2-{[7-(3,5-Dimethylphenyl)-2-methylimidazo[1,2-c]pyrimidin-5-yl]amino}ethyl)-3-nitropyridine-2,6-diamine

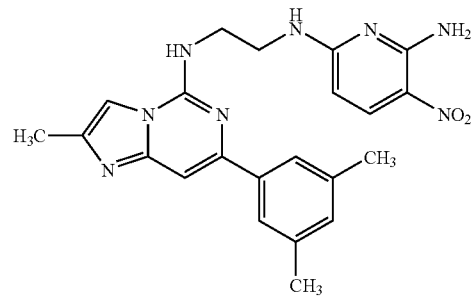

In analogy to the procedure described for Example 7, 4 mg (3% of theory) of the product are obtained starting from 120 mg (0.32 mmol) of $N^6$-{2-[(7-chloro-2-methylimidazo[1,2-c]pyrimidin-5-yl)amino]ethyl}-3-nitropyridine-2,6-diamine (Example 31A) by coupling with 57 mg (0.38 mmol) of (3,5-dimethylphenyl)boronic acid and subsequent purification by preparative HPLC.

LCMS (method 1): $R_t$=1.44 min. (m/z=433 (M+H)$^+$)

$^1$H-NMR (400 MHz, DMSO-d$_6$): d=8.59 (s, br, 1H), 8.12 (s, br, 1H), 8.03 (t, 1H), 7.92 (s, 1H), 7.81 (d, 1H), 7.70 (s, 1H), 7.6 (s, br, 1H), 7.49 (s, 1H), 7.13 (s, 1H), 5.79 (d, 1H), 3.89 (m, 2H), 3.73 (m, 2H), 2.44 (s, 3H), 2.32 (s, 6H).

Example 106

$N^6$-(2-{[7-(2,3-Dimethylphenyl)-2-methylimidazo[1,2-c]pyrimidin-5-yl]amino}ethyl)-3-nitropyridine-2,6-diamine trifluoroacetate

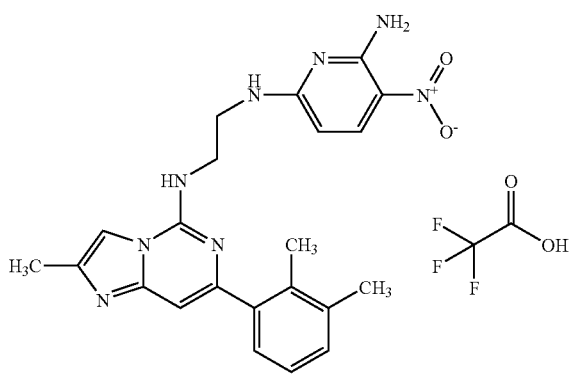

In analogy to the procedure described for Example 7, 14 mg (19% of theory) of the product are obtained starting from 50 mg (0.13 mmol) of $N^6$-{2-[(7-chloro-2-methylimidazo[1,2-c]pyrimidin-5-yl)amino]ethyl}-3-nitropyridine-2,6-diamine (Example 31A) by coupling with 24 mg (0.16 mmol) of (2,3-dimethylphenyl)boronic acid and subsequent purification by preparative HPLC.

LCMS (method 6): $R_t$=1.15 min. (m/z=433 (M+H)$^+$)

$^1$H-NMR (400 MHz, DMSO-d$_6$): d=8.69 (s, br, 1H), 8.0 (t, br, 1H), 7.95 (s, 1H), 7.84 (d, 1H), 7.45 (s, br, 1H), 7.12-7.29 (m, 3H), 7.07 (s, 1H), 5.81 (d, 1H), 3.77 (m, 2H), 3.64 (m, 2H), 2.46 (s, 3H), 2.29 (s, 3H), 2.23 (s, 3H).

Example 107

N-(2-{[7-(2,4-Dichlorophenyl)imidazo[1,2-c]pyrimidin-5-yl]oxy}ethyl)-5-(trifluoromethyl)-pyridine-2-amine

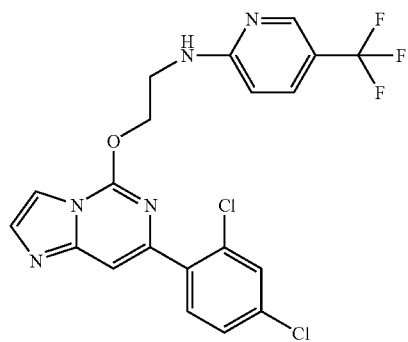

In analogy to the procedure described for Example 90, 46 mg (59% of theory) of the product are obtained starting from 50 mg (0.17 mmol) of 5-chloro-7-(2,4-dichlorophenyl)imidazo-[1,2-c]pyrimidine (Example 6A) by reaction with 48 mg (0.23 mmol) of 2-{[5-(trifluoromethyl)pyridin-2-yl]amino}ethanol, which can be prepared in analogy to the synthesis of Example 48A from 2-chloro-5-(trifluoromethyl)pyridine and aminoethanol, after subsequent purification by preparative HPLC.

LCMS (method 7): $R_t$=3.78 min. (m/z=468 (M+H)$^+$)

Example 108

6-[(2-{[7-(2,4-Dichlorophenyl)imidazo[1,2-c]pyrimidin-5-yl]oxy}ethyl)amino]pyridine-3-carbonitrile

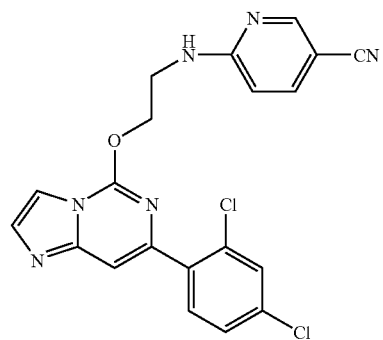

In analogy to the procedure described for Example 90, 35 mg (48% of theory) of the product are obtained starting from 50 mg (0.17 mmol) of 5-chloro-7-(2,4-dichlorophenyl)imidazo-[1,2-c]pyrimidine (Example 6A) by reaction with 38 mg (0.23 mmol) of 6-[(2-hydroxyethyl)amino]pyridine-3-carbonitrile, which can be prepared in analogy to the synthesis of Example 48A from 6-chloropyridine-3-carbonitrile and aminoethanol, after subsequent purification by preparative HPLC.

LCMS (method 3): $R_t$=2.31 min. (m/z=425 (M+H)$^+$)

$^1$H-NMR (400 MHz, DMSO-d$_6$): d=8.33 (d, 1H), 7.87 (t, 1H), 7.84 (s, 1H), 7.75 (d, 1H), 7.6-7.7 (m, 3H), 7.51-7.56 (m, 2H), 6.54 (d, 1H), 4.77 (t, 2H), 3.85 (dd, 2H).

Example 109

5-({2-[(5-Cyanopyridin-2-yl)amino]ethyl}amino)-7-(2,4-dichlorophenyl)imidazo-[1,2-c]pyrimidine-2-carboxylic acid

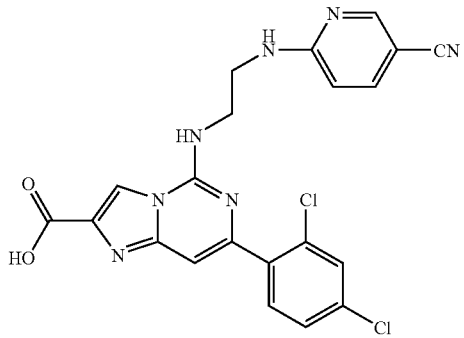

1 g (2.59 mmol) of ethyl 7-chloro-5-({2-[(5-cyanopyridin-2-yl)amino]ethyl}amino)imidazo[1,2-c]pyrimidine-2-carboxylate (Example 59A), 580 mg (2.98 mmol) of (2,4-dichlorophenyl)boronic acid and 716 mg (5.18 mmol) of potassium carbonate are introduced into a mixture of 25 ml of 1,2-dimethoxyethane and 10 ml of water under argon, and the mixture is carefully degassed before 300 mg (0.26 mmol) of tetrakis(triphenylphosphine)palladium(0) are added. The mixture is heated at 120° C. for 16 h. Filtration and subsequent purification by preparative HPLC result in 185 mg (14% of theory) of the product as a solid.

LCMS (method 8): $R_t$=1.01 min. (m/z=468 (M+H)$^+$)

$^1$H-NMR (400 MHz, DMSO-d$_6$): d=8.66 (s, 1H), 8.36 (d, 1H), 8.35 (t, 1H), 7.77 (m, 1H), 7.73 (d, 1H), 7.63 (d, 1H), 7.59 (dd, 1H), 7.52 (dd, 1H), 7.13 (s, 1H), 6.50 (d, 1H), 7.36-7.8 (m, 4H).

Example 110

5-({2-[(5-Cyanopyridin-2-yl)amino]ethyl}amino)-7-[4-(trifluoromethyl)phenyl]imidazo-[1,2-c]pyrimidine-2-carboxylic acid

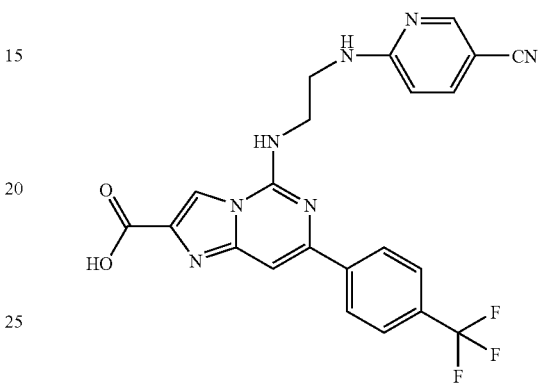

In analogy to the preparation of Example 109, the desired product is prepared by Pd-catalysed coupling starting from ethyl 7-chloro-5-({2-[(5-cyanopyridin-2-yl)amino]ethyl}amino)-imidazo[1,2-c]pyrimidine-2-carboxylate (Example 59A) and [4-(trifluoromethyl)phenyl]boronic acid.

LCMS (method 8): $R_t$=1.03 min. (m/z=468 (M+H)$^+$)

$^1$H-NMR (400 MHz, DMSO-d$_6$): d=8.69 (s, 1H), 8.44 (m, 2H), 8.24 (d, 2H), 7.79 (d, 3H), 7.59 (m, 1H), 7.56 (s, 1H), 6.48 (d, 1H), 3.85 (dd, 2H), 3.66-3.74 (m, 2H).

The following amides are prepared under standard coupling conditions (HATU, DIEA in DMF) starting from Example 109 or Example 110 with the appropriate amines:

| Example | Structure | Characterization |
|---|---|---|
| 111 | 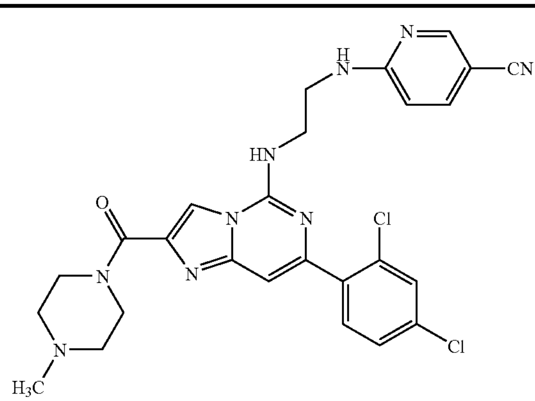 | LC/MS (method 1): $R_t$ = 1.42 min<br>MS (ESIpos): m/z = 550 (M + H)$^+$. |

-continued

| Example | Structure | Characterization |
|---------|-----------|------------------|
| 112 | 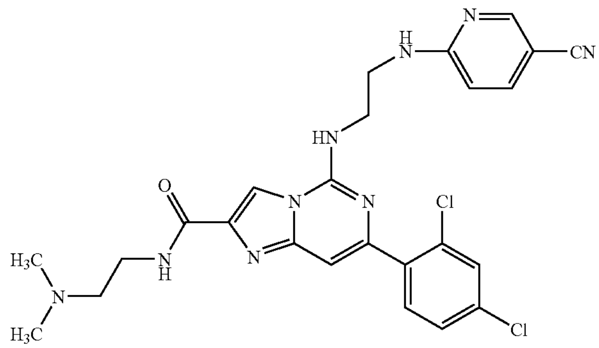 | LC/MS (method 1): R$_t$ = 1.45 min<br>MS (ESIpos): m/z = 538 (M + H)$^+$. |
| 113 | 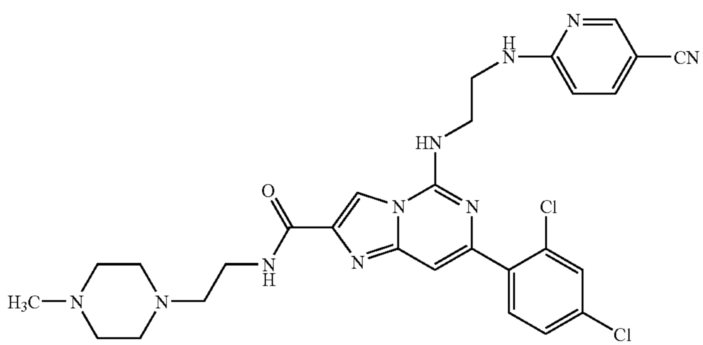 | LC/MS (method 6): R$_t$ = 1.29 min<br>MS (ESIpos): m/z = 593 (M + H)$^+$. |
| 114 | 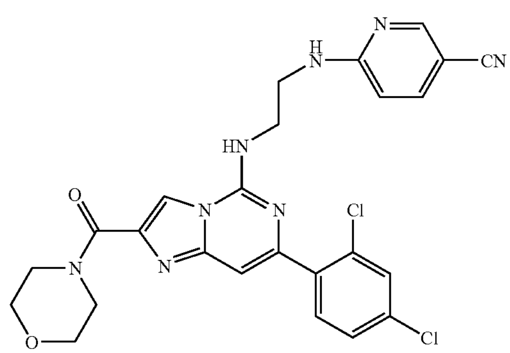 | LC/MS (method 3): R$_t$ = 2.48 min<br>MS (ESIpos): m/z = 537 (M + H)$^+$. |
| 115 | 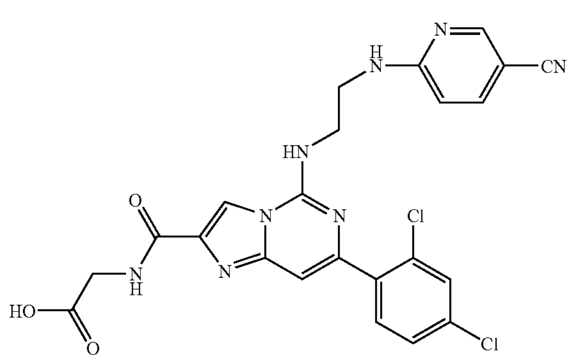 | LC/MS (method 6): R$_t$ = 1.82 min<br>MS (ESIpos): m/z = 525 (M + H)$^+$. |

-continued

| Example | Structure | Characterization |
|---|---|---|
| 116 | 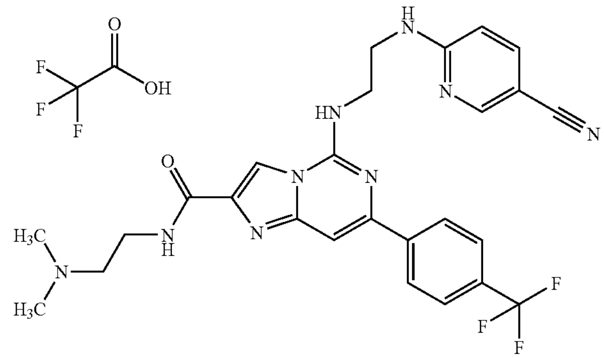 | LC/MS (method 3): R$_t$ = 1.66 min<br>MS (ESIpos): m/z = 538 (M + H)$^+$. |
| 117 | 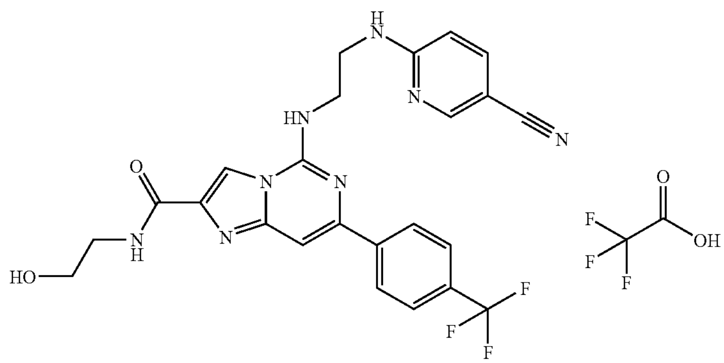 | LC/MS (method 6): R$_t$ = 1.77 min<br>MS (ESIpos): m/z = 511 (M + H)$^+$. |
| 118 | 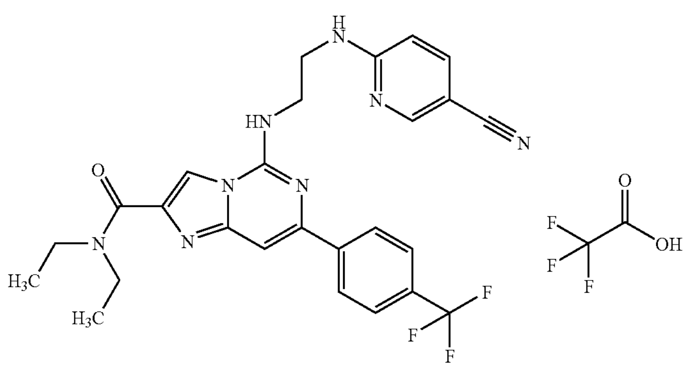 | LC/MS (method 6): R$_t$ = 2.11 min<br>MS (ESIpos): m/z = 523 (M + H)$^+$. |
| 119 | 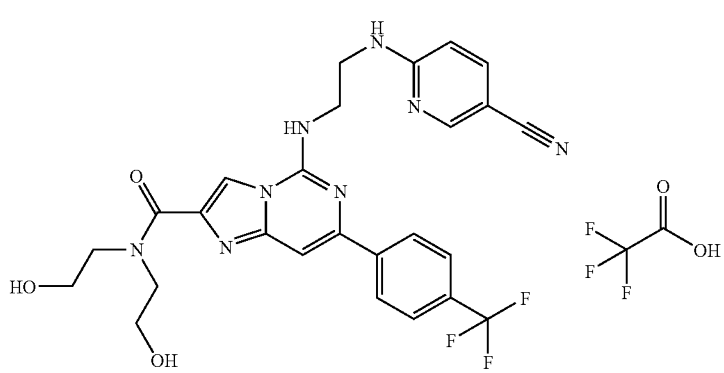 | LC/MS (method 3): R$_t$ = 2.12 min<br>MS (ESIpos): m/z = 555 (M + H)$^+$. |

-continued
| Example | Structure | Characterization |
|---|---|---|
| 120 | 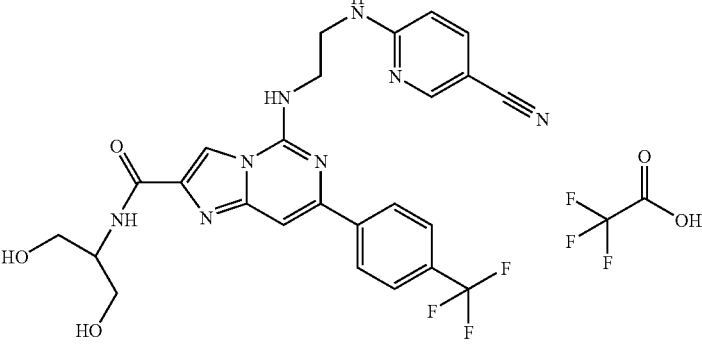 | LC/MS (method 6): R$_t$ = 1.70 min<br>MS (ESIpos): m/z = 541 (M + H)$^+$. |
| 121 | 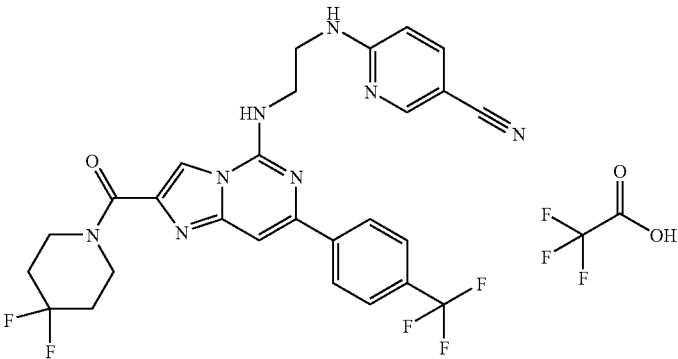 | LC/MS (method 6): R$_t$ = 2.17 min<br>MS (ESIpos): m/z = 571 (M + H)$^+$. |
| 122 | 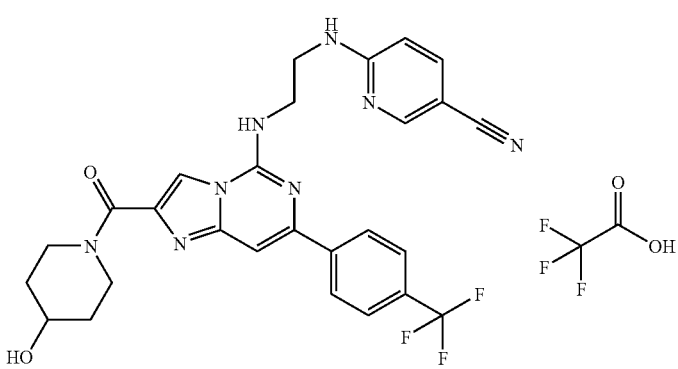 | LC/MS (method 3): R$_t$ = 2.18 min<br>MS (ESIpos): m/z = 551 (M + H)$^+$. |

Example 123

6-({1-[7-(2,4-Dichlorophenyl)imidazo[1,2-c]pyrimidin-5-yl]piperidin-3-yl}amino)pyridine-3-carbonitrile trifluoroacetate

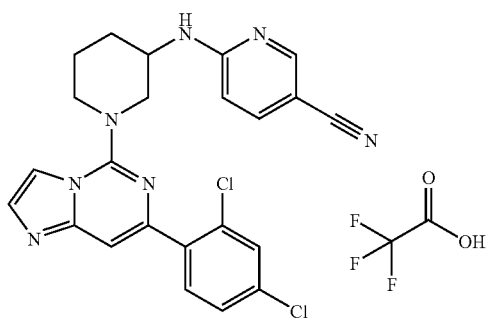

28.4 mg (0.095 mmol) of 5-chloro-7-(2,4-dichlorophenyl)imidazo[1,2-c]pyrimidine (Example 6A) are dissolved in 2 ml of DMSO, and 25 mg (0.124 mmol) of 6-(piperidin-3-ylamino)pyridine-3-carbonitrile hydrochloride (Example 61A) and 36.9 mg (0.29 mmol) of DIEA are added. The mixture is heated in a microwave at 150° C. for 2 h. After this time, water is added, and the precipitate which separates out is filtered off with suction. It is further purified by preparative HPLC. 55 mg (98% of theory) of the product are obtained as a solid.

LCMS (method 1): $R_t$=1.89 min. (m/z=464 (M+H)$^+$)

$^1$H-NMR (400 MHz, DMSO-d$_6$): d=8.51 (d, 1H), 8.28 (s, 1H), 8.13 (s, 1H), 7.73-7.82 (m, 3H), 7.69 (dd, 1H), 7.58-7.63 (m, 2H), 6.61 (d, 1H), 4.08-4.22 (m, 2H), 3.94 (d, 2H), 3.24 (t, 1H), 2.98 (dd, 1H), 2.03-2.14 (m, 1H), 1.92-2.02 (m, 1H), 1.75-1.89 (m, 1H), 1.62-1.74 (m, 1H).

Enantiomer separation of 6-({1-[7-(2,4-dichlorophenyl)imidazo[1,2-c]pyrimidin-5-yl]piperidin-3-yl}amino)pyridine-3-carbonitrile trifluoroacetate (Example 123) is carried out under the following conditions:

A sample of Example 123 (50 mg) is taken up in 2 ml of methanol and 6 ml of tert-butyl methyl ether and chromatographed on a Daicel Chiralpak IA-H 250 mm×20 mm column (flow rate: 15 ml/min; detection at 220 nm; volume injected: 450 µl; eluent: methanol:tert-butyl methyl ether (10:90), temperature: 25° C.). Two fractions are isolated:

Example Ent-A-123: 20 mg of product are isolated in >98% ee.

Retention time 6.55 min

Example Ent-B-123: 16 mg of product are isolated in >95% ee.

Retention time 6.94 min

The following products are obtained from the appropriate amines in analogy to the procedure described for Example 123:

| Example | Structure | Characterization |
|---|---|---|
| 124 | 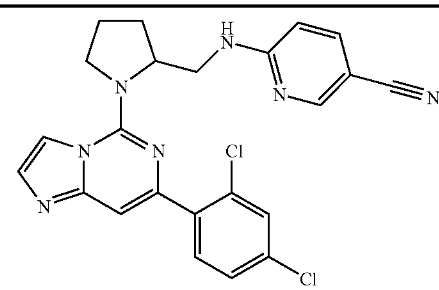 | LC/MS (method 8): $R_t$ = 1.00 min<br>MS (ESIpos): m/z = 464 (M + H)$^+$. |
| 125 | 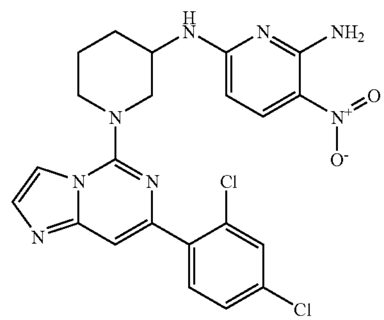 | LC/MS (method 8): $R_t$ = 1.10 min<br>MS (ESIpos): m/z = 499 (M + H)$^+$. |
| 126 | 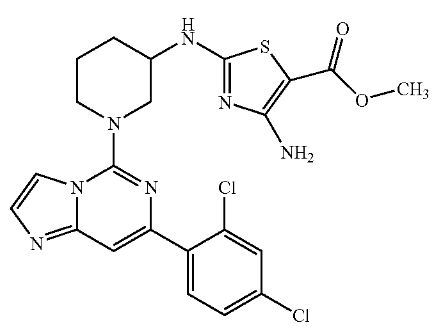 | LC/MS (method 6): $R_t$ = 1.61 min<br>MS (ESIpos): m/z = 518 (M + H)$^+$. |

-continued

| Example | Structure | Characterization |
|---|---|---|
| 127 | 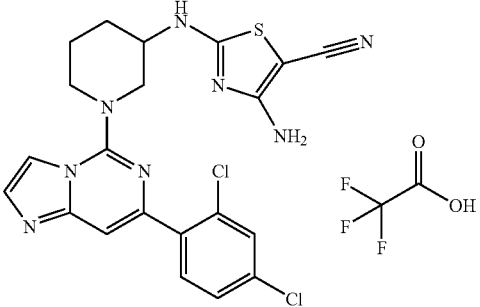 | LC/MS (method 3): $R_t$ = 1.93 min<br>MS (ESIpos): m/z = 485 (M + H)$^+$. |
| 128 | 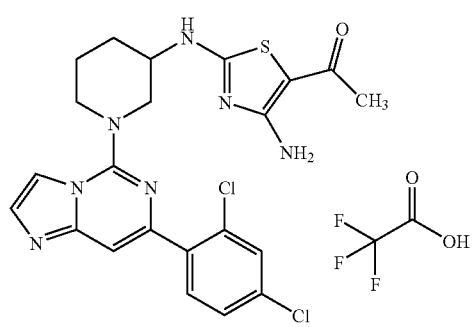 | LC/MS (method 6): $R_t$ = 1.47 min<br>MS (ESIpos): m/z = 502 (M + H)$^+$. |

Enantiomer separation of 6-[({1-[7-(2,4-dichlorophenyl)imidazo[1,2-c]pyrimidin-5-yl]-pyrrolidin-2-yl}methyl)amino]pyridine-3-carbonitrile (Example 124) is carried out under the following conditions:

A sample of Example 124 (110 mg) is taken up in 3 ml of ethanol and chromatographed on a Daicel Chiralcel OJ-H, 5 μm, 250 mm×20 mm column (flow rate: 15 ml/min; detection at 220 nm; volume injected: 500 μl; eluent: isohexane:ethanol (50:50), temperature: 45° C.). Two fractions are isolated:

Example Ent-A-124: 39 mg of product are isolated in >99% ee.

Retention time 4.54 min

Example Ent-B-124: 40 mg of product are isolated in >95% ee.

Retention time 5.55 min

Enantiomer separation of N$^6$-{1-[7-(2,4-dichlorophenyl)imidazo[1,2-c]pyrimidin-5-yl]piperidin-3-yl}-3-nitropyridine-2,6-diamine (Example 125) is carried out under the following conditions:

A sample of Example 125 (171 mg) is taken up in 8 ml of acetonitrile and 5 ml of tert-butyl methyl ether (TBME) and chromatographed on a Daicel Chiralpak IA, 5 μm, 250 mm×20 mm column (flow rate: 15 ml/min; detection at 220 nm; volume injected: 1500 μl; eluent: methanol:TBME (10:90), temperature: 30° C.). Two fractions are isolated:

Example Ent-A-125: 81 mg of product are isolated in >98% ee.

Retention time 4.58 min

Example Ent-B-125: 80 mg of product are isolated in >93% ee.

Retention time 6.01 min

Enantiomer separation of 1-[4-amino-2-({1-[7-(2,4-dichlorophenyl)imidazo[1,2-c]pyrimidin-5-yl]piperidin-3-yl}amino)-1,3-thiazol-5-yl]ethanone trifluoroacetate (Example 128) is carried out under the following conditions:

A sample of Example 128 (50 mg) is taken up in 2 ml of acetonitrile and 2 ml of methanol and chromatographed on a Daicel Chiralpak IA-H 250 mm×20 mm column (flow rate: 15 ml/min; detection at 320 nm; volume injected: 500 μl; eluent: methanol:tert-butyl methyl ether (20:80), temperature: 25° C.). Two fractions are isolated:

Example Ent-A-128: 20 mg of product are isolated in >99% ee.

Retention time 5.31 min

Example Ent-B-128: 16 mg of product are isolated in >95% ee.

Retention time 6.72 min

The following products are obtained from the appropriate amines in analogy to the procedure described for Example 123:

| Example | Structure | Characterization |
|---------|-----------|------------------|
| 129 | 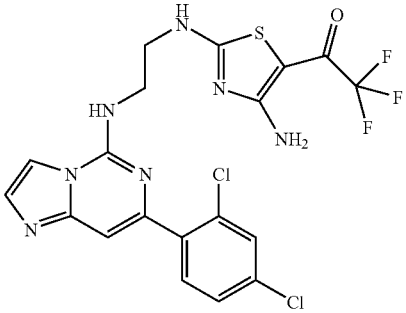 | LC/MS (method 6): R$_t$ = 1.38 min<br>MS (ESIpos): m/z = 516 (M + H)$^+$. |
| 130 | 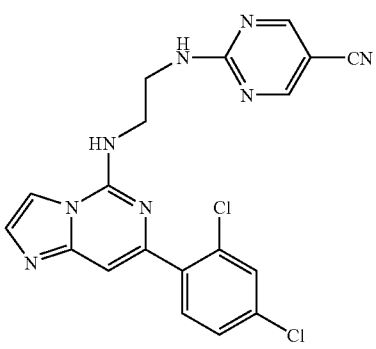 | LC/MS (method 3): R$_t$ = 1.69 min<br>MS (ESIpos): m/z = 425 (M + H)$^+$. |
| 131 | 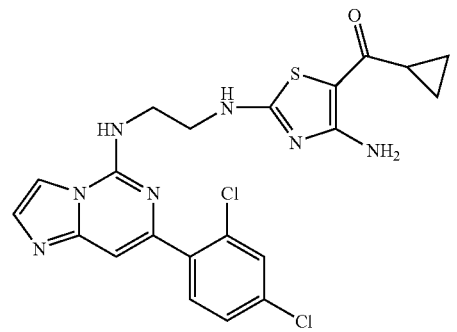 | LC/MS (method 3): R$_t$ = 1.76 min<br>MS (ESIpos): m/z = 488 (M + H)$^+$. |
| 132 | 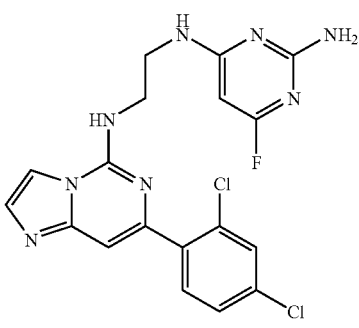 | LC/MS (method 3): R$_t$ = 1.73 min<br>MS (ESIpos): m/z = 433 (M + H)$^+$. |
| 133 | 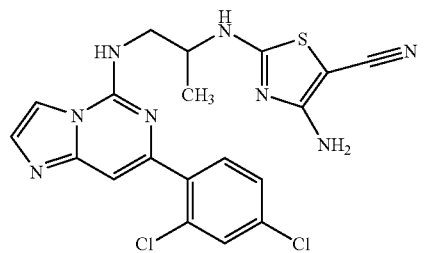 | LC/MS (method 3): R$_t$ = 1.64 min<br>MS (ESIpos): m/z = 459 (M + H)$^+$. |

| Example | Structure | Characterization |
|---|---|---|
| 134 | 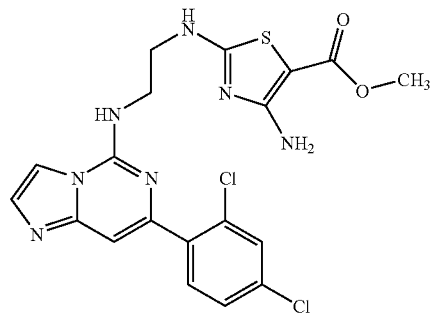 | LC/MS (method 6): R$_t$ = 1.24 min<br>MS (ESIpos): m/z = 478 (M + H)$^+$. |
| 135 | 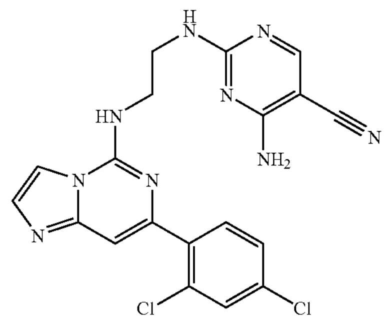 | LC/MS (method 8): R$_t$ = 0.84 min<br>MS (ESIpos): m/z = 441 (M + H)$^+$. |
| 136 | 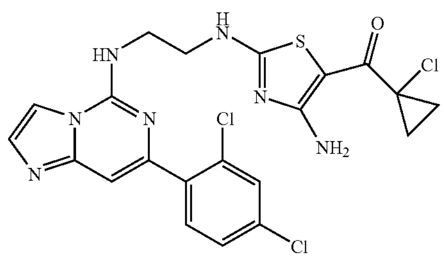 | LC/MS (method 8): R$_t$ = 1.00 min<br>MS (ESIpos): m/z = 522 (M + H)$^+$. |
| 137 | 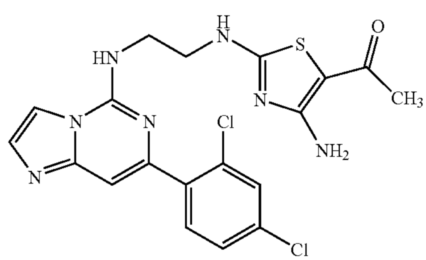 | LC/MS (method 8): R$_t$ = 0.88 min<br>MS (ESIpos): m/z = 462 (M + H)$^+$. |
| 138 | 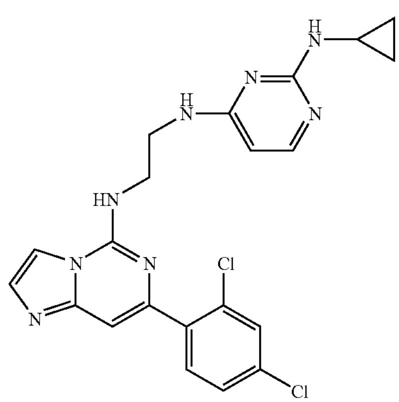 | LC/MS (method 3): R$_t$ = 1.80 min<br>MS (ESIpos): m/z = 455 (M + H)$^+$. |

| Example | Structure | Characterization |
|---|---|---|
| 139 | 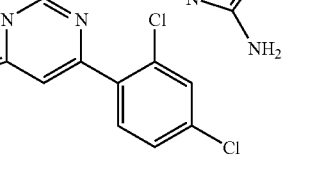 | LC/MS (method 3): $R_t$ = 1.36 min<br>MS (ESIpos): m/z = 465 (M + H)$^+$. |
| 140 | 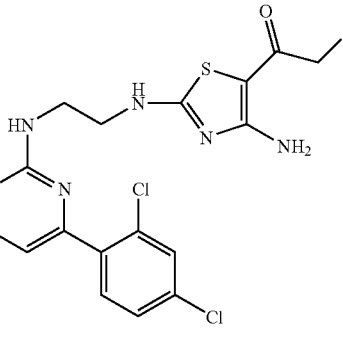 | LC/MS (method 3): $R_t$ = 1.62 min<br>MS (ESIpos): m/z = 456 (M + H)$^+$. |
| 141 | 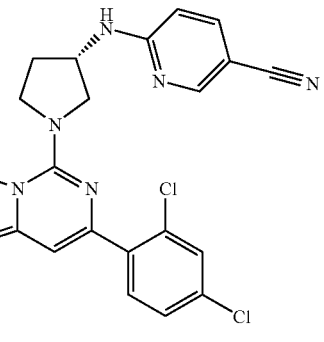 | LC/MS (method 3): $R_t$ = 2.06 min<br>MS (ESIpos): m/z = 450 (M + H)$^+$. |
| 142 | 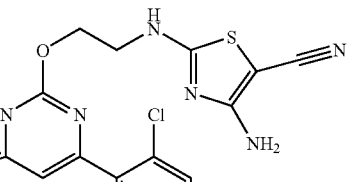 | LC/MS (method 8): $R_t$ = 0.99 min<br>MS (ESIpos): m/z = 446 (M + H)$^+$. |

Example 143

N-[7-(2,4-Dichlorophenyl)imidazo[1,2-c]pyrimidin-5-yl]-N'-(5-nitro-1,3-thiazol-2-yl)ethane-1,2-diamine

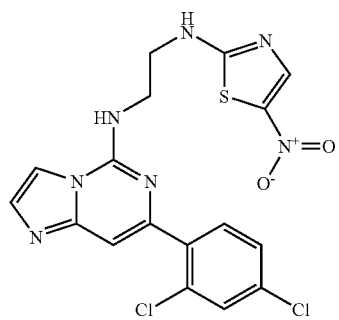

100 mg (0.238 mmol) of the amine (Example 8A) are introduced into 3 ml of DMSO, 76 mg (0.357 mmol) of 2-bromo-5-nitro-1,3-thiazole and 154 mg (1.19 mmol) of DIEA are added, and the mixture is heated in a microwave at 130° C. for 30 min. Purification by preparative HPLC results in 35 mg (33% of theory) of the product as a solid.

LCMS (method 9): $R_t$=1.70 min. (m/z=450 (M+H)$^+$)

$^1$H-NMR (400 MHz, DMSO-$d_6$): d=9.42 (s, br, 1H), 8.22 (s, 1H), 8.15 (t, 1H), 7.97 (s, 1H), 7.66 (s, 1H), 7.62 (d, 2H), 7.47 (dd, 1H), 7.13 (s, 1H), 3.74-3.82 (m, 2H), 3.63-3.73 (m, 2H).

Example 144

2-Amino-6-[(2-{[7-(2,4-dichlorophenyl)-2-(trifluoromethyl)imidazo[1,2-c]pyrimidin-5-yl]amino}-ethyl)amino]pyridine-3-carbonitrile trifluoroacetate

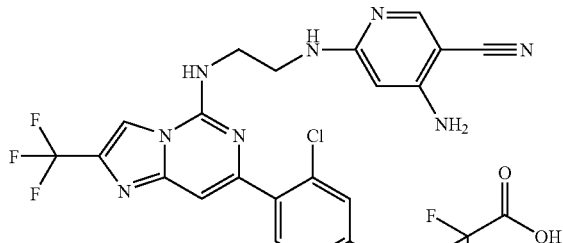

In analogy to the procedure described for Example 7, 47 mg (29% of theory) of the product are obtained as a solid starting from 100 mg (0.25 mmol) of 2-amino-6-[(2-{[7-chloro-2-(trifluoromethyl)imidazo[1,2-c]pyrimidin-5-yl]amino}ethyl)amino]pyridine-3-carbonitrile (Example 62A) by coupling with 52.9 mg (0.277 mmol) of (2,4-dichlorophenyl)boronic acid and subsequent purification by preparative HPLC.

LCMS (method 3): $R_t$=2.66 min. (m/z=507 (M+H)$^+$)

$^1$H-NMR (400 MHz, DMSO-$d_6$): d=8.61 (s, 1H), 8.26 (t, 1H), 7.74 (d, 1H), 7.63 (d, 1H), 7.52 (dd, 1H), 7.3 (s, br, 1H), 7.27 (d, 1H), 7.19 (s, 1H), 6.29 (s, br, 2H), 5.76 (d, 1H), 3.68 (dd, 2H), 3.52-3.62 (m, br, 2H).

Example 145

6-[(2-{[7-(2,4-Dichlorophenyl)-2-(morpholin-4-ylmethyl)imidazo[1,2-c]pyrimidin-5-yl]amino}-ethyl)amino]pyridine-3-carbonitrile trifluoroacetate

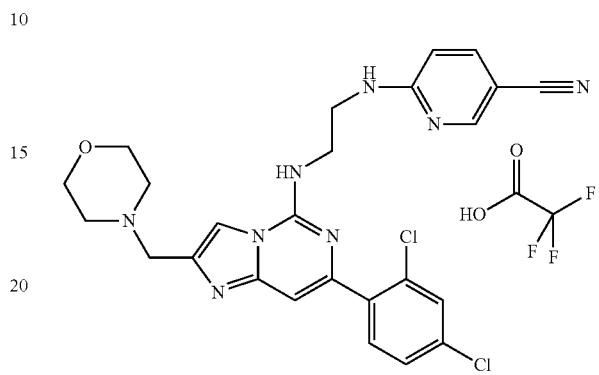

122 mg (0.268 mmol) of the chloropyrimidine of Example 95A are introduced into 3 ml of DMSO, 112 mg (0.4 mmol) of 6-[(2-aminoethyl)amino]pyridine-3-carbonitrile and 69 mg (0.54 mmol) of DIEA are added, and the mixture is heated in a microwave at 150° C. for 1.5 h.

Purification by preparative HPLC results in 23 mg (13% of theory) of the product as a solid.

LCMS (method 9): $R_t$=1.70 min. (m/z=450 (M+H)$^+$)

$^1$H-NMR (400 MHz, DMSO-$d_6$): d=8.34 (d, 1H), 8.30 (t, 1H), 8.10 (s, 1H), 7.77 (s, br, 1H), 7.74 (d, 1H), 7.65 (d, 1H), 7.60 (dd, 1H), 7.53 (dd, 1H), 7.12 (s, 1H), 6.51 (d, 1H), 4.49 (s, 2H), 4.2-4.7 (m, 4H), 3.72-3.95 (m, 2H), 3.6-3.73 (m, 4H), 3.28 (m, 4H).

Example 146

6-{[2-({7-(2,4-Dichlorophenyl)-2-[(4-methylpiperazin-1-yl)methyl]imidazo[1,2-c]pyrimidin-5-yl}-amino)ethyl]amino}pyridine-3-carbonitrile trifluoroacetate

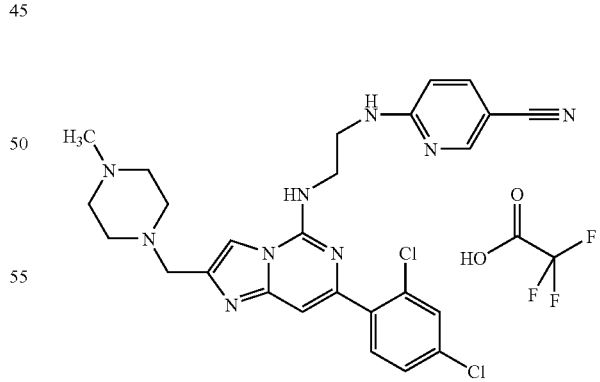

40 mg (0.081 mmol) of the chloropyrimidine of Example 96A are introduced into 2 ml of DMSO, 34 mg (0.122 mmol) of 6-[(2-aminoethyl)amino]pyridine-3-carbonitrile and 21 mg (0.16 mmol) of DIEA are added, and the mixture is heated in a microwave at 150° C. for 1 h. Purification by preparative HPLC results in 1.2 mg (2% of theory) of the product as a solid.

LCMS (method 8): $R_t$=0.93 min. (m/z=536 (M+H)$^+$)

$^1$H-NMR (400 MHz, DMSO-d$_6$): d=8.35 (d, 1H), 8.21 (s, br, 1H), 7.96 (s, 1H), 7.77 (s, br, 1H), 7.74 (d, 1H), 7.64 (d, 1H), 7.60 (dd, 1H), 7.53 (dd, 1H), 7.10 (s, 1H), 6.49 (d, 1H), 3.55-3.8 (m, 9H), 2.9-3.2 (m, 6H), 2.78 (m, 2H).

Example 147

N$^6$-[2-({7-(2,4-Dichlorophenyl)-2-[(dimethylamino)methyl]imidazo[1,2-c]pyrimidin-5-yl}amino)-ethyl]-3-nitropyridine-2,6-diamine trifluoroacetate

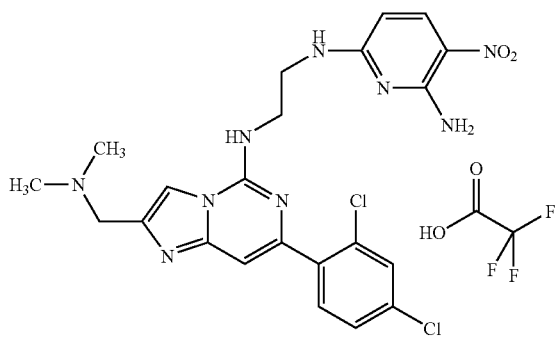

In analogy to the procedure described for Example 7, 1 mg (6% of theory) of the product is obtained starting from 11 mg (0.027 mmol) of N$^6$-[2-({7-chloro-2-[(dimethylamino)-methyl]imidazo[1,2-c]pyrimidin-5-yl}amino)ethyl]-3-nitropyridine-2,6-diamine (Example 100A) by coupling with 6 mg (0.032 mmol) of (2,4-dichlorophenyl)boronic acid and subsequent purification by preparative HPLC.

LCMS (method 1): $R_t$=1.43 min. (m/z=516 (M+H)$^+$)

$^1$H-NMR (400 MHz, DMSO-d$_6$): d=10 (s, br, 1H), 8.22 (s, br, 1H), 8.10 (s, 1H), 8.06 (m, 1H), 7.89 (d, 1H), 7.72 (s, 1H), 7.66 (d, 1H), 7.52-7.63 (m, 1H), 7.5 (d, 1H), 7.13 (s, 1H), 5.87 (d, 1H), 4.43 (s, 2H), 3.72 (d, 4H), 2.81 (s, 6H).

Example 148

2-Amino-6-[(2-{[7-(2,4-dichlorophenyl)imidazo[1,2-c]pyrimidin-5-yl]amino}ethyl)amino]-pyridine-3-carbonitrile

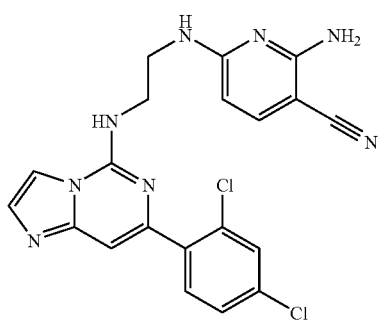

In analogy to the procedure described for Example 5, the desired product is obtained starting from 5-chloro-7-(2,4-dichlorophenyl)imidazo[1,2-c]pyrimidine (Example 6A) and 2-amino-6-[(2-aminoethyl)amino]pyridine-3-carbonitrile dihydrochloride (Example 111A).

LCMS (method 3): $R_t$=1.70 min. (m/z=439 (M+H)$^+$)

Example 149

1-{2-Amino-6-[(2-{[7-(2,4-dichlorophenyl)imidazo[1,2-c]pyrimidin-5-yl]amino}ethyl)amino]-pyridin-3-yl}-2,2,2-trifluoroethanone hydrochloride

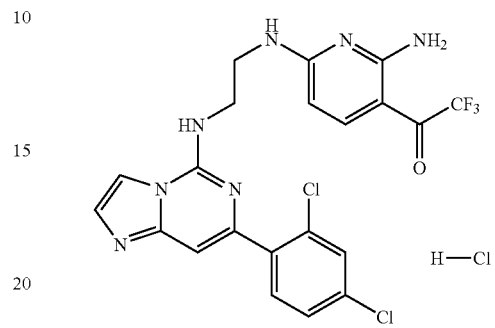

In analogy to the procedure described for Example 5, the desired product is obtained starting from 5-chloro-7-(2,4-dichlorophenyl)imidazo[1,2-c]pyrimidine (Example 6A) and 1-{2-amino-6-[(2-aminoethyl)amino]pyridin-3-yl}-2,2,2-trifluoroethanone hydrochloride (Example 115A).

LCMS (method 8): $R_t$=1.05 min. (m/z=510 (M+H—HCl)$^+$)

Example 150

1-{2-Amino-6-[(2-{[7-(2,4-dichlorophenyl)imidazo[1,2-c]pyrimidin-5-yl]amino}ethyl)amino]-pyridin-3-yl}ethanone hydrochloride

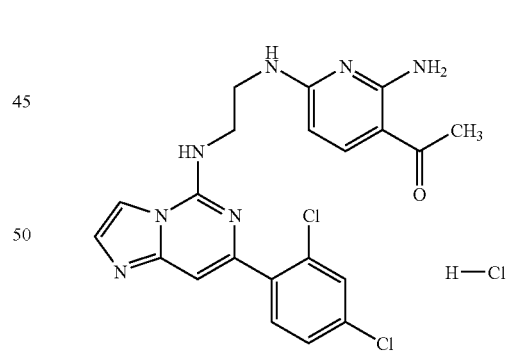

32 mg (0.01 mmol) of tert-butyl {3-acetyl-6-[(2-{[7-(2,4-dichlorophenyl)imidazo[1,2-c]pyrimidin-5-yl]amino}ethyl)amino]pyridin-2-yl}carbamate are dissolved in dioxane (2 ml), and 4M hydrogen chloride in dioxane (2 ml) are added. After stirring at RT for 3 h, the solvent is concentrated in a rotary evaporator, and the residue is purified by preparative HPLC. 11 mg (39% of theory) of the product are obtained as a solid.

LCMS (method 8): $R_t$=0.80 min. (m/z=456 (M+H—HCl)$^+$)

Example 151

Methyl 2-amino-6-[(2-{[7-(2,4-dichlorophenyl)imidazo[1,2-c]pyrimidin-5-yl]amino}ethyl)amino]pyridine-3-carboxylate

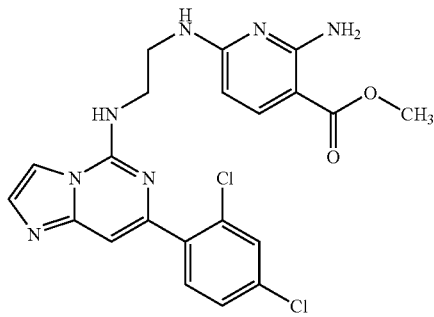

In analogy to the procedure described for Example 5, the desired product is obtained from 5-chloro-7-(2,4-dichlorophenyl)imidazo[1,2-c]pyrimidine (Example 6A) and methyl 2-amino-6-[(2-aminoethyl)amino]pyridine-3-carboxylate (Example 120A).
LCMS (method 6): $R_t$=1.10 min. (m/z=472 (M+H)$^+$)

Example 152

Ethyl 2-amino-6-[(2-{[7-(2,4-dichlorophenyl)imidazo[1,2-c]pyrimidin-5-yl]amino}ethyl)amino]-pyridine-3-carboxylate

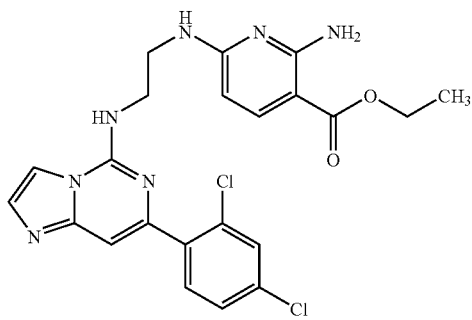

In analogy to the procedure described for Example 5, the desired product is obtained starting from 5-chloro-7-(2,4-dichlorophenyl)imidazo[1,2-c]pyrimidine (Example 6A) and ethyl-2-amino-6-[(2-aminoethyl)amino]pyridine-3-carboxylate.
LCMS (method 3): $R_t$=1.49 min. (m/z=468 (M+H)$^+$)

Example 153

6-[(2-{[3-Bromo-7-(2,4-dichlorophenyl)imidazo[1,2-c]pyrimidin-5-yl]amino}ethyl)amino]-pyridine-3-carbonitrile

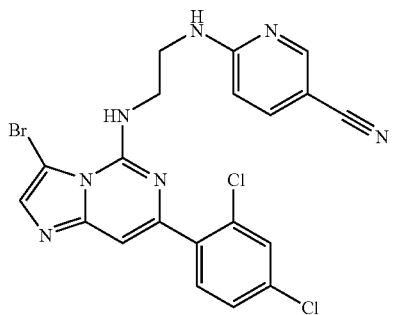

In analogy to the procedure described for Example 5, the desired product is obtained as a solid in 46% yield starting from 3-bromo-5-chloro-7-(2,4-dichlorophenyl)imidazo[1,2-c]pyrimidine (Example 121A) and 6-[(2-aminoethyl)amino]pyridine-3-carbonitrile (Example 13A).
LCMS (method 3): $R_t$=2.63 min. (m/z=504 (M+H)$^+$)

Example 154

6-[(2-{[3-Chloro-7-(2,4-dichlorophenyl)imidazo[1,2-c]pyrimidin-5-yl]amino}ethyl)amino]-pyridine-3-carbonitrile

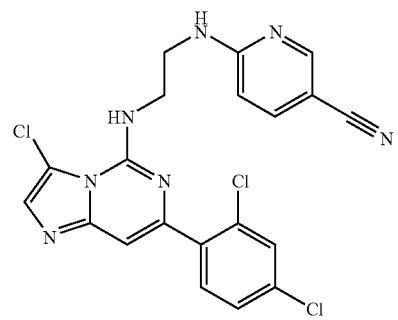

In analogy to the procedure described for Example 5, the desired product is obtained as a solid in 52% yield starting from 3,5-dichloro-7-(2,4-dichlorophenyl)imidazo[1,2-c]pyrimidine (Example 122A) and 6-[(2-aminoethyl)amino]pyridine-3-carbonitrile (Example 13A).
LCMS (method 6): $R_t$=2.10 min. (m/z=458 (M+H)$^+$)

Example 155

6-[(2-{[3,8-Dibromo-7-(2,4-dichlorophenyl)imidazo[1,2-c]pyrimidin-5-yl]amino}ethyl)amino]-pyridine-3-carbonitrile

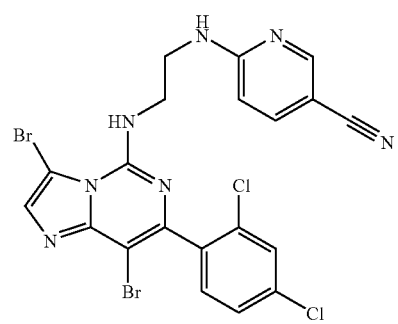

In analogy to the procedure described for Example 5, the desired product is obtained in 75% yield starting from 3,8-dibromo-5-chloro-7-(2,4-dichlorophenyl)imidazo[1,2-c]pyrimidine (Example 125A) and 2-amino-6-[(2-aminoethyl)amino]pyridine-3-carbonitrile (Example 13A).
LCMS (method 8): $R_t$=1.37 min. (m/z=580 (M+H)$^+$)

Example 156

6-[(2-{[3,8-Dichloro-7-(2,4-dichlorophenyl)imidazo[1,2-c]pyrimidin-5-yl]amino}ethyl)amino]-pyridine-3-carbonitrile

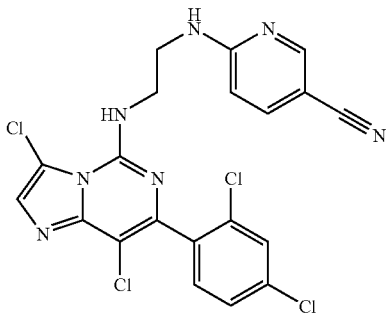

In analogy to the procedure described for Example 5, the desired product is obtained in 48% yield starting from 3,5,8-trichloro-7-(2,4-dichlorophenyl)imidazo[1,2-c]pyrimidine (Example 126A) and 2-amino-6-[(2-aminoethyl)amino]pyridine-3-carbonitrile (Example 13A).

LCMS (method 3): $R_t$=2.67 min. (m/z=492 (M+H)$^+$)

Example 157

6-{[2-({2-(Morpholin-4-ylmethyl)-7-[4-(trifluoromethyl)phenyl][1,2,4]triazolo[1,5-c]pyrimidin-5-yl}amino)ethyl]amino}pyridine-3-carbonitrile

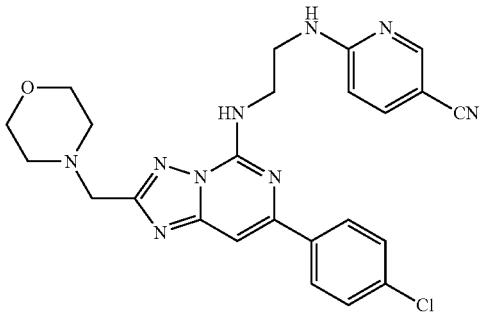

300 mg (0.75 mmol) of 5-chloro-2-(morpholin-4-ylmethyl)-7-[4-(trifluoromethyl)-phenyl][1,2,4]triazolo[1,5-c]pyrimidine (Example 151A) and 180 mg (0.91 mmol) of 6-[(2-aminoethyl)amino]pyridine-3-carbonitrile (Example 13A) are introduced into DMSO (4 ml), 0.79 ml (4.5 mmol) of DIEA is added, and the reaction solution is irradiated in a microwave reactor at 140° C. for 30 min. The reaction mixture is diluted with ethyl acetate, and the organic phase is washed with saturated sodium bicarbonate solution, ammonium chloride solution and saturated sodium chloride solution, dried and concentrated. The residue is taken up in acetonitrile (4 ml), and the solid which precipitates is filtered off and dried. 300 mg (76% of theory) of the product are obtained as a solid.

LCMS (method 8): $R_t$=1.04 min. (m/z=524 (M+H)$^+$)

$^1$H-NMR (400 MHz, DMSO-d$_6$): d=8.47 (t 1H), 8.43 (m, 1H), 8.19 (d, 2H), 7.77 (d, 2H), 7.63 (s, 1H), 7.73 (br m, 1H), 6.43 (br m, 1H), 3.85 (m, 2H), 3.74 (s, 2H), 3.67 (m, 2H), 3.61 (m, 4H), 3.28 (m, 4H).

Example 158

6-[(2-{[7-(2,4-Dichlorophenyl)-2-(morpholin-4-ylmethyl)[1,2,4]triazolo[1,5-c]pyrimidin-5-yl]-amino}ethyl)amino]pyridine-3-carbonitrile

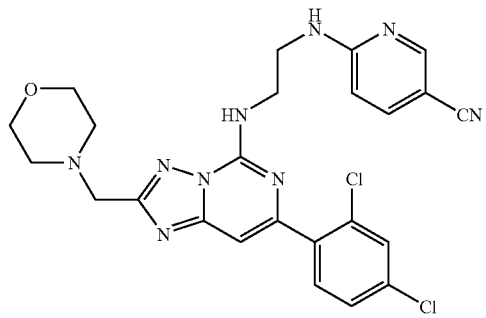

100 mg (0.25 mmol) of 5-chloro-7-(2,4-dichlorophenyl)-2-(morpholin-4-ylmethyl)[1,2,4]-triazolo[1,5-c]pyrimidine (Example 150A) and 60 mg (0.30 mmol) of 6-[(2-aminoethyl)amino]pyridine-3-carbonitrile (Example 13A) are introduced into DMSO (4 ml), 0.26 ml (1.5 mmol) of DIEA is added, and the reaction solution is irradiated in a microwave reactor at 140° C. for 45 min. The reaction mixture is purified by preparative HPLC. 62 mg (46% of theory) of the product are obtained as a solid.

LCMS (method 3): $R_t$=1.72 min. (m/z=524 (M+H)$^+$)

Example 159

Ethyl 5-({2-[(5-cyanopyridin-2-yl)amino]ethyl}amino)-7-[4-(trifluoromethyl)phenyl][1,2,4]-triazolo[1,5-c]pyrimidine-2-carboxylate

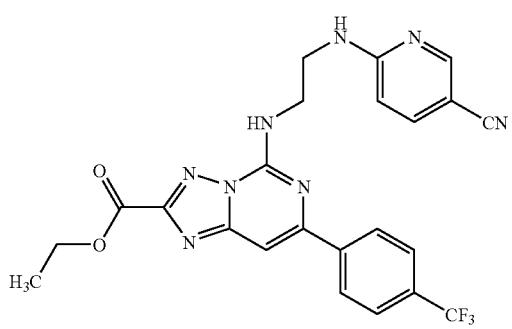

200 mg (0.52 mmol) of ethyl 5-chloro-7-(4-trifluoromethylphenyl)[1,2,4]triazolo[1,5-c]pyrimidine-2-carboxylate (Example 149A) and 123 mg (0.62 mmol) of 6-[(2-aminoethyl)amino]pyridine-3-carbonitrile (Example 13A) are introduced into DMSO (2 ml), 0.54 ml (3.1 mmol) of DIEA is added, and the reaction solution is irradiated in a microwave reactor at 90° C. for 30 min. The reaction mixture is purified by preparative HPLC. 98 mg (38% of theory) of the product are obtained as a solid.

LCMS (method 8): $R_t$=1.31 min. (m/z=497 (M+H)$^+$)

$^1$H-NMR (400 MHz, DMSO-d$_6$): d=8.79 (t, 1H), 8.45 (m, 1H), 8.20 (d, 2H), 7.86 (s, 1H), 7.79 (d, 2H), 7.77 (s, 1H), 7.50 (br m, 1H), 6.40 (br m, 1H), 4.43 (q, 2H), 3.86 (m, 2H), 3.67 (m, 2H), 1.37 (t, 3H).

Example 160

Ethyl 5-({2-[(6-amino-5-cyanopyridin-2-yl)amino]ethyl}amino)-7-[4-(trifluoromethyl)phenyl]-[1,2,4]triazolo[1,5-c]pyrimidine-2-carboxylate

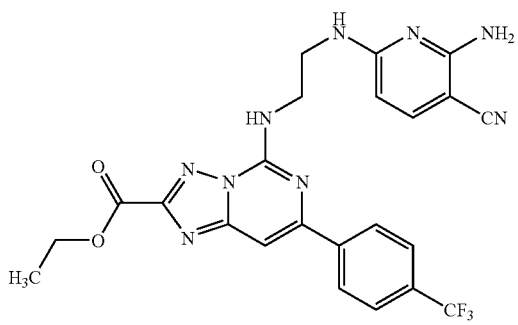

200 mg (0.52 mmol) of ethyl 5-chloro-7-(4-trifluoromethylphenyl)[1,2,4]-triazolo[1,5-c]pyrimidine-2-carboxylate (Example 149A) and 133 mg (0.62 mmol) of 2-amino-6-[(2-aminoethyl)amino]pyridine-3-carbonitrile dihydrochloride (Example 111A) are introduced into DMSO (2 ml), 0.54 ml (3.1 mmol) of DIEA is added, and the reaction solution is irradiated in a microwave reactor at 90° C. for 30 min. The reaction mixture is purified by preparative HPLC. 98 mg (38% of theory) of the product are obtained as a solid.

LCMS (method 8): $R_t$=1.30 min. (m/z=512 (M+H)$^+$)

$^1$H-NMR (400 MHz, DMSO-d$_6$): d=8.73 (t, 1H), 8.24 (d, 2H), 7.81 (d, 2H), 7.77 (s, 1H), 7.32 (br m, 1H), 7.22 (br m, 1H), 6.31 (br s, 1H), 5.68 (br m, 1H), 4.44 (q, 2H), 3.85 (m, 2H), 3.58 (m, 2H), 1.37 (t, 3H).

The following products are obtained in analogy to the procedures described for Example 5 or Example 7 (or explicitly stated otherwise):

| Example | Structure | Characterization |
|---|---|---|
| 161 | 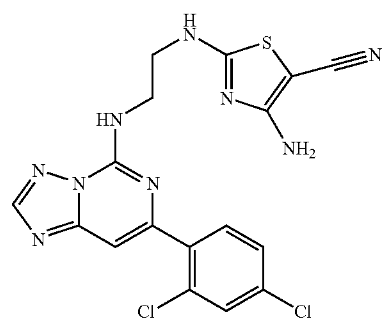 | LC/MS (method 6): $R_t$ = 1.76 min<br>MS (ESIpos): m/z = 446 (M + H)$^+$. |
| 162 | 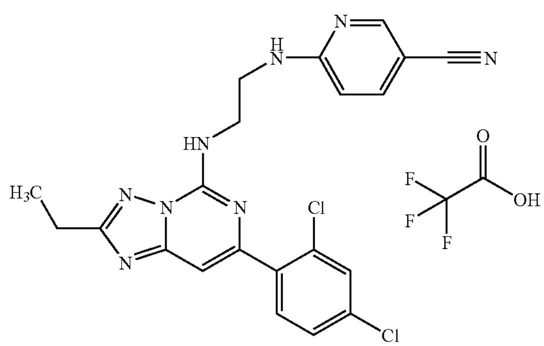 | LC/MS (method 6): $R_t$ = 2.14 min<br>MS (ESIpos): m/z = 453 (M + H)$^+$. |
| 163 | 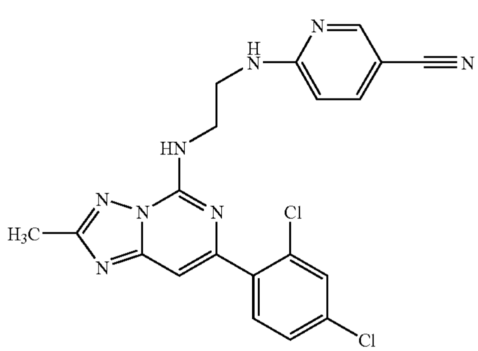 | LC/MS (method 8): $R_t$ = 1.25 min<br>MS (ESIpos): m/z = 439 (M + H)$^+$. |

| Example | Structure | Characterization |
|---|---|---|
| 164 | 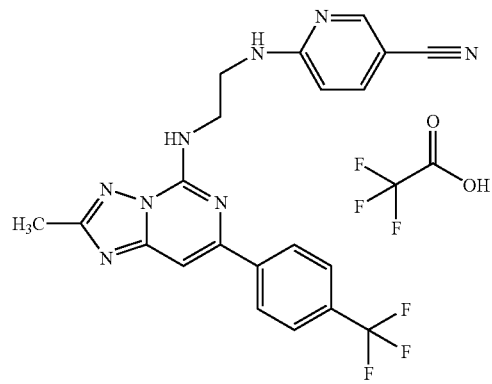 | LC/MS (method 3): $R_t$ = 2.61 min<br>MS (ESIpos): m/z = 439 (M + H)$^+$. |
| 165 | 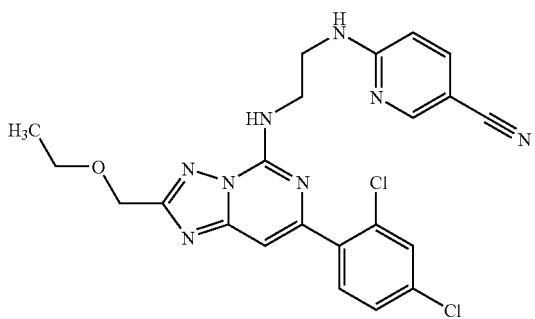 | LC/MS (method 8): $R_t$ = 1.30 min<br>MS (ESIpos): m/z = 483 (M + H)$^+$. |
| 166 | 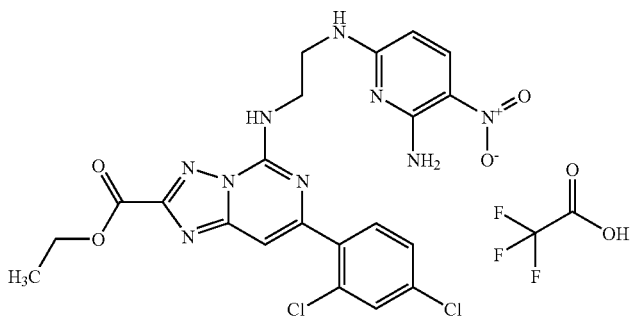 | LC/MS (method 8): $R_t$ = 1.33 min<br>MS (ESIpos): m/z = 532 (M + H)$^+$. |
| 167 | 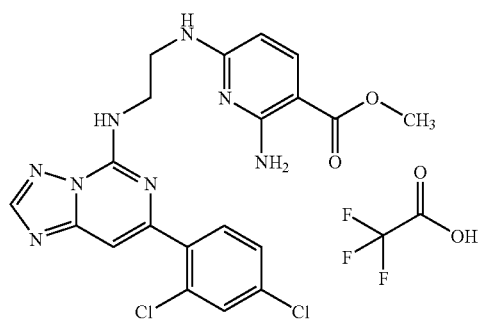 | LC/MS (method 3): $R_t$ = 2.01 min<br>MS (ESIpos): m/z = 473 (M + H)$^+$. |

-continued
| Example | Structure | Characterization |
|---|---|---|
| 168 | 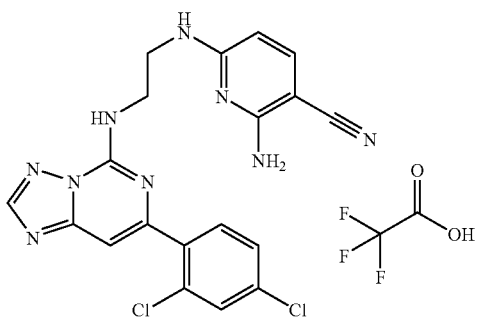 | LC/MS (method 8): $R_t$ = 1.20 min<br>MS (ESIpos): m/z = 440 (M + H)$^+$. |
| 169 | 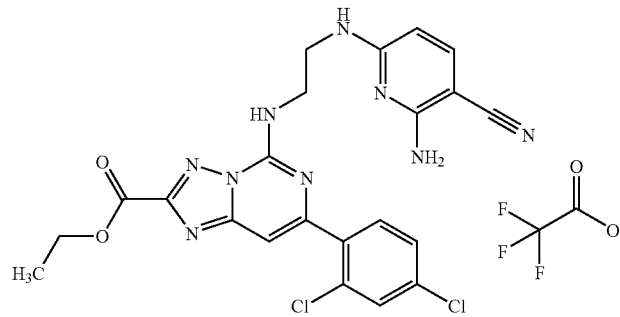 | LC/MS (method 6): $R_t$ = 2.11 min<br>MS (ESIpos): m/z = 512 (M + H)$^+$. |
| 170 | 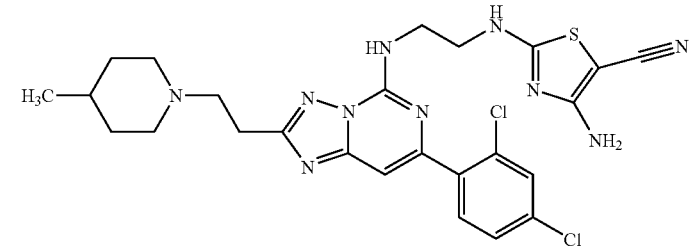 | LC/MS (method 3): $R_t$ = 1.66 min<br>MS (ESIpos): m/z = 571 (M + H)$^+$. |
| 171 | 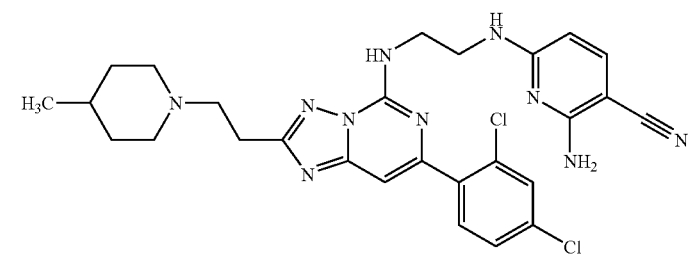 | LC/MS (method 3): $R_t$ = 1.73 min<br>MS (ESIpos): m/z = 565 (M + H)$^+$. |
| 172 | 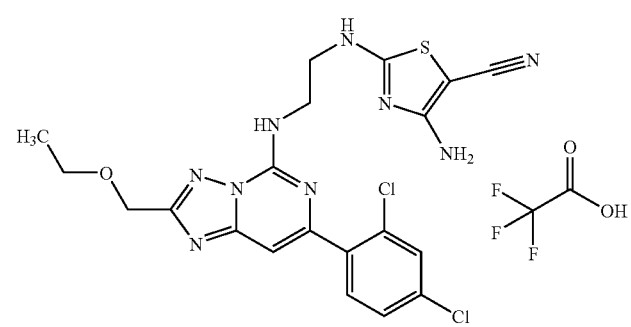 | LC/MS (method 8): $R_t$ = 1.21 min<br>MS (ESIpos): m/z = 504 (M + H)$^+$. |

-continued

| Example | Structure | Characterization |
|---|---|---|
| 173 | 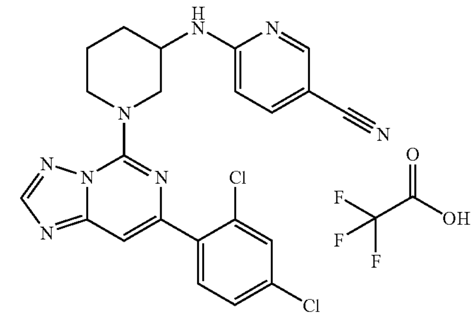 | LC/MS (method 8): R$_t$ = 1.38 min<br>MS (ESIpos): m/z = 465 (M + H)$^+$. |
| 174 | 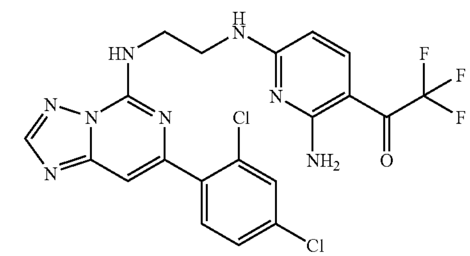 | LC/MS (method 9): R$_t$ = 2.56 min<br>MS (ESIpos): m/z = 511 (M + H)$^+$. |
| 175 | 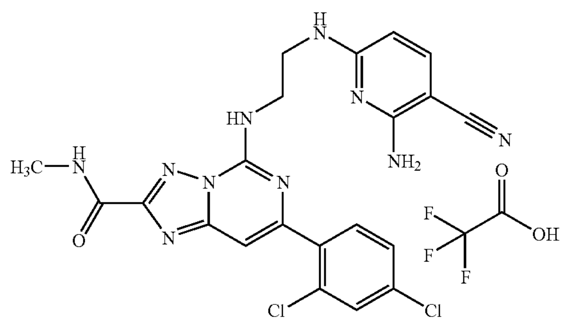 | LC/MS (method 6): R$_t$ = 1.85 min<br>MS (ESIpos): m/z = 497 (M + H)$^+$. |
| 176 | 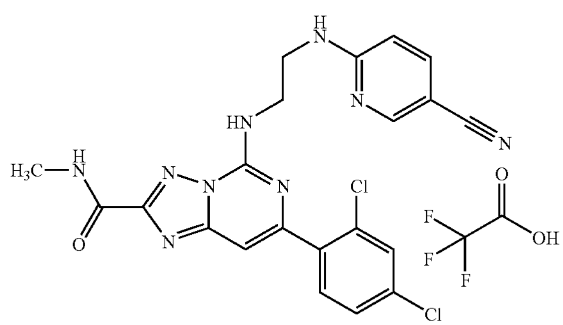 | LC/MS (method 6): R$_t$ = 1.85 min<br>MS (ESIpos): m/z = 482 (M + H)$^+$. |
| 177 | 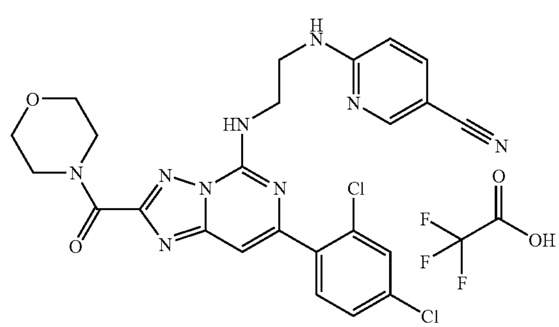 | LC/MS (method 9): R$_t$ = 2.21 min<br>MS (ESIpos): m/z = 538 (M + H)$^+$. |

-continued

| Example | Structure | Characterization |
|---|---|---|
| 178 | 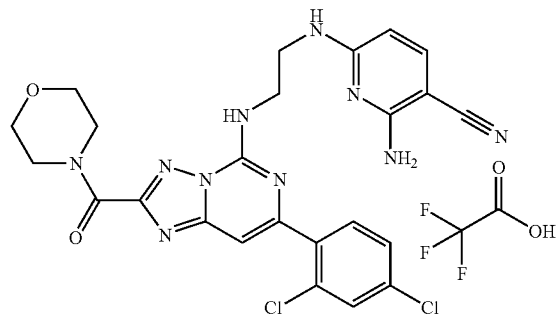 | LC/MS (method 8): R$_t$ = 1.18 min<br>MS (ESIpos): m/z = 553 (M + H)$^+$. |
| 179 | 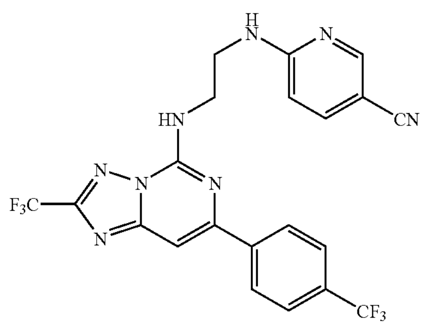 | LC/MS (method 8): R$_t$ = 1.28 min<br>MS (ESIpos): m/z = 453 (M + H)$^+$.<br>$^1$H-NMR (400 MHz, DMSO-d$_6$): d = 8.59(s, 1H), 8.43(d, 2H), 7.93(d, 2H), 2.59(s, 3H). |
| 180 | 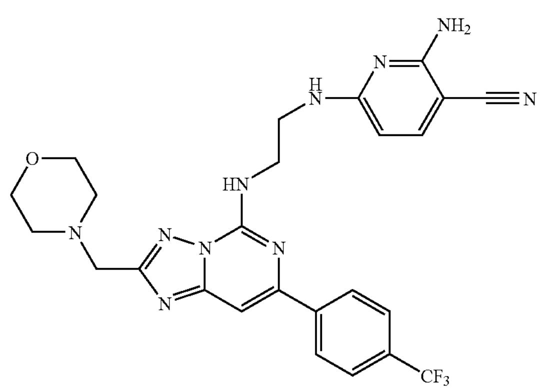 | LC/MS (method 8): R$_t$ = 1.02 min<br>MS (ESIpos): m/z = 539 (M + H)$^+$. |
| 181 | 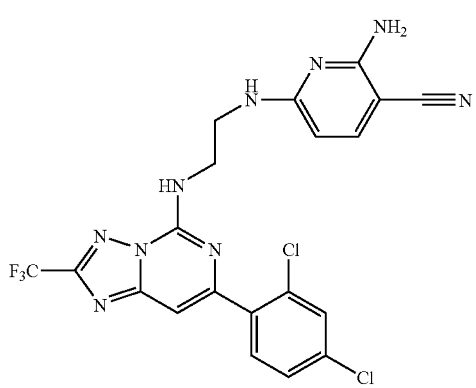 | LC/MS (method 3): R$_t$ = 2.82 min<br>MS (ESIpos): m/z = 508 (M + H)$^+$. |

-continued

| Example | Structure | Characterization |
|---|---|---|
| 182 | 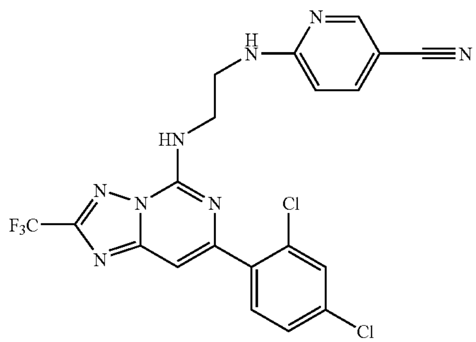 | LC/MS (method 8): R$_t$ = 1.47 min<br>MS (ESIpos): m/z = 493 (M + H)$^+$. |
| 183 | 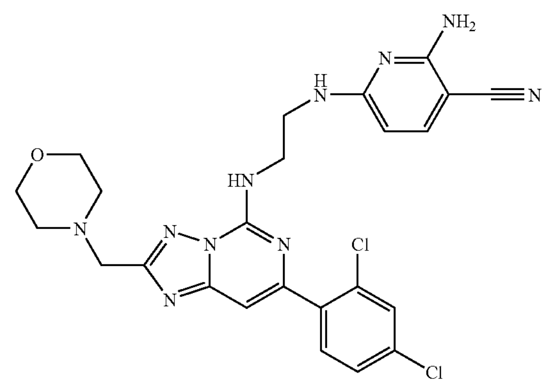 | LC/MS (method 3): R$_t$ = 1.70 min<br>MS (ESIpos): m/z = 539 (M + H)$^+$. |
| 184 | 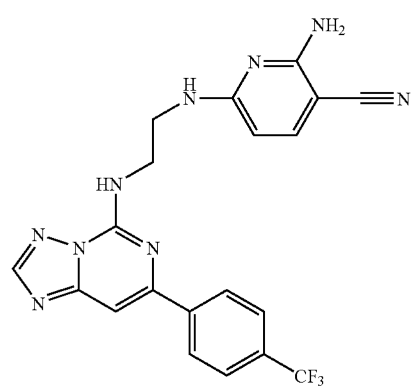 | LC/MS (method 3): R$_t$ = 2.40 min<br>MS (ESIpos): m/z = 440 (M + H)$^+$.<br>$^1$H-NMR (400 MHz, DMSO-d$_6$): d = 8.55(s, 1H), 8.51(m, 1H), 8.26(d, 2H), 7.80(d, 2H), 7.74(s, 1H), 7.35 (br m, 1H), 7.25(br m, 1H), 6.35(br m, 2H), 5.73(br m, 1H), 3.84(br m, 2H), 3.59(br m, 2H). |
| 185 | 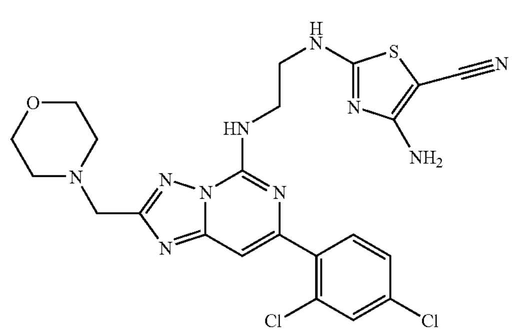 | LC/MS (method 6): R$_t$ = 1.30 min<br>MS (ESIpos): m/z = 545 (M + H)$^+$.<br>$^1$H-NMR (400 MHz, DMSO-d$_6$): d = 8.50(m, 2H), 7.75(d, 1H), 7.63(d, 1H), 7.53(dd, 1H), 7.22(s, 1H), 6.69 (s, 2H), 3.74(s, 2H), 3.72(m, 2H), 3.58(m, 4H), 3.53(m, 2H), 1.40(s, 4H). |

-continued

| Example | Structure | Characterization |
|---|---|---|
| 186 | 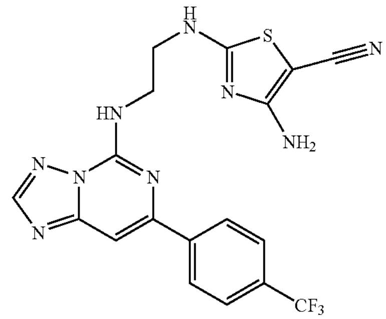 | LC/MS (method 6): R$_t$ = 1.78 min<br>MS (ESIpos): m/z = 446 (M + H)$^+$.<br>$^1$H-NMR (400 MHz, DMSO-d$_6$): d =<br>8.57(s, 1H), 8.50(m, 2H), 8.27(d, 2H), 7.81(d, 2H), 7.77(s, 1H), 3.86 (m, 2H), 3.58(m, 2H). |
| 187 | 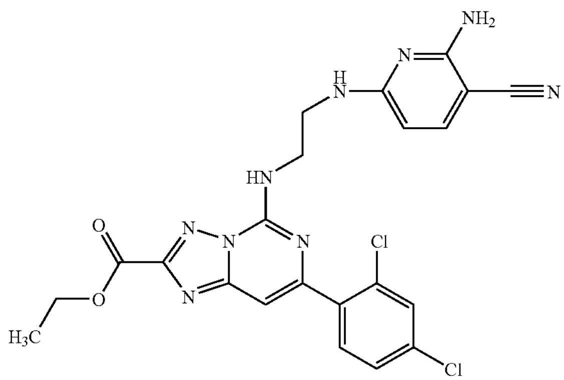 | LC/MS (method 8): R$_t$ = 1.31 min<br>MS (ESIpos): m/z = 512 (M + H)$^+$. |
| 188 | 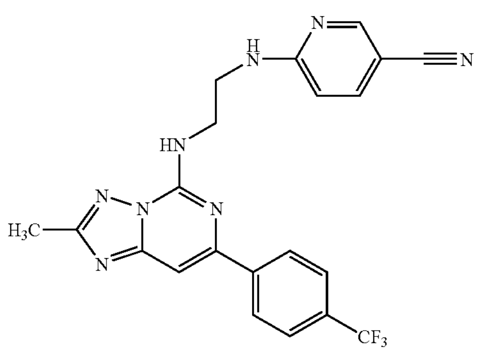 | LC/MS (method 8): R$_t$ = 1.25 min<br>MS (ESIpos): m/z = 439 (M + H)$^+$. |
| 189 | 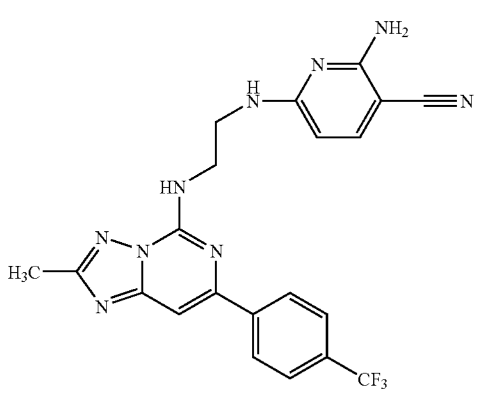 | LC/MS (method 8): R$_t$ = 1.23 min<br>MS (ESIpos): m/z = 454 (M + H)$^+$. |

-continued

| Example | Structure | Characterization |
| --- | --- | --- |
| 190 | 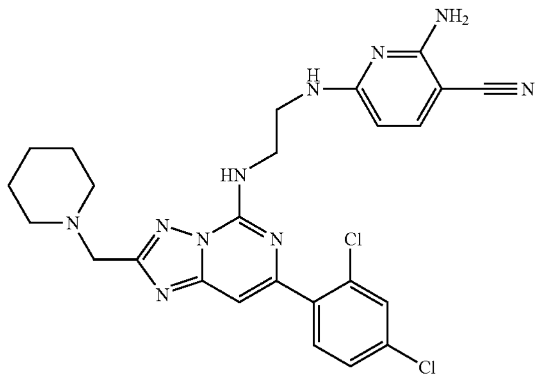 | LC/MS (method 8): R$_t$ = 1.03 min<br>MS (ESIpos): m/z = 537 (M + H)$^+$. |
| 191 | 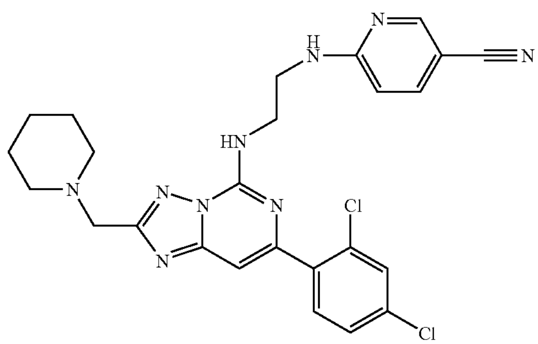 | LC/MS (method 9): R$_t$ = 1.79 min<br>MS (ESIpos): m/z = 522 (M + H)$^+$. |
| 192 | 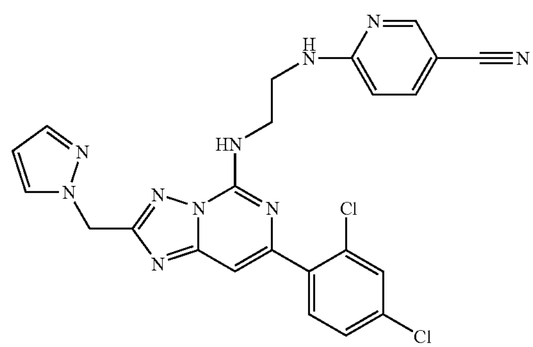 | LC/MS (method 8): R$_t$ = 1.24 min<br>MS (ESIpos): m/z = 505 (M + H)$^+$. |
| 193 | 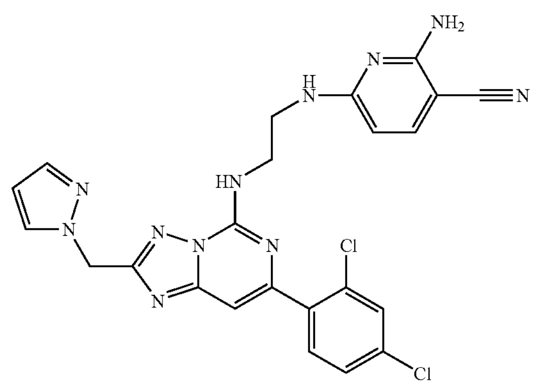 | LC/MS (method 3): R$_t$ = 2.44 min<br>MS (ESIpos): m/z = 520 (M + H)$^+$. |

-continued
| Example | Structure | Characterization |
|---|---|---|
| 194 | 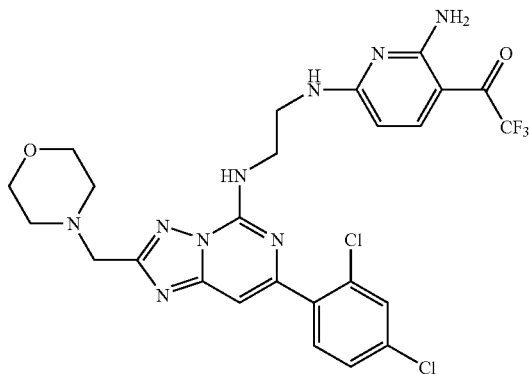 | LC/MS (method 6): $R_t$ = 1.64 min<br>MS (ESIpos): m/z = 610 (M + H)$^+$. |
| 195 | 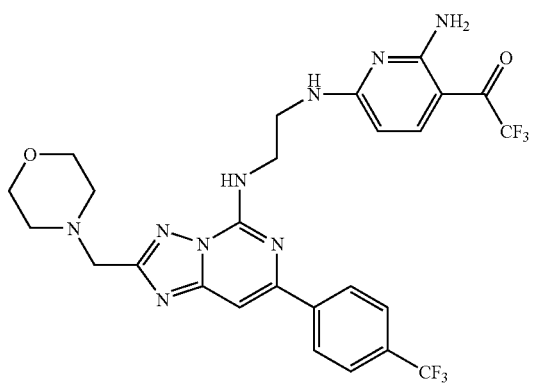 | LC/MS (method 6): $R_t$ = 1.60 min<br>MS (ESIpos): m/z = 610 (M + H)$^+$. |
| 196 | 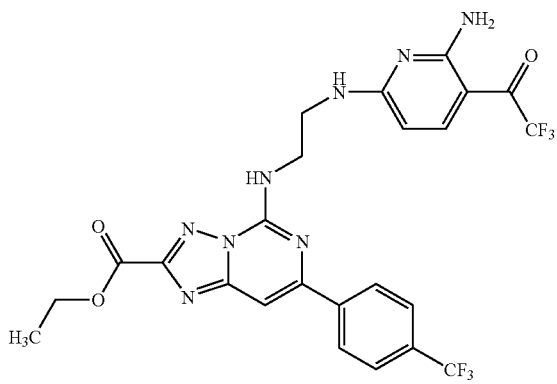 | LC/MS (method 6): $R_t$ = 2.47 min<br>MS (ESIpos): m/z = 583 (M + H)$^+$. |
| 197 | 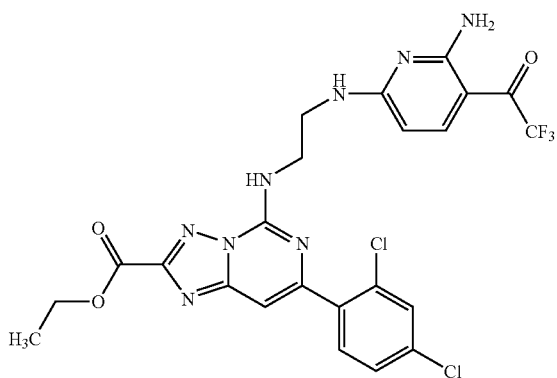 | LC/MS (method 6): $R_t$ = 2.52 min<br>MS (ESIpos): m/z = 583 (M + H)$^+$. |

-continued

| Example | Structure | Characterization |
|---|---|---|
| 198 | 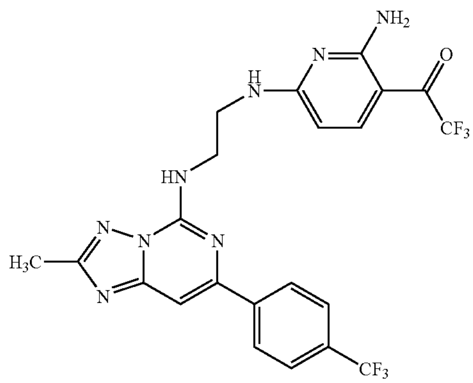 | LC/MS (method 6): $R_t$ = 2.30 min<br>MS (ESIpos): m/z = 525 (M + H)$^+$. |
| 199 | 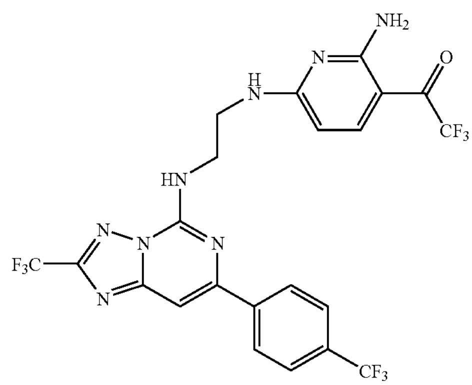 | LC/MS (method 6): $R_t$ = 2.61 min<br>MS (ESIpos): m/z = 579 (M + H)$^+$. |
| 200 | 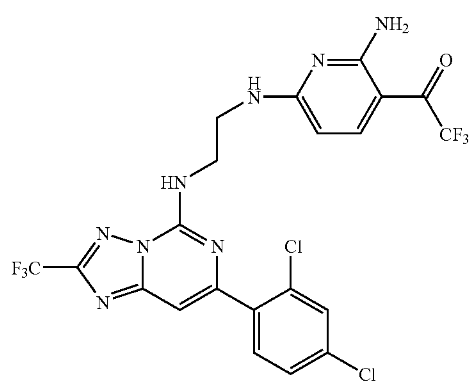 | LC/MS (method 6): $R_t$ = 2.68 min<br>MS (ESIpos): m/z = 579 (M + H)$^+$. |
| 201 | 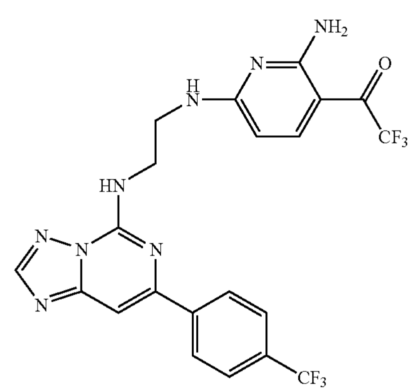 | LC/MS (method 6): $R_t$ = 2.25 min<br>MS (ESIpos): m/z = 511 (M + H)$^+$. |

| Example | Structure | Characterization |
|---|---|---|
| 202 | 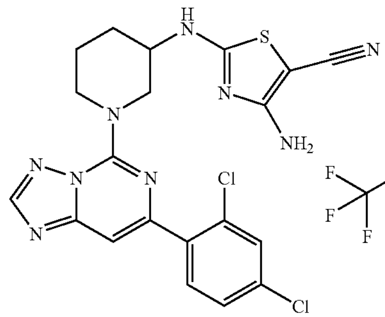 | LC/MS (method 8): $R_t$ = 1.26 min<br>MS (ESIpos): m/z = 486 (M + H)$^+$. |
| 203 | 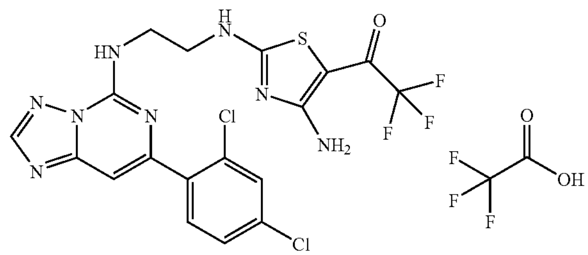 | LC/MS (method 3): $R_t$ = 2.46 min<br>MS (ESIpos): m/z = 517 (M + H)$^+$. |
| 204 | 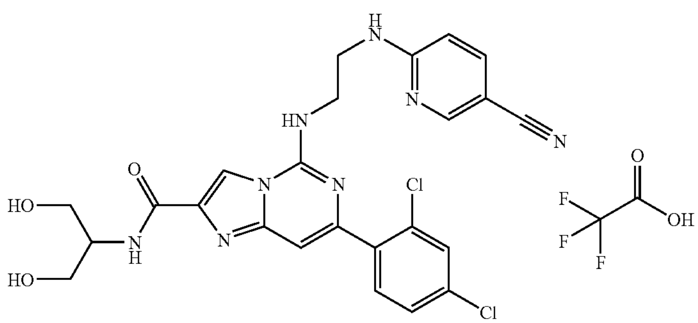 | LC/MS (method 8): $R_t$ = 1.09 min<br>MS (ESIpos): m/z = 541 (M + H)$^+$. |
| 205 | 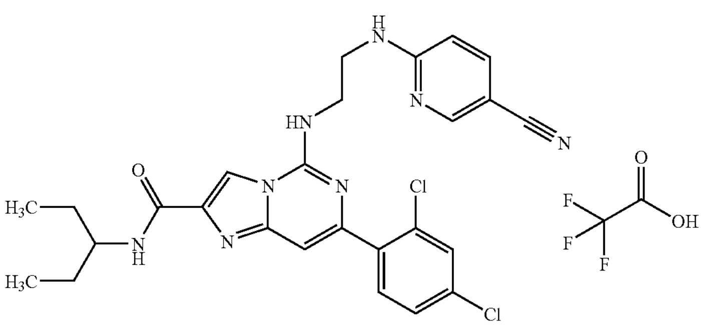 | LC/MS (method 8): $R_t$ = 1.47 min<br>MS (ESIpos): m/z = 537 (M + H)$^+$. |

B) Assessment of the Physiological Activity

The suitability of the compounds according to the invention for treating haematological disorders can be shown in the following assay systems:

In Vitro Assay

The inhibitory activity of active substances is determined in a biochemical assay. The ingredients required for this purpose are mixed in a black 384-well microtitre plate with transparent base (from Greiner, catalogue number 781092). The requirements in this connection for each well of the 384-well microtitre plate are 5 nM GSK3β (from Upstate, catalogue number xy), 40 μM GSK3B substrate GSM (sequence H-RRRPASVPPSPSLSRHS-(pS)-HQRR, from Upstate, catalogue number 2-533), 30 μM nicotinamide adenine dinucleotide NADH (Roche Diagnostics, catalogue number 10107735), 50 μM adenosine triphosphate ATP (from Sigma, catalogue number A7966), and 2 mM phosphoenolpyruvate (from Roche, catalogue number 128112). The required reaction buffer in which the biochemical reaction takes place consists of 50 mM Trizma hydrochloride tris-HCl pH: 7.5 (from Sigma, catalogue number T3253), 5 mM magnesium chloride MgCl$_2$ (from Sigma, catalogue number M8266), 0.2 mM DL-dithiothreitol DTT (from Sigma, catalogue number D9779), 2 mM ethylenediaminethertetraacid EDTA (from Sigma, catalogue number E6758), 0.01% Triton X-100 (from Sigma, catalogue number T8787) and 0.05% bovine serum albumin BSA (from Sigma, catalogue number B4287).

Active substances are dissolved in dimethyl sulphoxide DMSO (from Sigma, catalogue number D8418) in a concentration of 10 mM. Active substances are added in serial concentrations of 10 µM, 1 µM, 0.1 µM, 0.01 µM, 0.001 µM, 0.0001 µM, 0.00001 µM, 0.000001 µM to the mixtures of the biochemical reaction. As control, dimethyl sulphoxide is added instead of substance in a final concentration of 0.1%.

The reaction is incubated at 30° C. for 2 hours and then the resulting fluorescence is measured in a Tecan Safire-XFLUOR4 instrument, version V4.50 (serial number 12901300283) with the specifications: measurement mode—fluorescence measured from below, extinction wavelength 340 nm, emission wavelength 465 nm, slit width extinction 5 nm, slit width emission 5 nm, gain mode 120, delay 0 µs, number of light flashes per measurement 3, and an integration time of 40 µs.

The GSK3β activity is measured in fluorescence units, with the values of uninhibited kinase being set equal to 100% and of completely inhibited kinase set equal to 0%. The activity of the active substances is calculated in relation to these 0% and 100%.

TABLE A

| Example No. | IC$_{50}$ [nM] |
| --- | --- |
| 1 | 34 |
| 4 | 5 |
| 5 | 15 |
| 6 | 44 |
| 7 | 183 |
| 8 | 178 |
| 32 | 148 |
| 36 | 15 |
| 38 | 23 |
| 39 | 23 |
| 40 | 24 |
| 53 | 81 |
| 56 | 91 |
| 57 | 93 |
| 63 | 173 |
| 66 | 196 |
| 65 | 188 |
| 77 | 17 |
| 81 | 8 |
| 93 | 72 |
| 111 | 89 |
| 112 | 54 |
| 113 | 41 |
| 115 | 5 |
| 117 | 94 |
| 120 | 124 |
| 128 | 3 |
| 129 | 7 |
| 131 | 6 |
| 134 | 22 |
| 137 | 5 |
| 140 | 4 |
| 145 | 62 |
| 147 | 24 |
| 148 | 12 |
| 149 | 10 |
| 150 | 11 |
| 153 | 14 |
| 154 | 19 |
| 167 | 61 |
| 180 | 50 |
| 185 | 39 |
| 186 | 27 |
| 194 | 0.7 |
| 202 | 5 |
| 203 | 3 |
| Ent. B 123 | 22 |

CD34+ Proliferation Assays for Testing GSK3β Inhibitors

Adult haematopoietic stem cells are characterized by the specific expression of membrane-associated proteins. These surface markers are provided with an appropriate number appropriate for their molecular weight. This class also includes the molecule which is referred to as CD34 and which serves for the identification, characterization and isolation of adult haematopoietic stem cells. These stem cells can moreover be isolated from bone marrow, peripheral blood or umbilical cord blood. These cells have limited viability in in vitro cultures but can be stimulated to proliferation and differentiation by various additions to the culture medium. CD34-positive cells are used here in order to test the influence of substances on the activity of glycogen synthase kinase 3. For this purpose, in a first step, mononuclear cells are isolated from umbilical cord blood by differential centrifugation steps.

For this purpose, umbilical cord blood is diluted 1:4 with phosphate-buffered saline solution. 50 milliliter centrifugation vessels are charged with 17 milliliters of Ficoll (density 1.077, Ficoll Paque Plus; Pharmacia, catalogue number 17-1440-02). 30 milliliters of the 1:4 diluted umbilical cord blood are layered thereon and then centrifuged at 400×g at room temperature for 30 minutes. The brakes of the centrifuge are disengaged during this. Owing to the centrifugation, the mononuclear cells collect in the interphase. This is removed with the aid of a 30 milliliter pipette and transferred into a new 50 milliliter centrifugation vessel, and the volume is then made up to 30 ml with phosphate-buffered saline solution. These cells are centrifuged at 300×g with the brake engaged at room temperature for 10 minutes. The supernatant is discarded and the resulting cell pellet is resuspended in 30 milliliters of phosphate-buffered saline solution. These cells are again centrifuged at 200×g with brake engaged at 20° C. for 15 minutes.

To isolate the CD34-positive cells from the enriched mononuclear cells resuspended in a concentration of 1×10$^8$ cells per 300 microliters of MACS buffer (0.5% endotoxin-free bovine serum albumin in phosphate-buffered saline solution). 100 microliters of FCR blocking reagent (Miltenyi Biotec, catalogue number 130-046-702) and 100 microliters of CD34 microbeads (Miltenyi Biotec, catalogue number 130-046-702) are added. This suspension is incubated at 4° C. for 30 minutes. The cells are then diluted with 20 times the volume of MACS buffer and centrifuged at 300×g for 10 minutes. The supernatant is discarded and the cells are resuspended in 500 microliters of MACS buffer. The cells treated in this way are loaded onto an LS column (Miltenyi Biotec, catalogue number 130-042-401) and purified using a Midi MACS magnet (Miltenyi Biotec, catalogue number 130-042-303).

The number of CD34-positive cells is carried out by counting the cells using a Neubauer chamber. The purity of the cells is determined by standard protocols using the fluorescent activated cell sorting method (Becton Dickinson, BD FACS™ Sample Prep Assistant SPAII Upgrade Kit, catalogue number 337642).

To determine the influence of modulating the GSK3 activity, CD34-positive cells are incubated in a 96-well microtitre plate at 37° C. and 5% carbon dioxide for 7 days and then the proliferation rates are determined on the basis of the cell counts.

For this purpose, 5000 CD34-positive cells are taken in 100 microliters of IMDM medium (Life Technology, catalogue number 12440-046), 10% foetal calf serum (Life Technology, catalogue number 10082-139) and 20 nanograms per milliliter of stem cell factor (R&D, catalogue number 255-SC-010) in each well of a 96 U-bottom well microtitre plate (Greiner Bio-One, catalogue number 650 180). In addition, the cells are also mixed various concentrations of substances dissolved in dimethyl sulphoxide (Sigma Aldrich, catalogue number D5879-1L). This entails 4 wells in each case with the stated cell count of 5000 CD34-positive cells per well being provided with 10 micromol, 4 wells with 5 micromol, 4 wells with 2.5 micromol, 4 wells with 1.25 micromol, 4 wells with 0.625 micromol, 4 wells with 0.3125 micromol, 4 wells with 0.156 micromol, 4 wells with 0.078 micromol and as control 4 wells with 0.1% dimethyl sulphoxide as final concentration.

These cells treated in this way are incubated in a cell culture incubator at 37° C. and 5% carbon dioxide for 7 days. The proliferation rate is determined by renewed counting of the cells using a Neubauer counting chamber, with the cells provided only with the stem cell factor being set as 100% value, and all other values being related to this value.

In Vivo Assay

The investigations of the in vivo effect of the compounds according to the invention take place using 6-week old male C57BL/6 mice (Charles River, Sulzfeld, Germany) weighing 18-22 g. These animals are kept appropriate for the species with 12-hour light and dark cycles under constant climatic conditions and with water and mouse feed ad libitum. The concentrations of chemotherapeutics used are administered to the animals in accordance with the manufacturers' statements by intraperitoneal (i.p.) injections in the caudal third of the abdomen. The same procedure is applied to the substances relevant to the invention. Blood samples are taken from the retrobulbar venous plexus using Pasteur pipettes. The number of neutrophilic granulocytes is determined completely automatically using flow cytometry systems.

C) Exemplary Embodiments Of Pharmaceutical Compositions

The substances according to the invention can be converted into pharmaceutical preparations in the following ways:

Tablet:
Composition:
100 mg of the compounds of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg. Diameter 8 mm, radius of curvature 12 mm

Production:
The mixture of the compound of Example 1, lactose and starch is granulated with a 5% strength solution (m/m) of the PVP in water. The granules are dried and then mixed with magnesium stearate for 5 min. This mixture is compressed with a conventional tablet press (see above for format of the tablet).

Oral Suspension:
Composition:
1000 mg of the compound of Example 1, 1000 mg of ethanol (96%), 400 mg of Rhodigel (xanthan gum) (from FMC, USA) and 99 g of water.

10 ml of oral suspension correspond to a single dose of 100 mg of the compound according to the invention.

Production:
The Rhodigel is suspended in ethanol, and the compound of Example 1 is added to the suspension. The water is added while stirring. The mixture is stirred for about 6 h until the swelling of the Rhodigel is complete.

Solution which can be Administered Intravenously:
Composition:
1 mg of the compound of Example 1, 15 g of polyethylene glycol 400 and 250 g of water for injections.

Production:
The compound of Example 1 is dissolved together with polyethylene glycol 400 in the water by stirring. This solution is sterilized by filtration (pore diameter 0.22 μm) and dispensed under aseptic conditions into heat-sterilized infusion bottles. These are closed with infusion stoppers and crimped caps.

The invention claimed is:
1. A compound of the formula

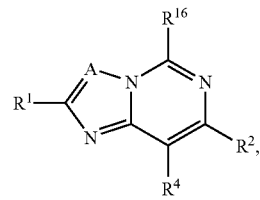

in which
A is CR$^{15}$,
where
R$^{15}$ is hydrogen, bromine or chlorine,
R$^1$ is hydrogen, hydroxy, amino, hydroxycarbonyl, aminocarbonyl, trifluoromethyl, trifluoromethoxy, cyano, $C_1$-$C_4$-alkyl, $C_1$-$C_4$-alkoxy, $C_1$-$C_6$-alkylamino, $C_1$-$C_4$-alkylcarbonyl, $C_1$-$C_4$-alkoxycarbonyl, $C_1$-$C_6$-alkylaminocarbonyl, dihydroxypropyl-aminocarbonyl, dihydroxybutylaminocarbonyl, dihydroxypentylaminocarbonyl, $C_1$-$C_4$-alkylcarbonylamino, $C_1$-$C_4$-alkylsulphonylamino, 5- or 6-membered heterocyclylcarbonyl, —CH$_2$R$^{13}$ or —CH$_2$CH$_2$R$^{14}$,
where alkoxy, alkylamino, alkylcarbonyl, alkoxycarbonyl, alkylaminocarbonyl, alkylcarbonylamino and alkylsulphonylamino may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino and 5- or 6-membered heterocyclyl,
in which heterocyclyl may be substituted by 1 to 3 substituents, where the substituents are selected independently of one another from the group consisting of halogen, hydroxy, oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl,
and
where heterocyclylcarbonyl may be substituted by 1 to 3 substituents,
where the substituents are selected independently of one another from the group consisting of halogen, hydroxy, oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl,
and
where
R$^{13}$ is hydroxy, amino, cyano, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino, 5- or 6-membered heterocyclyl or 5- or 6-membered heteroaryl,
in which alkoxy, alkylamino, alkoxycarbonyl, alkylaminocarbonyl and alkylcarbonylamino may be substituted by a substituent, where the substituent is selected from the group consisting of hydroxy, amino, hydroxycarbonyl, aminocarbonyl, $C_1$-$C_4$- alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino, and in which heterocyclyl and heteroaryl may be substituted by 1 to 3 substituents, where the substituents are selected independently of one another from the group consisting of halogen, hydroxy, oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl, and
where $R^{14}$ is hydroxy, amino, cyano, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl, $C_1$-$C_4$-alkylcarbonylamino, 5- or 6-membered heterocyclyl or 5- or 6-membered heteroaryl, in which alkoxy, alkylamino, alkoxycarbonyl, alkylaminocarbonyl and alkylcarbonylamino may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino, and in which heterocyclyl and heteroaryl may be substituted by 1 to 3 substituents, where the substituents are selected independently of one another from the group consisting of halogen, hydroxy, oxo, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl and $C_1$-$C_4$-alkylaminocarbonyl, $R^2$ is $C_6$-$C_{10}$-aryl or 5- to 10-membered heteroaryl, where aryl and heteroaryl may be substituted by 1 to 3 substituents, where the substituents are selected independently of one another from the group consisting of hydroxy, hydroxymethyl, amino, halogen, cyano, trifluoromethyl, trifluoromethoxy, aminocarbonyl, $C_1$-$C_4$-alkyl, $C_1$-$C_4$-alkoxy, $C_1$-$C_4$-alkoxymethyl, $C_1$-$C_4$-alkylamino, $C_1$-$C_4$-alkylaminomethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulphonyl, $C_1$-$C_4$-alkylsulphonylamino, $C_1$-$C_4$-alkylaminosulphonyl, phenyl, benzyloxy, 5-or 6-membered heterocyclyl, 5- or 6-membered heterocyclylcarbonyl, 5-or 6-membered heterocyclylmethyl and 5- or 6-membered heteroaryl, in which phenyl, benzyloxy, heterocyclyl, heterocyclylcarbonyl, heterocyclylmethyl and heteroaryl may be substituted by 1 to 3 substituents, where the substituents are selected independently of one another from the group consisting of halogen, cyano, trifluoromethyl, trifluoromethoxy, aminocarbonyl, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_1$-$C_4$-alkylcarbonylamino, or two of the substituents on the aryl form together with the carbon atoms to which they are bonded a 1,3-dioxolane or 1,4-dioxane, $R^4$ is hydrogen, halogen, cyano, trifluoromethyl, $C_1$-$C_3$-alkyl, methylthio or cyclopropyl, $R^{16}$ is a group of the formula

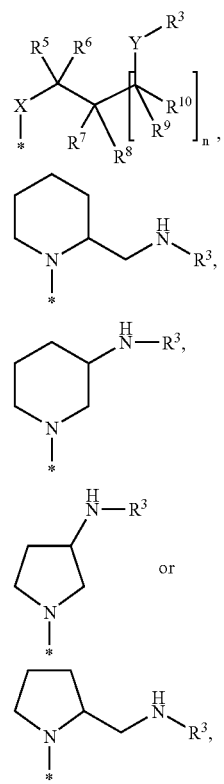

where

* is the point of attachment to the heterocycle, n is the number 0 or 1,

X is $NR^{11}$, S or O, where $R^{11}$ is hydrogen, $C_1$-$C_3$-alkyl or cyclopropyl, Y is $NR^{12}$, S or O, where $R^{12}$ is hydrogen, $C_1$-$C_3$-alkyl or cyclopropyl, $R^3$ is 2-pyridyl, pyrimid-2-yl, 2-aminopyrimid-4-yl, 2-cyclopropylaminopyrimid-4-yl, 2-methylaminopyrimid-4-yl, 2-ethylaminopyrimid-4-yl, 1,3-thiazol-2-yl, 1,3-thiazol-4-yl or 1,3-thiazol-5-yl, where 2-pyridyl, pyrimid-2-yl, 2-aminopyrimid-4-yl, 1,3-thiazol-2-yl, 1,3-thiazol-4-yl and 1,3-thiazol-5-yl are substituted by 1 to 3 substituents, where the substituents are selected independently of one another from the group consisting of halogen, cyano, nitro, amino, trifluoromethyl, trifluoromethoxy, aminocarbonyl, trifluoromethylcarbonyl, $C_1$-$C_4$-alkyl, $C_1$-$C_4$-alkoxy, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_3$-$C_6$-cycloalkylcarbonyl, in which alkyl, alkoxy, alkylamino, alkylcarbonyl, alkoxycarbonyl, alkylaminocarbonyl and cycloalkylcarbonyl may be substituted by a substituent, where the substituent is selected from the group consisting of halogen, cyano, hydroxy, amino, trifluoromethyl and $C_3$-$C_6$-cycloalkyl, or $R^3$ is a group of the formula

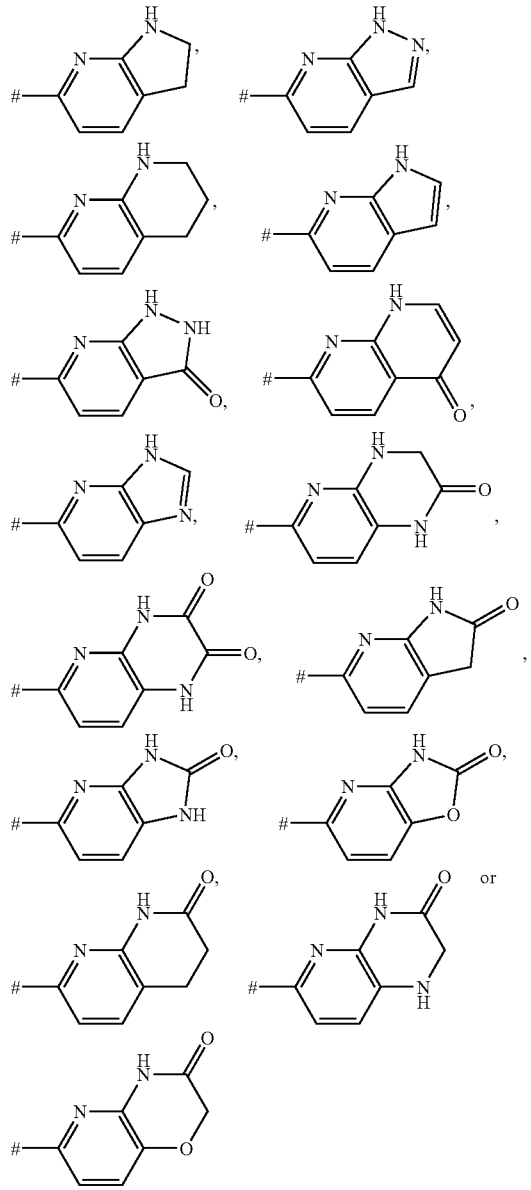

where # is the point of attachment to Y, $R^5$ is hydrogen, $C_1$-$C_3$-alkyl or cyclopropyl, $R^6$ is hydrogen or $C_1$-$C_3$-alkyl, $R^7$ is hydrogen, $C_1$-$C_3$-alkyl or cyclopropyl, $R^8$ is hydrogen or $C_1$-$C_3$-alkyl, $R^9$ is hydrogen, $C_1$-$C_3$-alkyl or cyclopropyl, $R^{10}$ is hydrogen or $C_1$-$C_3$-alkyl, or a salt thereof.

2. The compound according to claim 1, wherein

A is $CR^{15}$, where $R^{15}$ is hydrogen, $R^1$ is hydrogen, trifluoromethyl, cyano, $C_1$-$C_4$-alkyl, $C_1$-$C_6$-alkylaminocarbonyl, dihydroxypropylaminocarbonyl, dihydroxybutylaminocarbonyl, dihydroxypentylaminocarbonyl, pyrrolidinylcarbonyl, piperidinylcarbonyl, morpholinylcarbonyl, piperazinylcarbonyl, —$CH_2R^{13}$ or —$CH_2CH_2R^{14}$, where alkylaminocarbonyl may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, pyrrolidinyl, piperidinyl, morpholinyl and piperazinyl, in which pyrrolidinyl, piperidinyl, morpholinyl and piperazinyl may be substituted by 1 to 3 substituents, where the substituents are selected independently of one another from the group consisting of halogen, hydroxy, oxo, $C_1$-$C_4$-alkyl, $C_1$-$C_4$-alkoxy and $C_1$-$C_4$-alkylamino, and where pyrrolidinylcarbonyl, piperidinylcarbonyl, morpholinylcarbonyl and piperazinyl-carbonyl may be substituted by 1 to 3 substituents, where the substituents are selected independently of one another from the group consisting of halogen, hydroxy, oxo, $C_1$-$C_4$-alkyl, $C_1$-$C_4$-alkoxy and $C_1$-$C_4$-alkylamino, and where $R^{13}$ is hydroxycarbonyl, $C_1$-$C_4$-alkoxy, $C_1$-$C_4$-alkylamino, $C_1$-$C_4$-alkylaminocarbonyl, pyrrolidinyl, piperidinyl, morpholinyl, piperazinyl, pyrazolyl, imidazolyl, triazolyl or pyridyl, in which alkoxy, alkylamino and alkylaminocarbonyl may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino, and in which pyrrolidinyl, piperidinyl, morpholinyl, piperazinyl, pyrazolyl, imidazolyl, triazolyl and pyridyl may be substituted by 1 to 3 substituents, where the substituents are selected independently of one another from the group consisting of halogen, hydroxy, oxo, $C_1$-$C_4$-alkyl, $C_1$-$C_4$-alkoxy and $C_1$-$C_4$-alkylamino, and where $R^{14}$ is hydroxycarbonyl, $C_1$-$C_4$-alkoxy, $C_1$-$C_4$-alkylamino, $C_1$-$C_4$-alkylaminocarbonyl, pyrrolidinyl, piperidinyl, morpholinyl, piperazinyl, pyrazolyl, imidazolyl, triazolyl or pyridyl, in which alkoxy, alkylamino and alkylaminocarbonyl may be substituted by a substituent, where the substituent is selected from the group consisting of hydroxy, amino, hydroxycarbonyl, aminocarbonyl, $C_1$-$C_4$-alkoxy, $C_1$-$C_4$-alkylamino, $C_1$-$C_4$-alkoxycarbonyl, $C_1$-$C_4$-alkylaminocarbonyl and $C_1$-$C_4$-alkylcarbonylamino, and in which pyrrolidinyl, piperidinyl, morpholinyl, piperazinyl, pyrazolyl, imidazolyl, triazolyl and pyridyl may be substituted by 1 to 3 substituents, where the substituents are selected independently of one another from the group consisting of halogen, hydroxy, oxo, $C_1$-$C_4$-alkyl, $C_1$-$C_4$-alkoxy and $C_1$-$C_4$-alkylamino, $R^2$ is phenyl, where phenyl may be substituted by 1 to 3 substituents, where the substituents are selected independently of one another from the group consisting of hydroxy, halogen, cyano, trifluoromethyl, trifluoromethoxy, aminocarbonyl, $C_1$-$C_4$-alkyl, $C_1$-$C_4$-alkoxy, $C_1$-$C_4$-alkoxymethyl, $C_1$-$C_4$-alkylaminomethyl, $C_1$-$C_4$-alkylcarbonyl, $C_1$-$C_4$-alkoxycarbonyl, $C_1$-$C_4$-alkylaminocarbonyl, $C_1$-$C_4$-alkylcarbonylamino, $C_1$-$C_4$-alkylsulphonyl, $C_1$-$C_4$-alkylsulphonylamino, $C_1$-$C_4$-alkylaminosulphonyl, phenyl, pyrrolidinyl, piperidinyl, morpholinyl, piperazinyl, pyrrolidinylmethyl, piperidinylmethyl, morpholinylmethyl and piperazinylmethyl, in which phenyl, pyrrolidinyl, piperidinyl, morpholinyl, piperazinyl, pyrrolidinylmethyl, piperidinylmethyl, morpholinylmethyl and piperazinylmethyl may be substituted by 1 to 3 substituents, where the substituents are selected independently of one another from the group consisting of halogen, cyano, trifluoromethyl, trifluoromethoxy and $C_1$-$C_4$-alkyl, $R^4$ is hydrogen or chlorine,
$R^{16}$ is a group of the formula

[structure]

where
* is the point of attachment to the heterocycle,
n is the number 0,
X is $NR^{11}$, S or O,
where
$R^{11}$ is hydrogen or methyl,
Y is $NR^{12}$, S or O,
where
$R^{12}$ is hydrogen or methyl,
$R^3$ is 2-pyridyl, pyrimid-2-yl, 2-aminopyrimid-4-yl, 2-cyclopropylaminopyrimid-4-yl, 2-methylaminopyrimid-4-yl, 2-ethylaminopyrimid-4-yl, 1,3-thiazol-2-yl, 1,3-thiazol-4-yl or 1,3-thiazol-5-yl,
where 2-pyridyl, pyrimid-2-yl, 2-aminopyrimid-4-yl, 1,3-thiazol-2-yl, 1,3-thiazol-4-yl and 1,3-thiazol-5-yl are substituted by 1 to 3 substituents, where the substituents are selected independently of one another from the group consisting of halogen, cyano, nitro, amino, trifluoromethyl, trifluoromethoxy, aminocarbonyl, trifluoromethylcarbonyl, $C_1$-$C_4$-alkylamino, $C_1$-$C_4$-alkylcarbonyl, $C_1$-$C_4$-alkoxycarbonyl, $C_1$-$C_4$-alkylaminocarbonyl and $C_3$-$C_6$-cycloalkylcarbonyl,
in which alkylamino, alkylcarbonyl, alkoxycarbonyl, alkylaminocarbonyl and cycloalkylcarbonyl may be substituted by a substituent, where the substituent is selected from the group consisting of halogen, cyano, hydroxy, amino, trifluoromethyl and $C_3$-$C_6$-cycloalkyl, $R^5$ is hydrogen or methyl,
$R^6$ is hydrogen,
$R^7$ is hydrogen or methyl,
$R^8$ is hydrogen,
$R^9$ is hydrogen,
$R^{10}$ is hydrogen,
or a salt thereof.

3. The compound according to claim 1, wherein
A is $CR^{15}$,
where
$R^{15}$ is hydrogen,
$R^1$ is hydrogen, methyl or —$CH_2R^{13}$,
where
$R^{13}$ is morpholinyl,
$R^2$ is phenyl,
where phenyl may be substituted by 1 to 3 substituents, where the substituents are selected independently of one another from the group consisting of chlorine, fluorine, trifluoromethyl, trifluoromethoxy and methyl,
$R^4$ is hydrogen,
$R^{16}$ is a group of the formula

[structure]

where
* is the point of attachment to the heterocycle,
n is the number 0,
X is $NR^{11}$,
where
$R^{11}$ is hydrogen,
Y is $NR^{12}$,
where
$R^{12}$ is hydrogen,
$R^3$ is 2-pyridyl or 1,3-thiazol-2-yl,
where 2-pyridyl and 1,3-thiazol-2-yl are substituted by 1 to 2 substituents, where the substituents are selected independently of one another from the group consisting of cyano, nitro, amino, trifluoromethylcarbonyl and methylcarbonyl,
$R^5$ is hydrogen or methyl,
$R^6$ is hydrogen,
$R^7$ is hydrogen or methyl,
$R^8$ is hydrogen,
$R^9$ is hydrogen,
$R^{10}$ is hydrogen,
or a salt thereof.

4. A pharmaceutical composition comprising a compound according to claim 1 in combination with an inert, non-toxic, pharmaceutically suitable excipient.

5. A method for preparing a compound of the formula (I) or one of its salts, its solvates or solvates of its salts according to claim 1, comprising reacting

[A] a compound of the formula

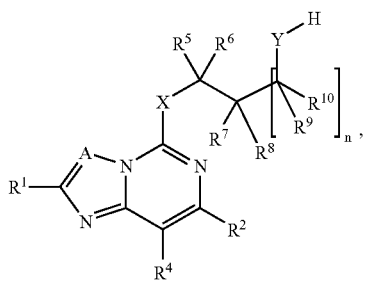
(II)

in which
A, n, X, Y, R$^1$, R$^2$, R$^4$, R$^5$, R$^6$, R$^7$, R$^8$, R$^9$ and R$^{10}$ have the meaning indicated in claim 1,
with a compound of the formula

R$^3$—X$^1$ (III), in which
R$^3$ has the meaning indicated in claim 1, and
X$^1$ is halogen, preferably chlorine or fluorine,
or reacting

[B] a compound of the formula

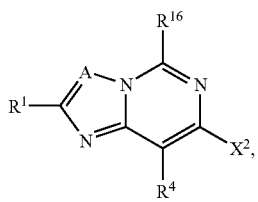
(IV)

in which
A, R$^1$, R$^4$ and R$^{16}$ have the meaning indicated in claim 1, and
X$^2$ is iodine, bromine, chlorine or trifluoromethanesulphonyl, preferably iodine or bromine,
with a compound of the formula

Q-R$^2$ (V), in which
R$^2$ has the meaning indicated in claim 1, and
Q is —B(OH)$_2$, a boronic acid ester, preferably boronic acid pinacol ester, or —BF$_3^-$K$^+$,
under Suzuki coupling conditions,
or reacting

[C] a compound of the formula

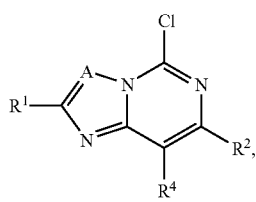
(VI)

in which
A, R$^1$, R$^2$ and R$^4$ have the meaning indicated in claim 1,
with a compound of the formula

H—R$^{16}$ (IX), in which
R$^{16}$ has the meaning indicated in claim 1.

* * * * *